United States Patent
Baldwin et al.

(10) Patent No.: US 7,566,786 B2
(45) Date of Patent: *Jul. 28, 2009

(54) QUINOLINE DERIVATIVES AS PHOSPHODIESTERASE INHIBITORS

(75) Inventors: Ian Robert Baldwin, Stevenage (GB); Michael David Barker, Stevenage (GB); Anthony William Dean, Stevenage (GB); Colin David Eldred, Stevenage (GB); Brian Evans, Stevenage (GB); Sharon Lisa Gough, Stevenage (GB); Stephen Barry Guntrip, Stevenage (GB); Julie Nicole Hamblin, Stevenage (GB); Stuart Holman, Stevenage (GB); Paul Jones, Stevenage (GB); Mika Kristian Lindvall, Stevenage (GB); Christopher James Lunniss, Stevenage (GB); Tracy Jane Redfern, Stevenage (GB); Alison Judith Redgrave, Stevenage (GB); John Edward Robinson, Stevenage (GB); Michael Woodrow, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 420 days.

This patent is subject to a terminal disclaimer.

(21) Appl. No.: 10/557,079

(22) PCT Filed: May 19, 2004

(86) PCT No.: PCT/EP2004/005494

§ 371 (c)(1),
(2), (4) Date: May 23, 2006

(87) PCT Pub. No.: WO2004/103998

PCT Pub. Date: Dec. 2, 2004

(65) Prior Publication Data

US 2007/0142373 A1    Jun. 21, 2007

(30) Foreign Application Priority Data

May 21, 2003   (GB) ................................. 0311688.6
Nov. 10, 2003  (GB) ................................. 0326187.2

(51) Int. Cl.
    *C07D 215/38*   (2006.01)
    *C07D 215/44*   (2006.01)
(52) U.S. Cl. ........................ 546/159; 546/160; 546/162; 514/313
(58) Field of Classification Search .................. 546/159, 546/160, 162; 514/313
    See application file for complete search history.

(56) References Cited

U.S. PATENT DOCUMENTS 5,215,999 A * 6/1993 Uchida et al. ................ 514/313

FOREIGN PATENT DOCUMENTS

| EP | 0480052 | 4/1992 |
|---|---|---|
| EP | 0498723 A1 | 8/1992 |
| JP | 03/005355 A | 1/2003 |
| WO | 91/14677 A1 | 3/1991 |
| WO | 95/11592 A1 | 5/1995 |
| WO | 98/02434 A1 | 1/1998 |
| WO | 98/13350 A1 | 4/1998 |
| WO | WO 98/57936 | 12/1998 |
| WO | 00/12497 A2 | 3/2000 |
| WO | 00/18740 A1 | 4/2000 |
| WO | 00/18761 A | 4/2000 |
| WO | 02/08224 A1 | 1/2002 |
| WO | WO 02/20489 | 3/2002 |
| WO | 0226713 A1 | 4/2002 |
| WO | 02/36570 A1 | 5/2002 |
| WO | 02/44166 A1 | 6/2002 |
| WO | 02/094203 A2 | 11/2002 |
| WO | WO 02/092571 | 11/2002 |
| WO | 02/102315 A2 | 12/2002 |
| WO | 03/035621 A1 | 5/2003 |
| WO | 03/045920 A1 | 6/2003 |
| WO | 03/048152 A2 | 6/2003 |
| WO | 03/064431 A2 | 8/2003 |
| WO | 03/082827 A1 | 10/2003 |
| WO | 04/000828 A1 | 12/2003 |
| WO | 2004/067513 A1 | 8/2004 |
| WO | 2004/080463 A1 | 9/2004 |

OTHER PUBLICATIONS

Joshua O Odingo; Inhibitors of PDE4: a review of recent patent literature; Expert Opin Ther. Patents; 2005; 15(7); 773-787; Ashley Publications.

* cited by examiner

*Primary Examiner*—D. Margaret Seaman
(74) *Attorney, Agent, or Firm*—J. Scott Young

(57) ABSTRACT

There are provided according to the invention novel compounds of formula (I)

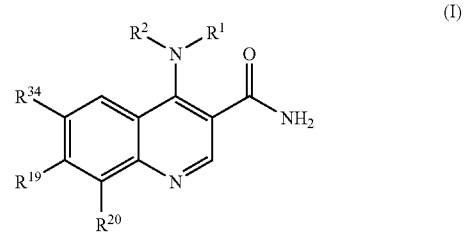

or pharmaceutically acceptable salts thereof, wherein R1, R2, R19, R20, and R34 are as described in the specification, processes for preparing them, formulations containing them and their use in therapy for the treatment of inflammatory diseases.

23 Claims, No Drawings

QUINOLINE DERIVATIVES AS PHOSPHODIESTERASE INHIBITORS

CROSS-REFERENCE TO RELATED APPLICATIONS

This application is filed pursuant to 35 U.S.C. § 371 as a United States National Phase Application of International Application No. PCT/EP2004/005494 filed May 19, 2004, which claims priority from GB 0311688.6 filed May 21, 2003 and GB 0326187.2 filed Nov. 10, 2003.

FIELD OF THE INVENTION

The present invention relates to quinoline compounds, processes for their preparation, intermediates usable in these processes, and pharmaceutical compositions containing the compounds. The invention also relates to the use of the quinoline compounds in therapy, for example as inhibitors of phosphodiesterases and/or for the treatment and/or prophylaxis of inflammatory and/or allergic diseases such as chronic obstructive pulmonary disease (COPD), asthma, rheumatoid arthritis or allergic rhinitis.

BACKGROUND OF THE INVENTION

WO 02/20489 A2 (Bristol-Myers-Squibb Company) discloses 4-aminoquinoline derivatives wherein the 4-amino group $NR^4R^5$ may represent an acyclic amino group wherein $R^4$ and $R^5$ may each independently represent hydrogen, alkyl, cycloalkyl, aryl, heteroaryl etc.; $NR^4R^5$ may alternatively represent an aliphatic heterocyclic group. The compounds are disclosed as inhibitors of cGMP phosphodiesterase, especially type 5 (PDE5).

EP 0 480 052 (Otsuka Pharmaceutical Co. Ltd.) discloses 4-aminoquinoline-3-carboxamides wherein the 4-amino group $NHR^4$ may represent an amino group wherein $R^4$ represents phenyl, tetrahydronaphthyl or naphthyl, optionally substituted with alkyl, halogen, alkoxy etc.; and the 3-carboxamide group $CONR^2R^3$ represents a primary, secondary or tertiary carboxamide group. The compounds are disclosed as inhibitors of gastric acid secretion, and as cytoprotective agents; inhibition of the ATPase activated by $H^+$ and $K^+$ at the gastric wall cells is also disclosed.

It is desirable to find new compounds which bind to, and preferably inhibit, phosphodiesterase type IV (PDE4).

SUMMARY OF THE INVENTION

According to the invention there is provided a compound of formula (I) or a pharmaceutically acceptable salt thereof:

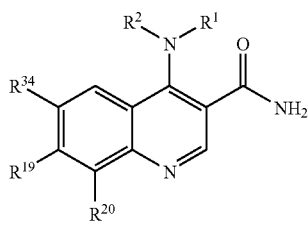

(I)

wherein:
$R^1$ is
$C_{1-6}$ alkyl;
$C_{3-7}$cycloalkyl or $C_{3-7}$cycloalkyl($C_{1-4}$alkyl)- wherein the $C_{3-7}$cycloalkyl is optionally substituted by one or more substituents selected from =O and OH;

$C_{4-7}$cycloalkyl fused to an aryl ring;

Aryl or aryl($C_{1-6}$alkyl)- wherein the aryl is optionally substituted by one or more substituents selected from $C_{1-6}$alkyl, $C_{1-6}$alkylCONR$^6$—, $C_{1-6}$alkylCO—, halogen, —CF$_3$, —(CH$_2$)$_m$OH, —OCF$_3$, $C_{1-6}$alkoxy-, $C_{1-6}$alkoxy($C_{1-4}$alkyl)-, $C_{1-6}$alkoxy$C_{2-6}$alkoxy-, $C_{1-6}$alkoxycarbonyl, —CN, $R^4R^5$NCO, $R^7R^6$N—, $R^9R^{10}$NCONR$^{11}$—, HO(CH$_2$)$_{2-6}$O—, $R^{12}R^{13}$NSO$_2$(CH$_2$)$_m$-, (4-morpholinyl)$C_{2-8}$alkoxy, —NR$^{14}$SO$_2C_{1-6}$alkyl, aryloxy, heteroaryl (optionally substituted by $C_{1-6}$alkyl), CO$_2$H, $R^{21}R^{22}$N($C_{1-4}$alkyl)-, $C_{1-6}$alkoxyCONR$^{23}$(CH$_2$)m—, aryl(optionally substituted by $C_{1-6}$alkyl);

Aryl fused to a $C_{4-7}$cycloalkyl ring, wherein the cycloalkyl ring is optionally substituted by one or more =O;

Aryl fused to a heterocyclyl ring, wherein the heterocyclyl ring is optionally substituted by one or more substituents selected from =O, —COC$_{1-4}$alkyl, $C_{1-4}$alkyl;

Heteroaryl or heteroaryl($C_{1-6}$alkyl)- wherein the heteroaryl is optionally substituted by one or more substituents selected from: $C_{1-6}$alkyl, aryl($C_{1-4}$alkyl), $C_{1-6}$alkoxy, halogen, $C_{1-6}$alkoxyCO; or Heterocyclyl optionally fused to an aryl or heteroaryl ring;

$R^2$ is hydrogen or $C_{1-6}$alkyl;

$R^{34}$ is hydrogen or a group of formula:

wherein $R^3$ is $C_{1-6}$alkyl optionally substituted by one or more substituents selected from —OH, —NR$^{16}$COR$^{15}$, —NR$^{17}$R$^{18}$, —CO$_2$R$^{24}$, $C_{1-6}$alkoxyCONR$^{25}$—, —CONR$^{26}$R$^{27}$, $C_{1-6}$alkoxy-, $C_{1-6}$alkylSO$_2$NR$^{33}$-, or a group having one of the following formulae;

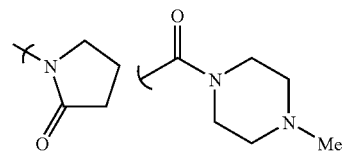

$C_{3-7}$cycloalkyl;

Aryl or aryl($C_{1-6}$alkyl)- wherein the aryl is optionally substituted by one or more substituents selected from $C_{1-6}$alkyl-, halogen-, $C_{1-6}$alkoxy-, —CO$_2$R$^{28}$, —CH$_2$CO$_2$H, —OH, aryl (optionally substituted by a $C_{1-6}$ alkoxy group), heteroaryl, —CONR$^{29}$R$^{30}$, $C_{3-7}$cycloalkoxy, $C^{3-7}$cycloalkyl($C_{1-6}$alkoxy)-, —CF$_3$;

Heteroaryl or heteroaryl($C_{1-6}$alkyl)- wherein the heteroaryl is optionally substituted by one or more $C_{1-6}$alkyl or —CONR$^{29}$R$^{30}$ groups; or Heterocyclyl which is optionally substituted by one of more substituents selected from $C_{1-6}$alkyl-, $C_{1-6}$alkylCO—, $C_{3-7}$cycloalkylCO—, heteroarylCO- (optionally substituted by one or more $C_{1-4}$alkyl- groups), $C_{1-6}$alkoxyCO—, arylCO—, $R^{31}R^{32}$NCO—, $C_{1-6}$alkylSO$_2$—, arylSO$_2$, -heteroarylSO$_2$ (optionally substituted by one or more $C_{1-4}$alkyl or $C_{1-4}$alkylCONH— groups) The heterocyclyl is linked to the $S(=O)_n$ moiety through a carbon atom.

m is 0-6 n is 0, 1 or 2;

$R^{19}$ is hydrogen, $C_{1-6}$alkyl or a group of formula:

$R^{20}$ is hydrogen, $C_{1-6}$alkyl, halogen or $C_{1-6}$alkoxy;

$R^{4-18}$, $R^{21-25}$, $R^{28}$ and $R^{31-33}$ all independently represent H, $C_{1-6}$alkyl;

$R^{26}$ and $R^{27}$ independently represent H, $C_{1-6}$ alkyl, $C_{3-7}$cycloalkyl or heterocyclyl;

$R^{29}$ and $R^{30}$ independently represent H, $C_{1-6}$alkyl optionally substituted by OH;

$R^7$ and $R^8$ together with the nitrogen atom to which they are attached may form a heterocyclyl ring;

$R^9$ and $R^{10}$ together with the nitrogen atom to which they are attached may form a heterocyclyl ring;

$R^{17}$ and $R^{18}$ together with the nitrogen atom to which they are attached may form a heterocyclyl ring such as morpholine;

$R^{21}$ and $R^{22}$ together with the nitrogen atom to which they are attached may form a heterocyclyl ring;

$R^{26}$ and $R^{27}$ together with the nitrogen atom to which they are attached may form a heterocyclyl ring;

$R^{29}$ and $R^{30}$ together with the nitrogen atom to which they are attached may form a heterocyclyl ring such as morpholine;

$R^{31}$ and $R^{32}$ together with the nitrogen atom to which they are attached may form a heterocyclyl ring;

with the proviso that $R^{34}$ and $R^{19}$ cannot both represent $R^3S(=O)_n—$.

DETAILED DESCRIPTION

As used herein, the term "alkyl" refers to straight or branched hydrocarbon chains containing the specified number of carbon atoms. For example, $C_{1-6}$alkyl means a straight or branched alkyl chain containing at least 1, and at most 6, carbon atoms. Examples of "alkyl" as used herein include, but are not limited to, methyl, ethyl, n-propyl, iso-propyl, n-butyl, sec-butyl, iso-butyl, t-butyl, n-pentyl and n-hexyl. A $C_{1-4}$alkyl group is preferred, for example methyl, ethyl or isopropyl. The said alkyl groups may be optionally substituted with one or more fluorine atoms, for example, trifluoromethyl.

As used herein, the term "alkoxy" refers to a straight or branched chain alkoxy group, for example, methoxy, ethoxy, prop-1-oxy, prop-2-oxy, but-1-oxy, but-2-oxy, 2-methylprop-1-oxy, 2-methylprop-2-oxy, pentoxy or hexyloxy. A $C_{1-4}$alkoxy group is preferred, for example methoxy or ethoxy. The said alkoxy groups may be optionally substituted with one or more fluorine atoms, for example, trifluoromethoxy.

As used herein, the term "cycloalkyl" refers to a non-aromatic hydrocarbon ring containing the specified number of carbon atoms. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$-cycloalkyl group is preferred, for example cyclopentyl or cyclohexyl.

When used herein, the term "aryl" refers to, unless otherwise defined, a mono- or bicyclic carbocyclic aromatic ring system containing up to 10 carbon atoms in the ring system, for instance phenyl or naphthyl, optionally fused to a $C_{4-7}$cycloalkyl or heterocyclyl ring.

As used herein, the terms "heteroaryl ring" and "heteroaryl" refer to, unless otherwise defined, a monocyclic five- to seven-membered heterocyclic aromatic ring containing one or more heteroatoms selected from oxygen, nitrogen and sulfur. In a particular aspect such a ring contains 1-3 heteroatoms. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The terms "heteroaryl ring" and "heteroaryl" also refer to fused bicyclic heterocyclic aromatic ring systems containing at least one heteroatom selected from oxygen, nitrogen and sulfur, preferably from 1-4 heteroatoms, more preferably from 1 to 3 heteroatoms. Preferably, the fused rings each independently have five or six ring atoms. Examples of fused aromatic rings include, but are not limited to, quinolinyl, isoquinolinyl, quinazolinyl, quinoxalinyl, cinnolinyl, naphthyridinyl, indolyl, indazolyl, pyrrolopyridinyj, benzofuranyl, benzothienyl, benzimidazolyl, benzoxazolyl, benzisoxazolyl, benzothiazolyl, benzisothiazolyl, benzoxadiazolyl and benzothiadiazolyl. The heteroaryl may attach to the rest of the molecule through any atom with a free valence.

As used herein, the term "heterocyclyl" refers to a monocyclic three- to seven-membered saturated or non-aromatic, unsaturated ring containing at least one heteroatom selected from oxygen, nitrogen and sulfur. In a particular aspect such a ring contains 1 or 2 heteroatoms. Preferably, the heterocyclyl ring has five or six ring atoms. Examples of heterocyclyl groups include, but are not limited to, aziridinyl, azetidinyl, pyrrolidinyl, piperidinyl, imidazolidinyl, pyrazolidinyl, piperazinyl, morpholinyl, thiomorpholinyl, diazepinyl, azepinyl, tetrahydrofuranyl, tetrahydropyranyl, and 1,4-dioxanyl.

As used herein, the terms "halogen" or "halo" refer to fluorine, chlorine, bromine and iodine. Preferred halogens are fluorine, chlorine and bromine. Particularly preferred halogens are fluorine and chlorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated. Where one or more substituents are referred to, this will refer for instance to 1 to 4 substituents, and preferably to 1 or 2 substituents.

In one embodiment, $R^1$ is selected from:

$C_{3-7}$ cycloalkyl, in particular cyclohexyl;

Aryl optionally substituted by one or more substituents selected from: $C_{1-6}$alkyl, halogen, $C_{1-6}$alkoxy, $C_{1-6}$alkoxy $(C_{1-4}$alkyl)-, —CN, —$(CH_2)_m$OH, —$CF_3$, $C_{1-6}$alkoxy$C_{2-6}$ alkoxy-, $R^4R^5$NCO, $C_{1-6}$alkylCONR$^8$—, $R^7R^8N$—, $C_{1-6}$-alkoxycarbonyl, HO$(CH_2)_{2-6}$O—, $C_{1-6}$alkylCO—, heteroaryl (optionally substituted by $C_{1-6}$alkyl) particularly oxazolyl, pyrazolyl or 1,2,4oxadiazolyl;

Aryl($C_{1-2}$alkyl) wherein the aryl is optionally substituted by —OH;

Aryl fused to a $C_{5-8}$ cycloalkyl ring wherein the cycloalkyl is optionally substituted by (=O);

Aryl fused to a heterocyclyl ring, wherein the heterocyclyl ring is optionally substituted by one or more substituents selected from =O, $C_{1-4}$alkyl;

Heteroaryl optionally substituted by one or more $C_{1-6}$alkyl, halogen (in particular chlorine or fluorine) or $C_{1-6}$alkoxy groups in particular wherein heteroaryl represents benzothiazolyl, benzisoxazolyl, benzimidazolyl, indazolyl, pyridyl and pyrazolyl;

Heteroaryl($C_{1-2}$alkyl) wherein the heteroaryl is optionally substituted by one or more $C_{1-6}$alkyl groups, in particular wherein heteroaryl represents pyridyl, pyrazolyl; or Heterocyclyl, in particular tetrahydropyranyl.

Examples of suitable aryl fused to a $C_{5-6}$ cycloalkyl ring include:

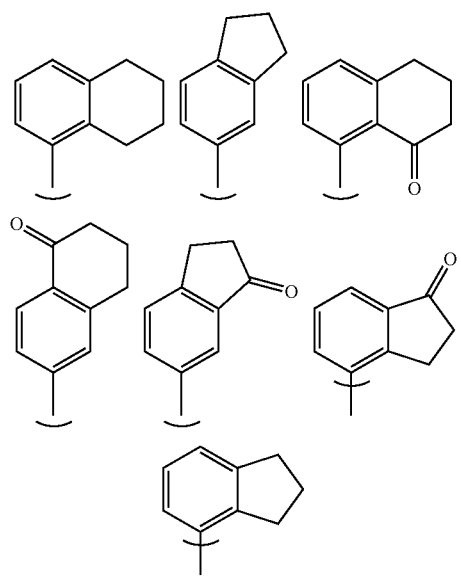

Examples of suitable aryl fused to heterocyclyl rings include:

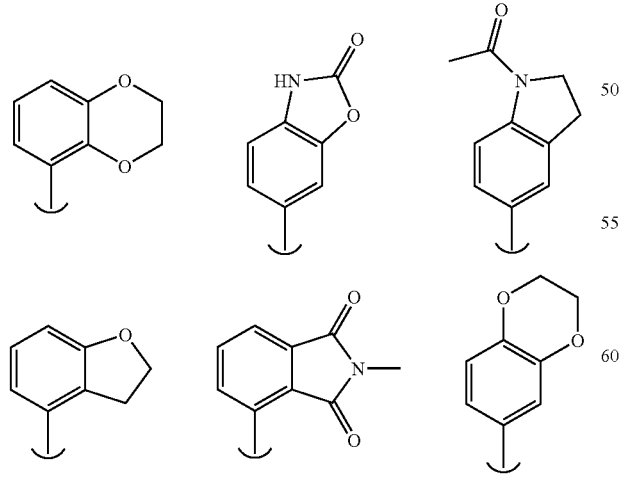

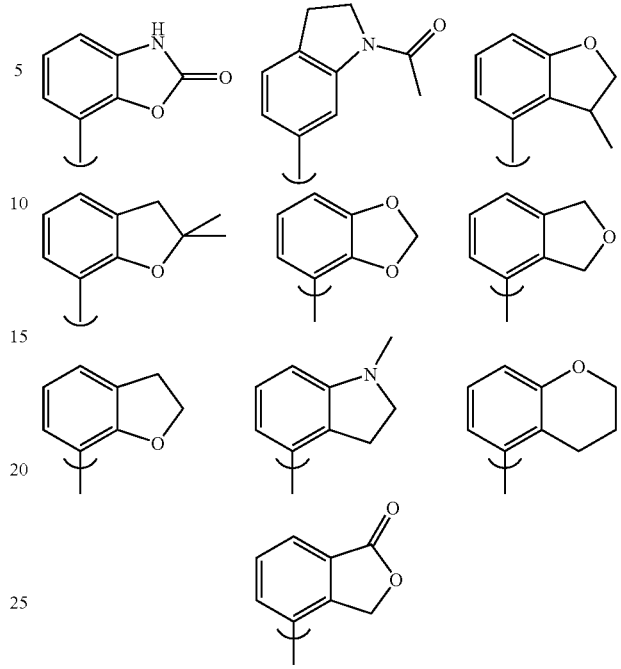

The following aryl fused to heterocyclyl rings are further embodiments:

In a further embodiment, $R^1$ is selected from:

Aryl optionally substituted by one or more substituents selected from: methyl, ethyl, fluorine, chlorine, —CN, —$CH_2OH$, —OMe, —OH, —$NMe_2$, —$O(CH_2)_{2OH}$, —$CF_3$, —COMe, 1,2,4-oxadiazolyl substituted by methyl; particular substitued aryl groups include; 3-(methyloxy)phenyl, 3-methylphenyl, 3-cyanophenyl, 3-fluorophenyl, 3-chlorophenyl, 4-fluoro-3-(methyloxy)phenyl, 3-acetylphenyl, 4-hydroxy-3-(methyloxy)phenyl, 2-fluoro-3-chlorophenyl, 2,3-difluorophenyl, 3,5-difluorophenyl;

Aryl fused to a cyclohexane or cyclopentane ring, wherein the cyclopentane ring is optionally substituted by (=O); in particular the following fused systems:

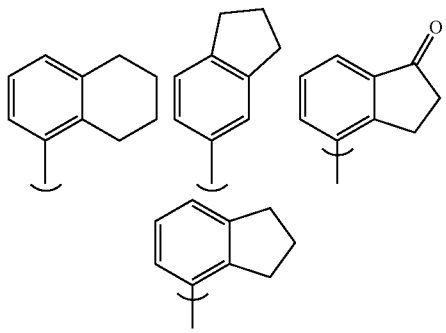

Aryl fused to a heterocyclyl ring, optionally substituted by methyl; in particular the following heterocyclyl ring fused aryl systems:

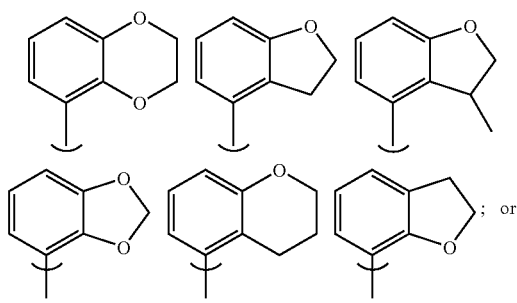

Heteroaryl optionally substituted by one or more methyl, ethyl, flourine, chlorine or methoxy groups; in particular a pyridyl, benzimidazolyl, pyrazolyl or indazolyl group optionally substituted by one or more methyl, ethyl, flourine, chlorine, or methoxy groups;preferably 1-methyl-1H-benzimidazolyl-6-yl, 1-methyl-1H-indazol-6-yl, 5-(methyloxy)-3-pyridinyl, 3-pyridinyl, 1-ethyl-1H-pyrazol-5-yl, 5-methyl-3-pyridinyl, 1,3-benzothiazol-6-yl, 5-fluoro-3-pyridinyl, or 5-chloro-3-pyridinyl.

In one embodiment, $R^2$ is hydrogen.

In one embodiment $R^3$ is selected from:

$C_{1-6}$ alkyl which is optionally substituted by one or more substituents selected from —$NR^{16}COR^{15}$; OH—, $C_{1-6}$alkoxyCONR$^{25}$—, —CONR$^{28}R^{27}$, —NH$_2$, —NR$^{17}R^{18}$, —CO$_2R^{24}$, $C_{1-6}$alkoxy; or a group having one of the following formulae:

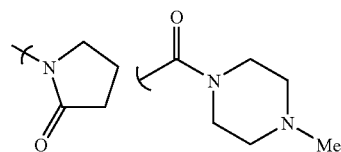

$C_{3-7}$cycloalkyl;

Aryl optionally substituted by one or more substituents selected from $C_{1-6}$alkyl-, halogen-, $C_{1-6}$alkoxy-, —CO$_2R^{28}$, —OH, —CONR$^{29}R^{30}$, $C_{3-7}$cycloalkoxy, $C_{3-7}$cycloalkyl ($C_{1-6}$ alkoxy);

Aryl($C_1$alkyl) wherein the aryl is optionally substituted by one or more $C_{1-6}$alkoxy groups;

Heteroaryl or heteroaryl($C_{1-6}$alkyl) which is optionally substituted by one or more $C_{1-6}$alkyl or —CONR$^{29}R^{30}$ groups; or Heterocyclyl which is optionally substituted by one or more substituents selected from $C_{1-6}$alkyl-, $C_{1-6}$alkylCO—, $C_{3-7}$cycloalkylCO—, heteroarylCO— (optionally substituted by one or more $C_{1-4}$alkyl- groups), $C_{1-6}$alkoxyCO—, arylCO—, $C_{1-6}$alkylSO$_2$—.

In an alternative embodiment $R^3$ is selected from:

methyl, ethyl, n-propyl, tert-butyl, isopropyl, MeCONH(CH$_2$)$_2$—, Me$_2$NCO(CH$_2$)$_2$—;

Cyclopentyl;

Aryl optionally substituted by one or more methoxy, methyl, —CONH$_2$ or —CONMe$_2$ groups; in particular: 4-(methyloxy)phenyl, phenyl, 3-[(dimethylamino)carbonyl]phenyl, 4-methylphenyl, 3-[(methyloxy)carbonyl]phenyl, 3,4-bis(methyloxy)phenyl, 3,4,5-tris(methyloxy)phenyl, 3-(ethyloxy)phenyl;

Heterocyclyl which is optionally substituted by one of more substituents selected from MeCO—, cyclopropylCO, 2-furylCO—, or MeSO$_2$—; in particular wherein the heterocyclyl group is tetrahydropyran-4-yl; a tetrahydrofuran-3-yl; or piperidinyl substituted by one or more substituents selected from MeCO—, cyclopropylCO, 2-furylCO—, or MeSO$_2$—, especially 1-acetyl-4-piperidinyl, 1-(2-furanylcarbonyl)-4-piperidinyl, 1-(cyclopropylcarbonyl)-4-piperidinyl;

Heteroaryl wherein the heteroaryl represents 3-pyridyl which is optionally substituted by CONMe$_2$, especially 5-[(dimethylamino)carbonyl]-3-pyridinyl.

In one embodiment $R^9$ and $R^{10}$ together with the nitrogen to which they are attached represent 4-morpholinyl.

In one embodiment $R^4$, $R^5$, $R^{6,}$ $R^7$, $R^8$, $R^{11-16}$, and $R^{21-25}$ and $R^{28-33}$ are independently selected from hydrogen and methyl.

In one embodiment $R^{26}$ and $R^{27}$ are independently selected from hydrogen, methyl, cyclopropyl, or 4-tetrahydropyranyl; or $R^{26}$ and $R^{27}$ together with the nitrogen to which they are attached form a heterocyclyl ring, in particular pyrrolidinyl or morpholinyl.

In one embodiment $R^{19}$ is hydrogen, $C_{1-6}$alkyl or MeSO$_2$—. In a further embodiment $R^{19}$ is hydrogen or methyl, especially hydrogen.

In one embodiment $R^{20}$ is hydrogen, halogen or $C_{1-6}$alkyl. Alternatively $R^{20}$ is hydrogen, chlorine, fluorine, methyl or ethyl. In a further embodiment $R^{20}$ is methyl, ethyl or chlorine.

In one embodiment m is 0 or 1.

In one embodiment n is 1 or 2, especially 2.

In one embodiment $R^{34}$ represents a group of formula:

It is to be understood that the present invention covers all combinations of substituent groups referred to herein above.

It is to be understood that the present invention covers all combinations of particular and preferred groups described herein above.

Particular compounds according to the invention include those mentioned in the examples and their pharmaceutically acceptable salts. Specific examples which may be mentioned include:

Example 7: 4-[(3-methylphenyl)amino]-6-(methylsulfonyl)-3-quinolinecarboxamide,

Example 8: 4-[(3-cyanophenyl)amino]-6-(methylsulfonyl)-3-quinolinecarboxamide,

Example 20: 4-(2,3-dihydro-1-benzofuran-4-ylamino)-6-(methylsulfonyl)-3-quinolinecarboxamide, Example 27: 4-{[3-(methyloxy)phenyl]amino}-6-(methylsulfonyl)-3-quinolinecarboxamide, Example 32: 4-{[4-fluoro-3-(methyloxy)phenyl]amino}-6-(methylsulfonyl)-3-quinolinecarboxamide, Example 35: 4-[(3-chlorophenyl)amino]-6-(methylsulfonyl)-3-quinolinecarboxamide, Example 43: 4-(1,3-benzothiazol-6-ylamino)-6-(phenylsulfonyl)-3-quinolinecarboxamide, Example 45: 4-[(1-methyl-1H-benzimidazol-6-yl)amino]-6-(phenylsulfonyl)-3-quinolinecarboxamide, Example 52: 4-[(3-cyanophenyl)amino]-6-(phenylsulfonyl)-3-quinolinecarboxamide, Example 66: 4-(2,3-dihydro-1-benzofuran-4-ylamino)-6-(phenylsulfonyl)-3-quinolinecarboxamide, Example 74: 4-{[3-(methyloxy)phenyl]amino}-6-(phenylsulfonyl)-3-quinolinecarboxamide, Example 89: 6-(cyclopentylsulfonyl)-4-[(3-fluorophenyl)amino]-3-quinolinecarboxamide, Example 128: 4-{[3-(methyloxy)phenyl]amino}-6-{[4-(methyloxy)phenyl]sulfonyl}-3-quinolinecarboxamide, Example 129: 6-[(1,1-dimethylethyl)sulfonyl]-4-{[3-(methyloxy)phenyl]amino}-3-quinolinecarboxamide, Example 130: 6-{[2-(acetylamino)ethyl]sulfonyl}-4-{[3-(methyloxy)phenyl]amino}-3-quinolinecarboxamide.

Example 133: 6-[(1,1-dimethylethyl)thio]-4-{[3-(methyloxy)phenyl]amino}-3-quinolinecarboxamide, Example 135: 6-{[2-(acetylamino)ethyl]thio}-4-{[3-(methyloxy)phenyl]amino}-3-quinolinecarboxamide, Example 163: 4-[(1-methyl-1H-indazol-6-yl)amino]-6-(phenylsulfonyl)-3-quinolinecarboxamide, Example 167: 4-{[4-hydroxy-3-(methyloxy)phenyl]amino}-6-(phenylsulfonyl)-3-quinolinecarboxamide, Example 174: 4-[(3-acetylphenyl)amino]-6-(phenylsulfonyl)-3-quinolinecarboxamide, Example 184: 8-methyl-4-{[3-(methyloxy)phenyl]amino}-6-(phenylsulfonyl)-3-quinolinecarboxamide, Example 185: 4-{[4-fluoro-3-(methyloxy)phenyl]amino}-8-methyl-6-(phenylsulfonyl)-3-quinolinecarboxamide, Example 186: 7-methyl-4-{[3-(methyloxy)phenyl]amino}-6-(methylsulfonyl)-3-quinolinecarboxamide, Example 265: 8-methyl-4-{[3-(methyloxy)phenyl]amino}-6-{[4-(methyloxy)phenyl]sulfonyl}-3-quinolinecarboxamide, Example 266: 4-(2,3-dihydro-1-benzofuran-4-ylamino)-8-methyl-6-{[4-(methyloxy)phenyl]sulfonyl}-3-quinolinecarboxamide, Example 267: 4-[(3-acetylphenyl)amino]-8-methyl-6-{[4-(methyloxy)phenyl]sulfonyl}-3-quinolinecarboxamide Example 268: 8-methyl-4-[(1-methyl-1H-indazol-6-yl)amino]-6-{[4-(methyloxy)phenyl]sulfonyl}-3-quinolinecarboxamide Example 269: 4-(2,3-dihydro-1,4-benzodioxin-5-ylamino)-8-methyl-6-{[4-(methyloxy)phenyl]sulfonyl}-3-quinolinecarboxamide Example 270: 4-[(3-chlorophenyl)amino]-8-methyl-6-{[4-(methyloxy)phenyl]sulfonyl}-3-quinolinecarboxamide Example 271: 4-[(3-cyanophenyl)amino]-8-methyl-6-{[4-(methyloxy)phenyl]sulfonyl}-3-quinolinecarboxamide Example 272: 4-(1,3-benzothiazol-6-ylamino)-8-methyl-6-{[4-(methyloxy)phenyl]sulfonyl}-3-quinolinecarboxamide Example 273: 4-[(3-fluorophenyl)amino]-8-methyl-6-{[4-(methyloxy)phenyl]sulfonyl}-3-quinolinecarboxamide Example 285: 4-(2,3-dihydro-1-benzofuran-4-ylamino)-8-methyl-6-[(4-methylphenyl)sulfonyl]-3-quinolinecarboxamide Example 287: 8-methyl-4-[(1-methyl-1H-indazol-6-yl)amino]-6-[(4-methylphenyl)sulfonyl]-3-quinolinecarboxamide Example 292: 8-methyl-4-{[3-(methyloxy)phenyl]amino}-6-[(4-methylphenyl)sulfonyl]-3-quinolinecarboxamide Example 294: 4-{[4-fluoro-3-(methyloxy)phenyl]amino}-8-methyl-6-(methylsulfonyl)-3-quinolinecarboxamide Example 303: 8-methyl-4-[(1-methyl-1H-indazol-6-yl)amino]-6-(phenylsulfonyl)-3-quinolinecarboxamide Example 307: 4-(2,3-dihydro-1-benzofuran-4-ylamino)-8-methyl-6-(methylsulfonyl)-3-quinolinecarboxamide Example 308: 8-methyl-6-(methylsulfonyl)-4-(3-pyridinylamino)-3-quinolinecarboxamide Example 309: 8-methyl-4-[(1-methyl-1H-indazol-6-yl)amino]-6-(methylsulfonyl)-3-quinolinecarboxamide Example 311: 4-[(3-fluorophenyl)amino]-8-methyl-6-(methylsulfonyl)-3-quinolinecarboxamide Example 312: 4-[(3-cyanophenyl)amino]-8-methyl-6-(methylsulfonyl)-3-quinolinecarboxamide Example 315: 4-[(1-ethyl-1H-pyrazol-5-yl)amino]-8-methyl-6-(methylsulfonyl)-3-quinolinecarboxamide Example 316: 8-methyl-4-{[5-(methyloxy)-3-pyridinyl]amino}-6-(methylsulfonyl)-3-quinolinecarboxamide Example 317: 8-methyl-4-[(5-methyl-3-pyridinyl)amino]-6-(methylsulfonyl)-3-quinolinecarboxamide Example 369: 8-chloro-4-[(3-methylphenyl)amino]-6-(methylsulfonyl)-3-quinolinecarboxamide Example 370: 8-chloro-4-{[4-fluoro-3-(methyloxy)phenyl]amino}-6-(methylsulfonyl)-3-quinolinecarboxamide Example 371: 8-chloro-4-(2,3-dihydro-1-benzofuran-4-ylamino)-6-(methylsulfonyl)-3-quinolinecarboxamide Example 372: 8-chloro-4-[(3-cyanophenyl)amino]-6-(methylsulfonyl)-3-quinolinecarboxamide Example 373: 8-chloro-4-[(3-fluorophenyl)amino]-6-(methylsulfonyl)-3-quinolinecarboxamide Example 374: 8-chloro-4-[(1-methyl-1H-indazol-6-yl)amino]-6-(methylsulfonyl)-3-quinolinecarboxamide Example 379: methyl 3-[(3-(aminocarbonyl)-8-methyl-4-{[3-(methyloxy)phenyl]amino}-6-quinolinyl)sulfonyl]benzoate Example 380: 6-{[3,4-bis(methyloxy)phenyl]sulfonyl}-8-methyl-4-{[3-(methyloxy)phenyl]amino}-3-quinolinecarboxamide Example 381: 8-methyl-4-{[3-(methyloxy)phenyl]amino}-6-{[3,4,5-tris(methyloxy)phenyl]sulfonyl}-3-quinolinecarboxamide hydrochloride Example 382: 6-{[3,4-bis(methyloxy)phenyl]sulfonyl}-4-{[3-(methyloxy)phenyl]amino}-3-quinolinecarboxamide Example 383: 6-{[3-(ethyloxy)phenyl]sulfonyl}-8-methyl-4-{[3-(methyloxy)phenyl]amino}-3-quinolinecarboxamide Example 392: 6-{[2-(acetylamino)ethyl]sulfonyl}-8-methyl-4-{[3-(methyloxy)phenyl]amino}-3-quinolinecarboxamide, Example 399: 6-({3-[(dimethylamino)carbonyl]phenyl}sulfonyl)-8-methyl-4-{[3-(methyloxy)phenyl]amino}-3-quinolinecarboxamide, Example 400: 6-({3-[(dimethylamino)carbonyl]phenyl}sulfonyl)-4-{[3-(methyloxy)phenyl]amino}-3-quinolinecarboxamide, Example 408: 4-[(3-cyanophenyl)amino]-6-({3-[(dimethylamino)carbonyl]phenyl}sulfonyl)-8-methyl-3-quinolinecarboxamide, Example 409: 6-({3-[(dimethylamino)carbonyl]phenyl}sulfonyl)-8-methyl-4-[(1-methyl-1H-benzimidazol-6-yl)amino]-3-quinolinecarboxamide Example 414: 4-(2,3-dihydro-1-benzofuran-4-ylamino)-6-({3-[(dimethylamino)carbonyl]phenyl}sulfonyl)-8-methyl-3-quinolinecarboxamide Example 426: 6-[(1-acetyl-4-piperidinyl)sulfonyl]-4-{[3-(methyloxy)phenyl]amino}-3-quinolinecarboxamide Example 442: 6-{[1-(2-furanylcarbonyl)-4-piperidinyl]sulfonyl}-8-methyl-4-{[3-(methyloxy)phenyl]amino}-3-quinolinecarboxamide Example 443: 4-[(3-cyanophenyl)amino]-6-{[1-(2-furanylcarbonyl)-4-piperidinyl]sulfonyl}-8-methyl-3-quinolinecarboxamide Example 445: 6-{[1-(cyclopropylcarbonyl)-4-piperidinyl]sulfonyl}-8-methyl-4-{[3-(methyloxy)phenyl]amino}-3-quinolinecarboxamide Example 446: 4-(2,3-dihydro-1-benzofuran-4-ylamino)-6-{[1-(2-furanylcarbonyl)-4-piperidinyl]sulfonyl}-8-methyl-3-quinolinecarboxamide Example 447: 6-{[1-(cyclopropylcarbonyl)-4-piperidinyl]sulfonyl}-4-(2,3-dihydro-1-benzofuran-4-ylamino)-8-methyl-3-quinolinecarboxamide Example 451: 6-[1-acetyl-4-piperidinyl)sulfonyl]-4-{[4-fluoro-3-(methyloxy)phenyl]amino}-8-methyl-3-quinolinecarboxamide Example 457: 4-(2,3-dihydro-1-benzofuran-4-ylamino)-8-methyl-6-({2-[(methylsulfonyl)amino]ethyl}sulfonyl)-3-quinolinecarboxamide Example 459: 6-{[1-(2-furanylcarbonyl)-4-piperidinyl]sulfonyl}-8-methyl-4-[(1-methyl-1H-benzimidazol-6-yl)amino]-3-quinolinecarboxamide Example 475: 6-{[3-(dimethylamino)-3-oxopropyl]sulfonyl}-4-{[4-fluoro-3-(methyloxy)phenyl]amino}-8-methyl-3-quinolinecarboxamide Example 500: 4-[(2,3-difluorophenyl)amino]-8-methyl-6-(methylsulfonyl)-3-quinolinecarboxamide Example 501: 4-[(3-chloro-2-fluorophenyl)amino]-8-methyl-6-(methylsulfonyl)-3-quinolinecarboxamide Example 502: 4-[(3,5-difluorophenyl)amino]-8-methyl-6-(methylsulfonyl)-3-quinolinecarboxamide Example 539: 4-[(5-fluoro-3-pyridinyl)amino]-8-methyl-6-(methylsulfonyl)-3-quinolinecarboxamide Example 540: 4-[(5-chloro-3-pyridinyl)amino]-8-methyl-6-(methylsulfonyl)-3-quinolinecarboxamide Example 546: 6-({5-[(dimethylamino)carbonyl]-3-pyridinyl}sulfonyl)-8-methyl-4-{[3-(methyloxy)phenyl]amino}3-quinolinecarboxamide hydrochloride Example 579: 8-methyl-6-[(1-methylethyl)sulfonyl]-4-(3-pyridinylamino)-3-quinolinecarboxamide Example 580; 6-[(1,1-dimethylethyl)sulfonyl]-8-methyl-4-(3-pyridinylamino)-3-quinolinecarboxamide Example 584: 4-[(1-ethyl-1H-pyrazol-5-yl)amino]-8-methyl-6-[(1-methylethyl)sulfonyl]-3-quinolinecarboxamide Example 585: 6-[(1,1-dimethylethyl)sulfonyl]-4-[(1-ethyl-1H-pyrazol-5-yl)amino]-8-methyl-3-quinolinecarboxamide Example 588: 4-(2,3-dihydro-1-benzofuran-4-ylamino)-8-methyl-6-(methylsulfinyl)-3-quinolinecarboxamide Example 590: 4-[(5-chloro-3-pyridinyl)amino]-6-[(1,1-dimethylethyl)sulfonyl]-3-quinolinecarboxamide Example 591: 8-ethyl-4-{[4-fluoro-3-(methyloxy)phenyl]amino}-6-(methylsulfonyl)-3-quinolinecarboxamide Example 592: 8-ethyl-4-[(3-fluorophenyl)amino]-6-(methylsulfonyl)-3-quinolinecarboxamide Example 593: 4-[(3-cyanophenyl)amino]-8-ethyl-6-(methylsulfonyl)-3-quinolinecarboxamide Example 598: 8-ethyl-4-[(1-methyl-1H-indazol-6-yl)amino]-6-(methylsulfonyl)-3-quinolinecarboxamide Example 599: 4-(2,3-dihydro-1-benzofuran-4-ylamino)-8-ethyl-6-(methylsulfonyl)-3-quinolinecarboxamide Example 600: 8-ethyl-6-(methylsulfonyl)-4-(3-pyridinylamino)-3-quinolinecarboxamide Example 624: 4-(2,3-dihydro-1-benzofuran-4-ylamino)-8-fluoro-6-(methylsulfonyl)-3-quinolinecarboxamide Example 666: 8-chloro-4-[(5-chloro-3-pyridinyl)amino]-6-(ethylsulfonyl)-3-quinolinecarboxamide Example 667: 8-chloro-4-[(5-chloro-3-pyridinyl)amino]-6-(propylsulfonyl)-3-quinolinecarboxamide Example 668: 8-chloro-4-[(5-chloro-3-pyridinyl)amino]-6-[(1-methylethyl)sulfonyl]-3-quinolinecarboxamide Example 669: 8-chloro-4-[(5-chloro-3-pyridinyl)amino]-6-[(1,1-dimethylethyl)sulfonyl]-3-quinolinecarboxamide Example 670: 4-[(5-chloro-3-pyridinyl)amino]-8-methyl-6-[(1-methylethyl)sulfonyl]-3-quinolinecarboxamide Example 671: 6-(ethylsulfonyl)-4-[(5-fluoro-3-pyridinyl)amino]-8-methyl-3-quinolinecarboxamide Example 674: 6-[(1,1-dimethylethyl)sulfonyl]-4-[(5-fluoro-3-pyridinyl)amino]-8-methyl-3-quinolinecarboxamide Example 676: 8-chloro-4-[(5-fluoro-3-pyridinyl)amino]-6-[(1-methylethyl)sulfonyl]-3-quinolinecarboxamide Example 677: 8-chloro-6-[(1,1-dimethylethyl)sulfonyl]-4-[(5-fluoro-3-pyridinyl)amino]-3-quinolinecarboxamide Example 678: 4-[(5-chloro-3-pyridinyl)amino]-6-(ethylsulfonyl)-8-methyl-3-quinolinecarboxamide Example 679: 4-[(5-chloro-3-pyridinyl)amino]-8-methyl-6-(propylsulfonyl)-3-quinolinecarboxamide Example 680: 4-[(5-chloro-3-pyridinyl)amino]-6-[(1,1-dimethylethyl)sulfonyl]-8-methyl-3-quinolinecarboxamide and pharmaceutically acceptable salts thereof.

Preferred compounds include:

8-methyl-4-{[3-(methyloxy)phenyl]amino}-6-{[4-(methyloxy)phenyl]sulfonyl}-3-quinolinecarboxamide, 4-(2,3-dihydro-1-benzofuran-4-ylamino)-8-methyl-6-(methylsulfonyl)-3-quinolinecarboxamide 8-methyl-4-[(1-methyl-1H-indazol-6-yl)amino]-6-(methylsulfonyl)-3-quinolinecarboxamide, 4-[(3-cyanophenyl)amino]-8-methyl-6-(methylsulfonyl)-3-quinolinecarboxamide, 8-methyl-4-[(5-methyl-3-pyridinyl)amino]-6-(methylsulfonyl)-3-quinolinecarboxamide 6-({3-[(dimethylamino)carbonyl]phenyl}sulfonyl)-8-methyl-4-{[3-(methyloxy)phenyl]amino}-3-quinolinecarboxamide hydrochloride 6-({3-[(dimethylamino)carbonyl]phenyl}sulfonyl)-4-{[3-(methyloxy)phenyl]amino}-3-quinolinecarboxamide, 4-[(3-cyanophenyl)amino]-6-({3-[(dimethylamino)carbonyl]phenyl}sulfonyl)-8-methyl-3-quinolinecarboxamide, 4(2,3-dihydro-1-benzofuran-4-ylamino)-6-{[1-(2-fura-nylcarbonyl)-4-piperidinyl]sulfonyl}-8-methyl-3-quinolinecarboxamide 4-(2,3-dihydro-1-benzofuran-4-ylamino)-8-methyl-6-({2-[(methylsulfonyl) amino]ethyl}sulfonyl)-3-quinolinecarboxamide 4-[(3,5-difluorophenyl)amino]-8-methyl-6-(methylsulfonyl)-3-quinolinecarboxamide 6-({5-[(dimethylamino)carbonyl]-3-pyridinyl}sulfonyl)-8-methyl-4-{[3-(methyloxy)phenyl]amino}-3-quinolinecarboxamide hydrochloride 4-[(1-ethyl-1H-pyrazol-5-yl)amino]-8-methyl-6-[(1-methylethyl)sulfonyl]-3-quinolinecarboxamide 6-[(1,1-dimethylethyl)sulfonyl]-4-[(5-fluoro-3-pyridinyl)amino]-8-methyl-3-quinolinecarboxamide 8-chloro-6-[(1,1-dimethylethyl)sulfonyl]-4-[(5-fluoro-3-pyridinyl)amino]-3-quinolinecarboxamide and pharmaceutically acceptable salts thereof.

Salts of the compounds of the present invention are also encompassed within the scope of the invention. Because of their potential use in medicine, the salts of the compounds of formula (I) are preferably pharmaceutically acceptable salts. Suitable pharmaceutically acceptable salts can include acid or base addition salts. A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, acetic, fumaric, citric, tartaric, benzoic, ρ-toluenesulfonic, methanesulfonic or naphthalenesulfonic acid), optionally in a suitable solvent such as an organic solvent, to give the salt which is usually isolated for example by crystallisation and filtration. A pharmaceutically acceptable acid addition salt of a compound of formula (I) can be for example a hydrobromide, hydrochloride, sulfate, nitrate, phosphate, succinate, maleate, acetate, fumarate, citrate, tartrate, benzoate, ρ-toluenesulfonate, methanesulfonate or naphthalenesulfonate salt. A pharmaceutically acceptable base addition salt can be formed by reaction of a compound of formula (I) with a suitable inorganic or organic base, optionally in a suitable solvent such as an organic solvent, to give the base addition salt which is usually isolated for example by crystallisation and filtration. Other non-pharmaceutically acceptable salts, eg. oxalates or trifluoroacetates, may be used, for example in the isolation of compounds of the invention, and are included within the scope of this invention. The invention includes within its scope all possible stoichiometric and non-stoichiometric forms of the salts of the compounds of formula (I).

Also included within the scope of the invention are all solvates, hydrates and complexes of compounds and salts of the invention.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Process a

Compounds of formula (I), wherein $R^{34}$, $R^{19}$, $R^{20}$, $R^1$ and $R^2$ are as defined above, may be prepared from compounds of formula II;

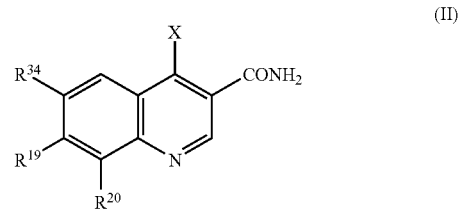

(II)

wherein $R^{34}$, $R^{19}$, and $R^{20}$ are as defined above, and X represents a halogen atom, by treatment with an amine of formula $R^1R^2NH$, wherein $R^1$ and $R^2$ are as defined above.

Suitable conditions for process a) include stirring in a suitable solvent such as acetonitrile, N,N-dimethylformamide or ethanol, at a suitable temperature, such as between room temperature and the reflux temperature of the solvent, for example at 80° C., optionally in the presence of a suitable base such as N,N-diisopropylethylamine, or in the presence of an acid catalyst such as the salt of an amine base, such as pyridine hydrochloride. Alternatively, process a) may be carried out under microwave irradiation, at a suitable power such as 100-30 W, for example at 150 W, in a suitable solvent such as N-methyl-2-pyrrolidinone or N,N-dimethylformamide, at a suitable temperature such as 60-200° C., for example at 150° C.

Compounds of formula (II), wherein $R^{34}$, $R^{19}$, $R^{20}$ and X are as defined above, may be prepared from compounds of formula (IV);

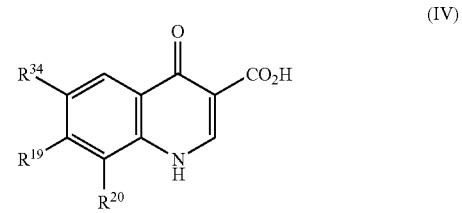

(IV)

wherein $R^{34}$, $R^{19}$, and $R^{20}$ are as defined above, by treatment with a suitable chlorinating agent, such as thionyl chloride, in the presence of a suitable catalyst such as N,N-dimethylformamide, followed by treatment with ammonia under suitable conditions, such as 880 ammonia at room temperature.

Compounds of formula (IV), wherein $R^{34}$, $R^{19}$, and $R^{20}$ are as defined above, may be prepared from compounds of formula (V);

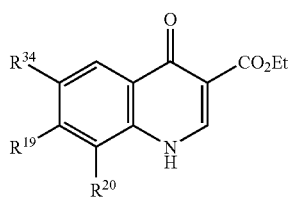

wherein $R^{34}$, $R^{19}$, and $R^{20}$ are as defined above, by hydrolysis with a suitable base, such as aqueous sodium hydroxide, in a suitable solvent, such as ethanol, at a suitable temperature such as room temperature.

Compounds of formula (V), wherein $R^{34}$, $R^{19}$, and $R^{20}$ are as defined above, may be prepared from compounds of formula (VI);

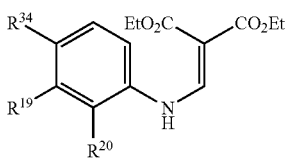

wherein $R^{34}$, $R^{19}$, and $R^{20}$ are as defined above, by heating in a suitable solvent, such as diphenyl ether, at a suitable temperature such as 200-300° C., for example at 250° C. The preparation of compounds of formulae (IV), (V), and (VI) wherein $R^{34}$ represents $MeSO_2$—, $R^{19}$ represents H and $R^{20}$ represents H have been previously described in patent application WO 02/068394 A1 (Glaxo Group Limited).

Compounds of formula (VI), wherein $R^{34}$, $R^{19}$, and $R^{20}$ are as defined above, may be prepared from compounds of formula (VII), wherein $R^{34}$, $R^{19}$, and $R^{20}$ are as defined above, and the compound of formula (VIII);

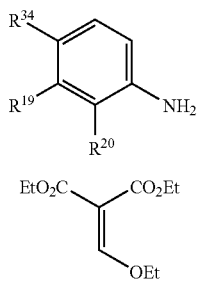

Suitable conditions include heating together compounds of formulae (VII) and (VIII) in a suitable solvent such as ethanol or in the absence of solvent, at a suitable temperature, such as 60-100° C., for example at 80° C.

Compounds of formula (VII) wherein $R^{34}$, $R^{19}$, and $R^{20}$ are as defined above may be prepared by reduction of compounds of formula (XIV), wherein $R^{34}$, $R^{19}$, and $R^{20}$ are as defined above;

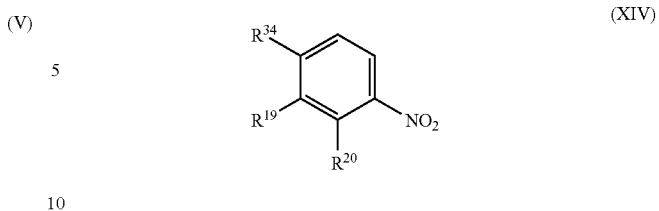

suitable conditions where n=1 or 2 include catalytic hydrogenation with hydrogen and a suitable catalyst, such as palladium on carbon, in a suitable solvent such as acetic acid. Suitable conditions where n=0 include reduction with a reducing agent such as iron in dilute acetic acid, at a suitable temperature such as 85-90° C.

Compounds of formula (XIV), wherein $R^{34}$ represents $R^3S(=O)_n$—, $R^{19}$ represents hydrogen or $C_{1-6}$alkyl, n is 0 or 2, and $R^{20}$ is as defined above, may be prepared from compounds of formula (XV), wherein $R^{19}$ represents hydrogen or $C_{1-6}$alkyl and $R^{20}$ is as defined above and compounds of formula (XVI) wherein $R^3$ is defined above and n=0 or 2;

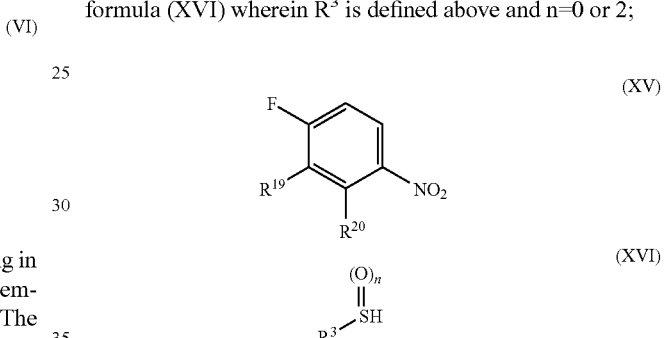

Suitable conditions where n=0 include treatment of the compound of formula (XV) with a thiol of formula (XVI) (n=0) in the presence of a suitable base such as potassium carbonate, in a suitable solvent such as acetonitrile, at a suitable temperature such as room temperature. Where n=2, suitable conditions include treatment of the compound of formula (XV) with the sodium salt of a sulphinic acid of formula (XVI) (n=2), in a suitable solvent such as dimethylacetamide, at a suitable temperature such as 30-100° C., for example at 50° C.

Alternatively, compounds of formula (XIV) where n represents 2 may be prepared from compounds of formula (XIV) where n represents 0 by oxidation with a suitable oxidising agent, such as oxone, in a suitable solvent such as a mixture of methanol and water, at a suitable temperature such as room temperature. Compounds of formula (XIV) where n represents 1 may be prepared from compounds of formula (XIV) where n represents 0 by oxidation with a suitable oxidising agent, such as ceric ammonium nitrate, in the presence of a suitable solid support such as hydrated silica gel, in a suitable solvent such as methylene chloride, at a suitable temperature such as 20-40° C., for example at room temperature.

Compounds of formula $R^1R^2NH$ may contain amine or acid groups which are suitably protected. Examples of suitable protecting groups and the means for their removal are well known in the art, see for instance T. W. Greene and P. G. M. Wuts 'Protective Groups in Organic Synthesis' ($3^{rd}$ Ed., J. Wiley and Sons, 1999). Addition or removal of such protecting groups may be accomplished at any suitable stage in the synthesis of compounds of formula (I).

Compounds of formula (II) wherein $R^{34}$ represents $R^3S(=O)_n-$, n represents 0, $R^{19}$ represents hydrogen or $C_{1-6}$alkyl, X represents chlorine and $R^{20}$ is as defined above may alternatively be prepared from compounds of formula (IX), wherein X represents chlorine, Y represents iodine, Z represents hydrogen or $C_{1-6}$alkyl, and $R^{20}$ is as defined above, by treatment with a trialkylstannane of formula $R^3SSnW_3$, wherein W represents a $C_{1-6}$alkyl group such as an n-butyl group. Suitable conditions include heating in the presence of a suitable catalyst, such as a palladium catalyst, for example tetrakistriphenylphosphine palladium (0), in a suitable solvent such as toluene, at a suitable temperature such as between 80° C. and 150° C., for example at 110° C.

Process b

Compounds of formula (I), wherein $R^1$, $R^2$, $R^{34}$, $R^{19}$, and $R^{20}$ are as defined above, and n=0, may alternatively be prepared from compounds of formula (III);

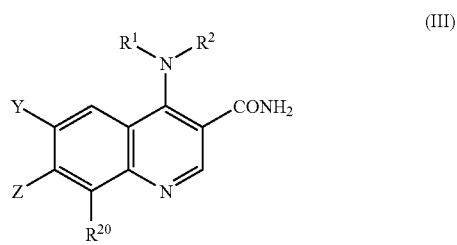

wherein $R^1$, $R^2$ and $R^{20}$ are as defined above, and Z represents hydrogen, $C_{1-6}$alkyl or halogen for example chlorine and Y represents hydrogen, chlorine, bromine or iodine, by treatment with a thiol of formula $R^3SH$, or the sodium salt thereof, $R^3SNa$, wherein $R^3$ is as defined above, with the proviso that at least one of Y and Z represent halogen.

Suitable conditions for process b) include heating in a suitable solvent such as toluene or N,N-dimethylformamide, at a suitable temperature such as 60-150° C., for example at 110° C., in the presence of a suitable catalyst, such as a palladium catalyst, for example tris(dibenzylideneacetone) palladium (II), and a suitable ligand, such as a phosphine ligand, for example (oxydi-2,1-phenylene)bis(diphenylphosphine), and in the presence of a suitable base such as potassium tert-butoxide.

Alternatively, conditions for process b) include heating in a suitable solvent such as 1,3-dimethyl-3,4,5,6-tetrahydro-2(1H)-pyrimidinone or dimethoxyethane, at a suitable temperature such as 60-150° C., for example at 85° C., optionally in the presence of a suitable catalyst, such as a copper catalyst, for example copper (I) iodide, and in the presence of a suitable base such as potassium phosphate or potassium carbonate and optionally in the presence of a suitable ligand for example N,N-diethylsalicylamide.

Compounds of formula (III), wherein $R^1$, $R^2$, $R^{20}$, Y and Z are as defined above, may be prepared from compounds of formula (IX), wherein $R^{20}$, X, Y and Z are as defined above, by treatment with an amine of formula $R^1R^2NH$, wherein $R^1$ and $R^2$ are as defined above;

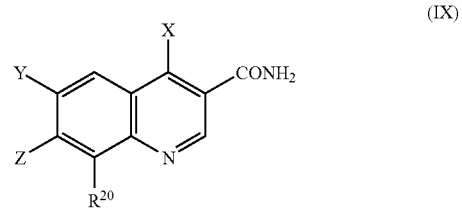

suitable conditions include stirring in a suitable solvent such as acetonitrile, at a suitable temperature, such as between room temperature and the reflux temperature of the solvent, for example at 80° C., optionally in the presence of a base such a N,N-diisopropylethylamine, or in the presence of an acid catalyst such as pyridine hydrochloride. Alternatively, preparation of compounds of formula (III) from compounds of formula (IX) may be carried out under microwave irradiation, at a suitable power such as 100-300 W, for example at 150 W, in a suitable solvent such as N-methyl-2-pyrrolidinone, at a suitable temperature such as 60-200° C. for example at 150° C.

The compounds of formula (IX) may be prepared according to the following synthetic scheme, Scheme 1, wherein $R^{19}$, $R^{20}$, Y and Z are as defined above:

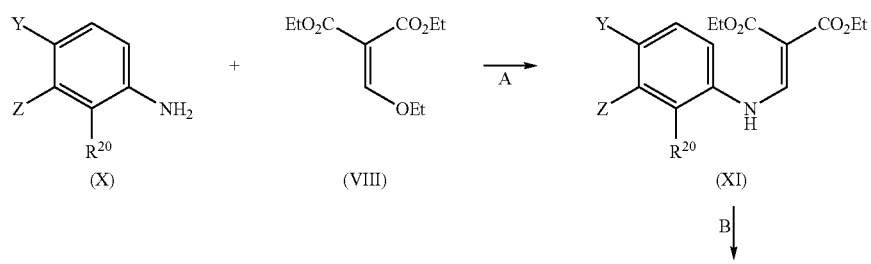

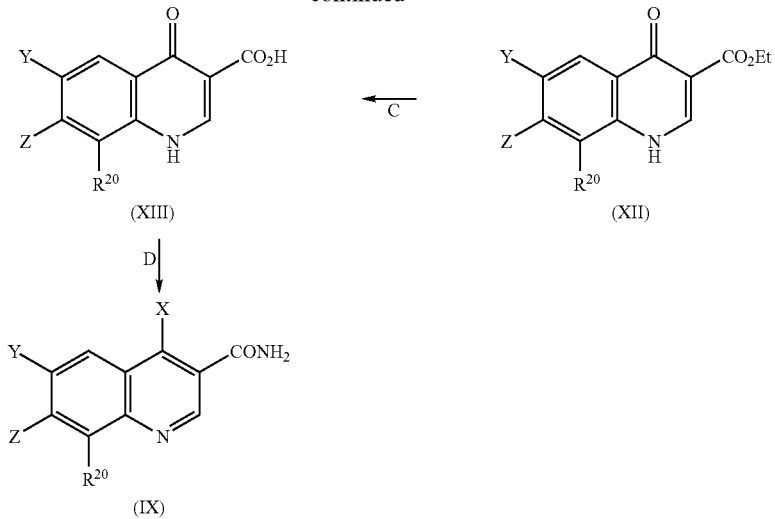

Suitable conditions for the reactions of Scheme 1 are: (A) heating together compounds of formulae (X) and (VIII) in the absence of solvent, at a suitable temperature, such as 60-100° C., for example at 80° C.; (B) heating compounds of formula (XI) in a suitable solvent, such as diphenyl ether, at a suitable temperature such as 200-300° C., for example at 250° C.; (C) hydrolysis of compounds of formula (XII) with a suitable base, such as aqueous sodium hydroxide, in a suitable solvent, such as ethanol, at a suitable temperature such as room temperature; (D) treatment of compounds of formula (XIII) with a suitable halogenating agent, such as a chlorinating agent, for example thionyl chloride, in the presence of a suitable catalyst such as N,N-dimethylformamide, followed by treatment with ammonia under suitable conditions, such as 880 ammonia at room temperature.

Preparation of the compounds of formulae (XI) and (XII) wherein Y represents iodine and Z and $R^{20}$ both represent hydrogen have been previously described in: *Indian Journal of Chemistry, Section B: Organic Chemistry Including Medicinal Chemistry,* 2002, 41B(3), 650-652. Preparation of the compound of formula (XIII) wherein Y represents iodine and Z and $R^{20}$ both represent hydrogen has been previously described in: PCT Int. Appl. (1999), WO9932450 A1.

Compounds of formula (X) are either known compounds (for example available from commercial suppliers such as Aldrich) or may be prepared by conventional means.

Compounds of formula (V), wherein $R^{34}$ represents $R^3S$ (=O)$_n$—, $R^{19}$ represents hydrogen or $C_{1-6}$alkyl, $R^{20}$ is as defined above and n=0, may be prepared by treatment of compounds of formula (XII), wherein Y and $R^{20}$ are as defined above and Z represents hydrogen or $C_{1-6}$alkyl with a thiol of formula $R^3SH$, wherein $R^3$ is as defined above, according to the following scheme:

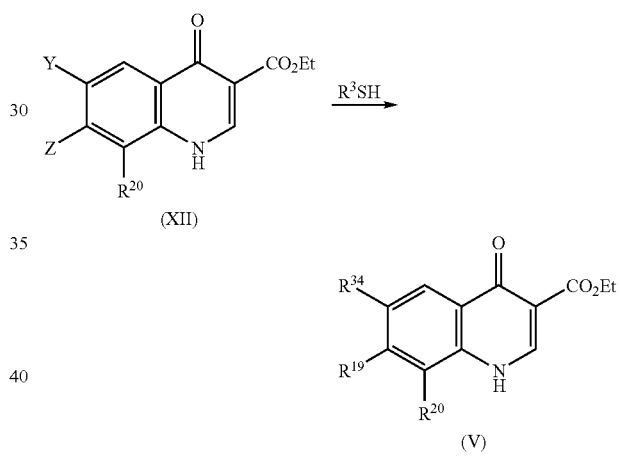

Suitable conditions for preparation of compounds of formula (V) from compounds of formula (XII) and a thiol of formula $R^3SH$ include heating in a suitable solvent such as toluene, at a suitable temperature such as 60-120° C., for example at 110° C., in the presence of a suitable catalyst, such as a palladium catalyst, for example tris(dibenzylideneacetone) palladium (II), and a suitable ligand, such as a phosphine ligand, for example (oxydi-2,1-phenylene)bis(diphenylphosphine), and in the presence of a suitable base such as potassium tert-butoxide.

Compounds of formulae $R^1R^2NH$ and $R^3SH$ are either known compounds (for example available from commercial suppliers such as Aldrich) or may be prepared by conventional means.

Certain compounds of formula $R^3SH$ may be prepared from compounds of formula $R^3SSR^3$. Suitable conditions include treatment with a suitable reducing agent such as a phosphine, for example triphenylphosphine, in the presence of an acid such as concentrated hydrochloric acid, in a suitable solvent such as a mixture of water and 1,4-dioxane, at a suitable temperature such as between 20° C. and 100° C., for example at 40° C. Alternatively certain compounds of formula $R^3SH$ may be prepared from compounds of formula $R^3SO_2Cl$. Suitable conditions include treatment with a suitable reducing agent such as a phosphine, for example triphenylphosphine, in a suitable solvent such as 1,4-dioxane, at a suitable temperature such as between 0° C. and 50° C., for example at 20° C.

Compounds of formula $R^1R^2NH$ may be used in the free base form, or in the form of a suitable salt, such as a hydrochloride salt. Where the free base form is commercially available, suitable salt forms may be prepared by conventional means. Similarly, where a salt form is commercially available, the free base form may be prepared by conventional means.

Compounds of formula $R^3SH$ may contain amine or acid groups which are suitably protected. Examples of suitable protecting groups and the means for their removal are well known in the art, see for instance T. W. Greene and P. G. M. Wuts 'Protective Groups in Organic Synthesis' (3$^{rd}$ Ed., J. Wiley and Sons, 1999). Addition or removal of such protecting groups may be accomplished at any suitable stage in the synthesis of compounds of formula (I).

Process c

Compounds of formula (I) may also be prepared by a process of interconversion between compounds of formula (I). For example, compounds of formula (I) where n=2 may be prepared from compounds of formula (i) wherein n=0 or 1, by treatment with a suitable oxidising agent, such as oxone, in a suitable solvent such N,N-dimethylformamide or a mixture of N,N-dimethylformamide and anisole, at a suitable temperature such as room temperature. Compounds of formula (I) where n=1 may be prepared from compounds of formula (I) where n=0 by oxidation with a suitable oxidising agent, such as oxone or ceric ammonium nitrate, in the presence of a suitable solid support such as hydrated silica gel, in a suitable solvent such as methylene chloride, at a suitable temperature such as 20-40° C., for example at room temperature.

Alternative processes of interconversion between compounds of formula (I) may include, for example oxidation, reduction, hydrolysis, alkylation, dealkylation, amide bond formation, protection, deprotection, sulphonamide formation or substitution, using methods for functional group interconversion well known to those skilled in the art.

Process d

As a particular example of a process of interconversion, compounds of formula (I), wherein $R^{34}$ represents $R^3S(=O)_n$—, $R^3$ represents an aryl group substituted by —$CONR^{29}R^{30}$, $R^{19}$ represents hydrogen or $C_{1-6}$alkyl, and wherein $R^1$, $R^2$, $R^{20}$, $R^{29}$, $R^{30}$ and n are as defined above, may alternatively be prepared from corresponding compounds of formula (I) in which $R^3$ represents an aryl group substituted by —COOH, namely compounds of formula (XVII);

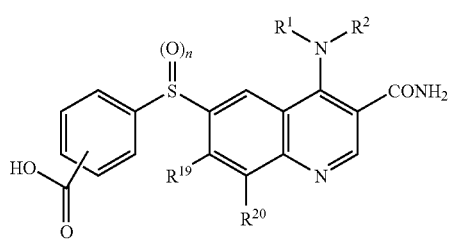

(XVII)

wherein $R^{19}$ represents hydrogen or $C_{1-6}$alkyl, and $R^1$, $R^2$, $R^{20}$ and n are as defined above, by coupling with a primary or secondary amine, in a suitable solvent, such as N,N-dimethylformamide, in the presence of a suitable amide coupling reagent, such as O-(7-azabenzotriazol-1-yl)-N,N,N'N'-tetramethyluronium hexafluorophosphate, optionally in the presence of a suitable base, such as N,N-diisopropylethylamine, at a suitable temperature, such as room temperature. (Step (I))

Compounds of formula (XVII), wherein $R^{19}$ represents hydrogen or $C_{1-6}$alkyl, and $R^1$, $R^2$, $R^{20}$ and n are as defined above, may be prepared from compounds of formula XVIII;

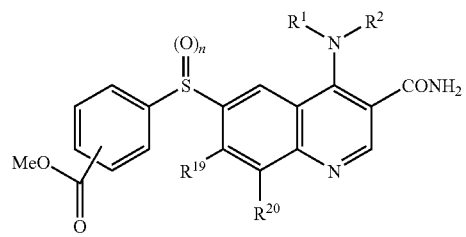

(XVIII)

wherein $R^{19}$ represents hydrogen or $C_{1-6}$alkyl, and $R^1$, $R^2$, $R^{20}$ and n are as defined above, by hydrolysis with a suitable base, such as aqueous sodium hydroxide, in a suitable solvent, such as ethanol, at a suitable temperature such as 75° C.( Step (II))

Compounds of formula (XVIII) wherein n=2 may be prepared from compounds of formula (XVIII) wherein n=0, by treatment with a suitable oxidising agent, such as oxone, in a suitable solvent such as N,N-dimethylformamide, at a suitable temperature such as room temperature. (Step (III))

Compounds of formula (XVIII), wherein $R^{19}$ represents hydrogen or $C_{1-6}$alkyl, $R^1$, $R^2$ and $R^{20}$ are as defined above, and n=0, may be prepared from compounds of formula (III) wherein Z represents hydrogen or $C_{1-6}$alkyl by treatment with a suitable thiol such as methyl 3-mercaptobenzoate or methyl 4-mercaptobenzoate (both commercially available from Toronto). Suitable conditions for this include heating in a suitable solvent such as 1,3-dimethyl-3,4,5,6-tetrahydro-2(1H)-pyrimidinone, at a suitable temperature such as 60-150° C., for example at 85° C., in the presence of a suitable catalyst, such as a copper catalyst, for example copper (I) iodide, and in the presence of a suitable base such as potassium phosphate or potassium carbonate, optionally in the presence of a suitable ligand for example N,N-diethylsalicylamide. (Step (IV))

The order of the steps comprising this process may be arranged in a number of different ways. For example the order of steps (II) and (III) may be reversed so that compounds of formula (I) may be prepared by step (IV) followed by step (II) followed by step (III) followed by step (I).

By a similar process, compounds of formula (I), wherein $R^{34}$ represents $R^3S(=O)_n$— and $R^3$ represents a $C_{1-6}$ alkyl group substituted by —$CONR^{26}R^{27}$ and wherein $R^{19}$ represents hydrogen or $C_{1-6}$alkyl, and $R^1$, $R^2$, $R^{20}$, $R^{26}$, $R^{27}$ and n are as defined above, may alternatively be prepared from compounds of formula (III) where Z represents hydrogen or $C_{1-6}$alkyl and a suitable thiol such as ethyl 3-mercaptopropionate (commercially available from Aldrich) as shown in the scheme below:

Steps (I) to (IV) of Scheme 2 use conditions as described in process d above.

The order of the steps comprising this process may be arranged in a number of different ways. For example the order of steps may be changed so that compounds of formula (I) may be prepared from compounds of formula (III) by step (IV) followed by step (II) followed by step (III) followed by step (I).

Alternatively the order of steps may be changed so that compounds of formula (I) may be prepared by step (IV) followed by step (II) followed by step (I) followed by step (III).

Scheme 2

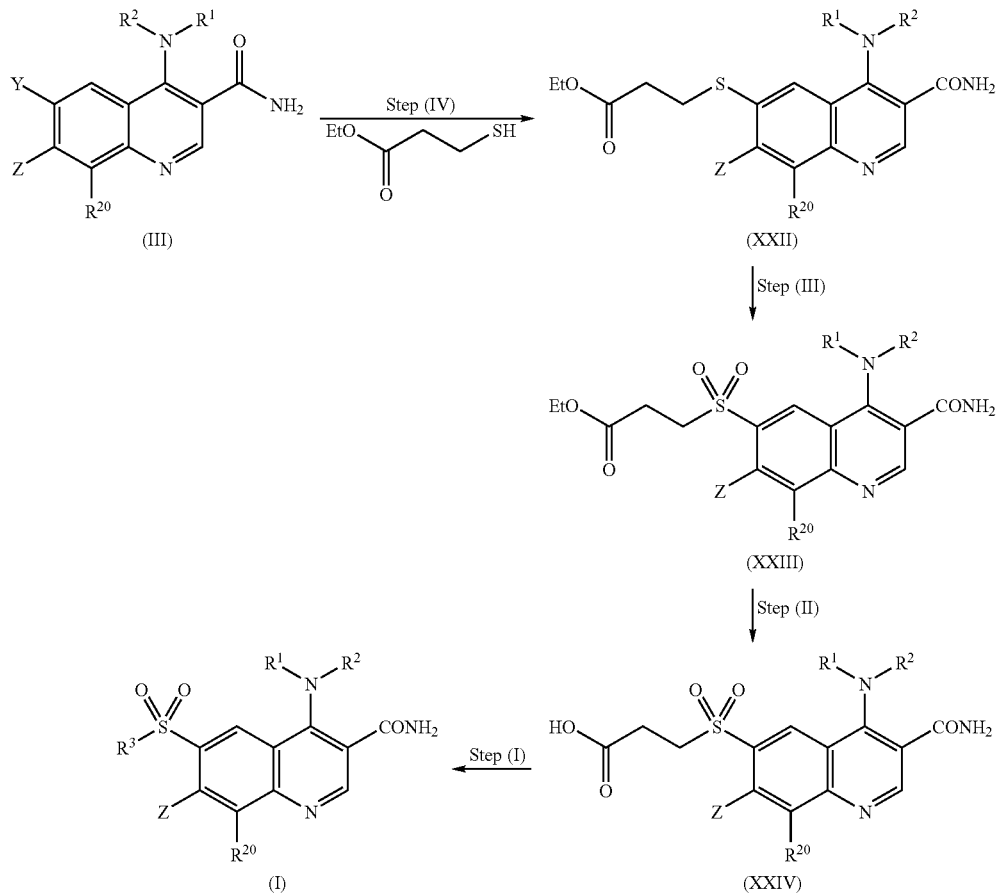

wherein $R^3$ is $R^{28}R^{27}NCO(CH_2)_2$—.

Process e

As a particular example of a process of interconversion, compounds of formula (I), wherein $R^{34}$ represents $R^3S(=O)_n$— and $R^3$ represents a piperidinyl group which is substituted by a substituent selected from $C_{1-6}$alkyl-, $C_{1-6}$alkylCO—, $C_{3-7}$cycloalkylCO—, heteroarylCO— (optionally substituted by one or more $C_{1-4}$alkyl- groups), $C_{1-6}$alkoxyCO—, arylCO—, $R^{31}R^{32}$NCO—, $C_{1-6}$alkylSO$_2$—, arylSO$_2$— or heteroarylSO$_2$— (optionally substituted by one or more $C_{1-4}$alkyl or $C_{1-4}$alkylCONH— groups) and wherein $R^1$, $R^2$, $R^{20}$, $R^{31}$, $R^{32}$ and n are as defined above and $R^{19}$ represents hydrogen or $C_{1-6}$alkyl, may alternatively be prepared from compounds of formula (XIX);

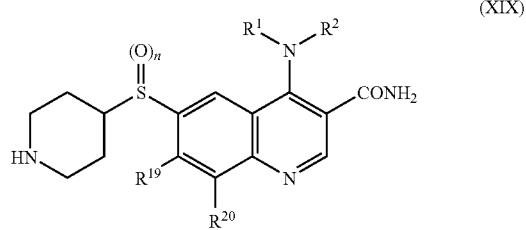

(XIX)

wherein $R^1$, $R^2$, $R^{20}$ and n are as defined above and $R^{19}$ represents hydrogen or $C_{1-6}$alkyl, by treatment with an electrophile, such as an acylating agent, such as an acid chloride, in a suitable solvent, such as 1,4-dioxane, in the presence of a suitable base, such as an amine base, for example triethylamine, at a suitable temperature, such as room temperature. Alternative electrophiles that may be used for this process include sulphonyl chlorides, alkyl chloroformates, alkyl halides and acid anhydrides.

Alternatively, compounds of formula (I), wherein $R^{34}$ represents $R^3S(=O)_n$— and $R^3$ represents a piperidinyl which is substituted by a substituent selected from $C_{1-6}$alkylCO—, $C_{3-7}$cycloalkylCO—, heteroarylCO— (optionally substituted by one or more $C_{1-4}$alkyl- groups), or arylCO—, and wherein $R^1$, $R^2$, $R^{20}$ and n are as defined above and $R^{19}$ represents hydrogen or $C_{1-6}$alkyl, may alternatively be prepared from compounds of formula (XIX), by coupling with a carboxylic acid, in a suitable solvent, such as N,N-dimethylformamide, in the presence of a suitable amide coupling reagent, such as O-(7-azabenzotriazol-1-yl)-N,N,N', N'-tetramethyluronium hexafluorophosphate, optionally in the presence of a suitable base, such as N,N-diisopropylethylamine, at a suitable temperature, such as room temperature. (Step (I))

Compounds of formula (XIX), wherein $R^1$, $R^2$, $R^{20}$ and n are as defined above and $R^{19}$ represents hydrogen or $C_{1-6}$alkyl, may be prepared from compounds of formula (XX);

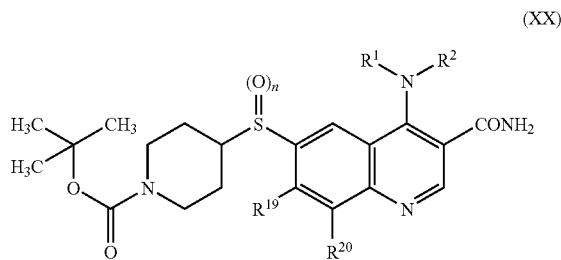

wherein $R^1$, $R^2$, $R^{20}$ and n are as defined above and $R^{19}$ represents hydrogen or $C_{1-6}$alkyl, by treatment with a suitable reagent, such as a strong acid, for example trifluoroacetic acid, at a suitable temperature, such as room temperature (Step (II)).

Compounds of formula (XX) wherein $R^1$, $R^2$, and $R^{20}$ are as defined above, $R^{19}$ represents hydrogen or $C_{1-6}$alkyl, and n=2, may be prepared from compounds of formula (XX) wherein n=0, by treatment with a suitable oxidising agent, such as oxone, in a suitable solvent such as N,N-dimethylformamide, at a suitable temperature such as room temperature (Step (III)).

Compounds of formula (XX) wherein $R^1$, $R^2$, and $R^{20}$ are as defined above, $R^{19}$ represents hydrogen or $C_{1-6}$alkyl, and n=0, may be prepared from compounds of formula (III) wherein $R^1$, $R^2$, Y and $R^{20}$ are as defined above and Z represents hydrogen or $C_{1-6}$alkyl, by treatment with 1,1-dimethylethyl 4-mercapto-1-piperidinecarboxylate (prepared as described in U.S. Pat. No. 5,317,025A) (Step (IV)).

Suitable conditions for this process include heating in a suitable solvent such as dimethylformamide, at a suitable temperature such as 60-150° C., for example at 110° C., in the presence of a suitable catalyst, such as a palladium catalyst, for example tris(dibenzylideneacetone) palladium (II), and a suitable ligand, such as a phosphine ligand, for example (oxydi-2,1-phenylene)bis(diphenylphosphine), and in the presence of a suitable base such as potassium tert-butoxide.

The order of the steps comprising this process may be arranged in a number of different ways. For example the order of steps may be changed so that compounds of formula (I) may be prepared by step (IV) followed by step (II) followed by step (I) followed by step (III).

Similarly, compounds of formula (I) wherein $R^{34}$ represents $R^3S(=O)_n-$ and $R^3$ represents a $C_{1-6}$alkyl which is substituted by $-NR^{17}R^{18}$, $-NR^{16}COR^{15}$, $C_{1-6}$alkoxy-$CONR^{25}-$ or $C_{1-6}$alkylSO$_2$NR$^{33}-$ and wherein $R^1$, $R^2$, $R^{20}$, $R^{15}$, $R^{17}$, $R^{18}$ and n are as defined above, $R^{19}$ represents hydrogen or $C_{1-6}$alkyl, and $R^{16}$, $R^{25}$ and $R^{33}$ represent hydrogen may alternatively be prepared from compounds of formula (III), wherein $R^1$, $R^2$, Y and $R^{20}$ are as defined above and Z represents hydrogen or $C_{1-6}$alkyl, and a thiol such as tert-butyl-N-(2-mercaptoethyl)carbamate (Aldrich), as is illustrated in the following Scheme (Scheme 3):

Steps (I) to (IV) of Scheme 3 use conditions as described in process e above.

SCHEME 3

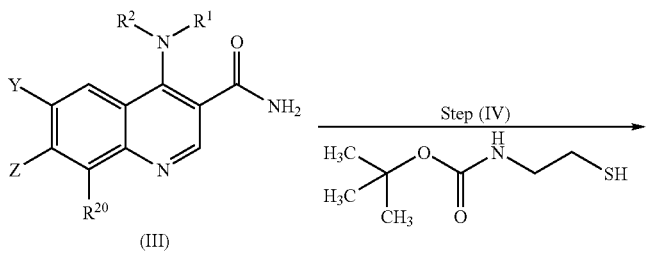

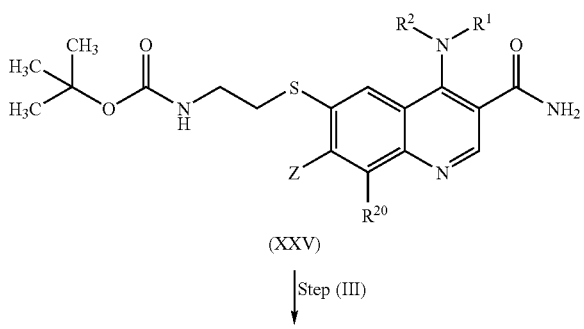

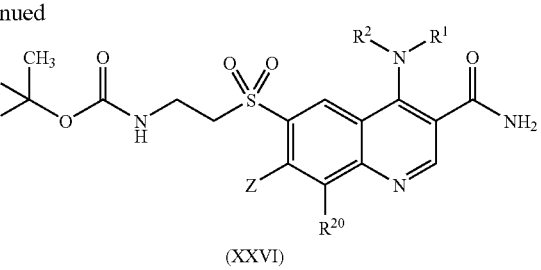

(XXVI)

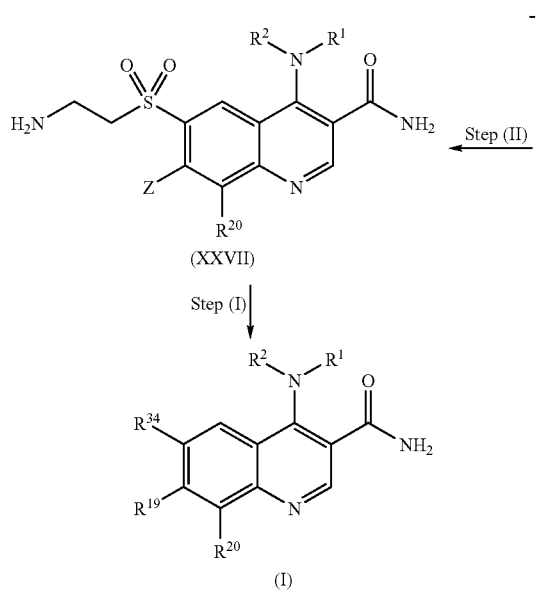

(XXVII)

(I)

wherein $R^{34}$ represents $C_{1-6}$alky)SO2-, wherein the $C_{1-6}$alkyl group is substituted by $R^{15}CONR^{16}$—, $C_{1-6}$alkoxy-$CONR^{25}$—, $C_{1-6}$alkylSO$_2$NR$^{33}$— or $R^{17}R^{18}N$—.

Process f

As a particular example of a process of interconversion compounds of formula (I), wherein $R^{34}$ represents $R^3S(=O)_n$— and $R^3$ represents an aryl group substituted by a $C_{1-6}$alkoxy-, $C_{3-7}$cycloalkoxy- or $C_{3-7}$cycloalkyl($C_{1-6}$alkoxy)- group, $R^1$, $R^2$, $R^{20}$ and n are as defined above, and $R^{19}$ represents hydrogen or $C_{1-6}$alkyl, may alternatively be prepared from compounds of formula (XXI);

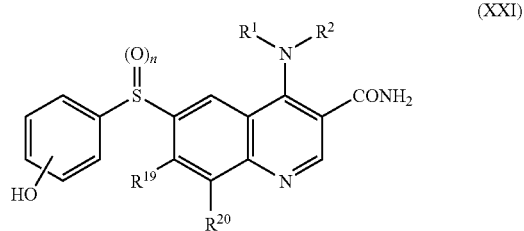

(XXI)

wherein $R^1$, $R^2$, $R^{20}$ and n are as defined above and $R^{19}$ represents hydrogen or $C_{1-6}$alkyl, by coupling with a suitable alkylating agent, in a suitable solvent, such as acetonitrile, in the presence of a suitable base, such as potassium carbonate, at a suitable temperature, such as 0 to 100° C., for example the reflux temperature of the solvent.

Alternatively compounds of formula (I) wherein $R^{34}$ represents $R^3S(=O)_n$— and $R^3$ represents an aryl group substituted by a $C_{1-6}$alkoxy-, $C_{3-7}$cycloalkoxy- or $C_{3-7}$cycloalkyl ($C_{1-6}$alkoxy)- group, $R^1$, $R^2$, $R^{20}$ and n are as defined above, and $R^{19}$ represents hydrogen or $C_{1-6}$alkyl, may be prepared from compounds of formula (XXI) by coupling with a suitable alcohol in a suitable solvent such as tetrahydrofuran, at a suitable temperature such as room temperature in the presence of a suitable coupling agent such as di-tert butylazodicarboxylate.

Compounds of formula (XXI) wherein n=2 may be prepared from compounds of formula (XXI) wherein n=0, by treatment with a suitable oxidising agent, such as oxone, in a suitable solvent such as N,N-dimethylformamide, at a suitable temperature such as room temperature.

Compounds of formula (XXI) wherein $R^1$, $R^2$, and $R^{20}$ are as defined above, $R^{19}$ represents hydrogen or $C_{1-6}$alkyl, and n=0, may be prepared from compounds of formula (III) wherein $R^1$, $R^2$, $R^{20}$ and Y are as defined above, and wherein Z represents hydrogen or $C_{1-6}$alkyl, by treatment with 4{[tert-butyl(dimethyl)silyl]oxy}benzenethiol (prepared according to EP 465802 A1). Suitable conditions for this process include heating in a suitable solvent such as dimethylformamide, at a suitable temperature such as 60-150° C., for example at 110° C., in the presence of a suitable catalyst, such as a palladium catalyst, for example tris(dibenzylideneacetone) palladium (II), and a suitable ligand, such as a phosphine ligand, for example (oxydi-2,1-phenylene)bis(diphenylphosphine), and in the presence of a suitable base such as potassium tert-butoxide, followed by deprotection with a suitable fluoride source such as tetrabutylammonium fluoride in a suitable solvent such as tetrahydrofuran at a suitable temperature such as room temperature.

The order of the steps comprising this process may be arranged in a number of different ways.

Process g

Compounds of formula (I) may also be prepared by a process of deprotection of protected derivatives of compounds of formula (I). Examples of suitable protecting groups and the means for their removal are well known in the art, see for instance T. W. Greene and P. G. M. Wuts 'Protective Groups in Organic Synthesis' (3$^{rd}$ Ed., J. Wiley and Sons, 1999).

As an example of this, compounds of formula (I) containing a primary or secondary amine group may be prepared from compounds of formula (I) where that amine group is protected, such as a carbamate group, for example as a tert-butyl carbamate, by deprotecting under appropriate conditions, such as treating with a strong acid, for example trifluoroacetic acid.

Process h

As a particular example of a process of interconversion, compounds of formula (I), wherein $R^{34}$ represents $R^3S(=O)_n$— and $R^3$ represents $C_{1-6}$alkoxyethyl-, $R^1$, $R^2$, $R^{20}$ and n are as defined above, and $R^{19}$ represents hydrogen or $C_{1-6}$alkyl may be prepared from compounds of formula (XXVIII);

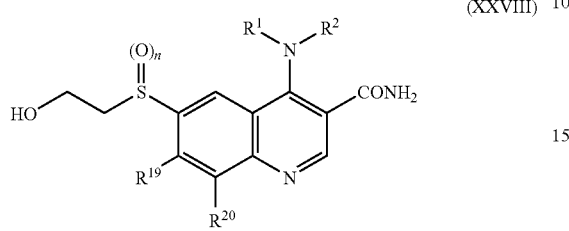

(XXVIII)

wherein $R^1$, $R^2$, $R^{20}$ and n are as defined above and $R^{19}$ represents hydrogen or $C_{1-6}$alkyl, by alkylation with a suitable alkylating agent, in a suitable solvent, such as N,N-dimethylformamide, in the presence of a suitable base, such as sodium hydride, at a suitable temperature, such as 0 to 30° C., for example at room temperature.

Alternatively compounds of formula (I) wherein $R^{34}$ represents $R^3S(=O)_n$— and $R^3$ represents $C_{1-6}$alkoxyethyl-, $R^1$, $R^2$, $R^{20}$ and n are as defined above, and $R^{19}$ represents hydrogen or $C_{1-6}$alkyl may be prepared from compounds of formula (XXVIII) wherein $R^1$, $R^2$, $R^{20}$ and n are as defined above and $R^{19}$ represents hydrogen or $C_{1-6}$alkyl, by coupling with a suitable alcohol in a suitable solvent such as tetrahydrofuran, at a suitable temperature such as room temperature in the presence of a suitable coupling agent such as di-tert butylazodicarboxylate.

Compounds of formula (XXVIII) wherein $R^1$, $R^2$, and $R^{20}$ are as defined above, $R^{19}$ represents hydrogen or $C_{1-6}$alkyl, and n=2 may be prepared from compounds of formula (XXVIII) wherein n=0, by treatment with a suitable oxidising agent, such as oxone, in a suitable solvent such as N,N-dimethylformamide, at a suitable temperature such as room temperature.

Compounds of formula (XXVIII) wherein $R^1$, $R^2$ and $R^{20}$ are as defined above, $R^{19}$ represents hydrogen or $C_{1-6}$alkyl, and n is 0, may be prepared from compounds of formula (III) wherein $R^1$, $R^2$, $R^{20}$ and Y are as defined above and Z represents hydrogen or $C_{1-6}$alkyl, by treatment with 2-mercaptoethanol (available from Aldrich). Suitable conditions for this process include heating in a suitable solvent such as N,N-dimethylformamide, at a suitable temperature such as 60-150° C., for example at 110° C., in the presence of a suitable catalyst, such as a palladium catalyst, for example tris(dibenzylideneacetone) palladium (II), and a suitable ligand, such as a phosphine ligand, for example (oxydi-2,1-phenylene)bis(diphenylphosphine), and in the presence of a suitable base such as potassium tert-butoxide.

The order of the steps comprising this process may be arranged in a number of different ways.

Process i

Compounds of formula (I) wherein $R^{34}$ represents hydrogen, $R^{19}$ represents $R^3S(=O)_n$—, and $R^1$, $R^2$, $R^{20}$ and n are as defined above, may be prepared from compounds of formula (XXIX) wherein Y represents chlorine, bromine or iodine, in particular iodine, n=1 or 2, and $R^1$, $R^2$, $R^3$ and $R^{20}$ are as defined above, by hydrogenation using a suitable hydrogenation process such as palladium on carbon in a suitable solvent such as ethanol.

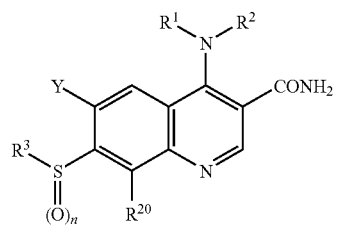

(XXIX)

Compounds of formula (XXIX) wherein Y represents chlorine, bromine or iodine, in particular iodine, n=1 or 2, and $R^1$, $R^2$, $R^3$ and $R^{20}$ are as defined above, may be prepared from compounds of formula (XXIX) wherein n=0 by treatment with a suitable oxidising agent such as oxone in a suitable solvent such as N,N-dimethylformamide of a mixture of N,N-dimethylformamide and anisole at a suitable temperature such as room temperature.

Compounds of formula (XXIX) wherein Y represents chlorine, bromine or iodine, in particular iodine, $R^1$, $R^2$, $R^3$ and $R^{20}$ are as defined above, and n=0 may be prepared from compounds of formula (III) wherein $R^1$, $R^2$ and $R^{20}$ are as defined above, Y represents chlorine, bromine or iodine, especially iodine, and Z represents chlorine, bromine or iodine, especially chlorine, and a thiol of formula $R^3SH$ by heating in a suitable solvent such as 1,3-dimethyl-3,4,5,6-tetrahydro-2 (1H)-pyrimidinone, at a suitable temperature such as 60-150° C. for example at 100° C. in the presence of a suitable base such as potassium carbonate.

Process j

As a particular example of a process of interconversion, compounds of formula (I), wherein $R^{34}$ represents $R^3S(=O)_n$— and wherein $R^3$ represents:

![structure]

and wherein $R^1$, $R^2$, $R^{20}$, and n are as defined above, and $R^{19}$ represents hydrogen or $C_{1-6}$alkyl, may be prepared from compounds of formula (XXVII) in scheme 3, wherein $R^1$, $R^2$, and $R^{20}$ are as defined above and Z represents hydrogen or $C_{1-6}$alkyl, by treatment with a suitable alkylating agent such as ethyl 4-bromobutyrate in a suitable solvent such as 1,4-dioxane at a suitable temperature such as 120° C.

The present invention also provides a compound of formula (I) or a pharmaceutically acceptable salt thereof for use as an active therapeutic substance in a mammal such as a human. The compound or salt can be for use in the treatment and/or prophylaxis of any of the conditions described herein and/or for use as a phosphodiesterase inhibitor, for example for use as a phosphodiesterase 4 (PDE4) inhibitor. "Therapy" may include treatment and/or prophylaxis.

Also provided is the use of a compound of formula (I) or a pharmaceutically acceptable salt thereof in the manufacture of a medicament (e.g. pharmaceutical composition) for the treatment and/or prophylaxis of an inflammatory and/or allergic disease in a mammal such as a human.

Also provided is a method of treatment and/or prophylaxis of an inflammatory and/or allergic disease in a mammal (e.g. human) in need thereof, which comprises administering to the mammal (e.g. human) a therapeutically effective amount of a compound of formula (I) as herein defined or a pharmaceutically acceptable salt thereof.

Phosphodiesterase 4 inhibitors are believed to be useful in the treatment and/or prophylaxis of a variety of diseases, especially inflammatory and/or allergic diseases, in mammals such as humans, for example: asthma, chronic bronchitis, emphysema, atopic dermatitis, urticaria, allergic rhinitis (seasonal or perennial), vasomotor rhinitis, nasal polyps, allergic conjunctivitis, vernal conjunctivitis, occupational conjunctivitis, infective conjunctivitis, eosinophilic syndromes, eosinophilic granuloma, psoriasis, rheumatoid arthritis, chronic obstructive pulmonary disease (COPD) including chronic bronchitis and emphysema, septic shock, ulcerative colitis, Crohn's disease, reperfusion injury of the myocardium and brain, chronic glomerulonephritis, endotoxic shock, adult respiratory distress syndrome, multiple sclerosis or memory impairment (including Alzheimer's disease).

In the treatment and/or prophylaxis, the inflammatory and/or allergic disease is preferably chronic obstructive pulmonary disease (COPD) including chronic bronchitis and emphysema, asthma, rheumatoid arthritis, psoriasis or allergic rhinitis in a mammal (e.g. human). More preferably, the treatment and/or prophylaxis is of COPD including chronic bronchitis and emphysema or asthma in a mammal (e.g. human). PDE4 inhibitors are thought to be effective in the treatment of asthma (e.g. see M. A. Giembycz, *Drugs,* February 2000, 59(2), 193-212; Z. Huang et al., *Current Opinion in Chemical Biology,* 2001, 5, 432-438; and refs cited therein) and COPD (e.g. see S. L. Wolda, *Emerging Drugs,* 2000, 5(3), 309-319; Z. Huang et al., *Current Opinion in Chemical Biology,* 2001, 5, 432-438; and refs cited therein). COPD is often characterised by the presence of airflow obstruction due to chronic bronchitis and/or emphysema (S. L. Wolda, *Emerging Drugs,* 2000, 5(3), 309-319).

For use in medicine, the compounds of the present invention are usually administered as a pharmaceutical composition.

The present invention therefore provides in a further aspect a pharmaceutical composition comprising a compound of formula (I) or a pharmaceutically acceptable salt thereof and one or more pharmaceutically acceptable carriers and/or excipients.

The pharmaceutical composition can be for use in the treatment and/or prophylaxis of any of the conditions described herein.

The compounds of formula (I) and/or the pharmaceutical composition may be administered, for example, by oral, parenteral (e.g. intravenous, subcutaneous, or intramuscular), inhaled, nasal, transdermal or rectal administration, or as topical treatments (e.g. ointments or gels). Accordingly, the pharmaceutical composition is preferably suitable for oral, parenteral (e.g. intravenous, subcutaneous or intramuscular), inhaled or nasal administration. More preferably, the pharmaceutical composition is suitable for inhaled or oral administration, e.g. to a mammal such as a human. Inhaled administration involves topical administration to the lung, e.g. by aerosol or dry powder composition.

A pharmaceutical composition suitable for oral administration can be liquid or solid; for example it can be a solution, a syrup, a suspension or emulsion, a tablet, a capsule or a lozenge.

A liquid formulation will generally consist of a suspension or solution of the compound or pharmaceutically acceptable salt in a suitable pharmaceutically acceptable liquid carrier(s), for example an aqueous solvent such as water, ethanol or glycerine, or an oil, or a non-aqueous solvent, such as a surfactant, such as polyethylene glycol. The formulation may also contain a suspending agent, preservative, flavouring and/or colouring agent.

A pharmaceutical composition suitable for oral administration being a tablet can comprise one or more pharmaceutically acceptable carriers and/or excipients suitable for preparing tablet formulations. Examples of such carriers include lactose and cellulose. The tablet can also or instead contain one or more pharmaceutically acceptable excipients, for example binding agents, lubricants such as magnesium stearate, and/or tablet disintegrants.

A pharmaceutical composition suitable for oral administration being a capsule can be prepared using encapsulation procedures. For example, pellets containing the active ingredient can be prepared using a suitable pharmaceutically acceptable carrier and then filled into a hard gelatin capsule. Alternatively, a dispersion, suspension or solution can be prepared using any suitable pharmaceutically acceptable carrier, for example an aqueous solution, aqueous gum or an oil and the dispersion, suspension or solution then filled into a hard or soft gelatin capsule.

The compounds of formula (I) and/or the pharmaceutical composition may be administered by a controlled or sustained release formulation as described in WO 00/50011.

A parenteral composition can comprise a solution or suspension of the compound or pharmaceutically acceptable salt in a sterile aqueous carrier or parenterally acceptable oil. Alternatively, the solution can be lyophilised; the lyophilised parenteral pharmaceutical composition can be reconstituted with a suitable solvent just prior to administration.

Compositions for nasal or inhaled administration may conveniently be formulated as aerosols, solutions, suspensions, drops, gels or dry powders.

For compositions suitable and/or adapted for inhaled administration, it is preferred that the compound or salt of formula (I) is in a particle-size-reduced form, and more preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a chlorofluorocarbon (CFC) or hydrofluorocarbon (HFC). Suitable CFC propellants include dichlorodifluoromethane, trichlorofluoromethane and dichlorotetrafluoroethane. Suitable HFC propellants include 1,1,1,2,3,3,3-heptafluoropropane and 1,1,1,2-tetrafluoroethane. The aerosol dosage forms can also take the form of a pump-atomiser.

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

In the pharmaceutical composition, each dosage unit for oral or parenteral administration preferably contains from 0.01 to 3000 mg, more preferably 0.5 to 1000 mg, of a compound of the formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds or salts of the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base.

The compounds, salts and/or pharmaceutical compositions according to the invention may also be used in combination with one or more other therapeutically active agents, for example, a $\beta_2$ adrenoreceptor agonist, an anti-histamine, an anti-allergic agent, an anti-inflammatory agent (including a steroid), an anticholinergic agent or an antiinfective agent (e.g. antibiotics or antivirals).

The invention thus provides, in a further aspect, a combination comprising a compound of formula (I) or a pharmaceutically acceptable salt thereof with one or more other therapeutically active agents, for example, a $\beta_2$-adrenoreceptor agonist, an anti-histamine, an anti-allergic agent, an anti-inflammatory agent (including a steroid), an anticholinergic agent or an antiinfective agent (e.g. antibiotics or antivirals).

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period, such as salmeterol or formoterol.

Examples of anti-histamines include methapyrilene or loratadine.

Examples of anti-inflammatory steroids include fluticasone propionate and budesonide.

Examples of anticholinergic compounds which may be used in combination with a compound of formula (I) or a pharmaceutically acceptable salt thereof are described in WO 03/011274 A2 and WO 02/069945 A2/US 2002/0193393 A1 and US 2002/052312 A1. For example, anticholinergic agents include muscarinic M3 antagonists, such as ipratropium bromide, oxitropium bromide or tiotropium bromide.

Other suitable combinations include, for example, combinations comprising a compound of formula (I) or a pharmaceutically acceptable salt thereof together with other anti-inflammatory agents such as an anti-inflammatory corticosteroid; or a non-steroidal anti-inflammatory drug (NSAID) such as a leukotriene antagonist (e.g. montelukast), an iNOS inhibitor, a tryptase inhibitor, an elastase inhibitor, a beta-2 integrin antagonist, an adenosine a2a agonist, a chemokine antagonist such as a CCR3 antagonist, or a 5-lipoxygenase inhibitor; or an antiinfective agent (e.g. an antibiotic or an antiviral). An iNOS inhibitor is preferably for oral administration. Suitable iNOS inhibitors (inducible nitric oxide synthase inhibitors) incluse those disclosed in WO 93/13055, WO 98/30537, WO 02/50021, WO 95/34534 and WO 99/62875. Suitable CCR3 inhibitors include those disclosed in WO 02/26722.

The combinations referred to above may conveniently be presented for use in the form of a pharmaceutical composition and thus a pharmaceutical composition comprising a combination as defined above together with one or more pharmaceutically acceptable carriers and/or excipients represent a further aspect of the invention.

The individual compounds of such combinations may be administered either sequentially or simultaneously in separate or in combined pharmaceutical compositions.

All publications, including but not limited to patents and patent applications, cited in this specification are herein incorporated by reference as if each individual publication were specifically and individually indicated to be incorporated by reference herein as though fully set forth.

The various aspects of the invention will now be described by reference to the following Biological Test Methods and Examples. These Examples are merely illustrative and are not to be construed as a limitation of the scope of the present invention.

Biological Test Methods

PDE3, PDE4B, PDE4D, PDE5 and PDE6 Primary Assay Methods

The activity of the compounds can be measured as described below. Preferred compounds of the invention are selective PDE4 inhibitors, i.e. they inhibit PDE4 (e.g. PDE4B and/or PDE4D) more strongly than they inhibit other PDE's such as PDE3 and/or PDE5.

1. PDE Enzyme Sources and Literature References.

Human recombinant PDE4B, in particular the 2B splice variant thereof (HSPDE4B2B), is disclosed in WO 94/20079 and also in M. M. McLaughlin et al., "A low Km, rolipram-sensitive, cAMP-specific phosphodiesterase from human brain: cloning and expression of cDNA, biochemical characterisation of recombinant protein, and tissue distribution of mRNA", *J. Biol. Chem.*, 1993, 268, 6470-6476. For example, in Example 1 of WO 94/20079, human recombinant PDE4B is described as being expressed in the PDE-deficient yeast *Saccharomyces cerevisiae* strain GL62, e.g. after induction by addition of 150 μM $CuSO_4$, and 100,000×g supernatant fractions of yeast cell lysates are described for use in the harvesting of PDE4B enzyme.

Human recombinant PDE4D (HSPDE4D3A) is disclosed in P. A. Baecker et al., "Isolation of a cDNA encoding a human rolipram-sensitive cyclic AMP phoshodiesterase (PDE $IV_D$)", *Gene*, 1994,138, 253-256.

Human recombinant PDE5 is disclosed in K. Loughney et al., "Isolation and characterisation of cDNAs encoding PDE5A, a human cGMP-binding, cGMP-specific 3',5'-cyclic nucleotide phosphodiesterase", *Gene,* 1998, 216, 139-147.

PDE3 was purified from bovine aorta. Its presence in the tissue was reported by H. Coste and P. Grondin in "Characterisation of a novel potent and specific inhibitor of type V phosphodiesterase", *Biochem. Pharmacol.,* 1995, 50,1577-1585.

PDE6 was purified from bovine retina. Its presence in this tissue was reported by: P. Catty and P. Deterre in "Activation and solubilization of the retinal cGMP-specific phosphodiesterase by limited proteolysis", *Eur. J. Biochem.,* 1991, 199, 263-269; A. Tar et al. in "Purification of bovine retinal cGMP phosphodiesterase", *Methods in Enzymology,* 1994, 238, 3-12; and/or D. Srivastava et al. in "Effects of magnesium on cyclic GMP hydrolysis by the bovine retinal rod cyclic GMP phosphodiesterase", *Biochem. J.,* 1995, 308, 653-658.

2. Inhibition of PDE3, PDE4B, PDE4D, PDE5 or PDE6 Activity: Radioactive Scintillation Proximity Assay (SPA)

The ability of compounds to inhibit catalytic activity at PDE4B or 4D (human recombinant), PDE3 (from bovine aorta), PDE5 (human recombinant) or PDE 6 (from bovine retina) was determined by Scintillation Proximity Assay (SPA) in 96-well format. Test compounds (preferably as a solution in DMSO, e.g. 2 microlitre (µl) volume) were preincubated at ambient temperature in Wallac Isoplates (code 1450-514) with PDE enzyme in 50 mM Tris-HCl buffer pH 7.5, 8.3 mM $MgCl_2$, 1.7 mM EGTA, 0.05% (w/v) bovine serum albumin for 10-30 minutes. The enzyme concentration was adjusted so that no more than 20% hydrolysis of the substrate occurred in control wells without compound, during the incubation. For the PDE3, PDE4B and PDE4D assays [5',8-$^3$H]adenosine 3',5'-cyclic phosphate (Amersham Pharmacia Biotech, code TRK.559 or Amersham Biosciences UK Ltd, Pollards Wood, Chalfont St Giles, Buckinghamshire HP8 4SP, UK) was added to give 0.05 µCi per well and ~10 nM final concentration. For the PDE5 and PDE6 assays [8-$^3$H]guanosine 3',5'-cyclic phosphate (Amersham Pharmacia Biotech, code TRK.392) was added to give 0.05 µCi per well and ~36 nM final concentration. Plates e.g. containing approx. 100 µl volume of assay mixture were mixed on an orbital shaker for 5 minutes and incubated at ambient temperature for 1 hour. Phosphodiesterase SPA beads (Amersham Pharmacia Biotech, code RPNQ 0150) suspended in buffer were added (~1 mg per well) to terminate the assay. Plates were sealed and shaken and allowed to stand at ambient temperature for 35 minutes to 1 hour to allow the beads to settle. Bound radioactive product was measured using a WALLAC TRILUX 1450 Microbeta scintillation counter. For inhibition curves, 10 concentrations (e.g. 1.5 nM-30 µM) of each compound were assayed; more potent compounds were assayed over lower concentration ranges (assay concentrations were generally between 30 µM and 50 fM). Curves were analysed using ActivityBase and XLfit (ID Business Solutions Limited, 2 Ocean Court, Surrey Research Park, Guildford, Surrey GU2 7QB, United Kingdom). Results were expressed as $pIC_{50}$ values.

Alternatively, the activity of the compounds can be measured in the following Fluorescence Polarisation (FP) assay:

3. Inhibition of PDE4B or PDE4D Activity: Fluorescence Polarisation (FP) Assay

The ability of compounds to inhibit catalytic activity at PDE4B (human recombinant) and PDE4D (human recombinant) was determined by IMAP Fluorescence Polarisation (FP) assay (Molecular Devices code: R8062) in 384-well format. Test compounds (small volume, e.g. 0.5 µl, of solution in DMSO) were preincubated at ambient temperature in black 384-well microtitre plates (supplier: NUNC, code 262260) with PDE enzyme in 10 mM Tris-HCl buffer pH 7.2, 10 mM $MgCl_2$, 0.1% (w/v) bovine serum albumin. 0.05% $NaN_3$ for 10-30 minutes. The enzyme level was set so that reaction was linear throughout the incubation.

Fluorescein adenosine 3',5'-cyclic phosphate (Molecular Devices code: R7091) was added to give ~40 nM final concentration. Plates were mixed on an orbital shaker for 10 seconds and incubated at ambient temperature for 40 minutes. IMAP binding reagent (Molecular Devices code: R7207) was added (60 µl of a 1 in 400 dilution in binding buffer of the kit stock suspension) to terminate the assay. Plates were allowed to stand at ambient temperature for 1 hour. The FP ratio of parallel to perpendicular light was measured using an Analyst™ plate reader (from Molecular Devices Ltd). For inhibition curves, 11 concentrations (0.5 nM-30 µM) of each compound were assayed; more potent compounds were assayed over lower concentration ranges (assay concentrations were generally between 30 µM and 50 fM). Curves were analysed using ActivityBase and XLfit (ID Business Solutions Limited). Results were expressed as $pIC_{50}$ values. For a given PDE4 inhibitor, the PDE4B (or PDE4D) inhibition values measured using the SPA and FP assays can differ slightly. However, in a regression analysis of 100 test compounds, the $pIC_{50}$ inhibition values measured using SPA and FP assays have been found generally to agree within 0.5 log units for PDE4B and PDE4D (linear regression coefficient 0.966 for PDE4B and 0.971 for PDE4D; David R. Mobbs et al, "Comparison of the IMAP Fluorescence Polarisation Assay with the Scintillation Proximity Assay for Phosphodiesterase Activity", poster presented at 2003 Molecular Devices UK & Europe User Meeting, 2nd Oct. 2003, Down Hall, Harlow, Essex, United Kingdom).

Examples of compounds of the invention described above inhibit the catalytic activity at the PDE4B (human recombinant) enzyme with $pIC_{50}$ values in the range 6.0-11.7. Biological Data obtained for some of the Examples (PDE4B and PDE5 inhibitory activity) is as follows:

| Example No. | PDE4B mean $pIC_{50}$ | PDE5 mean $pIC_{50}$ |
|---|---|---|
| 27 | 8.4 | 4.8 |
| 70 | 7.3 | 5.0 |
| 92 | 7.7 | <4.5 |
| 125 | 6.6 | 5.5 |
| 265 | 11.3 | 5.2 |
| 307 | 10.5 | <4.6 |
| 309 | 10.1 | <4.9 |
| 312 | 9.4 | <4.5 |
| 369 | 9.5 | 5.1 |
| 380 | 11.4 | <7.0 |
| 399 | >11.6 | 5.6 |
| 400 | 11.0 | <5.0 |
| 408 | 11.4 | 4.9 |
| 446 | 11.3 | <4.5 |
| 457 | 11.0 | <5.5 |
| 502 | 8.9 | <5 |
| 546 | 10.7 | 4.7 |

4. Emesis:

Many known PDE4 inhibitors cause emesis and/or nausea to greater or lesser extents (e.g. see Z. Huang et al., *Current Opinion in Chemical Biology,* 2001, 5, 432-438, see especially pages 433-434 and references cited therein). Therefore, it would be preferable but not essential that a PDE4 inhibitory compound of the invention causes only limited or manageable emetic side-effects. Emetic side-effects can for example be measured by the emetogenic potential of the compound when administered to ferrets; for example one can measure the time to onset, extent, frequency and/or duration of vomiting and/or writhing in ferrets after oral or parenteral administration of the compound. See for example A. Robichaud et al., "Emesis induced by inhibitors of PDE IV in the ferret" *Neuropharmacology*, 1999, 38, 289-297, erratum *Neuropharmacology*, 2001, 40, 465465.

EXAMPLES

In this section, "intermediates" represent syntheses of intermediate compounds intended for use in the synthesis of the "Examples".

Abbreviations used herein:
HPLC high performance liquid chromatography
NMR nuclear magnetic resonance
LC/MS liquid chromatography/mass spectroscopy
TLC thin layer chromatography
SPE solid phase extraction column. Unless otherwise specified the solid phase will be silica gel. C18 SPE refers to reverse phase SPE columns (eg Varian Bond Elut C18 columns). Aminopropyl SPE refers to a silica SPE column with aminopropyl residues immobilised on the solid phase (eg. IST Isolute™ columns). It is thought that compounds isolated by SPE are free bases.
SCX solid phase extraction (SPE) column with benzene sulfonic acid residues immobilised on the solid phase (eg. IST lsolute™ columns). When eluting with ammonia/methanol, it is thought that compounds isolated by SCX are free bases.

General Experimental Details

LC/MS (Liquid Chromatography/Mass Spectroscopy)
Waters ZQ mass spectrometer operating in positive ion electrospray mode, mass range 100-1000 amu.
UV wavelength: 215-330 nm
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mM ammonium acetate
Gradient: Mixtures of Solvent A and Solvent B are used according to the following gradient profiles (expressed as % Solvent A in the mixture): 0% A/0.7 min, 0-100% A/3.5 min, 100% A/1.1 min, 100-0% A/0.2 min Mass Directed Automated Preparative HPLC Column, Conditions and Eluent Method A
The preparative column used was a Supelcosil ABZplus (10 cm×2.12 cm internal diameter; particle size 5 μm)
UV detection wavelength : 200-320 nm
Flow rate: 20 ml/min
Injection Volume: 0.5 ml
Solvent A: 0.1 % formic acid
Solvent B: 95% acetonitrile+0.05% formic acid
Gradient systems: mixtures of Solvent A and Solvent B are used according to a choice of 5 generic gradient profiles (expressed as % Solvent B in the mixture), ranging from a start of 0 to 50% Solvent B, with all finishing at 100% Solvent B to ensure total elution. It is thought that compounds isolated by this method are free bases, unless the $R^1$ or $R^3$ groups contain basic moieties, in which case formate salts may be formed.

Mass Directed Automated Preparative HPLC Column, Conditions and Eluent

Method B
The preparative column used was a Supelcosil ABZplus (10 cm×2.12 cm internal diameter; particle size 5 μm)
UV detection wavelength: 200-320 nm
Flow rate: 20 ml/min
Injection Volume: 0.5 ml
Solvent A: water+0.1% trifluoroacetic acid
Solvent B: acetonitrile+0.1% trifluoroacetic acid
Gradient systems: mixtures of Solvent A and Solvent B are used according to a choice of 5 generic gradient profiles (expressed as % Solvent B in the mixture), ranging from a start of 0 to 50% Solvent B, with all finishing at 100% Solvent B to ensure total elution. It is thought that compounds isolated by this method are trifluoroacetate salts.

Mass Directed Automated Preparative HPLC Column, Conditions and Eluent

Method C
This is identical to method A. After purification but before solvent removal an excess (between a few drops and 0.5 ml) of dilute hydrochloric acid is added to the product containing fractions.
It is thought that compounds isolated by this method are hydrochloride salts.

Product Isolation by Filtration Directly from the Reaction Mixture
It is thought that compounds isolated by this method from reactions involving displacement of a 4-chloroquinoline intermediate with an amine of formula $R^1R^2NH$ are hydrochloride salts.

'Hydrophobic Frit'
This refers to a Whatman PTFE filter medium (frit), pore size 5.0 μm, housed in a polypropylene tube.

Oasis Cartridge
This refers to a Waters Oasis™ HLB Liquid Phase Extraction Cartridge Evaporation of Product Fractions After Purification
Reference to column chromatography, SPE and preparative HPLC purification includes evaporation of the product containing fractions to dryness by an appropriate method.

Aqueous Ammonia Solutions
'880 Ammonia' or '0.880 ammonia' refers to concentrated aqueous ammonia (specific gravity 0.880).

INTERMEDIATES AND EXAMPLES

All reagents not detailed in the text below are commercially available from established suppliers such as Sigma-Aldrich.

Intermediate 1. 1-(Cyclopentylthio)-4-nitrobenzene

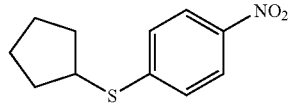

Cyclopentanethiol (1.0 g) (available from Aldrich) was dissolved in acetonitrile (10 ml) and potassium carbonate (1.35 g) was added. After 5 min, 1-fluoro-4-nitrobenzene (1.38 g) (available from Aldrich) was added and the mixture was stirred at room temperature overnight. The mixture was diluted with water and extracted with ether. The organic layer was washed with 1M aqueous sodium hydroxide (20 ml), water (20 ml), and 1M aqueous hydrochoric acid (20 ml). The organic layer was separated and the solvent evaporated in vacuo to give the title compound as a yellow liquid (0.7 g).

$^1$HNMR (CDCl$_3$) δ 8.12 (2H,m), 7.33 (2H,m), 3.75 (1H, m), 2.19 (2H,m), 1.87-162 (6H,m).

Intermediate 2.
1-(Cyclopentylsulfonyl)-4-nitrobenzene

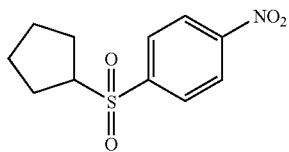

Intermediate 1 (0.7 g) was dissolved in methanol (20 ml) and the solution cooled to 0° C. A solution of oxone (1.93 g) in water (20 ml) was added and the mixture was stirred under nitrogen for 2 h at room temperature. The mixture was extracted with dichloromethane, the layers were separated (hydrophobic frit), and the organic layer evaporated to give the title compound as a yellow oil which crystallised on standing (0.79 g).

LC/MS R$_t$ 3.05 min, m/z 273 [MNH$_4^+$]

Intermediate 3. 4-(Cyclopentylsulfonyl)aniline

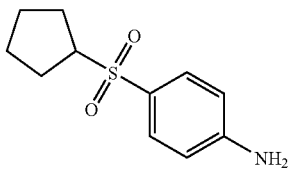

Intermediate 2 (13.1 g) was dissolved in acetic acid (150 ml) and hydrogenated over palladium on activated carbon (1.6 g) with stirring overnight. The mixture was filtered through Celite filter aid, and the filtrate was evaporated to give a yellow/green oil. The oil was taken up in methanol and an insoluble precipitate filtered off; the filtrate was evaporated in vacuo to give a yellow solid. Trituration with ether and filtration gave the title compound as a pale yellow solid (8.1 g).

LC/MS R$_t$ 2.5 min, m/z 243 [MNH$_4^+$]

Intermediate 4. Diethyl ({[4-cyclopentylsulfonyl) phenyl]amino}methylidene)propanedioate

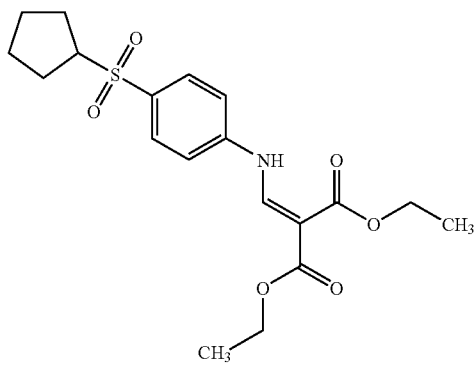

Intermediate 3 (10.8 g) (*Helvetica Chimica Acta* 1983, 66(4), 1046-52) and diethyl (ethoxymethylene)malonate (11.4 g) (available from Aldrich) were heated at 130° C. for 2 h. After cooling, the brown oil was scratched around the edge of the flask which caused the oil to solidify. Trituration with methanol gave a beige solid, which was filtered off to give the title compound (12.3 g). The filtrate was evaporated in vacuo to give a brown oil. Purification by chromatography on silica gel, eluting with 5% ethyl acetate/cyclohexane followed by 10% ethyl acetate/cyclohexane, gave an orange solid; trituration with methanol and filtration gave the title compound as a yellow solid (2.5 g; total yield 14.8 g).

LC/MS R$_t$ 3.27 min m/z 396 [MH$^+$]

Intermediate 5. Ethyl 6-(cyclopentylsulfonyl)-4-oxo-1,4-dihydro-3-quinolinecarboxylate

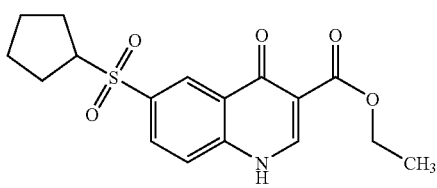

Intermediate 4 (14.7 g) was dissolved in diphenyl ether (150 ml) and the solution heated at 250° C. for 30 min. After cooling, the mixture was diluted with cyclohexane and the resulting precipitate filtered off and washed with further cyclohexane to give the title compound as a beige solid (10.9 g).

LC/MS R$_t$ 2.46 min m/z 350 [MH$^{30}$]

Intermediate 6. 6-(Cyclopentylsulfonyl)-4-oxo-1,4-dihydro-3-quinolinecarboxylic acid

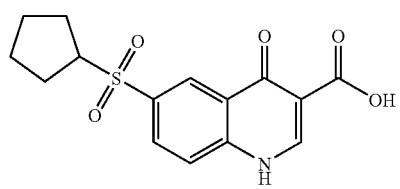

Intermediate 5 (10.9 g) was dissolved in ethanol (100 ml) and 2M sodium hydroxide (100 ml), and the mixture was heated under reflux for 3 h. After cooling, the solvent was evaporated in vacuo and the residue was dissolved in water and washed with ethyl acetate. The aqueous layer was acidified with 2M hydrochloric acid to between pH 5 and pH 6 which caused a precipitate to form. The precipitate was filtered off, washed with water, and dried in vacuo overnight to give the title compound as a beige solid (9.47 g).

LC/MS R$_t$ 2.65 min m/z 322 [MH$^+$]

Intermediate 7. 4-Chloro-6-(cyclopentylsulfonyl)-3-quinolinecarboxamide

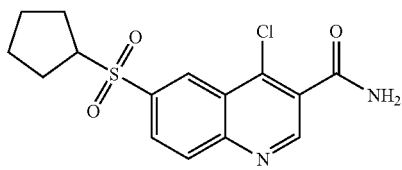

Intermediate 6 (1.43 g) was suspended in thionyl chloride (20 ml) and N,N-dimethylformamide (5 drops) was added. The mixture was heated under reflux for 2 h. After cooling, the thionyl chloride was evaporated in vacuo and the resulting residue was azeotroped with toluene. 0.880 Ammonia (25 ml) was added dropwise to the yellow solid (caution: exotherm), and the suspension was stirred at room temperature for 16 h. The resulting precipitate was filtered off, washed with water, and dried in vacuo to give the title compound (0.71 g).

LC/MS $R_t$ 2.47 min m/z 339 [MH$^+$]
Similarly prepared were the following:

Intermediate 30. 4-Chloro-6-[(1-methylethyl)sulfonyl]-3-quinolinecarboxamide

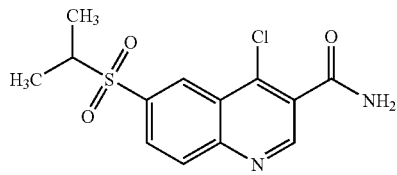

This was made in the same manner as Intermediate 7 starting from 4-[(1-methylethyl)sulfonyl]aniline (*Helvetica Chimica Acta* (1983), 66(4), 1046-52).

LC/MS $R_t$ 2.27 min n/z 313 [MH$^+$]

The following were also made in the same manner as Intermediate 7, with the proviso that the intermediates of formula

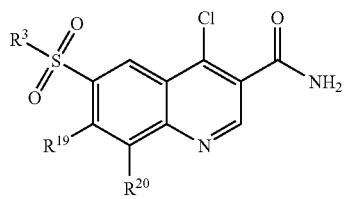

were prepared from the appropriate 4-fluoronitrobenzene in a similar manner to Intermediate 15:

| Intermediate No. | R$^3$— | R$^{19}$— | R$^{20}$— | Starting material/source | LCMS MH$^+$ | LCMS $R_t$ (min) |
|---|---|---|---|---|---|---|
| Intermediate 8 | Ph— | H— | H— | 4-(phenylsulfonyl)aniline/Maybridge | 347 | 2.58 |
| Intermediate 9 | Me— | H— | H— | 4-(methylsulphonyl)aniline/Salor | 285 | 2.00 |
| Intermediate 16 | Ph— | H— | Me— | Intermediate 15 | 361 | 2.78 |
| Intermediate 17 | Me— | Me— | H— | 1-fluoro-2-methyl-4-nitrobenzene/Aldrich | 299 | 2.19 |
| Intermediate 95 | $^t$Bu— | H— | H— | 4-[(1,1-dimethylethyl)sulphonyl]aniline/Helvetica Chimica Ada (1983), 66(4), 1046-52 | 327 | 2.40 |

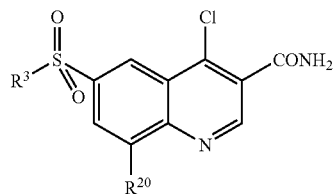

| Intermediate Number | R³SO₂— | R²⁰— | Starting Nitroaryl Compound/ Supplier | Starting Sulfinic Acid/Supplier | LCMS MH⁺ | LCMS R$_t$ (min) |
|---|---|---|---|---|---|---|
| Intermediate 31 | CH₃–O–C₆H₄–S(O)₂– | H— | 4-fluoro nitrobenzene/ Aldrich | Sodium 4-(methyloxy) benzenesulfinate/ WO 9830566 A1 | 379 | 2.72 |
| Intermediate 32 | CH₃–O–C₆H₄–S(O)₂– | Me— | 5-fluoro-2-nitrotoluene/ Aldrich | Sodium 4-(methyloxy) benzenesulfinate/ WO 9830566 A1 | 391 | 2.91 |
| Intermediate 34 | H₃C–C₆H₄–S(O)₂– | Me— | 5-fluoro-2-nitrotoluene/ Aldrich | Sodium 4-methylbenzene sulfinate/Aldrich | 375 | 2.93 |
| Intermediate 33 | MeSO₂— | Me— | 5-fluoro-2-nitrotoluene/ Aldrich | Methanesulfinic acid sodium salt/ Lancaster | 299 | 2.12 |
| Intermediate 50 | MeSO₂— | MeO— | 4-fluoro-2-(methyloxy)-1-nitrobenzene/ Maybridge | Methanesulfinic acid sodium salt/ Lancaster | 315 | 1.99 |

Intermediate 10. Diethyl {[(4-iodophenyl)amino]methylidene}propanedioate

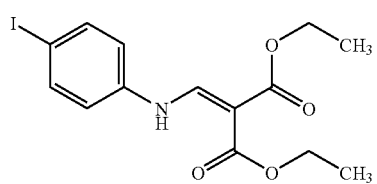

A mixture of 4-iodoaniline (208 g) (available from Aldrich) and diethyl (ethoxymethylene)malonate (210 ml) (available from Aldrich) was heated to ca. 60° C., whereupon the mixture set solid. Heating was continued to 100° C., and then the mixture was removed from heating and broken up. Heating was continued at 100° C. for 1 h, and the solid was collected, washed with cyclohexane (1 L) and ethanol (2×500 ml), and dried in vacuo at 40° C. overnight to give the title compound as a white solid (356 g).

LC/MS R$_t$ 3.57 min m/z 390 [MH⁺]

Intermediate 11. Ethyl 6-iodo-4-oxo-1,4-dihydro-3-quinolinecarboxylate

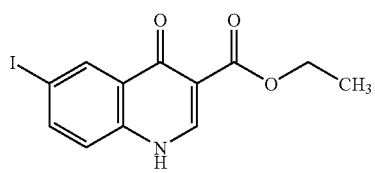

Diphenyl ether (175 ml) was heated to reflux temperature, and Intermediate 10 was gradually added down an air condenser. Once all the reagent had been added the mixture was heated under reflux for a further 30 min. The mixture was then cooled and 2-methylpentane (200 ml) was added. The solid formed was collected by filtration to give the title compound (24.6 g).

$^1$HNMR (DMSO) δ 8.58 (1H,s), 8.42(1H,d), 7.99 (1H,dd), 7.44(1H,d), 4.21(2H,q), 1.28 (3H,t)

Intermediate 12.
6-Iodo-4-oxo-1,4-dihydro-3-quinolinecarboxylic acid

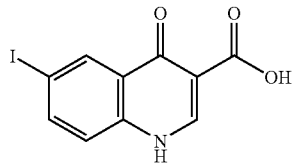

Sodium hydroxide (9.8 g) was dissolved in water (61 ml) and ethanol (30 ml) was added. The resultant solution was added to Intermediate 11, and the mixture was heated under reflux for 60 min with stirring under nitrogen. Concentrated hydrochloric acid was added, giving a white precipitate. After stirring for 16 h, the precipitate was filtered off, washed with water and dried in vacuo to give the title compound as a white solid (8.15 g).

LC/MS $R_t$ 3.01min m/z 316 [MH$^+$]

Intermediate 13.
4-Chloro-6-iodo-3-quinolinecarboxamide

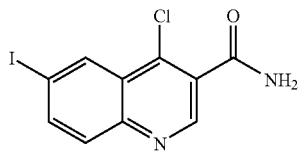

Intermediate 12 (8.1 g) was added portionwise to stirred thionyl chloride (60 ml). N,N-dimethylformamide (3 drops) was added and the mixture was heated under reflux with stirring under nitrogen for 1.75 h. The excess thionyl chloride was evaporated in vacuo and the residue was azeotroped with toluene (2×50 ml). The resulting pale yellow solid was added portionwise to stirred 0.880 ammonia (250 ml), and the mixture stirred at room temperature for 1.5 h. The solid was filtered off, washed with water and dried in vacuo at 60° C. for 16 h to give the title compound as a white solid (7.94 g).

LC/MS $R_t$ 2.72min m/z 332 [MH$^+$]

The following were made in the same manner as Intermediate 13:

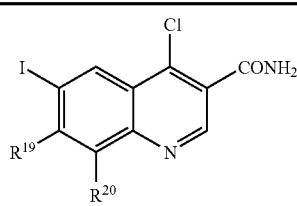

| Intermediate Number | R$^{19}$— | R$^{20}$— | Starting Material | LCMS MH$^+$ | LCMS $R_t$ (min) |
|---|---|---|---|---|---|
| Intermediate 48 | H— | Me— | 4-iodo-2-methylaniline/Aldrich | 347 | 3.06 |

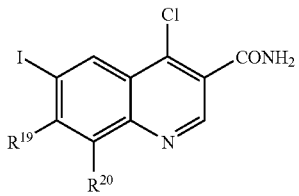

| Intermediate Number | R$^{19}$— | R$^{20}$— | Starting Material | LCMS MH$^+$ | LCMS $R_t$ (min) |
|---|---|---|---|---|---|
| Intermediate 49 | H— | Cl— | 2-chloro-4-iodoaniline/Avocado | 367 | 2.99 |
| Intermediate 72 | H— | Et— | Intermediate 73 | 361 | 3.22 |
| Intermediate 87 | H— | F— | 2-Fluoro-4-iodoaniline/Aldrich | 352 | 2.65 |
| Intermediate 67 | Cl— | H— | from 3-chloro-4-iodoaniline/Aldrich | 367 | 3.07 |

Intermediate 68.
4.7-Dichloro-8-methyl-3-quinolinecarboxamide

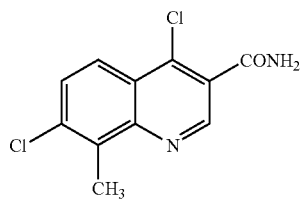

Intermediate 68 was prepared from 2-methyl-3-chloroaniline (Aldrich) in a similar manner to Intermediate 13.

LC/MS $R_t$ 3.00 min m/z 255 [MH$^+$]

Intermediate 14. 6-Iodo-4-{[3-(methyloxy)phenyl]amino}-3-quinolinecarboxamide hydrochloride

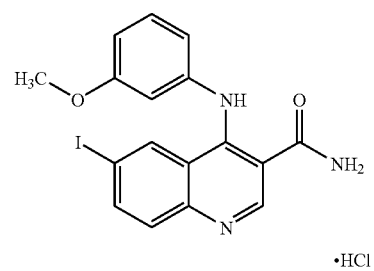

Intermediate 13 (5.0 g) was dissolved in ethanol (60 ml), 3-methoxyaniline (3.37 ml) (available from Aldrich) was added, and the mixture was heated under reflux for 2.5 h. The resulting precipitate was filtered off and washed with ether to give the title compound.

LC/MS $R_t$ 2.59 min m/z 420 [MH$^+$]

The following were made in the same manner as Intermediate 14, using acetonitrile as solvent:

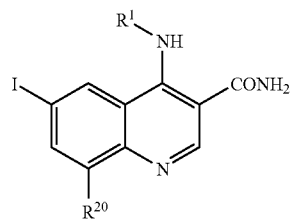

| Intermediate Number (a) | R¹NH— | R²⁰— | Starting Material | Amine/Source | LCMS MH⁺ | LCMS R$_t$ (min) |
|---|---|---|---|---|---|---|
| Intermediate 38 HCl | 3-methylanilino-N(CH₃)— | Cl— | Intermediate 49 | 3-methylaniline/ Aldrich | 438 | 3.56 |
| Intermediate 35 HCl | 4-fluoro-3-methoxy-N(CH₃)— | Me— | Intermediate 48 | 4-fluoro-3-methoxyaniline/ Apollo-Chem | 452 | 2.78 |
| Intermediate 36 HCl | 2,3-dihydrobenzofuran-4-yl-N(CH₃)— | Me— | Intermediate 48 | 2,3-dihydro-1-benzofuran-4-amine hydrobromide/ Journal of Heterocyclic Chemistry, (1980), 17(6), 1333-5. | 446 | 2.81 |
| Intermediate 39 HCl | 4-fluoro-3-methoxy-N(CH₃)— | Cl— | Intermediate 49 | 4-fluoro-3-methoxyaniline/ Apollo-Chem | 472 | 3.29 |
| Intermediate 40 HCl | 2,3-dihydrobenzofuran-4-yl-N(CH₃)— | Cl— | Intermediate 49 | 2,3-dihydro-1-benzofuran-4-amine hydrobromide/ Journal of Heterocyclic Chemistry (1980), 17(6), 1333-5. | 466 | 3.35 |
| Intermediate 41 HCl | 3-cyanophenyl-N(CH₃)— | Cl— | Intermediate 49 | 3-aminobenzonitrile/ Aldrich | 449 | 3.19 |

-continued

| Intermediate Number (a) | R¹NH— | R²⁰— | Starting Material | Amine/Source | LCMS MH⁺ | LCMS R$_t$ (min) |
|---|---|---|---|---|---|---|
| Intermediate 42 HCl | 3-fluorophenyl-NH— | Cl— | Intermediate 49 | 3-fluoroaniline/ Aldrich | 442 | 3.40 |
| Intermediate 43 HCl | 1-methyl-1H-indazol-6-yl-NH— | Cl— | Intermediate 49 | 1-methyl-1H-indazol-6-amine hydrochloride/ Synthetic Communications (1996), 26(13), 2443-2447. | 477 | 3.05 |
| Intermediate 44 HCl | 1-methyl-1H-benzimidazol-6-yl-NH— | Me— | Intermediate 48 | 1-methyl-1H-benzimidazol-6-amine/ Heterocycles (1991), 32(5), 1003-12. | 458 | 2.03 |
| Intermediate 45 HCl | 3-methoxyphenyl-NH— | Me— | Intermediate 48 | 3-methoxyaniline/ Aldrich | 434 | 2.75 |
| Intermediate 46 HCl | 3-cyanophenyl-NH— | Me— | Intermediate 48 | 3-aminobenzonitrile/ Aldrich | 429 | 2.93 |
| Intermediate 61 HCl | 3-fluorophenyl-NH— | Me— | Intermediate 48 | 3-fluoroaniline/ Aldrich | 422 | 3.02 |

-continued

| Intermediate Number (a) | R¹NH— | R²⁰— | Starting Material | Amine/Source | LCMS MH⁺ | LCMS R$_t$ (min) |
|---|---|---|---|---|---|---|
| Intermediate 74 HCl | 4-fluoro-2-methoxy-phenyl-NH- (F, OCH₃ substituents) | Et— | Intermediate 72 | 4-fluoro-3-methoxyaniline/ Apollo-Chem | 466 | 2.92 |
| Intermediate 75 HCl | 3-fluorophenyl-NH- | Et— | Intermediate 72 | 3-fluoroaniline/ Aldrich | 436 | 3.24 |
| Intermediate 76 HCl | 3-chlorophenyl-NH- | Et— | Intermediate 72 | 3-chloroaniline/ Aldrich | 452 | 3.44 |
| Intermediate 77 HCl | 3-cyanophenyl-NH- | Et— | Intermediate 72 | 3-aminobenzonitrile/ Aldrich | 443 | 3.12 |
| Intermediate 78 HCl | 3-methylphenyl-NH- | Et— | Intermediate 72 | 3-methylaniline/ Aldrich | 432 | 3.15 |
| Intermediate 79 HCl | 1-methyl-1H-indazol-6-yl-NH- | Et— | Intermediate 72 | 1-methyl-1H-indazol-6-amine hydrochloride/ Synthetic Communications (1996), 26(13). 2443-2447 | 472 | 2.8 |

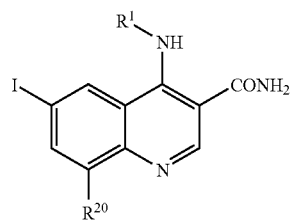

| Intermediate Number (a) | R¹NH— | R²⁰— | Starting Material | Amine/Source | LCMS MH⁺ | LCMS $R_t$ (min) |
|---|---|---|---|---|---|---|
| Intermediate 80 HCl | 2,3-dihydrobenzofuran-4-yl-N(Me)— | Et— | Intermediate 72 | 2,3-dihydro-1-benzofuran-4-amine hydrobromide/ Journal of Heterocyclic Chemistry (1980), 17(6), 1333-5. | 460 | 2.97 |
| Intermediate 88 HCl | 2,3-dihydrobenzofuran-4-yl-N(Me)— | F— | Intermediate 87 | 2,3-dihydro-1-benzofuran-4-amine hydrobromide/ Journal of Heterocyclic Chemistry (1980), 17(6), 1333-5. | 450 | 3.06 |
| Intermediate 89 HCl | 3-fluorophenyl-N(Me)— | F— | Intermediate 87 | 3-fluoroaniline/ Aldrich | 426 | 3.11 |
| Intermediate 90 HCl | 3-chlorophenyl-N(Me)— | F— | Intermediate 87 | 3-chloroaniline/ Aldrich | 442 | 3.19 |
| Intermediate 91 HCl | 3-methylphenyl-N(Me)— | F— | Intermediate 87 | 3-methylaniline/ Aldrich | 422 | 3.15 |

-continued

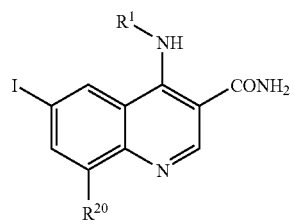

| Intermediate Number (a) | R¹NH— | R²⁰— | Starting Material | Amine/Source | LCMS MH⁺ | LCMS R$_t$ (min) |
|---|---|---|---|---|---|---|
| Intermediate 92 HCl | 3-cyanophenyl-NH— | F— | Intermediate 87 | 3-aminobenzonitrile/ Aldrich | 433 | 2.88 |
| Intermediate 93 HCl | 1-methyl-1H-indazol-6-yl-NH— | F— | Intermediate 87 | 1-methyl-1H-indazol-6-amine hydrochloride/ Synthetic Communications (1996), 26(13), 2443-2447 | 462 | 2.87 |
| Intermediate 94 HCl | 4-fluoro-3-methoxyphenyl-NH— | F— | Intermediate 87 | 4-fluoro-3-methoxyaniline/ Apollo-Chem | 456 | 3.11 |

(a) Salt form: HCl = hydrochloride

Intermediate 63. 7-Chloro-6-iodo-4-{[3-(methyloxy)phenyl]amino}-3-quinolinecarboxamide hydrochloride

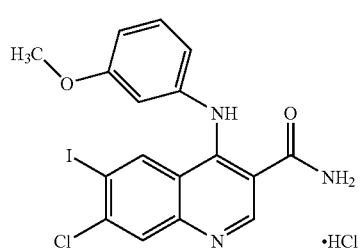

Intermediate 63 was prepared from Intermediate 67 in a similar manner to Intermediate 14, using acetonitrile as solvent.

LC/MS R$_t$ 3.15 min m/z 452 [MH⁺]

Intermediate 66. 7-Chloro-8-methyl-4-{[3-(methyloxy)phenyl]amino}-3-quinolinecarboxamide hydrochloride

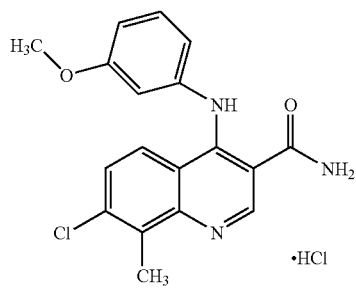

Intermediate 66 was prepared from Intermediate 68 using 3-methoxyaniline in a similar manner to Intermediate 14.

LC/MS R$_t$ 2.80 min m/z 342 [MH⁺]

Intermediate 104. 7-Chloro-4-(2,3-dihydro-1-benzofuran-4-ylamino)-8-methyl-3-quinolinecarboxamide hydrochloride

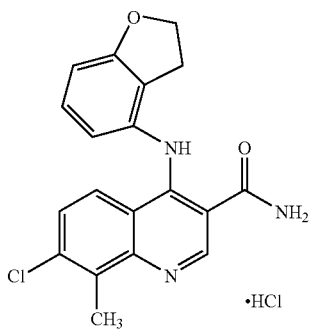

Intermediate 104 was prepared from Intermediate 68 using 2,3-dihydro-1-benzofuran-4-amine in a similar manner to Intermediate 14, using acetonitrile as solvent.
LC/MS $R_t$ 2.80 min m/z 354 [MH$^+$]

Intermediate 15. 3-Methyl-4-nitrophenyl phenyl sulphone

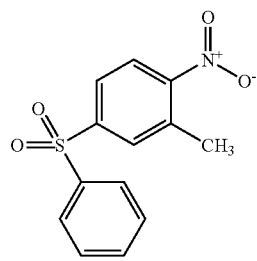

4-Fluoro-2-methyl-1-nitrobenzene (2.6 g) (available from Aldrich) and sodium benzenesulfinate (3.0 g) (available from Aldrich) were heated in N,N-dimethylacetamide (40 ml) at 50° C. for 16 h. After cooling the mixture was filtered, the filtrate collected and the solvent removed in vacuo. The residue was triturated with cyclohexane and the resultant precipitate collected by filtration to give the title compound as a white solid (3.5 g).
LC/MS $R_t$ 3.22 min m/z 295 [MNH$_4^+$]

Intermediate 18. 3-Amino-N-hydroxybenzenecarboximidamide

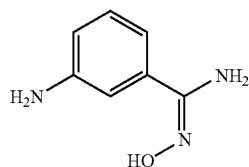

To a stirred solution of 3-aminobenzonitrile (4.0 g) (available from Aldrich) in ethanol (100 ml) was added hydroxylamine hydrochloride (4.7 g) and potassium carbonate (14.0 g) and the mixture heated under reflux for 22 h. After cooling to room temperature the mixture was filtered through 'hyflo' filter aid, the residue washed with ethanol, and the filtrates concentrated in vacuo to give the title compound as a viscous oil (5.3 g).
TLC SiO$_2$ (ethyl acetate) $R_f$=0.34

Intermediate 19. 3-(5-Methyl-1,2,4-oxadiazol-3-yl)aniline

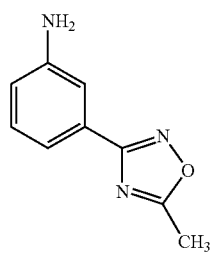

To a stirred solution of Intermediate 18 (5.3 g) in dry tetrahydrofuran (50 ml) was added 4 Å molecular sieves, followed by sodium hydride (60% dispersion in mineral oil; 1.5 g) and the mixture heated at 65° C. for 30 min. After cooling to room temperature methyl acetate (2.8 ml) was added and the mixture heated under reflux for 16 h. After cooling to 20° C. the mixture was added to water (100 ml) and extracted with ethyl acetate. The combined organic layers were washed with brine, dried over magnesium sulphate and concentrated in vacuo. The residue was purified by chromatography on silica gel, eluting with dichloromethane to give the title compound as a white solid (4.0 g).
TLC SiO$_2$ (30% ethyl acetate in cyclohexane) $R_f$=0.22

Intermediate 20. 1-[2-Amino-3-chloro-6-(methyloxy)phenyl]-2-chloroethanone

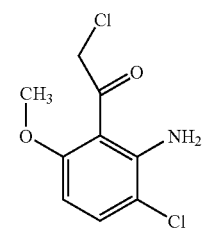

Boron trichloride (25 g) was added to dry dichloromethane (250 ml) at 0° C. and the resulting solution stirred for 10 min. A solution of 2-chloro-5-(methyloxy)aniline (30.6 g) (available from Pfaltz Bauer) in dichloromethane (100 ml) was added dropwise over 15 min to give a dark red/black mixture which was stirred for 20 min at 0° C. Chloroacetonitrile (29.5 ml) was added, followed by the portionwise addition of aluminum chloride (28.4 g). The mixture was stirred at room temperature for 1 h and then heated under reflux for 3 h. The mixture was cooled in an ice/water bath and 2M hydrochloric acid added, followed by 5M hydrochloric acid (200 ml). The resulting biphasic mixture was stirred at room temperature for 15 h and then heated at 80° C. for 30 min. After cooling to room temperature the organic layer was collected and the aqueous layer extracted with dichloromethane. The combined organic layers were washed with water, dried over sodium sulphate and concentrated in vacuo to give the title compound as a dark khaki solid (57.8 g).

TLC SiO$_2$ (30% ethyl acetate in cyclohexane) R$_f$=0.52

Intermediate 21.
4-Amino-5-chloro-1-benzofuran-3(2H)-one

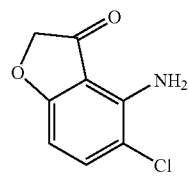

To a stirred suspension of aluminum chloride (77.6 g) in dry dichloromethane (300 ml) was added dropwise a solution of Intermediate 20 (45 g) in dichloromethane (250 ml). The mixture was heated under reflux for 6 h and then cooled to room temperature. The mixture was decomposed by the dropwise addition of 2M hydrochloric acid, then methanol and dichloromethane were added and the organic layer collected. The aqueous layer was extracted with dichloromethane and the combined organic layers dried over sodium sulphate and concentrated in vacuo. The residue was dissolved in boiling methanol and an excess of triethylamine added. The solvent was removed in vacuo and the residue absorbed onto silica gel. Purification by chromatography on silica gel eluting with a gradient of 20% to 50% ethyl acetate in cyclohexane gave the title compound as an orange/brown solid (46.9 g).

TLC SiO$_2$ (30% ethyl acetate in cyclohexane) R$_f$=0.66

Intermediate 22. N-(5-Chloro-3-oxo-2,3-dihydro-1-benzofuran-4-yl)-2,2,2-trifluoroacetamide

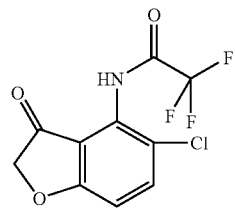

To a stirred solution of Intermediate 21 (2 g) in dichloromethane (35 ml) at 0° C. was added triethylamine (2.1 ml) and trifluoroacetic anhydride (2.1 ml) and the mixture stirred at 0° C. for 30 min, then at room temperature for 30 min. The mixture was quenched by the dropwise addition of water, the organic layer washed with water and the combined aqueous layers re-extracted with dichloromethane. The combined organic layers were dried over sodium sulphate and concentrated in vacuo. Purification by chromatography on silica gel, eluting with 10% ethyl acetate in cyclohexane, gave the title compound as a bright yellow/orange solid (1.0 g).

TLC SiO$_2$ (30% ethyl acetate in cyclohexane) R$_f$=0.69

Intermediate 23. N-(5-Chloro-3-methylidene-2,3-dihydro-1-benzofuran-4-yl)-2,2,2-trifluoroacetamide

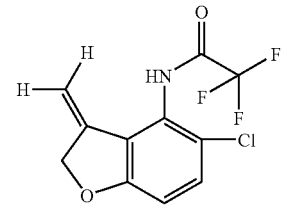

To a mixture of potassium tert-butoxide (2.0) and methyltriphenylphosphonium iodide (7.1 g) was added dry toluene (70 ml) and the mixture stirred at room temperature for 30 min, then heated under reflux for 30 min. The mixture was cooled to room temperature, a solution of Intermediate 22 (1.0 g) in toluene (30 ml) added dropwise and the mixture heated under reflux for 30 min. The mixture was cooled and quenched by the dropwise addition of saturated ammonium chloride solution. The mixture was partitioned between ethyl acetate and water and the organic phase washed with water. The combined aqueous layers were re-extracted with ethyl acetate and the combined organic layers dried over sodium sulphate and concentrated in vacuo to give a dark brown oil. Purification by column chromatography on silica gel, eluting with 10% ethyl acetate in cyclohexane, gave the title compound as a rose coloured solid (0.5 g).

TLC SiO$_2$ (30% ethyl acetate in cyclohexane) R$_f$=0.50

Intermediate 24. 2,2,2-Trifluoro-N-(3-methyl-2,3-dihydro-1-benzofuran-4-yl)acetamide

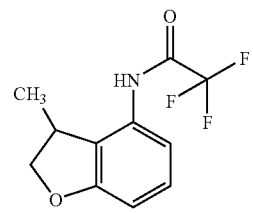

A solution of Intermediate 23 (0.10 g) in ethanol (20 ml) was added to 10% palladium on carbon (0.20 g) and the mixture stirred under an atmosphere of hydrogen for 20 h. The mixture was filtered through 'hyflo' filter aid, washed with ethanol and the solvent removed in vacuo to give the title compound as a white solid (0.092 g).

TLC SiO$_2$ (30% ethyl acetate in cyclohexane) R$_f$=0.53

Intermediate 25.
3-Methyl-2,3-dihydro-1-benzofuran-4-amine

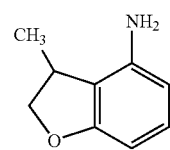

To a stirred solution of Intermediate 24 (0.087 g) in 2:2:1 tetrahydrofuran:methanol:water (5 ml) was added lithium hyroxide (0.149 g) and the mixture stirred at room temperature for 47 h, then at 60° C. for 2.5 h. The solvent was removed in vacuo and the residue partitioned between ethyl acetate and water. The aqueous layer was re-extracted with dichloromethane and the combined organic layers dried over sodium sulphate and concentrated in vacuo to give the title compound as a colourless oil (0.049 g).

TLC SiO$_2$ (30% ethyl acetate in cyclohexane) R$_f$=0.69

Intermediate 26.
3-(1-Methyl-1H-pyrazol-3-yl)aniline

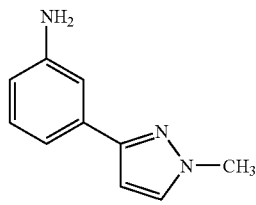

A solution of 3-(4-bromo-1-methyl-1H-pyrazol-3-yl) aniline (1.0 g) (available from Maybridge) in ethanol (20 ml) was added to a pre-hydrogenated suspension of 5% palladium on charcoal (0.5 g) in ethanol (40 ml). The resulting suspension was stirred under an atmosphere of hydrogen for 3 h. The mixture was filtered through 'hyflo' filter aid and the filter pad washed with ethanol (50 ml). The combined filtrate was evaporated in vacuo to give a brown gum. This gum was treated with 2M sodium carbonate solution (100 ml) and extracted with ethyl acetate (2×100 ml); the organic layer was dried over magnesium sulphate and the solvent removed in vacuo. Purification by chromatography on silica gel, eluting with diethyl ether, gave the title compound as a white crystalline solid (0.5 g).

TLC SiO$_2$ (diethyl ether) R$_f$=0.28

Intermediate 27.
1.2-Dimethyl-1H-benzimidazol-6-amine

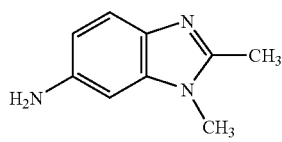

To a stirred solution of tin (II) chloride dihydrate (4.7 g) in concentrated hydrochloric acid (15 ml) was added 1,2-dimethyl-6-nitro-1H-benzimidazole (1 g) (*J. Chem. Soc.*,1931, 1143-1153), and the mixture was stirred at room temperature for 6 h. The mixture was poured onto ice and chloroform, and basified to pH 10 by the addition of 10M sodium hydroxide solution. The mixture was extracted several times with chloroform and the combined organic extracts dried and concentrated in vacuo to give a brown solid. This was crystallised from ethanol to give the title compound.

TLC SiO$_2$ (dichloromethane:methanol:880 ammonia 90:10:1) Rf 0.75.

Intermediate 28.
3-Mercapto-N,N-dimethylbenzamide

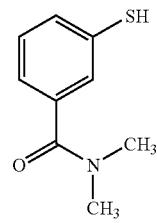

Iodine (1 g) was added to a stirred solution of 3-[(dimethylamino)carbonylbenzenesulfonyl chloride (2 g) (Borthwick et al, *J. Med. Chem* 2002, 45(1), 1-18) and triphenylphosphine (8.4 g) in 1,4-dioxane at 0° C. The mixture was stirred for 0.5 h at ambient temperature. The mixture was poured into a sodium sulphite solution (50 ml), extracted into ethyl acetate (2×30 ml) and washed with 2N sodium hydroxide solution (2×40 ml). The alkaline extracts were acidified and re-extracted into dichloromethane (3×50 ml). The extracts were washed with water (100 ml), dried (Na$_2$SO$_4$) and evaporated to give the title compound as a colourless solid (1.1 g).

LC/MS R$_t$ 2.32 min, m/z 182 [MH$^+$]

Intermediate 28.
3-Mercapto-N,N-dimethylbenzamide (alternative synthesis)

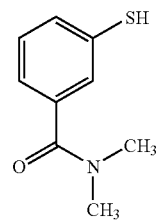

A solution of 3,3'-dithiobis(N,N-dimethylbenzamide) (Ger. Offen. (1978), DE 2821410) (54.2 g) in 1,4-dioxane (400 ml) and water (100 ml) was warmed to 35° C. and concentrated hydrochloric acid (3 ml) was added. Triphenylphosphine (55 g) was added portionwise over 25 min maintaining the temperature below 42° C., then the mixture was stirred at 40° C. for 2.5 h. After cooling to ambient temperature the mixture was concentrated to ca. 200 ml, and partitioned between 2N aqueous sodium hydroxide solution (250 ml) and ethyl acetate (500 ml). The aqueous phase was separated and washed with ethyl acetate (2×300 ml). The aqueous phase was acidified with 5N hydrochloric acid and extracted with ethyl acetate (3×400 ml). The organic extracts of the acidic aqueous phase were combined, dried over sodium sulphate, and the solvent evaporated to leave a solid. The solid was dissolved in hot ethyl acetate (100 ml) and 40-60 petrol (160 ml) was added to the hot solution. The solution was left to cool and the resulting solid filtered off, washed and dried to give the title compound (28.4 g)

LC/MS R$_t$ 2.24min m/z 182 [MH$^+$].

Intermediate 29. 6-({3-[(Dimethylamino)carbonyl]phenyl}thio)-4-[(3-methoxyphenyl)amino]-8-methylquinoline-3-carboxamide

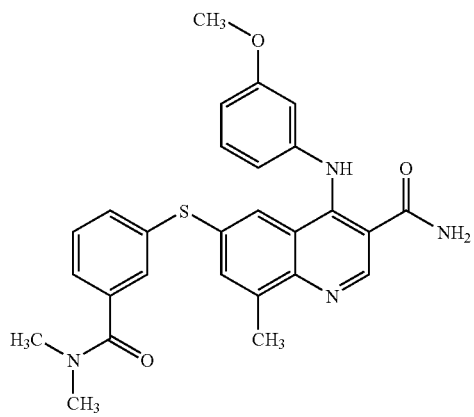

A stirred mixture of Intermediate 45 (0.5 g), Intermediate 28 (0.392 g), cuprous iodide (0.03 g) and potassium carbonate (0.38 g) in 1,3-dimethyltetrahydropyrimidin-2(1H)-one (7 ml) was heated at 100° C. for 16 h. The mixture was cooled, poured into water (100 ml) and extracted into ethyl acetate (3×40 ml). The extracts were washed with water (100 ml), dried ($Na_2SO_4$) and evaporated. The residual oil was triturated with ethyl acetate (10 ml) to give the title compound as a fawn coloured solid (0.263 g).

LC/MS $R_t$ 2.67 min, m/z 487 [$MH^+$]

Intermediate 37. 1,1-Dimethylethyl [(6-iodo-4-{[3-(methyloxy)phenyl]amino}-3-quinolinyl)carbonyl]carbamate

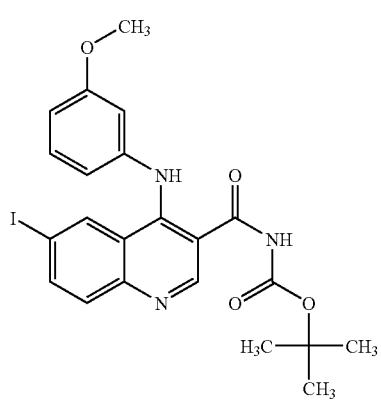

To a stirred suspension of Intermediate 14 (6.93 g) in dichloromethane (170 ml) was added N,N-dimethyl-4-aminopyridine (2.42 g) followed by di-tert-butyldicarbonate (18 g) (Aldrich). The solution was stirred at room temperature for 25 min, then quenched by addition of aqueous citric acid (200 ml) and stirred vigorously for 30 min. The organic layer was separated and the aqueous layer washed with dichloromethane (50 ml). The combined organic extracts were washed with brine (100 ml), dried over magnesium sulphate and concentrated in vacuo. The residue was triturated in diethyl ether to give a yellow solid which was collected by filtration, washed with diethyl ether (3×15 ml) and dried in vacuo to give the title compound as a yellow solid (6.6 g).

LC/MS $R_t$ 3.59 min m/z 520 [$MH^+$]

Intermediate 47. 6-[(4-{[tert-Butyl(dimethyl)silyl]oxy}phenyl)thio]-4-[(3-methoxyphenyl)amino]quinoline-3-carboxamide

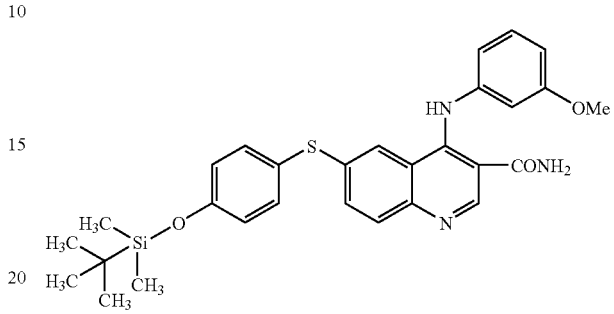

A stirred mixture of Intermediate 37 (0.8 g) and 4-{[tert-butyl(dimethyl)silyl]oxy} benzenethiol (0.74 g, EP465802A1), with (oxydi-2,1-phenylene)bis(diphenylphosphine) (0.05 g), potassium tert-butoxide (0.26 g) and tris(dibenzylideneacetone) dipalladium(0) (0.08 g) in toluene (30 ml) was heated at 106° C. for 18 h. The mixture was cooled, diluted with ethyl acetate (25 ml) and washed with a sodium carbonate solution (30 ml). The organic extracts were washed with water (30 ml), dried ($Na_2SO_4$) and concentrated in vacuo. The residue was purified by chromatography on silica gel using ethyl acetate/diethyl ether (7:3) as the eluent. The appropriate fractions were concentrated in vacuo to give the title compound as a yellow foam (0.38 g).

LC/MS $R_t$ 3.9 min, m/z 532 [$MH^+$]

Intermediate 51. 1,1-Dimethylethyl-4-amino-1H-indazole-1-carboxylate

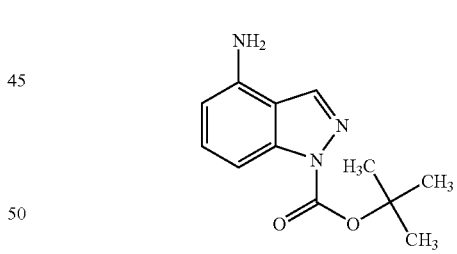

To a solution of 4-nitro-1H-indazole (1.57 g, *Journal of Heterocyclic Chemistry* 1979, 16(8), 1599-603) and di-tert-butyldicarbonate (2.33 g) in acetonitrile (30 ml) was added N,N-dimethyl-4-aminopyridine (0.059 g). The reaction mixture was stirred at room temperature for 30 min, then concentrated in vacuo to leave a brown solid which was purified by silica SPE, eluting sequentially with dichloromethane and diethyl ether to give 1,1-dimethylethyl 4-nitro-1H-indazole-1-carboxylate as a yellow solid (1.9 g).

LC/MS $R_t$ 3.26 min, m/z 263 [$MH^+$]

1,1-Dimethylethyl 4-nitro-1H-indazole-1-carboxylate (1.2 g) was dissolved in ethanol (150 ml) and stirred with 10% palladium on carbon (0.24 g) under an atmosphere of hydrogen (1 atmosphere pressure) for 18 h. The solution was filtered through a pad of celite and the filtrate concentrated in vacuo to give the title compound as a yellow-orange solid (1.03 g).

LC/MS $R_t$ 2.36 min, m/z 234 [MH$^+$]

Intermediate 52: Ethyl 3-[(3-(aminocarbonyl)-4-{[4-fluoro-3-(methyloxy)phenyl]amino}-8-methyl-6-quinolinyl)thio]propanoate

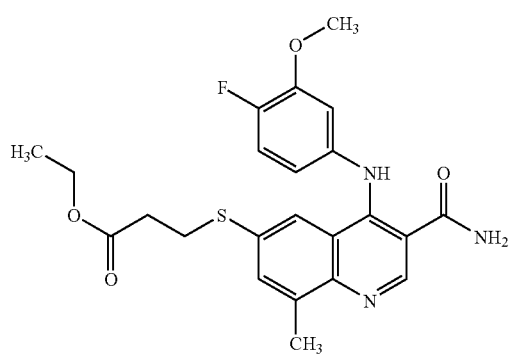

A mixture containing Intermediate 35 (1.4 g), ethyl 3-mercaptopropionate (0.74 g, available from Aldrich), potassium tert-butoxide (0.64 g), tris(dibenzylideneacetone)dipalladium(0) (0.26 g) and (oxydi-2,1-phenylene)bis(diphenylphosphine) (0.15 g) was dissolved in N,N-dimethylformamide (20 ml) and stirred under an atmosphere of nitrogen at 100° C. for 18 h. The solvents were concentrated in vacuo and the residue dissolved in methanol. This was purified by chromatography on an SPE column eluting with methanol and a solution of ammonia in methanol, to give the title compound as a brown foam (1.06 g).

LC/MS $R_t$ 2.69 min, m/z 458 [MH$^+$]

Similarly prepared were the following:

| Intermediate Number | R$^1$NH— | Starting Material | LCMS MH$^+$ | LCMS $R_t$ (min) |
|---|---|---|---|---|
| Intermediate 57 | (2,3-dihydrobenzofuran-4-yl)methylamino | Intermediate 36 | 452 | 2.67 |
| Intermediate 58 | (pyridin-3-yl)methylamino | Intermediate 62 | 411 | 2.36 |
| Intermediate 103 | (3-fluorophenyl)methylamino | Intermediate 61 | 428 | 2.86 |

Intermediate 53: 3-[(3-(Aminocarbonyl)-4-{[4-fluoro-3-(methyloxy)phenyl]amino}-8-methyl-6-quinolinyl)thio]propanoic acid

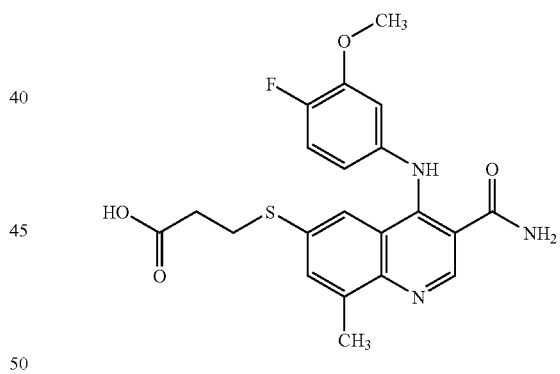

A solution of Intermediate 52 (0.95 g) in ethanol (10 ml) was treated with 2M sodium hydroxide (10 ml) and the resulting solution was left standing at room temperature overnight. The solvent was evaporated in vacuo. The residue was dissolved in water and acidified with 2M hydrochloric acid to pH 4. The resulting precipitate was filtered off, washed with water and dried in vacuo to give the title compound as an orange solid (0.8 g).

LC/MS $R_t$ 2.3 min, m/z 430 [MH$^+$]

67

Similarly prepared were the following:

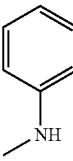

| Intermediate Number | R¹NH— | Starting Material | LCMS MH⁺ | LCMS $R_t$ (min) |
|---|---|---|---|---|
| Intermediate 59 | (3-fluoro-N-methylanilino) | Intermediate 103 | 400 | 2.39 |
| Intermediate 60 | (N-methyl-pyridin-3-ylamino) | Intermediate 58 | 383 | 2.10 |

Intermediate 54. 4-{[3-(Methyloxy)phenyl]amino}6-(4-piperidinylsulfonyl)-3-quinolinecarboxamide trifluoroacetate

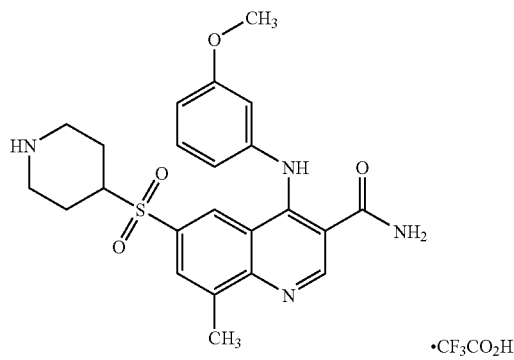

To a mixture containing Example 377 (0.64 g) in anisole (9 ml) was added a solution of 95% trifluoroacetic acid in water (16 ml). The mixture was stirred for 1.5 h at room temperature and was then concentrated in vacuo. The residue was co-evaporated with toluene (2×20 ml), triturated with ethyl acetate and filtered to give a yellow solid. This residue was again triturated with ethyl acetate and filtered to give the title compound as a yellow solid (0.570 g).

LC/MS $R_t$ 1.94 min, m/z 455 [MH⁺]

68

Intermediate 55. 1,1-Dimethylethyl 4-[(3-(aminocarbonyl)-4-{[4-fluoro-3-(methyloxy)phenyl]amino}8-methyl-6-quinolinyl)sulfonyl]-1-piperidinecarboxylate

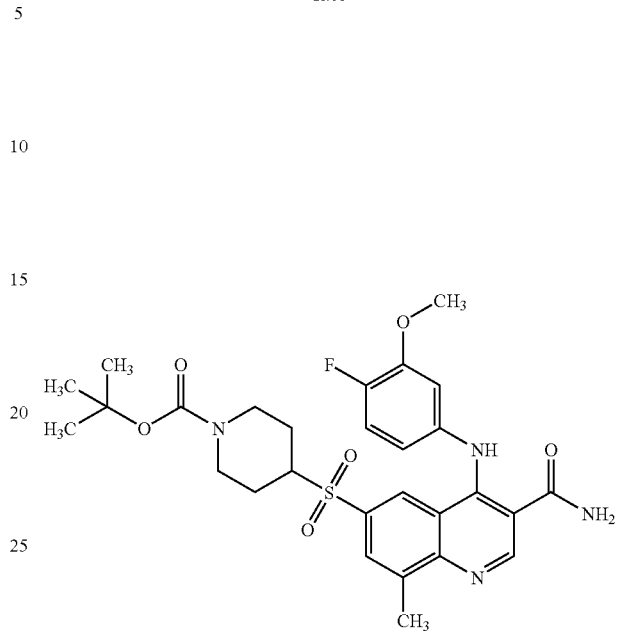

To a solution of Intermediate 35 (1.0 g) in N,N-dimethylformamide (30 ml) under an atmosphere of nitrogen was added 1,1-dimethylethyl 4-mercapto-1-piperidinecarboxylate (0.89 g, U.S. Pat. No. 5,317,025A), potassium tert-butoxide (0.46 g), tris(dibenzylideneacetone) dipalladium(0) (0.19 g) and (oxydi-2,1-phenylene)bis(diphenylphosphine) (0.11 g). The mixture was heated to 100° C. for 3 h, cooled and the solvent removed under reduced pressure. The residue was partitioned between ethyl acetate (100 ml) and water (100 ml) then dried over magnesium sulphate, filtered and concentrated in vacuo. The residue was purified by SPE (eluting with a gradient of 0 to 5% methanol in chloroform) to give intermediate 1,1-dimethylethyl 4-[(3-(aminocarbonyl)-4-{[4-fluoro-3-(methyloxy)phenyl]amino}-8-methyl-6-quinolinyl)thio]-1-piperidinecarboxylate as a yellow solid (1.1 g). This sulphide was dissolved in N,N-dimethylformamide (50 ml) and oxone (5.15 g) was added portionwise. The mixture was stirred at room temperature for 3 h, then quenched by addition of 1M sodium sulphite solution (500 ml). The mixture was extracted with chloroform (2×200 ml), and the organic layers were washed with 10% lithium chloride solution, dried over magnesium sulphate, filtered and concentrated to give the title compound as a pale yellow solid (0.71 g) after trituration with ether.

LC/MS $R_t$ 3.04 min, m/z 573 [MH⁺]

Similarly prepared from Intermediate 35 and 1,1-dimethylethyl (2-mercaptoethyl) carbamate (available from Aldrich) was:

69

Intermediate 56. 1,1-Dimethylethyl {2-[(3-(aminocarbonyl)-4-{[4-fluoro-3-(methyloxy)phenyl]amino}-8-methyl-6-quinolinyl)sulfonyl]ethyl}carbamate

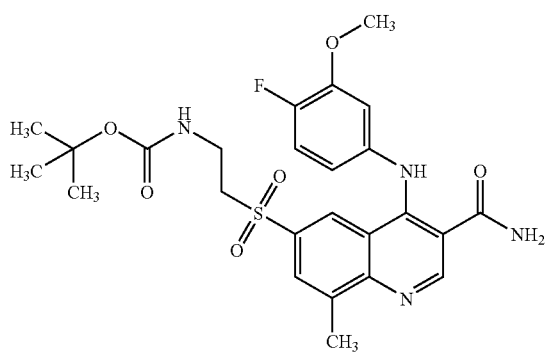

LC/MS $R_t$ 2.79 min, m/z 533 [MH$^+$]

70

Intermediate 62. 6-Iodo-8-methyl-4-(3-pyridinylamino)-3-quinolinecarboxamide hydrochloride

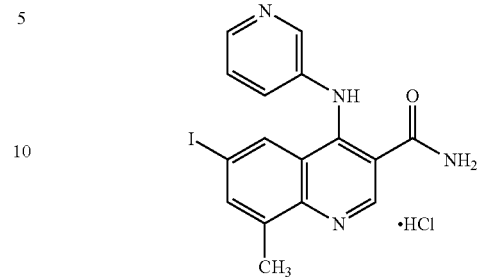

To a solution of Intermediate 48 (1.1 g) in N,N-dimethylformamide (20 ml) was added 3-aminopyridine (0.8 g, available from Aldrich) and pyridine hydrochloride (0.7 g, available from Aldrich). The mixture was heated at 80° C. under nitrogen for 2 days. The solvent was evaporated in vacuo. The residue was triturated with methanol and the precipitate filtered off to give the title compound as a brown solid (0.9 g).

LC/MS $R_t$ 2.32 min m/z 405 [MH$^+$].

Similarly prepared were the following:

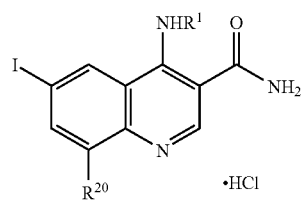

| Intermediate Number (a) (b) | R$^1$NH— | R$^{20}$— | Starting Material | Amine/ Supplier | LCMS MH$^+$ | LCMS $R_t$ (min) |
|---|---|---|---|---|---|---|
| Intermediate 81 HCl | ![pyridine-NHMe] | Et— | Intermediate 72 | 3-pyridinamine/ Aldrich | 419 | 2.52 |
| Intermediate 82 HCl | ![5-Cl-pyridine-NHMe] | Et— | Intermediate 72 | 5-chloro-3-pyridinamine/ Synchem OHG | 453 | 3.19 |
| Intermediate 83 HCl | ![5-F-pyridine-NHMe] | Et— | Intermediate 72 | 5-fluoro-3-pyridinamine/ Synchem OHG | 437 | 2.93 |

-continued

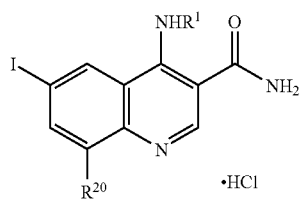

| Intermediate Number (a) (b) | R¹NH— | R²⁰— | Starting Material | Amine/ Supplier | LCMS MH⁺ | LCMS R$_t$ (min) |
|---|---|---|---|---|---|---|
| Intermediate 84 HCl | F-pyridin-3-yl-N(Me)H (5-F) | F— | Intermediate 87 | 5-fluoro-3-pyridinamine/ Synchem OHG | 427 | 2.6 |
| Intermediate 85 HCl | Cl-pyridin-3-yl-N(Me)H (5-Cl) | F— | Intermediate 87 | 5-chloro-3-pyridinamine/ Synchem OHG | 443 | 2.88 |
| Intermediate 86 HCl | pyridin-3-yl-N(Me)H | F— | Intermediate 87 | 3-pyridinamine/ Aldrich | 409 | 2.27 |
| 96 HCl | pyridin-3-yl-N(Me)H | Cl— | Intermediate 49 | 3-pyridinamine/ Aldrich | 425 | 2.52 |
| 97 HCl | Cl-pyridin-3-yl-N(Me)H (5-Cl) | Me— | Intermediate 48 | 5-chloro-3-pyridinamine/ Synchem OHG | 439 | 2.95 |
| 98 HCl | F-pyridin-3-yl-N(Me)H (5-F) | Me— | Intermediate 48 | 5-fluoro-3-pyridinamine/ Synchem OHG | 423 | 2.65 |
| 99 HCl | F-pyridin-3-yl-N(Me)H (5-F) | Cl— | Intermediate 49 | 5-fluoro-3-pyridinamine/ Synchem OHG | 443 | 2.91 |

-continued

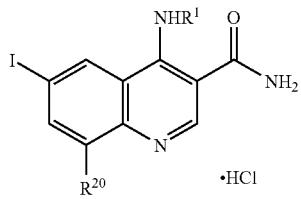

| Intermediate Number (a) (b) | R¹NH— | R²⁰— | Starting Material | Amine/ Supplier | LCMS MH⁺ | LCMS R$_t$ (min) |
|---|---|---|---|---|---|---|
| 100 HCl | Cl-pyridinyl-NH- | Cl— | Intermediate 49 | 5-chloro-3-pyridinamine/ Synchem OHG | 459 | 2.94 |
| 101 HCl | Me-ethylpyrazolyl-NH- | Me— | Intermediate 48 | 1-ethyl-1H-pyrazol-5-amine/ Aldrich | 422 | 2.58 |
| 102 HCl | Me-ethylpyrazolyl-NH- | Cl— | Intermediate 49 | 1-ethyl-1H-pyrazol-5-amine/ Aldrich | 442 | 2.86 |

(a) Salt form HCl = hydrochloride
(b) All products isolated by trituration with acetonitrile and filtration.

Intermediate 73. 2-Ethyl-4-iodoaniline

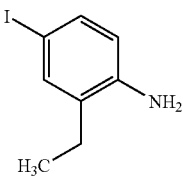

To a stirred solution of 2-ethylaniline (1.88 g, available from Aldrich) and sodium acetate (1.27 g) in acetic acid (20 ml) was added iodine monochloride (1 ml, available from Aldrich). The mixture was stirred at 20° C. for 90 min and then the solvent was removed in vacuo. The residue was partitioned between ethyl acetate (25 ml) and saturated aqueous sodium carbonate solution (25 ml). The organic layer was dried using a hydrophobic frit and the solvent was removed in vacuo. Purification by C18 SPE eluting with 20% acetonitrile in water gave the title compound as a purple solid (0.402 g). LC/MS R$_t$ 3.23 min, m/z 248 [MH⁺]

Intermediate 64. 7-({3-[(Dimethylamino)carbonyl]phenyl}thio)-6-iodo-4-{[3-(methyloxy)phenyl]amino}-3-quinolinecarboxamide

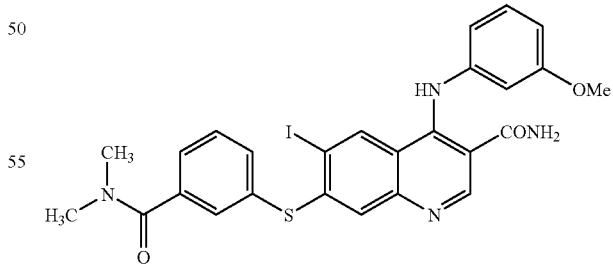

A stirred mixture of Intermediate 63 (0.4 g), Intermediate 28 (0.16 g) and potassium carbonate (0.38 g) in 1,3-dimethyl-3,4,5,6-tetrahydro-2(1H)-pyrimidinone (10 ml) was heated at 100° C. under nitrogen for 3 h. A further portion of Intermediate 28 (0.07 g) was added and the mixture stirred at 60° C. for 23 h. The cooled mixture was diluted with water (100 ml) and extracted with ethyl acetate (3×100 ml). The combined organic extracts were washed with water (2×70 ml) and brine (70 ml), dried over magnesium sulphate and concentrated in vacuo. The residue was purified by chromatography on silica gel eluting with methanol followed by mass directed preparative HPLC (Method A) to give the title compound as a yellow foam (0.12 g).

LC/MS R$_t$ 2.94 min, m/z 599 [MH$^+$]

Intermediate 65. 7-({3-[(Dimethylamino)carbonyl] phenyl}sulfinyl)-6-iodo-4-{[3-(methyloxy)phenyl] amino}-3-quinolinecarboxamide

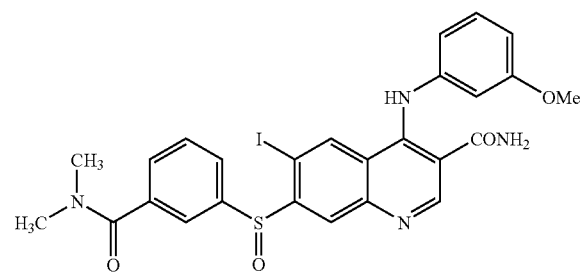

Oxone (0.5 g) was added portionwise to a stirred solution of Intermediate 64 (0.12 g) in N,N-dimethylformamide (5 ml). The solution was stirred at room temperature under nitrogen for 21 h. More oxone (0.5 g) was added and the mixture was stirred for a further 3 h, quenched with a solution of sodium sulphite (1.5 g) in water (15 ml), diluted with water (50 ml) and extracted with ethyl acetate (3×50 ml). The combined organic extracts were dried over magnesium sulphate and concentrated in vacuo to give the title compound as a yellow solid (0.15 g).

LC/MS R$_t$ 2.70 min, m/z 615 [MH$^+$]

Intermediate 69.
5-Mercapto-N,N-dimethyl-3-pyridinecarboxamide

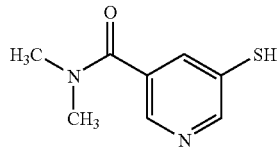

Sodium thiomethoxide (3 g) was added to a stirred solution of 5-bromo-N,N-dimethyl-3-pyridinecarboxamide (2.5g, WO2000055168) in N,N-dimethylformamide (40 ml) and the suspension stirred at 100° C. for 4 h. The solvent was concentrated in vacuo, the residue dissolved in 2M sodium hydroxide (35 ml) and water (50 ml), and the solution washed with chloroform (4×75 ml). The aqueous layer was acidified with 2M hydrochloric acid to pH 4 and extracted with chloroform (5×80 ml), and the combined organic layers were washed with brine (20 ml), dried over magnesium sulphate and concentrated in vacuo to give the title compound as an orange oil (1.8 g)

LC/MS R$_t$ 0.96 min, m/z 183 [MH$^+$].

Intermediate 70.
1-Methyl-4-nitro-2,3-dihydro-1H-indole

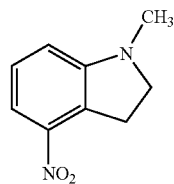

To a stirred solution of 1-methyl-4-nitro-1H-indole (3.8 g, Organic Process Research and Development 2001 5 (6) 604) and borane-tetrahydrofuran complex (1M in tetrahydrofuran, 86.3 ml) at 0° C. under an atmosphere of nitrogen was added, dropwise, trifluoroacetic acid (88 ml). The resulting mixture was allowed to warm to room temperature and stirred at room temperature for 90 min. The mixture was cautiously added to 2M sodium carbonate solution (750 ml) over 20 min and then stirred for 30 min. The mixture was extracted with ethyl acetate (2×300 ml), the combined organic extracts were dried over sodium sulphate and the solvent was removed in vacuo. Purification by column chromatography on silica gel, eluting with hexane : ethyl acetate (9:1) gave the title compound as a red solid (1.97 g).

TLC SiO$_2$ (hexane:ethyl acetate (4:1)) R$_f$=0.61

Intermediate 71.
1-Methyl-2,3-dihydro-1H-indol-4-amine

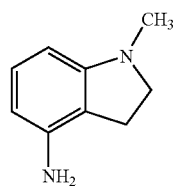

A solution of Intermediate 70 (0.50 g) in ethanol (30 ml) was added to 10% palladium on carbon (0.050 g) and the mixture was stirred under an atmosphere of hydrogen for 20 min. The mixture was filtered through 'hyflo' filter aid and the solvent removed in vacuo to give the title compound as a brown oil (0.405 g).

TLC SiO$_2$ (hexane:ethyl acetate (4:1)) R$_f$=0.25

EXAMPLES

Experimental details for the preparation of representative Examples are given in full below. Summary details for further Examples prepared by analagous methods are give in the accompanying tables,

Example 10

4-[(3-Fluorophenyl)amino]-6-(methylsulfonyl)-3-quinolinecarboxamide

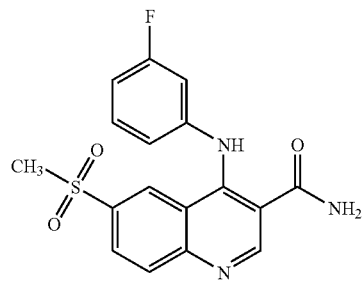

Intermediate 9 (0.014 g) was suspended in acetonitrile (3 ml), 3-fluoroaniline (0.0056 g, available from Aldrich) was added, and the mixture was heated under reflux for 16 h. After cooling to room temperature, the mixture was cooled in a refrigerator for 2 h, filtered, and the residue purified by mass directed preparative HPLC (Method A) to give the title compound (0.011 g).

LC/MS $R_t$ 1.95 min m/z 359 [MH$^+$]

Similarly prepared were the following:

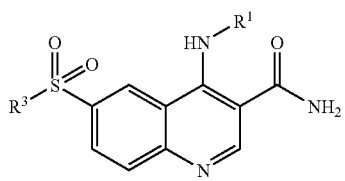

| Ex. No. (a) | R$^1$NH— | R$^3$SO$_2$— | Starting Material | Amine/Reagent Source | Isolation Method (b) | LCMS MH$^+$ | LCMS $R_t$ (min) |
|---|---|---|---|---|---|---|---|
| 1 HCl | (6-aminobenzothiazol-N-methylamino) | MeSO$_2$— | Intermediate 9 | 6-aminobenzothiazole/ Lancaster | (I) | 399 | 1.9 |
| 2 HCl | (3-(N-methyl-N-acetyl)amino-N-methylanilino) | MeSO$_2$— | Intermediate 9 | 3-amino-N-methyl acetanilide/ Merlin synthesis | (I) | 413 | 1.89 |
| 3 HCl | (3-NMe$_2$-N-methylanilino) | MeSO$_2$— | Intermediate 9 | N,N-dimethyl benzene-1,3-diamine hydrochloride/ Aldrich | (I) | 385 | 1.83 |
| 4 HCl | (3,5-dimethoxy-N-methylanilino) | MeSO$_2$— | Intermediate 9 | 3,5-dimethoxyaniline/ Aldrich | (I) | 402 | 2.05 |

-continued

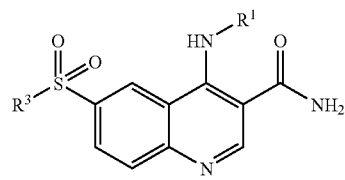

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 5 HCl | 5-NHMe-1,2-benzisoxazole | MeSO₂— | Intermediate 9 | 1,2-benzoisoxazol-5-amine/ Key organics Ltd (8W-0024) | (I) | 383 | 1.84 |
| 6 HCl | methyl 3-(NHMe)benzoate | MeSO₂— | Intermediate 9 | methyl 3-amino benzoate hydrochloride/ Fluka | (I) | 400 | 1.99 |
| 7 HCl | 3-methyl-N-methylaniline | MeSO₂— | Intermediate 9 | 3-methylaniline hydrochloride/ TCI-JP | (I) | 356 | 2 |
| 8 HCl | 3-cyano-N-methylaniline | MeSO₂— | Intermediate 9 | 3-aminobenzonitrile/ Aldrich | (I) | 367 | 2.26 |
| 9 | 3-(hydroxymethyl)-N-methylaniline | MeSO₂— | Intermediate 9 | 3-aminobenzyl alcohol/ Aldrich | (II) | 372 | 1.82 |
| 11 | 1-methyl-6-(NHMe)-1H-benzimidazole | MeSO₂— | Intermediate 9 | 1-methyl-1H-benzimidazol-6-amine/ Heterocycles, 1991, 32(5), 1003-12. | (II) | 396 | 1.65 |

-continued

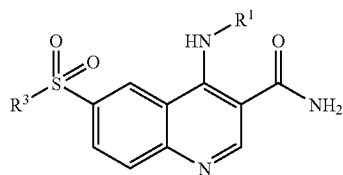

| Ex. No. (a) | R¹NH— | R³SO₂— | Starting Material | Amine/Reagent Source | Isolation Method (b) | LCMS MH⁺ | LCMS $R_t$ (min) |
|---|---|---|---|---|---|---|---|
| 12 | 3-Cl,4-F-C₆H₃-N(Me)H— | MeSO₂— | Intermediate 9 | 3-chloro-4-fluoroaniline/ ABCR | (II) | 394 | 2.37 |
| 13 HCl | PhN(Me)H— | MeSO₂— | Intermediate 9 | aniline/ Aldrich | (I) | 342 | 2.07 |
| 15 HCl | 6-(N-Me)benzoxazolin-2(3H)-one— | MeSO₂— | Intermediate 9 | 6-aminobenzoxazolinone/ WO 9845268 A1 | (I) | 399 | 1.99 |
| 16 HCl | 2,3-dihydro-1H-inden-5-yl-N(Me)H— | MeSO₂— | Intermediate 9 | 2,3-dihydro-1H-inden-5-ylamine hydrochloride/ Aldrich | (I) | 382 | 2.48 |
| 17 HCl | 2,3-dihydro-1,4-benzodioxin-6-yl-N(Me)H— | MeSO₂— | Intermediate 9 | 2,3-dihydro-benzodioxin-6-amine hydrochloride/ Aldrich | (I) | 400 | 2.18 |
| 18 HCl | 2,3-dihydro-1,4-benzodioxin-5-yl-N(Me)H— | MeSO₂— | Intermediate 9 | 2,3-dihydro-1,4-benzodioxin-5-amine hydrochloride/ WO 9703067 A1 | (I) | 400 | 2.2 |

-continued

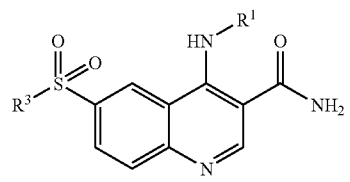

| Ex. No. (a) | R¹NH— | R³SO₂— | Starting Material | Amine/Reagent Source | Isolation Method (b) | LCMS MH⁺ | LCMS R$_t$ (min) |
|---|---|---|---|---|---|---|---|
| 19 HCl | (1,2,3,4-tetrahydronaphthalen-1-yl)methylamino | MeSO₂— | Intermediate 9 | 1-amino-5,6,7,8-tetrahydro napthalene/ Aldrich | (I) | 396 | 2.57 |
| 20 HCl | N-methyl-2,3-dihydrobenzofuran-4-amino | MeSO₂— | Intermediate 9 | 2,3-dihydro-1-benzofuran-4-amine hydrobromide/ Journal of Heterocyclic Chemistry, 1980, 17(6), 1333-5. | (I) | 384 | 2.23 |
| 21 | N-methyl-benzoxazol-2(3H)-one-7-amino | MeSO₂— | Intermediate 9 | 7-amino-1,3-benzoxazol-2(3H)-one/ Annales Universitatis Mariae Curie-Sklodowska, Sectio D: Medicine, 1980, Volume Date 1979, 35 121-8. | (II) | 399 | 1.93 |
| 22 HCl | 3-ethyl-N-methylaniline | MeSO₂— | Intermediate 9 | 3-ethylaniline/ Aldrich | (I) | 370 | 2.33 |
| 23 HCl | 3-isopropyl-N-methylaniline | MeSO₂— | Intermediate 9 | 3-isopropylaniline/ APIN | (I) | 384 | 2.5 |
| 24 HCl | 3-chloro-4-methoxy-N-methylaniline | MeSO₂— | Intermediate 9 | 3-chloro-4-methoxyaniline/ Aldrich | (I) | 406/408 | 2.2 |

-continued

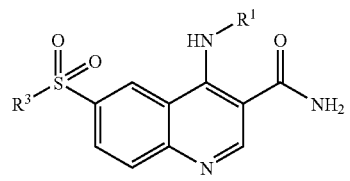

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 25 | 3-(methoxymethyl)benzylamine derivative | MeSO₂— | Intermediate 9 | 3-(methoxymethyl)aniline/ WO 0018721 A1 | (II) | 386 | 2.01 |
| 26 HCl | 2,5-dimethoxy derivative | MeSO₂— | Intermediate 9 | 2,5-dimethoxy aniline/ Aldrich | (I) | 402 | 2.37 |
| 27 HCl | 3-methoxy derivative | MeSO₂— | Intermediate 9 | 3-methoxyaniline/ Aldrich | (I) | 372 | 2.33 |
| 28 HCl | 3-hydroxy-4-methoxy derivative | MeSO₂— | Intermediate 9 | 3-hydroxy-4-methoxyaniline/ Aldrich | (I) | 388 | 2.0 |
| 29 HCl | 3-phenoxy derivative | MeSO₂— | Intermediate 9 | 3-phenoxyaniline/ Aldrich | (I) | 434 | 2.97 |
| 30 HCl | 3-hydroxy-2-methyl derivative | MeSO₂— | Intermediate 9 | 3-amino-2-methylphenol/ Aldrich | (I) | 372 | 2.2 |
| 31 HCl | 3-hydroxy derivative | MeSO₂— | Intermediate 9 | 3-aminophenol hydrochloride/ TCI-US | (I) | 358 | 2.04 |

-continued

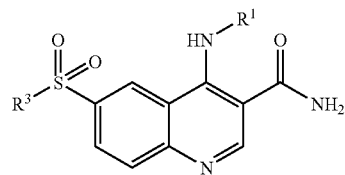

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 32 HCl | 4-fluoro-3-methoxy-N-methylanilino | MeSO₂— | Intermediate 9 | 4-fluoro-3-methoxyaniline/ Apollo-Chem | (I) | 390 | 1.92 |
| 33 HCl | 3-(2-hydroxyethoxy)-N-methylanilino | MeSO₂— | Intermediate 9 | 2-(3-amino phenoxy) ethanol hydrochloride/ J. Amer. Chem. Soc.; 1937, 59; 1716 | (I) | 402 | 1.8 |
| 34 HCl | 3-ethoxy-N-methylanilino | MeSO₂— | Intermediate 9 | 3-ethoxyaniline/ Aldrich | (I) | 386 | 2.04 |
| 35 HCl | 3-chloro-N-methylanilino | MeSO₂— | Intermediate 9 | 3-chloroaniline/ Aldrich | (I) | 376 | 2.09 |
| 36 HCl | 3-(2-methoxyethoxy)-N-methylanilino | MeSO₂— | Intermediate 9 | [3-(2-methoxy ethoxy)phenyl] amine hydrochloride/ EP 388165 A2 | (I) | 416 | 1.94 |
| 37 HCl | 4-methoxy-N-methylanilino | MeSO₂— | Intermediate 9 | 4-methoxyaniline/ Aldrich | (I) | 372 | 1.88 |

-continued

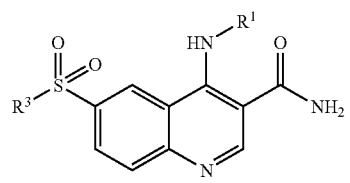

| Ex. No. (a) | R¹NH— | R³SO₂— | Starting Material | Amine/Reagent Source | Isolation Method (b) | LCMS MH⁺ | LCMS R$_t$ (min) |
|---|---|---|---|---|---|---|---|
| 38 HCl | HN-phenyl-3,4-di(OMe) | MeSO₂— | Intermediate 9 | 3,4-dimethoxy aniline/ Aldrich | (I) | 402 | 1.84 |
| 39 | MeHN-phenyl-3-OEt | PhSO₂— | Intermediate 8 | 3-ethoxyaniline/ Aldrich | (II) | 448 | 2.55 |
| 40 | MeHN-phenyl-3-O(CH₂)₂OMe | PhSO₂— | Intermediate 8 | [3-(2-methoxy ethoxy)phenyl] amine hydrochloride/ EP 388165 A2 | (II) | 478 | 1.42 |
| 41 | MeHN-phenyl-3-C(O)NHMe | PhSO₂— | Intermediate 8 | 3-amino-N-methyl benzamide/ TCI-US | (II) | 461 | 2.37 |
| 42 | MeHN-phenyl-4-OH | PhSO₂— | Intermediate 8 | 4-aminophenol hydrochloride/ Aldrich | (II) | 420 | 2.46 |
| 43 HCl | HN-benzothiazol-6-yl with N-Me | PhSO₂— | Intermediate 8 | 6-aminobenzothia-zole/ Lancaster | (I) | 461 | 2.67 |

-continued

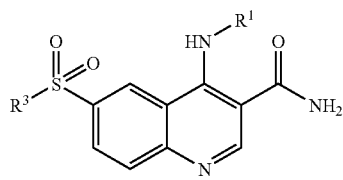

| Ex. No. (a) | R¹NH— | R³SO₂— | Starting Material | Amine/Reagent Source | Isolation Method (b) | LCMS MH⁺ | LCMS R$_t$ (min) |
|---|---|---|---|---|---|---|---|
| 44 HCl | (3-(N-methyl-N-methylacetamido)phenyl)methylamino | PhSO₂— | Intermediate 8 | N-(3-aminophenyl)-N-methyl acetamide/ Merlin Synthesis | (I) | 475 | 2.58 |
| 45 HCl | (1-methyl-1H-benzimidazol-6-yl)methylamino | PhSO₂— | Intermediate 8 | 1-methyl-1H-benzimidazol-6-amine/ Gwyn Ellis Heterocycles, 1991, 32(5), 1003-12. | (I) | 458 | 2.24 |
| 46 HCl | (3,5-dimethoxyphenyl)methylamino | PhSO₂— | Intermediate 8 | 3,5-dimethoxy aniline/ Aldrich | (I) | 464 | 2.89 |
| 47 HCl | (3-(methoxycarbonyl)phenyl)methylamino | PhSO₂— | Intermediate 8 | methyl 3-amino benzoate hydrochloride/ Fluka | (I) | 462 | 2.86 |
| 48 HCl | (4-(2-morpholinoethoxy)phenyl)methylamino | PhSO₂— | Intermediate 8 | 4-(2-morphalin-4-ylethoxy) aniline EP 410358 A1 | (I) | 533 | 2.1 |

-continued

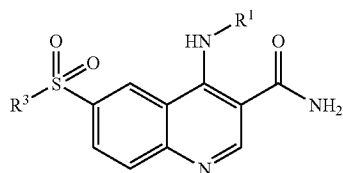

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 49 HCl | 3-fluoro-N-methylanilino | PhSO₂— | Intermediate 8 | 3-fluoroaniline/ Aldrich | (I) | 422 | 2.96 |
| 50 HCl | 3-chloro-4-fluoro-N-methylanilino | PhSO₂— | Intermediate 8 | 3-chloro-4-fluoroaniline/ Aldrich | (I) | 456 | 3.12 |
| 51 HCl | 3-methyl-N-methylanilino | PhSO₂— | Intermediate 8 | 3-methylaniline hydrochloride/ TCI-US | (I) | 418 | 2.87 |
| 52 HCl | 3-cyano-N-methylanilino | PhSO₂— | Intermediate 8 | 3-amino benzonitrile/ Aldrich | (I) | 429 | 2.91 |
| 53 | 4-(morpholine-4-carboxamido)-N-methylanilino | PhSO₂— | Intermediate 8 | N-(4-aminophenyl) morpholine-4-carboxamide/ Peakdale Molecular Ltd | (II) | 532 | 2.34 |
| 54 | 3-dimethylamino-N-methylanilino | PhSO₂— | Intermediate 8 | N,N-dimethyl benzene-1,3-diamine hydrochloride/ Aldrich | (II) | 447 | 2.75 |

-continued

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 55 | 3-(N-methylamino)-N-acetylaniline group | PhSO₂— | Intermediate 8 | N-(3-aminophenyl)acetamide hydrochloride/ Acros Chimica | (II) | 461 | 2.4 |
| 56 | 3-(N-methylamino)benzyl alcohol group | PhSO₂— | Intermediate 8 | 3-aminobenzyl alcohol/ Aldrich | (II) | 434 | 2.34 |
| 57 HCl | N-methylanilino group | PhSO₂— | Intermediate 8 | aniline/ Aldrich | (I) | 404 | 2.73 |
| 58 HCl | 1-acetylindolin-5-yl(methyl)amino | PhSO₂— | Intermediate 8 | 1-acetylindolin-5-amine/ Maybridge | (I) | 487 | 2.52 |
| 59 HCl | 2-oxo-2,3-dihydro-1,3-benzoxazol-6-yl(methyl)amino | PhSO₂— | Intermediate 8 | 6-amino-1,3-benzoxazol-2(3H)-one/ WO 9845268 A1 | (I) | 461 | 2.48 |
| 60 HCl | 1-acetylindolin-6-yl(methyl)amino | PhSO₂— | Intermediate 8 | 1-acetyl-6-aminoindoline/ SIGMA | (I) | 487 | 2.55 |

-continued

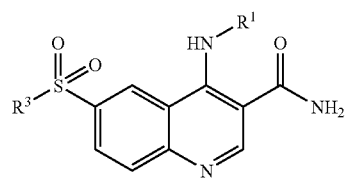

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 61 HCl | (3-methylamino-2,3-dihydro-1H-inden-1-one) | PhSO₂— | Intermediate 8 | 6-amino-2,3-dihydro-1H-inden-1-one/ J. Med. Chem. 2003, 46(3), 399-408. | (I) | 458 | 2.67 |
| 62 HCl | (N-methyl-1-oxo-1,2,3,4-tetrahydronaphthalen-6-amine) | PhSO₂— | Intermediate 8 | 6-amino-1,2,3,4-tetrahydronaphthalen-1-one/ Maybridge | (I) | 472 | 2.93 |
| 63 HCl | (N-methyl-2,3-dihydro-1,4-benzodioxin-6-amine) | PhSO₂— | Intermediate 8 | 2,3-dihydro-1,4-benzodioxin-6-amine hydrochloride/ Aldrich | (I) | 462 | 2.69 |
| 64 HCl | (N-methyl-5,6,7,8-tetrahydronaphthalen-1-amine) | PhSO₂— | Intermediate 8 | 1-amino-5,6,7,8-tetrahydronapthalene/ Aldrich | (I) | 458 | 3.07 |
| 65 HCl | (N-methyl-benzoxazol-2(3H)-one-7-amine) | PhSO₂— | Intermediate 8 | 7-amino-1,3-benzoxazol-2(3H)-one/ Medicine 1980, Volume Date 1979, 35, 121-8. | (I) | 461 | 2.64 |
| 66 HCl | (N-methyl-2,3-dihydro-1-benzofuran-4-amine) | PhSO₂— | Intermediate 8 | 2,3-dihydro-1-benzofuran-4-amine hydrobromide/ Journal of Heterocyclic Chemistry 1980, 17(6), 1333-5. | (I) | 446 | 2.84 |

-continued

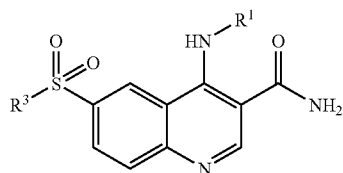

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 67 | | PhSO₂— | Intermediate 8 | 2,3-dihydro-1H-inden-5-amine hydrochloride/ Aldrich | (II) | 444 | 2.95 |
| 68 | | PhSO₂— | Intermediate 8 | 2,3-dihydro-1,4-benzodioxin-5-amine hydrochloride/ WO 9703067 A1 | (II) | 462 | 2.69 |
| 69 HCl | | PhSO₂— | Intermediate 8 | 3-ethylaniline/ Aldrich | (I) | 432 | 2.92 |
| 70 HCl | | PhSO₂— | Intermediate 8 | 3-isopropyl aniline/ APIN | (I) | 446 | 3.04 |
| 71 HCl | | PhSO₂— | Intermediate 8 | 3-chloro-4-methoxyaniline/ Aldrich | (I) | 468 | 2.76 |
| 72 HCl | | PhSO₂— | Intermediate 8 | 8-amino-3,4-dihydro-1(2H)-naphthalenone/ WO 0160826 A2 | (I) | 472 | 2.86 |
| 73 | | PhSO₂— | Intermediate 8 | 3-[(methyloxy)methyl]aniline/ WO 0018721 A1 | (II) | 448 | 2.60 |

-continued

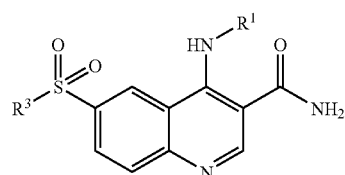

| Ex. No. (a) | R¹NH— | R³SO₂— | Starting Material | Amine/Reagent Source | Isolation Method (b) | LCMS MH⁺ | LCMS $R_t$ (min) |
|---|---|---|---|---|---|---|---|
| 74 HCl | 3-methoxy-N-methylanilino | PhSO₂— | Intermediate 8 | 3-(methyloxy) aniline/ Aldrich | (I) | 434 | 2.77 |
| 75 HCl | 3-(2-hydroxyethoxy)-N-methylanilino | PhSO₂— | Intermediate 8 | 2-[(3-aminophenyl) oxy]ethanol hydrochloride/ J. Amer. Chem. Soc.; 1937, 59, 1716 | (I) | 464 | 2.21 |
| 76 HCl | 4-(N-methylcarbamoyl)-N-methylanilino | PhSO₂— | Intermediate 8 | 4-amino-N-methyl benzamide/ Buttpark | (I) | 461 | 2.2 |
| 77 | 3-hydroxy-2-methyl-N-methylanilino | PhSO₂— | Intermediate 8 | 3-amino-2-methylphenol/ Aldrich | (II) | 434 | 2.57 |
| 78 HCl | 4-methoxy-N-methylanilino | PhSO₂— | Intermediate 8 | 4-methoxyaniline hydrochloride/ Acros | (I) | 434 | 2.32 |
| 79 HCl | 3-(trifluoromethoxy)-N-methylanilino | PhSO₂— | Intermediate 8 | 3-[(trifluoro methyl)oxy] aniline/ Aldrich | (I) | 487 | 2.8 |

-continued

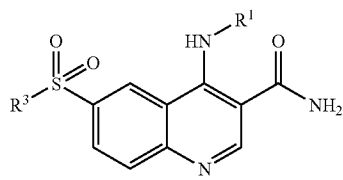

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 80 | 3-(4-morpholinyl)phenyl-N(Me)H | PhSO₂— | Intermediate 8 | 3-(4-morpholinyl) aniline/ Journal of Organic Chemistry 2002, 67(9), 3029-3036. | (II) | 489 | 2.72 |
| 81 | 3-hydroxyphenyl-N(Me)H | PhSO₂— | Intermediate 8 | 3-aminophenol hydrochloride/ TCI-US | (II) | 420 | 2.6 |
| 82 | 3,4-dimethoxyphenyl-N(Me)H | PhSO₂— | Intermediate 8 | [3,4-bis(methyloxy)phenyl]amine hydrochloride/ Aldrich | (II) | 463 | 2.58 |
| 83 HCl | benzothiazol-6-yl-N(Me)H | cyclopentyl-SO₂— | Intermediate 7 | 6-aminobenzothiazole/ Lancaster | (I) | 453 | 2.3 |
| 84 HCl | 3-(N-methyl-N-acetyl-amino)phenyl-N(Me)H | cyclopentyl-SO₂— | Intermediate 7 | N-(3-aminophenyl)-N-methyl acetamide/ Merlin synthesis | (I) | 467 | 2.29 |
| 85 HCl | 4-(morpholine-4-carboxamido)phenyl-N(Me)H | cyclopentyl-SO₂— | Intermediate 7 | N-(4-aminophenyl)-4-morpholine carboxamide/ Peakdale molecular Ltd | (I) | 524 | 2.21 |

-continued

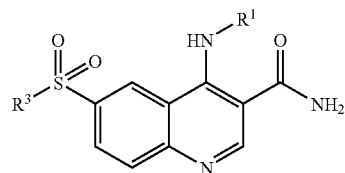

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 86 HCl | 3,5-dimethoxyphenyl-N(Me)H | cyclopentyl-SO₂-Me | Intermediate 7 | 3,5-dimethoxy aniline/ Aldrich | (I) | 456 | 2.51 |
| 87 HCl | 3-(methoxycarbonyl)phenyl-N(Me)H | cyclopentyl-SO₂-Me | Intermediate 7 | methyl 3-amino benzoate hydrochloride/ Fluka | (I) | 454 | 2.48 |
| 88 HCl | 3-(MeNHC(O))phenyl-N(Me)H | cyclopentyl-SO₂-Me | Intermediate 7 | 3-amino-N-methyl benzamide/ TCI-US | (I) | 453 | 2.17 |
| 89 HCl | 3-fluorophenyl-N(Me)H | cyclopentyl-SO₂-Me | Intermediate 7 | 3-fluoroanilline/ Aldrich | (I) | 414 | 2.53 |
| 90 HCl | 3-chloro-4-fluorophenyl-N(Me)H | cyclopentyl-SO₂-Me | Intermediate 7 | 3-chloro-4-fluoroaniline/ Aldrich | (I) | 448 | 2.72 |
| 91 HCl | 3-methylphenyl-N(Me)H | cyclopentyl-SO₂-Me | Intermediate 7 | (3-methylphenyl)amine hydrochloride/ TCI-US | (I) | 410 | 2.49 |

-continued

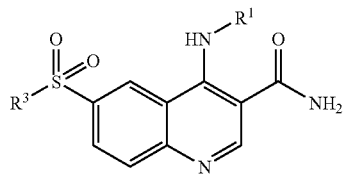

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 92 | Me₂N-C₆H₄-NH-Me (3-) | cyclopentyl-SO₂-Me | Intermediate 7 | N,N-dimethyl-1,3-benzenediamine hydrochloride/ Aldrich | (II) | 439 | 2.62 |
| 93 | 3-(MeNH)-C₆H₄-NHC(O)Me | cyclopentyl-SO₂-Me | Intermediate 7 | N-(3-aminophenyl)acetamide hydrochloride/ Acros | (II) | 453 | 2.25 |
| 94 | 2-Cl-C₆H₄-NHMe | cyclopentyl-SO₂-Me | Intermediate 7 | 2-chloroaniline/ Aldrich | (II) | 430 | 2.69 |
| 95 HCl | C₆H₅-NHMe | cyclopentyl-SO₂-Me | Intermediate 7 | aniline/Aldrich | (I) | 396 | 2.58 |
| 96 HCl | 1-methyl-benzimidazol-6-yl-NHMe | cyclopentyl-SO₂-Me | Intermediate 7 | 1-methyl-1H-benzlmidazol-6-amine/ Heterocycles 1991, 32(5), 1003-12. | (I) | 450 | 2.04 |
| 97 HCl | 3-Et-C₆H₄-NHMe | cyclopentyl-SO₂-Me | Intermediate 7 | 3-ethylaniline/ Aldrich | (I) | 424 | 2.81 |
| 98 HCl | 3-iPr-C₆H₄-NHMe | cyclopentyl-SO₂-Me | Intermediate 7 | 3-isopropyl aniline/ TCI-US | (I) | 438 | 3.0 |

-continued

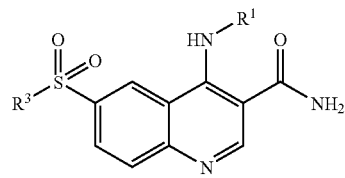

| Ex. No. (a) | R¹NH— | R³SO₂— | Starting Material | Amine/Reagent Source | Isolation Method (b) | LCMS MH⁺ | LCMS R$_t$ (min) |
|---|---|---|---|---|---|---|---|
| 99 HCl | 3-methoxy-N-methylanilino | cyclopentylsulfonyl | Intermediate 7 | 3-methoxy aniline/ Aldrich | (I) | 426 | 2.58 |
| 100 | N-methyl-3-pyridylamino | PhSO₂— | Intermediate 8 | 3-aminopyridine/ Aldrich | (II) | 405 | 2.41 |
| 145 HCl | 4-fluoro-3-methyl-N-methylanilino | MeSO₂— | Intermediate 9 | 4-fluoro-3-methylaniline/ Aldrich | (I) | 396 | 1.77 |
| 146 TFA | 2-methylbenzofuran-5-yl-N-methylamino | MeSO₂— | Intermediate 9 | 5-amino-2-methyl benzofuran hydrochloride/ Aldrich | (III) | 396 | 2.43 |
| 147 TFA | 1-methyl-1H-indazol-6-yl-N-methylamino | MeSO₂— | Intermediate 9 | 1-methyl-1H-indazol-6-amine hydrochloride/ Synthetic Communications, 1996, 26(13), 2443-2447. | (III) | 396 | 2.15 |
| 148 TFA | 1-methyl-1H-indazol-5-yl-N-methylamino | MeSO₂— | Intermediate 9 | 1-methyl-1H-indazole-5-amine/ Bionet Research Ltd | (III) | 396 | 2.06 |

-continued

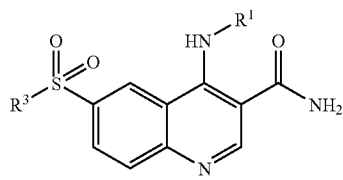

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 149 TFA | 5-(methylamino)-1-benzyl-1H-indazole group | MeSO₂— | Intermediate 9 | 1-(phenylmethyl)-1H-indazol-5-amine/ WO 0283654 A1 | (III) | 472 | 2.56 |
| 150 HCl | 3-(trifluoromethyl)-N-methylanilino | MeSO₂— | Intermediate 9 | 3-(trifluoromethyl)aniline/ Aldrich | (I) | 410 | 2.05 |
| 151 HCl | 3-acetyl-N-methylanilino | MeSO₂— | Intermediate 9 | 1-(3-aminophenyl)ethanone/ Aldrich | (I) | 384 | 1.71 |
| 152 HCl | 3-(5-methyl-1,2,4-oxadiazol-3-yl)-N-methylanilino | MeSO₂— | Intermediate 9 | 3-(5-methyl-1,2,4-oxadiazol-3-yl)aniline/ Intermediate 19 | (I) | 424 | 1.88 |
| 153 HCl | 3-[(N,N-dimethylsulfamoyl)methyl]-N-methylanilino | MeSO₂— | Intermediate 9 | 1-(3-aminophenyl)-N,N-dimethyl methane sulfonamide/ Peakdale molecular Ltd | (I) | 463 | 1.78 |

-continued

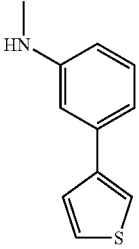

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 154 HCl | 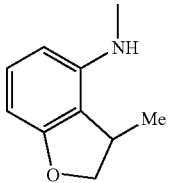 | MeSO₂— | Intermediate 9 | 3-(3-thienyl)aniline/ U.S. Pat. No. 6,211,220 B1 | (I) | 424 | 2.15 |
| 155 HCl | 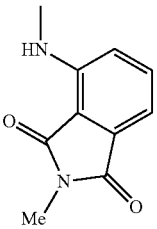 | MeSO₂— | Intermediate 9 | 3-methyl-2,3-dihydro-1-benzofuran-4-amine/ Intermediate 25 | (I) | 398 | 1.91 |
| 156 | 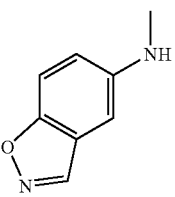 | MeSO₂— | Intermediate 9 | 4-amino-2-methyl-1H-isoindole-1,3(2H)-dione/ Archiv der Pharmazie (Weinheim, Germany) 1989, 322(7), 419-26. | (II) | 425 | 2.35 |
| 157 TFA | 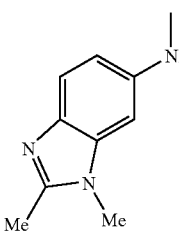 | PhSO₂— | Intermediate 8 | 1,2-benzisoxazol-5-amine/ Key organics Ltd | (III) | 445 | 2.61 |
| 158 TFA | 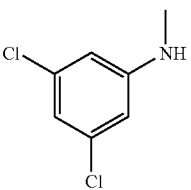 | PhSO₂— | Intermediate 8 | 1,2-dimethyl-1H-benzimidazol-6-amine/ Intermediate 27 | (III) | 472 | 2.15 |
| 159 TFA |  | PhSO₂— | Intermediate 8 | 3,5-dichloroaniline/ Aldrich | (III) | 472 | 3.35 |

-continued

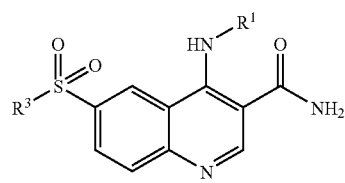

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 160 TFA | 2-methylbenzoxazol-5-yl-NH— | PhSO₂— | Intermediate 8 | 2-methyl-1,3-benzoxazol-5-amine/ Collection of Czechoslovak Chemical Communications 1996, 61(3), 371-380. | (III) | 459 | 2.33 |
| 161 TFA | 4-chloro-3-methoxyphenyl-NH— | PhSO₂— | Intermediate 8 | 4-chloro-3-methoxyaniline/ Wychem | (III) | 468 | 3.08 |
| 162 TFA | 2-methylbenzofuran-5-yl-NH— | PhSO₂— | Intermediate 8 | 5-amino-2-methyl benzofuran hydrochloride/ Sigma Aldrich | (III) | 458 | 2.92 |
| 163 TFA | 1-methyl-1H-indazol-6-yl-NH— | PhSO₂— | Intermediate 8 | 1-methyl-1H-indazol-6-amine hydrochloride/ Heterocycles, 1995, 41(3), 487-96. | (III) | 458 | 2.67 |
| 164 TFA | 5-fluoro-2-methoxyphenyl-NH— | PhSO₂— | Intermediate 8 | 5-fluoro-2-methoxyaniline/ Wychem | (III) | 452 | 2.92 |
| 165 TFA | 1-methyl-1H-indazol-5-yl-NH— | PhSO₂— | Intermediate 8 | 1-methyl-1H-indazol-5-amine/ Bionet Research Ltd | (III) | 458 | 2.51 |

-continued

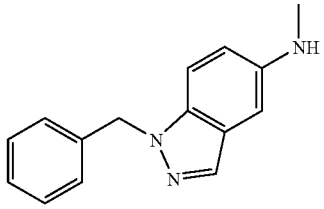

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 166 TFA | 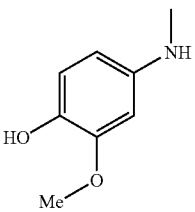 | PhSO₂— | Intermediate 8 | 1-(phenylmethyl)-1H-indazol-5-amine/ WO 0283654 A1 | (III) | 534 | 2.97 |
| 167 TFA | 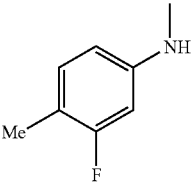 | PhSO₂— | Intermediate 8 | 4-amino-2-(methyloxy)phenol hydrochloride/ Journal of Chemical Research, Synopses 1988, (9), 284-5. | (III) | 450 | 2.42 |
| 168 TFA | 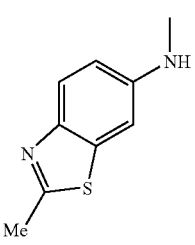 | PhSO₂— | Intermediate 8 | 3-fluoro-4-methylaniline/ Aldrich | (III) | 436 | 3.04 |
| 169 TFA | 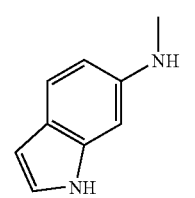 | PhSO₂— | Intermediate 8 | 2-methyl-1,3-benzothiazol-6-amine/ AsInEx Compound Collection | (III) | 475 | 2.73 |
| 170 TFA | 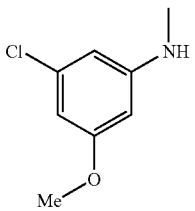 | PhSO₂— | Intermediate 8 | 1H-indol-6-amine/ Lancaster Synthesis | (III) | 443 | 2.7 |
| 171 TFA |  | PhSO₂— | Intermediate 8 | 3-chloro-5-(methyloxy)aniline/ J. Chem. Soc. Perkin 2, 1977, 14. | (III) | 468 | 3.17 |

-continued

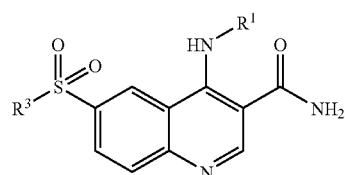

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 172 HCl | 3-(2-methylpyrimidin-4-yl)phenyl-NHMe | PhSO₂— | Intermediate 8 | 3-(2-methyl-4-pyrimidinyl)aniline/ Fluorochem | (I) | 496 | 2.23 |
| 173 HCl | 3-(trifluoromethyl)phenyl-NHMe | PhSO₂— | Intermediate 8 | 3-(trifluoromethyl)aniline/ Aldrich | (I) | 472 | 2.62 |
| 174 HCl | 3-acetylphenyl-NHMe | PhSO₂— | Intermediate 8 | 1-(3-aminophenyl)ethanone/ Aldrich | (I) | 446 | 2.2 |
| 175 HCl | 3-(1,3-oxazol-5-yl)phenyl-NHMe | PhSO₂— | Intermediate 8 | 3-(1,3-oxazol-5-yl)aniline/ Fluorochem | (I) | 471 | 2.24 |
| 176 HCl | 3-(1-methyl-1H-pyrazol-3-yl)phenyl-NHMe | PhSO₂— | Intermediate 8 | 3-(1-methyl-1H-pyrazol-3-yl)aniline/ Intermediate 26 | (I) | 484 | 2.27 |
| 177 HCl | 3-(5-methyl-1,2,4-oxadiazol-3-yl)phenyl-NHMe | PhSO₂— | Intermediate 8 | 3-(5-methyl-1,2,4-oxadiazol-3-yl)aniline/ Intermediate 19 | (I) | 486 | 2.34 |

-continued

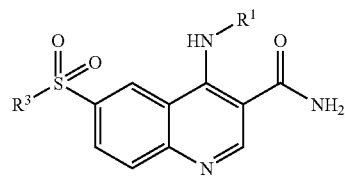

| Ex. No. (a) | R¹NH— | R³SO₂— | Starting Material | Amine/Reagent Source | Isolation Method (b) | LCMS MH⁺ | LCMS R$_t$ (min) |
|---|---|---|---|---|---|---|---|
| 178 HCl | HN-(3-methyl)phenyl-CH₂-SO₂-NMe₂ | PhSO₂— | Intermediate 8 | 1-(3-aminophenyl)-N,N-dimethyl methane sulfonamide/ Peakdale molecular Ltd | (I) | 525 | 2.23 |
| 179 HCl | 3-(3-thienyl)-N-methylanilino | PhSO₂— | Intermediate 8 | 3-(3-thienyl)aniline/ U.S. Pat. No. 6,211,220 B1 | (I) | 486 | 2.55 |
| 180 HCl | N-methyl-3-methyl-2,3-dihydrobenzofuran-4-yl | PhSO₂— | Intermediate 8 | 3-methyl-2,3-dihydro-1-benzofuran-4-amine/ Intermediate 25 | (I) | 460 | 2.36 |
| 181 HCl | N-methyl-2,2-dimethyl-2,3-dihydrobenzofuran-7-yl | PhSO₂— | Intermediate 8 | 2,2-dimethyl-2,3-dihydro-1-benzofuran-7-amine/ DE 3526510 A1 | (I) | 474 | 2.34 |

-continued

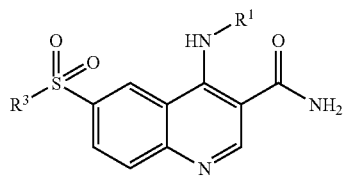

| Ex. No. (a) | R¹NH— | R³SO₂— | Starting Material | Amine/Reagent Source | Isolation Method (b) | LCMS MH⁺ | LCMS R_t (min) |
|---|---|---|---|---|---|---|---|
| 182 | HN-(2-(N-methyl phthalimidyl))- with N-Me | PhSO₂— | Intermediate 8 | 4-amino-2-methyl-1H-isoindole-1,3(2H)-dione/ Archiv der Pharmazie (Weinheim, Germany) 1989, 322(7), 419-26. | (II) | 487 | 2.85 |
| 183 | MeN(H)-(4-methoxy-2-naphthyl) | PhSO₂— | Intermediate 8 | [4-(methyloxy)-2-naphthalenyl]amine 4-methyl benzene sulfonate/ Sigma | (I) | 484 | 3.19 |
| 590 HCl | MeN(H)-(5-chloro-3-pyridyl) | Me₂C(Me)SO₂— (tert-butyl methyl sulfone) | Intermediate 95 | 5-chloro-3-pyridinamine/ Synchem OHG | (I) | 419 | 2.44 |
| 589 HCl | MeN(H)-(3-pyridyl) | Me₂C(Me)SO₂— | Intermediate 95 | 3-pyridinamine Aldrich | (I) | 385 | 1.96 |

(a) Salt forms: HCl = hydrochloride
TFA = trifluoroacetate
(b) Isolation Method:
(I) Filtered off directly from the reaction mixture.
(II) Mass Directed preparative HPLC Method A.
(III) Mass Directed preparative HPLC Method B.

The following compounds were prepared by a similar method to Example 10:

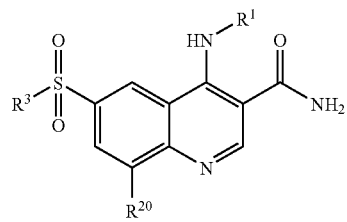

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 187 HCl | *tert*-butyl (3-aminophenyl)carbamate-derived (N-methyl) | MeSO₂— | H— | Intermediate 9 | 1,1-dimethylethyl (3-aminophenyl) carbamate/ J. Med. Chem. 2003, 46(9) 1661-1669 | (I) | 457 | 2.47 |
| 188 HCl | benzyl carbamate derived (N-methyl) | MeSO₂— | H— | Intermediate 9 | 1,1-dimethylethyl [(3-aminophenyl) methyl]carbamate/ J. Med. Chem. 2003, 46(9) 1661-1669 | (I) | 471 | 2.39 |
| 189 | 1,3-benzodioxol-5-yl(N-methyl)amino | MeSO₂— | H— | Intermediate 9 | 1,3-benzodioxol-5-amine/ Aldrich | (II) | 386 | 1.98 |
| 190 HCl | 3-(1,3-oxazol-5-yl)phenyl(N-methyl)amino | MeSO₂— | H— | Intermediate 9 | 3-(1,3-oxazol-5-yl)aniline/ Maybridge | (I) | 409 | 1.82 |
| 191 HCl | 3-(1-methyl-1H-pyrazol-3-yl)phenyl(N-methyl)amino | MeSO₂— | H— | Intermediate 9 | 3-(3-aminophenyl)-1-methyl-1H-pyrazole/ Buttpark | (I) | 422 | 1.88 |

-continued

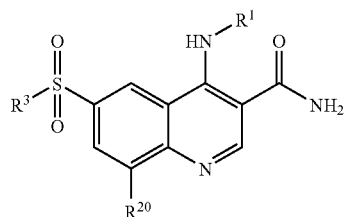

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 192 HCl | 3-chloro-2-fluoro-N-methylanilino | MeSO₂— | H— | Intermediate 9 | 3-chloro-2-fluoroaniline/ Aldrich | (I) | 394 | 2.46 |
| 193 HCl | 2,3-difluoro-N-methylanilino | MeSO₂— | H— | Intermediate 9 | 2,3-difluoroaniline/ Aldrich | (I) | 378 | 2.3 |
| 194 HCl | 3-cyano-N-methylanilino | MeSO₂— | H— | Intermediate 9 | 3-aminobenzonitrile/ Aldrich | (I) | 367 | 2.07 |
| 195 HCl | 3-cyano-4-fluoro-N-methylanilino | MeSO₂— | H— | Intermediate 9 | 5-amino-2-fluorobenzonitrile/ Maybridge | (I) | 385 | 2.15 |
| 196 HCl | 3-isopropoxy-N-methylanilino | MeSO₂— | H— | Intermediate 9 | 3-isopropoxyaniline/ Maybridge | (I) | 400 | 2.35 |
| 197 HCl | 4-fluoro-2-methyl-N-methylanilino | MeSO₂— | H— | Intermediate 9 | 2-amino-5-fluorotoluene/ Aldrich | (I) | 374 | 2.2 |

-continued

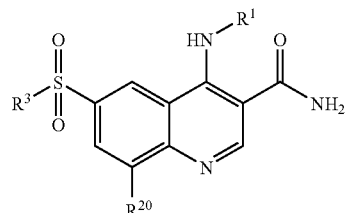

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 198 HCl | 2,4-difluoroanilino-N-methyl | MeSO₂— | H— | Intermediate 9 | 3,4-difluoroaniline/ Aldrich | (I) | 378 | 2.26 |
| 199 HCl | 4-fluoro-3-(trifluoromethyl)anilino-N-methyl | MeSO₂— | H— | Intermediate 9 | 4-fluoro-3-(trifluoromethyl) aniline/Avocado | (I) | 428 | 2.61 |
| 200 HCl | 2-fluoroanilino-N-methyl | MeSO₂— | H— | Intermediate 9 | 2-fluoroaniline/ Aldrich | (I) | 360 | 2.04 |
| 201 HCl | 2,4-difluoroanilino-N-methyl | MeSO₂— | H— | Intermediate 9 | 2,4-difluoroaniline/ Aldrich | (I) | 378 | 2.22 |
| 202 HCl | 2-chloro-4-fluoroanilino-N-methyl | MeSO₂— | H— | Intermediate 9 | 2-chloro-4-fluoroaniline/ Aldrich | (I) | 394 | 2.43 |
| 203 HCl | 3-pyridylamino-N-methyl | MeSO₂— | H— | Intermediate 9 | 3-aminopyridine/ Aldrich | (IV) | 343 | 1.69 |
| 204 HCl | 4-carboxyanilino-N-methyl | MeSO₂— | H— | Intermediate 9 | 4-aminobenzoic acid/Aldrich | (I) | 386 | 2 |

-continued

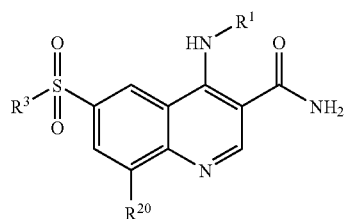

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 205 TFA | 4-chloro-3-methoxy-NH-phenyl (N-methyl) | MeSO₂— | H— | Intermediate 9 | 4-chloro-3-methoxyaniline/ Wychem | (III) | 406 | 2.49 |
| 206 TFA | 1-methyl-1H-benzimidazol-6-yl (N-methyl) | MeSO₂— | H— | Intermediate 9 | 1-methyl-1H-benzimidazol-6-amine/ Heterocycles. 1991, 32(5), 1003-12. | (III) | 396 | 1.77 |
| 207 TFA | 6-methoxy-1,3-benzothiazol-4-yl (N-methyl) | MeSO₂— | H— | Intermediate 9 | 6-(methyloxy)-1,3-benzothiazol-4-amine J. Am. Chem. Soc, 1939, 61(8), 2013-2017. | (III) | 429 | 2.35 |
| 208 TFA | 3-fluoro-5-(3-pyridinyl)phenyl (N-methyl) | MeSO₂— | H— | Intermediate 9 | 3-fluoro-5-(3-pyridinyl)aniline J. Med. Chem. 2000, 43(6), 1123-1134. | (III) | 437 | 2.34 |
| 209 TFA | 5-fluoro-2-methoxyphenyl (N-methyl) | MeSO₂— | H— | Intermediate 9 | 5-fluoro-2-methoxyaniline/ Wychem | (III) | 390 | 2.3 |

-continued

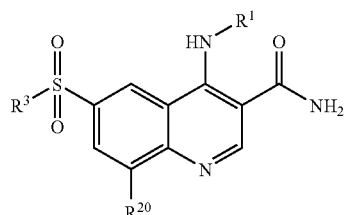

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 210 TFA | 1-methyl-1H-benzotriazol-5-yl(methyl)amino | MeSO₂— | H— | Intermediate 9 | 1-methyl-1H-1,2,3-benzotriazol-5-amine/ US 2003060453 A1 | (III) | 397 | 1.98 |
| 211 TFA | 3,5-difluorophenyl(methyl)amino | MeSO₂— | H— | Intermediate 9 | 3,5-difluoroaniline/ Aldrich | (III) | 378 | 2.51 |
| 212 TFA | 3-fluoro-4-methylphenyl(methyl)amino | MeSO₂— | H— | Intermediate 9 | 3-fluoro-4-methylaniline/ Aldrich | (III) | 374 | 2.43 |
| 213 TFA | 3-fluoro-4-hydroxyphenyl(methyl)amino | MeSO₂— | H— | Intermediate 9 | 4-amino-2-fluorophenol/ Apollo | (III) | 376 | 2.01 |
| 214 TFA | 4-methoxynaphthalen-2-yl(methyl)amino | MeSO₂— | H— | Intermediate 9 | 4-(methyloxy)-2-naphthalenamine/ Sigma | (III) | 422 | 2.73 |
| 215 TFA | 1H-indol-6-yl(methyl)amino | MeSO₂— | H— | Intermediate 9 | 6-aminoindole/ Lancaster | (III) | 381 | 2.25 |

-continued

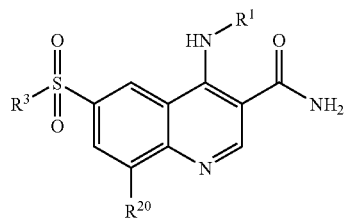

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 216 TFA | 4-(methylamino)-2-methoxy methyl benzoate group | MeSO₂— | H— | Intermediate 9 | methyl 4-amino-2-methoxy benzoate/ Avocado | (III) | 430 | 2.36 |
| 217 HCl | N-methyl-1,3-benzodioxol-4-amine group | MeSO₂— | H— | Intermediate 9 | 1,3-benzodioxol-4-amine J. Med. Chem. 1979, 22(11), 1354-7. | (I) | 386 | 2.06 |
| 218 HCl | 3-(methylamino)benzonitrile group | PhSO₂— | H— | Intermediate 8 | 3-aminobenzonitrile/ Aldrich | (I) | 429 | 2.80 |
| 219 | N-methyl-1,3-benzodioxol-5-amine group | PhSO₂— | H— | Intermediate 8 | 1,3-benzodioxol-5-amine/Aldrich | (II) | 448 | 2.63 |
| 220 | 3-(methylamino)-N,N-dimethylbenzenesulfonamide group | PhSO₂— | H— | Intermediate 8 | 3-amino-N,N-dimethylbenzene sulfonamide/WO 9737646 A1 | (II) | 511 | 2.94 |
| 221 | 3-(methylamino)benzenesulfonamide group | PhSO₂— | H— | Intermediate 8 | 3-aminobenzene sulfonamide/ Fluka | (II) | 483 | 2.6 |

-continued

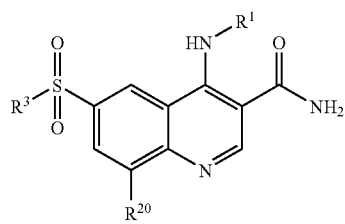

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 222 | 4-(N-methylsulfamoyl)-N-methylanilino | PhSO₂— | H— | Intermediate 8 | 4-amino-N-methylbenzene-sulfonamide/ Zelinsky BB | (II) | 497 | 2.51 |
| 223 TFA | 6-methoxy-N-methylbenzothiazol-4-ylamino | PhSO₂— | H— | Intermediate 8 | 6-(methyloxy)-1,3-benzothiazol-4-amine J. Am. Chem. Soc., 1939, 61(8), 2013-2017. | (III) | 491 | 2.92 |
| 224 TFA | 3-fluoro-5-(pyridin-3-yl)-N-methylanilino | PhSO₂— | H— | Intermediate 8 | 3-fluoro-5-(3-pyridinyl)aniline/ J. Med. Chem., 2000, 43(6), 1123-1134. | (III) | 499 | 2.89 |
| 225 TFA | N-methyl-1H-indazol-4-ylamino | PhSO₂— | H— | Intermediate 8 | Intermediate 51 | (III) | 444 | 3.21 |
| 226 TFA | 3,5-difluoro-N-methylanilino | PhSO₂— | H— | Intermediate 8 | 3,5-difluoroaniline/ Aldrich | (III) | 440 | 3.12 |

-continued

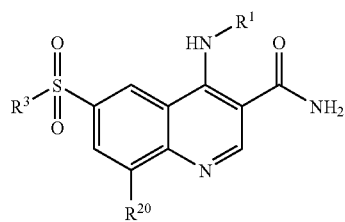

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 227 TFA | 4-(methylamino)-2-fluorophenol | PhSO₂— | H— | Intermediate 8 | 4-amino-2-fluorophenol/ Apollo | (III) | 438 | 2.56 |
| 228 TFA | N-methyl-3,4-difluoroaniline | PhSO₂— | H— | Intermediate 8 | 3,4-difluoroaniline/ Aldrich | (III) | 440 | 3.03 |
| 229 TFA | methyl 4-(methylamino)-2-methoxybenzoate | PhSO₂— | H— | Intermediate 8 | methyl 4-amino-2-methoxy benzoate/ Avocado | (III) | 492 | 2.89 |
| 230 HCl | 2-(3-(methylamino)phenoxy)ethanol | PhSO₂— | Me— | Intermediate 16 | 2-(3-aminophenoxy) ethanol/Key Organics Ltd. | (I) | 478 | 2.22 |
| 231 HCl | methyl 3-(methylamino)thiophene-2-carboxylate | PhSO₂— | Me— | Intermediate 16 | 3-aminothiophene-2-carboxylic acid methyl ester/ Avocado | (I) | 482 | 2.79 |

-continued

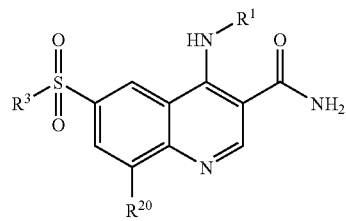

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 232 HCl | 4-methoxy-3-hydroxyphenyl(methyl)amino | PhSO₂— | Me— | Intermediate 16 | 5-amino-2-methoxyphenol/ Aldrich | (I) | 464 | 2.1 |
| 233 HCl | 5,6,7,8-tetrahydronaphthalen-1-yl(methyl)amino | PhSO₂— | Me— | Intermediate 16 | 5-aminotetralin/ Aldrich | (I) | 472 | 2.64 |
| 234 HCl | 3-(ethoxycarbonyl)phenyl(methyl)amino | PhSO₂— | Me— | Intermediate 16 | ethyl 3-aminobenzoate/ Aldrich | (I) | 490 | 2.66 |
| 235 HCl | 3-hydroxy-4-methylphenyl(methyl)amino | PhSO₂— | Me— | Intermediate 16 | 5-amino-2-methylphenol/ TCI America | (I) | 448 | 2.31 |
| 236 HCl | 3-((Boc-aminomethyl)phenyl)(methyl)amino | PhSO₂— | Me— | Intermediate 16 | 1-dimethylethyl [(3-aminophenyl) methyl]carbamate/ J. Med. Chem., 2003, 46(9), 1661-1669. | (I) | 547 | 2.64 |

-continued

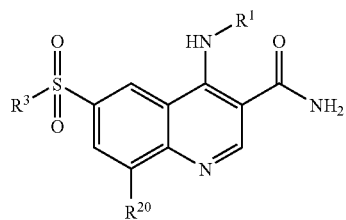

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 237 HCl | 4-(N-methylcarbamoyl)phenyl-NH(Me)— | PhSO₂— | Me— | Intermediate 16 | 4-amino-N-methylbenzamide/ Buttpark | (I) | 475 | 2.27 |
| 238 HCl | 3-(hydroxymethyl)phenyl-NH(Me)— | PhSO₂— | Me— | Intermediate 16 | 3-aminobenzyl alcohol/Aldrich | (I) | 448 | 2.13 |
| 239 TFA | 3-(N-methylcarbamoyl)phenyl-NH(Me)— | PhSO₂— | Me— | Intermediate 16 | 3-aminobenzoyl methylamide/ Buttpark | (III) | 475 | 2.55 |
| 240 TFA | 3-hydroxyphenyl-NH(Me)— | PhSO₂— | Me— | Intermediate 16 | 3-aminophenol/ Aldrich | (III) | 434 | 2.64 |
| 241 TFA | (1-ethylpyrazol-5-yl)-NH(Me)— | PhSO₂— | Me— | Intermediate 16 | 5-amino-1-ethylpyrazole/ Aldrich | (III) | 436 | 2.75 |

-continued

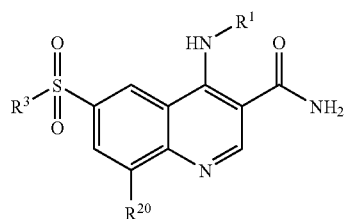

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 242 TFA | 4-fluoro-3-cyanophenyl-N(Me)H | PhSO₂— | Me— | Intermediate 16 | 3-cyano-4-fluoroaniline hydrochloride/ Combiblocks | (III) | 461 | 3.04 |
| 243 TFA | 1-acetylindolin-6-yl-N(Me)H | PhSO₂— | Me— | Intermediate 16 | 1-acetyl-6-aminoindoline/ Sigma | (III) | 501 | 2.59 |
| 244 HCl | 2,3-dihydrobenzofuran-4-yl-N(Me)H | iPrSO₂— | H— | Intermediate 30 | 2,3-dihydro-1-benzofuran-4-amine hydrobromide/ J. Heterocyclic Chem., 1980, 17(6), 1333-5. | (I) | 412 | 2.36 |
| 245 HCl | 3-acetylphenyl-N(Me)H | iPrSO₂— | H— | Intermediate 30 | 3-amino-acetophenone/ Aldrich | (I) | 412 | 2.33 |
| 246 HCl | 1-methyl-1H-indazol-6-yl-N(Me)H | iPrSO₂— | H— | Intermediate 30 | 1-methyl-1H-indazol-6-amine hydrochloride/ Synth. Comm., 1996. 26(13), 2443-2447. | (I) | 424 | 2.22 |

-continued

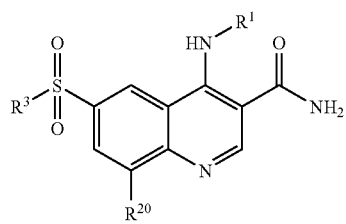

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 247 HCl | 4-fluoro-3-methoxy-N-methylanilino | iPrSO₂— | H— | Intermediate 30 | 4-fluoro-3-methoxyaniline/ Apollo-Chem | (I) | 418 | 2.38 |
| 248 HCl | 2,3-dihydro-1,4-benzodioxin-5-yl-N-methylamino | iPrSO₂— | H— | Intermediate 30 | 2,3-dihydro-1,4-benzodioxin-5-amine hydrochloride/ WO 9703067 A1 | (I) | 428 | 2.30 |
| 249 HCl | 3-chloro-N-methylanilino | iPrSO₂— | H— | Intermediate 30 | 3-chloroaniline/ Aldrich | (I) | 404 | 2.64 |
| 250 HCl | 3-cyano-N-methylanilino | iPrSO₂— | H— | Intermediate 30 | 3-aminobenzonitrile/ Aldrich | (I) | 395 | 2.40 |
| 251 HCl | 3-methyl-N-methylanilino | iPrSO₂— | H— | Intermediate 30 | 3-methylaniline hydrochloride/ TCI-US | (I) | 384 | 2.41 |
| 252 HCl | pyridin-3-yl-N-methylamino | iPrSO₂— | H— | Intermediate 30 | 3-aminopyridine/ Aldrich | (I) | 371 | 1.92 |

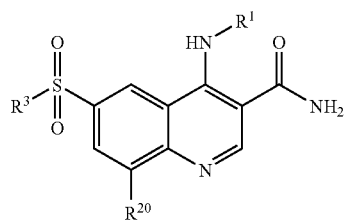

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 253 HCl | 6-(methylamino)benzothiazole | iPrSO₂— | H— | Intermediate 30 | 6-aminobenzo thiazole/ Lancaster | (I) | 427 | 2.20 |
| 254 HCl | 3-iodo-N-methylaniline | 4-methoxyphenylsulfonyl | H— | Intermediate 31 | 3-iodoaniline/ Aldrich | (I) | 560 | 3.06 |
| 255 HCl | 3-acetyl-N-methylaniline | 4-methoxyphenylsulfonyl | H— | Intermediate 31 | 3-amino-acetophenone/ Aldrich | (I) | 476 | 2.68 |
| 256 HCl | 1-methyl-6-(methylamino)benzimidazole | 4-methoxyphenylsulfonyl | H— | Intermediate 31 | 1-methyl-1H-benzimidazol-6-amine/ Heterocycles, 1991, 32(5), 1003-12. | (I) | 488 | 2.17 |
| 257 HCl | 2,3-dihydro-N-methylbenzofuran-4-amine | 4-methoxyphenylsulfonyl | H— | Intermediate 31 | 2,3-dihydro-1-benzofuran-4-amine hydrobromide/ J. Heterocyclic Chem., 1980, 17(6), 1333-5. | (I) | 476 | 2.76 |
| 258 HCl | 3-fluoro-N-methylaniline | 4-methoxyphenylsulfonyl | H— | Intermediate 31 | 3-fluoroaniline/ Aldrich | (I) | 452 | 2.89 |

-continued

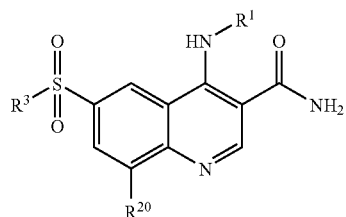

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 259 HCl | 4-fluoro-3-methoxyanilino (N-methyl) | 4-(methylsulfonyl)phenoxy methyl | H— | Intermediate 31 | 4-fluoro-3-methoxyaniline/ Apollo-Chem | (I) | 482 | 2.78 |
| 260 HCl | N-methyl-benzothiazol-6-ylamino | 4-(methylsulfonyl)phenoxy methyl | H— | Intermediate 31 | 6-aminobenzo thiazole/ Lancaster | (I) | 491 | 2.61 |
| 261 HCl | N-methyl-(1-methyl-1H-indazol-6-yl)amino | 4-(methylsulfonyl)phenoxy methyl | H— | Intermediate 31 | 1-methyl-1H-indazol-6-amine hydrochloride/ Synth. Comm., 1996, 26(13), 2443-2447. | (I) | 488 | 2.62 |
| 262 HCl | 3-cyanophenyl-N-methylamino | 4-(methylsulfonyl)phenoxy methyl | H— | Intermediate 31 | 3-aminobenzonitrile/ Aldrich | (I) | 459 | 2.86 |
| 263 HCl | 3-chlorophenyl-N-methylamino | 4-(methylsulfonyl)phenoxy methyl | H— | Intermediate 31 | 3-chloroaniline/ Aldrich | (I) | 468 | 3.02 |
| 264 HCl | 3-methylphenyl-N-methylamino | 4-(methylsulfonyl)phenoxy methyl | H— | Intermediate 31 | 3-methylaniline hydrochlorlde/ TCI-US | (I) | 448 | 2.78 |

-continued

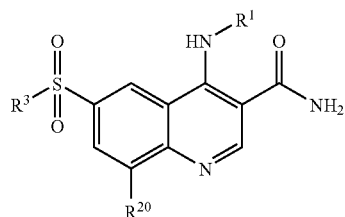

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 265 | 3-methoxyphenyl-NHMe | 4-(methylsulfonyl)phenoxy-CH₃ | Me— | Intermediate 32 | 3-methoxyaniline/ Aldrich | (II) | 478 | 3.04 |
| 266 TFA | 2,3-dihydrobenzofuran-4-yl-NHMe | 4-(methylsulfonyl)phenoxy-CH₃ | Me— | Intermediate 32 | 2,3-dihydro-1-benzofuran-4-amine hydrobromide/ J. Heterocyclic Chem., 1980, 17(6). 1333-5. | (III) | 490 | 2.45 |
| 267 TFA | 3-acetylphenyl-NHMe | 4-(methylsulfonyl)phenoxy-CH₃ | Me— | Intermediate 32 | 3-amino-acetophenone/ Aldrich | (III) | 490 | 2.41 |
| 268 TFA | 1-methyl-1H-indazol-6-yl-NHMe | 4-(methylsulfonyl)phenoxy-CH₃ | Me— | Intermediate 32 | 1-methyl-1H-indazol-6-amine hydrochloride/ Synth. Comm., 1996, 26(13), 2443-2447. | (III) | 502 | 2.36 |
| 269 TFA | 2,3-dihydro-1,4-benzodioxin-5-yl-NHMe | 4-(methylsulfonyl)phenoxy-CH₃ | Me— | Intermediate 32 | 2,3-dihydro-1,4-benzodioxin-5-amine hydrochloride/ WO 9703067 A1 | (III) | 506 | 2.36 |
| 270 TFA | 3-chlorophenyl-NHMe | 4-(methylsulfonyl)phenoxy-CH₃ | Me— | Intermediate 32 | 3-chloroaniline/ Aldrich | (III) | 482 | 2.72 |

-continued

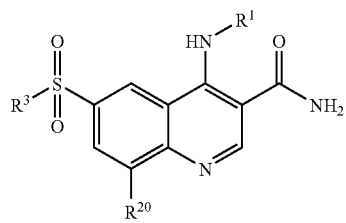

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 271 TFA | 3-(methylamino)benzonitrile | 4-(methylsulfonyl)anisole | Me— | Intermediate 32 | 3-aminobenzonitrile/ Aldrich | (III) | 473 | 2.62 |
| 272 TFA | N-methyl-benzothiazol-6-amine | 4-(methylsulfonyl)anisole | Me— | Intermediate 32 | 6-aminobenzothiazole/ Lancaster | (III) | 505 | 2.36 |
| 273 TFA | 3-fluoro-N-methylaniline | 4-(methylsulfonyl)anisole | Me— | Intermediate 32 | 3-fluoroaniline/ Aldrich | (III) | 466 | 2.6 |
| 274 HCl | 2-(3-(methylamino)phenoxy)ethanol | 4-(methylsulfonyl)anisole | H— | Intermediate 31 | 2-(3-aminophenoxy) ethanol hydrochloride/ J. Am. Chem. Soc., 1937, 59; 1716 | (I) | 494 | 2.15 |
| 275 HCl | 3-(methylamino)phenol | 4-(methylsulfonyl)anisole | H— | Intermediate 31 | 3-aminophenol/ Aldrich | (I) | 450 | 2.15 |

-continued

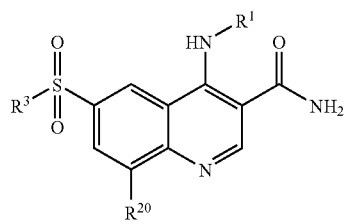

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 276 HCl | 3-(methylamino)benzoic acid ethyl ester | 4-methoxyphenyl methylsulfone | H— | Intermediate 31 | ethyl 3-aminobenzoate/ Aldrich | (I) | 506 | 2.51 |
| 277 HCl | 5-(methylamino)-2-methylphenol | 4-methoxyphenyl methylsulfone | H— | Intermediate 31 | 5-amino-2-methylphenol/ TCI America | (I) | 464 | 2.27 |
| 278 HCl | 4-(methylamino)-N-methylbenzamide | 4-methoxyphenyl methylsulfone | H— | Intermediate 31 | 4-amino-N-methylbenzamide/ Buttpark | (I) | 491 | 2.16 |
| 279 HCl | 3-(methylamino)benzyl alcohol | 4-methoxyphenyl methylsulfone | H— | Intermediate 31 | 3-aminobenzyl-alcohol/Aldrich | (I) | 464 | 2.07 |
| 280 TFA | methyl 3-(methylamino)thiophene-2-carboxylate | 4-methoxyphenyl methylsulfone | H— | Intermediate 31 | methyl 3-aminothiophene-2-carboxylate/ Avocado | (III) | 498 | 2.95 |

-continued

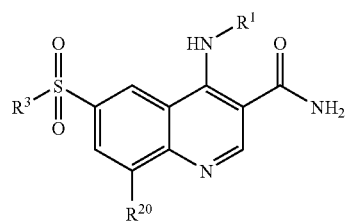

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 281 TFA | | | H— | Intermediate 31 | 5-amino-2-methoxyphenol/ Aldrich | (III) | 480 | 2.37 |
| 282 TFA | | | H— | Intermediate 31 | 3-amino-N-methylbenzamide/ Buttpark | (III) | 491 | 2.43 |
| 283 TFA | | | H— | Intermediate 31 | 1-amino-5,6,7,8-tetrahydro napthalene/ Aldrich | (III) | 488 | 2.96 |
| 284 TFA | | | H— | Intermediate 31 | 4-amino-2-methoxyphenol/ WO 2003049702 A2 | (III) | 480 | 2.34 |
| 285 TFA | | | Me— | Intermediate 34 | 2,3-dihydro-1-benzofuran-4-amine hydrobromide/ J. Heterocyclic Chem., 1980, 17(6), 1333-5. | (III) | 474 | 2.53 |

-continued

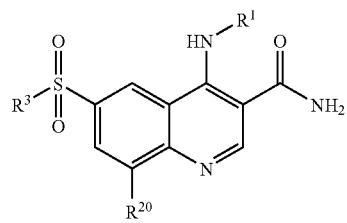

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 286 TFA | 3-(N-methylamino)acetophenone | 4-methylphenylsulfonyl (H₃C-C₆H₄-SO₂-CH₃) | Me— | Intermediate 34 | 3-amino-acetophenone/ Aldrich | (III) | 474 | 2.49 |
| 287 TFA | 1-methyl-6-(methylamino)-1H-indazole | 4-methylphenylsulfonyl | Me— | Intermediate 34 | 1-methyl-1H-indazol-6-amine hydrochloride/ Synth. Comm., 1996, 26(13), 2443-2447. | (III) | 486 | 2.41 |
| 288 TFA | 5-(methylamino)-2,3-dihydro-1,4-benzodioxin | 4-methylphenylsulfonyl | Me— | Intermediate 34 | 2,3-dihydro-1,4-benzodioxin-5-amine hydrochloride/ WO 9703067 A1 | (III) | 490 | 2.43 |
| 289 TFA | 3-chloro-N-methylaniline | 4-methylphenylsulfonyl | Me— | Intermediate 34 | 3-chloroaniline/ Aldrich | (III) | 466 | 2.82 |
| 290 TFA | 3-fluoro-N-methylaniline | 4-methylphenylsulfonyl | Me— | Intermediate 34 | 3-fluoroaniline/ Aldrich | (III) | 450 | 2.70 |
| 291 TFA | 3-(methylamino)benzonitrile | 4-methylphenylsulfonyl | Me— | Intermediate 34 | 3-aminobenzonitrile/ Aldrich | (III) | 457 | 2.71 |

-continued

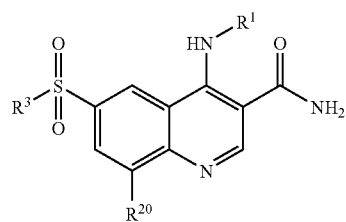

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 292 TFA | 3-methoxy-N-methylanilino | 4-methylphenylsulfonyl | Me— | Intermediate 34 | 3-methoxyaniline/ Aldrich | (III) | 462 | 2.51 |
| 293 HCl | 3-methoxy-N-methylanilino | MeSO₂— | Me— | Intermediate 33 | 3-methoxyaniline/ Aldrich | (I) | 386 | 2.20 |
| 294 HCl | 4-fluoro-3-methoxy-N-methylanilino | MeSO₂— | Me— | Intermediate 33 | 4-fluoro-3-methoxyaniline/ Apollo-Chem | (I) | 404 | 2.23 |
| 295 HCl | 3-methoxy-N-methylanilino | MeSO₂— | MeO— | Intermediate 50 | 3-methoxyaniline/ Aldrich | (I) | 402 | 2.09 |
| 296 HCl | 4-fluoro-3-methoxy-N-methylanilino | MeSO₂— | MeO— | Intermediate 50 | 4-fluoro-3-methoxyaniline/ Apollo-Chem | (I) | 420 | 2.12 |

-continued

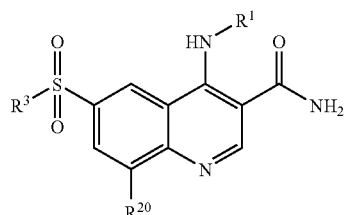

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 297 HCl | 3-(N-methylamino)acetophenone | PhSO₂— | Me— | Intermediate 16 | 3-amino-acetophenone/ Aldrich | (I) | 460 | 2.82 |
| 298 HCl | 1-methyl-6-(methylamino)-1H-benzimidazole | PhSO₂— | Me— | Intermediate 16 | 1-methyl-1H-benzimidazol-6-amine/ Heterocycles, 1991, 32(5), 1003-12. | (I) | 472 | 2.24 |
| 299 HCl | 2,3-dihydro-4-(methylamino)benzofuran | PhSO₂— | Me— | Intermediate 16 | 2,3-dihydro-1-benzofuran-4-amine hydrobromide/ J. Heterocyclic Chem., 1980, 17(6), 1333-5. | (I) | 460 | 2.90 |
| 300 HCl | 3-fluoro-N-methylaniline | PhSO₂— | Me— | Intermediate 16 | 3-fluoroaniline/ Aldrich | (I) | 436 | 3.07 |
| 301 TFA | 2,3-dihydro-5-(methylamino)-1,4-benzodioxin | PhSO₂— | Me— | Intermediate 16 | 2,3-dihydro-1,4-benzodioxin-5-amine hydrochloride/ WO 9703067 A1 | (III) | 476 | 2.77 |
| 302 HCl | 6-(methylamino)benzothiazole | PhSO₂— | Me— | Intermediate 16 | 6-aminobenzo thiazole/ Lancaster | (I) | 475 | 2.75 |

-continued

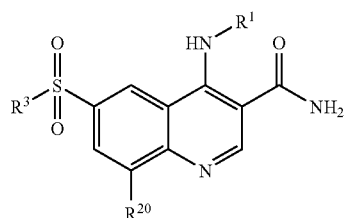

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 303 HCl | [1-methyl-1H-indazol-6-yl-NH-Me] | PhSO₂— | Me— | Intermediate 16 | 1-methyl-1H-indazol-6-amine hydrochloride/ Synth. Comm., 1996, 26(13), 2443-2447. | (I) | 472 | 2.74 |
| 304 HCl | [3-cyanophenyl-NH-Me] | PhSO₂— | Me— | Intermediate 16 | 3-aminobenzonitrile/ Aldrich | (I) | 443 | 3.01 |
| 305 HCl | [3-chlorophenyl-NH-Me] | PhSO₂— | Me— | Intermediate 16 | 3-chloroaniline/ Aldrich | (I) | 452 | 3.21 |
| 306 HCl | [3-methylphenyl-NH-Me] | PhSO₂— | Me— | Intermediate 16 | 3-methylaniline/ Aldrich | (I) | 432 | 2.93 |
| 307 HCl | [2,3-dihydrobenzofuran-4-yl-NH-Me] | MeSO₂— | Me— | Intermediate 33 | 2,3-dihydro-1-benzofuran-4-amine hydrobromide/ J. Heterocyclic Chem., 1980, 17(6), 1333-5. | (I) | 398 | 2.38 |
| 308 TFA | [pyridin-3-yl-NH-Me] | MeSO₂— | Me— | Intermediate 33 | 3-aminopyridine/ Aldrich | (III) | 357 | 1.95 |

-continued

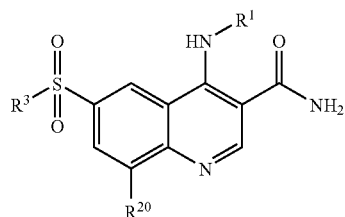

| Ex. No. (a) | R¹NH— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 309 HCl | 1-methyl-1H-indazol-6-yl(methyl)amino | MeSO₂— | Me— | Intermediate 33 | 1-methyl-1H-indazol-6-amine hydrochloride/ Synth. Comm., 1996, 26(13), 2443-2447. | (I) | 410 | 2.28 |
| 310 HCl | 3-chlorophenyl(methyl)amino | MeSO₂— | Me— | Intermediate 33 | 3-chloroaniline/ Aldrich | (I) | 390 | 2.68 |
| 311 HCl | 3-fluorophenyl(methyl)amino | MeSO₂— | Me— | Intermediate 33 | 3-fluoroaniline/ Aldrich | (I) | 374 | 2.49 |
| 312 HCl | 3-cyanophenyl(methyl)amino | MeSO₂— | Me— | Intermediate 33 | 3-aminobenzonitrile/ Aldrich | (I) | 381 | 2.44 |
| 313 HCl | 1-methyl-1H-benzimidazol-6-yl(methyl)amino | MeSO₂— | Me— | Intermediate 33 | 1-methyl-1H-benzimidazol-6-amine/ Heterocycles, 1991, 32(5), 1003-12. | (I) | 410 | 1.87 |
| 314 HCl | 3-methylphenyl(methyl)amino | MeSO₂— | Me— | Intermediate 33 | 3-methylaniline/ Aldrich | (I) | 370 | 2.40 |

-continued

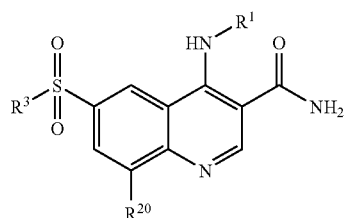

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 315 HCl | (1-ethyl-1H-pyrazol-5-yl)methylamino | MeSO₂— | Me— | Intermediate 33 | 1-ethyl-1H-pyrazol-5-amine/ Aldrich | (I) | 374 | 2.22 |
| 316 HCl | (5-methoxypyridin-3-yl)methylamino | MeSO₂— | Me— | Intermediate 33 | 5-(methyloxy)-3-pyridinamine/ Australian J. Chem., 1981, 34(4). 927-32 | (I) | 387 | 2.08 |
| 317 HCl | (5-methylpyridin-3-yl)methylamino | MeSO₂— | Me— | Intermediate 33 | 5-methyl-3-pyridinamine/ Synchem | (I) | 371 | 1.90 |
| 318 HCl | (3-cyano-4-fluorophenyl)methylamino | MeSO₂— | Me— | Intermediate 33 | 5-amino-2-fluorobenzonitrile/ Matrix Scientific | (I) | 399 | 2.38 |
| 329 HCl | (2-methoxybenzyl)methylamino | PhSO₂— | Me— | Intermediate 16 | 2-methoxybenzyl amine/Aldrich | (I) | 462 | 2.26 |
| 479 HCl | (1-methyl-1H-pyrazol-5-yl)methylamino | MeSO₂— | Me— | Intermediate 33 | 1-methyl-1H-pyrazol-5-amine/ Apollo Chem | (IV) | 360 | 2.09 |

-continued

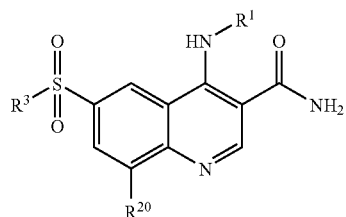

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 496 HCl | [benzodioxol-NHMe] | MeSO₂— | Me— | Intermediate 33 | 1,3-benzodioxol-4-amine/J. Med. Chem., 2002, 45(19), 4128-4139 | (I) | 400 | 2.22 |
| 497 HCl | [3-methyl-4-fluoro-NHMe phenyl] | MeSO₂— | Me— | Intermediate 33 | 4-fluoro-3-methylaniline/ Fluoro Chem | (I) | 388 | 2.35 |
| 498 HCl | [3-chloro-4-fluoro-NHMe phenyl] | MeSO₂— | Me— | Intermediate 33 | 3-chloro-4-fluoroaniline/ Aldrich | (IV) | 408 | 2.59 |
| 499 HCl | [5,6,7,8-tetrahydronaphthyl-NHMe] | MeSO₂— | Me— | Intermediate 33 | 5,6,7,8-tetrahydro-1-naphthalenamine/ Fluka | (I) | 410 | 2.57 |
| 500 HCl | [2,3-difluoro-NHMe phenyl] | MeSO₂— | Me— | Intermediate 33 | 2,3-difluoroaniline/ Aldrich | (IV) | 392 | 2.52 |
| 501 HCl | [3-chloro-2-fluoro-NHMe phenyl] | MeSO₂— | Me— | Intermediate 33 | 3-chloro-2-fluoroaniline/ Aldrich | (I) | 408 | 2.67 |
| 502 HCl | [3,5-difluoro-NHMe phenyl] | MeSO₂— | Me— | Intermediate 33 | 3,5-difluoroaniline Aldrich | (I) | 392 | 2.60 |

-continued

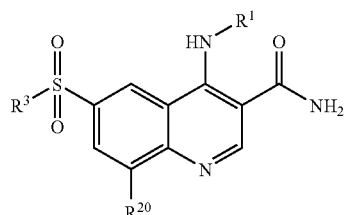

| Ex. No. (a) | R¹NH— | R³SO₂— | R²⁰— | Starting Material | Amine Reagent/ Source | Isolation Method (b) | LCMS MH⁺ | LCMS R_t (min) |
|---|---|---|---|---|---|---|---|---|
| 503 HCl | benzothiazol-6-yl-NH-CH₂- | MeSO₂— | Me— | Intermediate 33 | 1,3-benzothiazol-6-amine/ Maybridge | (I) | 413 | 2.13 |
| 504 HCl | 3,4-difluorophenyl-NH-CH₂- | MeSO₂— | Me— | Intermediate 33 | 3,4-difluoroaniline/ Aldrich | (I) | 392 | 2.43 |
| 505 HCl | 2,4-difluorophenyl-NH-CH₂- | MeSO₂— | Me— | Intermediate 33 | 2,4-difluoroaniline/ Aldrich | (I) | 392 | 2.33 |
| 508 HCl | 1-methyl-2,3-dihydro-1H-indol-4-yl-NH-CH₂- | MeSO₂— | Me— | Intermediate 33 | 1-methyl-2,3-dihydro-1H-indol-4-amine/ Intermediate 71 | (IV) | 411 | 2.2 |
| 509 HCl | 1-methyl-1H-indazol-4-yl-NH-CH₂- | MeSO₂— | Me— | Intermediate 33 | 1-methyl-1H-indazol-4-amine/ J. Med. Chem., 2002, 45(3), 740-743 | (I) | 410 | 2.21 |
| 510 HCl | 2,3-dihydro-1-benzofuran-7-yl-NH-CH₂- | MeSO₂— | Me— | Intermediate 33 | 2,3-dihydro-1-benzofuran-7-amine/ WO 9517401 A1 | (I) | 398 | 2.15 |
| 511 HCl | 2,3-dihydro-1H-inden-4-yl-NH-CH₂- | MeSO₂— | Me— | Intermediate 33 | 2,3-dihydro-1H-inden-4-amine/ Aldrich | (I) | 396 | 2.46 |

-continued

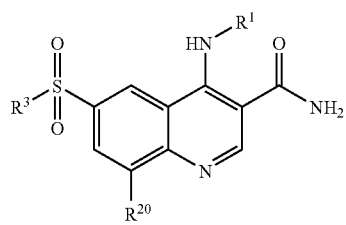

| Ex. No. (a) | R¹NH— | R³SO₂— | R²⁰— | Starting Material | Amine Reagent/ Source | Isolation Method (b) | LCMS MH⁺ | LCMS $R_t$ (min) |
|---|---|---|---|---|---|---|---|---|
| 512 HCl | ![structure: 4-(methylamino)-2,3-dihydro-1H-inden-1-one] | MeSO₂— | Me— | Intermediate 33 | 4-amino-2,3-dihydro-1H-inden-1-one/Davos | (IV) | 410 | 2.13 |
| 520 HCl | ![structure: N,2-dimethylpyridin-4-amine] | MeSO₂— | Me— | Intermediate 33 | 2-methyl-4-pyridinamine/ Asym Chem | (I) | 371 | 1.7 |
| 542 HCl | ![structure: N-methyl-1,3-dihydro-2-benzofuran-4-amine] | MeSO₂— | Me— | Intermediate 33 | 1,3-dihydro-2-benzofuran-4-amine/U.S. Pat. No. 4,521,241 | (I) | 398 | 2.16 |
| 587 HCl | ![structure: N-methyl-3,4-dihydro-2H-chromen-5-amine] | MeSO₂— | Me— | Intermediate 33 | 3,4-dihydro-2H-chromen-5-ylamine/J. Heterocyclic Chem., 1973, 10(4), 623-9 | (I) | 412 | 2.26 |

(a) Salt forms: HCl = hydrochloride
TFA = trifluoroacetate
(b) Isolation Method:
(I) Filtered off directly from the reaction mixture.
(II) Mass Directed preparative HPLC Method A.
(III) Mass Directed preparative HPLC Method B.
(IV) Mass Directed preparative HPLC Method C.

Example 14

4-[(3-Chlorophenyl)(methyl)amino]-6-(methylsulfonyl)-3-quinolinecarboxamide

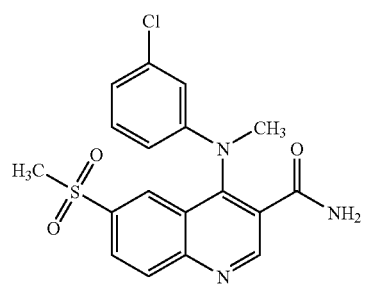

Intermediate 9 (0.023 g) was dissolved in 1-methyl-2-pyrrolidinone (1 ml), and 3-chloro-N-methylaniline (available from Avocado) (0.012 ml) was added. The mixture was stirred under microwave irradiation (power 150 W) for 10 min at 180° C. and for a further 10 min (power 150 W) at 150° C. Purification by mass directed HPLC (Method A) gave the title compound (0.015 g).

LC/MS $R_t$ 2.58 min m/z 390 [MH$^+$]

Example 112

4-({[2-(Methyloxy)phenyl]methyl}amino)-6-(phenylsulfonyl)-3-quinolinecarboxamide

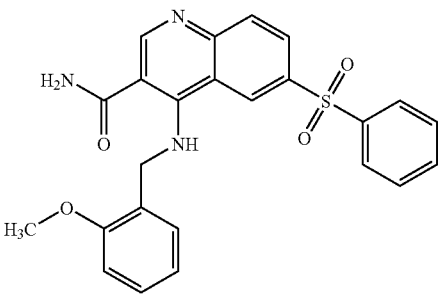

Intermediate 8 (0.017 g) was taken up in acetonitrile (1.5 ml) to give a slurry. 2-Methoxy benzylamine (available from Aldrich) (0.021 g) and N,N-diisopropylethylamine (0.050 ml) were added and the resultant mixture was heated under reflux for 16 h. The mixture was cooled, the solvent evaporated in vacuo and the residue purified by mass directed HPLC (Method A) to give the title compound (0.014 g).

LC/MS $R_t$ 2.73 min m/z 448 [MH$^+$]

Similarly prepared were the following:

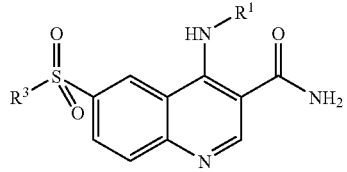

| Ex. No. (a) | R$^1$NH | R$^3$SO$_2$ | Starting Material | Amine reagent/ Source | Isolation Method (b) | LCMS MH$^+$ | LCMS $R_t$ (min) |
|---|---|---|---|---|---|---|---|
| 101 (c) HCl | benzyl-NH-methyl | MeSO$_2$— | Intermediate 9 | 1-phenylmethanamine/ Aldrich | (I) | 356 | 2.07 |
| 102 | tetrahydropyran-3-yl-NH-methyl | MeSO$_2$— | Intermediate 9 | tetrahydro-2H-pyran-3-amine hydrochloride/ Anales de Quimica, Serie C: Quimica Organica y Bioquimica, 1988, 64(2), 148-55. | (II) | 350 | 1.78 |
| 103 | (2-hydroxyphenyl)methyl-NH-methyl | PhSO$_2$— | Intermediate 8 | 2-(aminomethyl)phenol/ Buttpark | (I) | 434 | 2.56 |

-continued

| Ex. No. (a) | R¹NH | R³SO₂ | Starting Material | Amine reagent/ Source | Isolation Method (b) | LCMS MH⁺ | LCMS R_t (min) |
|---|---|---|---|---|---|---|---|
| 104 | (2,3-dihydro-1H-inden-2-yl)(methyl)amine | PhSO₂— | Intermediate 8 | 2,3-dihydro-1H-inden-2-amine hydrochloride/ Aldrich | (I) | 444 | 2.85 |
| 105 | N-methylcyclopropylamine | PhSO₂— | Intermediate 8 | cyclopropylamine/ Aldrich | (I) | 368 | 2.37 |
| 106 | N-methyl-4-(dimethylaminomethyl)benzylamine | PhSO₂— | Intermediate 8 | [4-(aminomethyl)phenyl]dimethylamine hydrochloride/ Aldrich | (I) | 461 | 2.69 |
| 107 | N-methyl-3-(methanesulfonamido)benzylamine | PhSO₂— | Intermediate 8 | N-[3-(aminomethyl)phenyl]methanesulfonamide trifluoroacetate/ J. Med. Chem., 1999, 42(14), 2504-2526. | (I) | 511 | 2.52 |
| 108 | 2-(methylamino)cyclohexanol | PhSO₂— | Intermediate 8 | 2-aminocyclohexanol/ TCI-US | (I) | 426 | 2.49 |
| 109 | N-methyl-(1-methyl-1H-pyrazol-4-yl)methylamine | PhSO₂— | Intermediate 8 | [(1-methyl-1H-pyrazol-4-yl)methyl]amine/ Zelinsky-BB; CA 400877-05-6 | (I) | 422 | 2.28 |
| 110 | N-methyl-(2-pyridinylmethyl)amine | PhSO₂— | Intermediate 8 | (2-pyridinylmethyl)amine hydrochloride/ Aldrich | (I) | 419 | 2.35 |

-continued

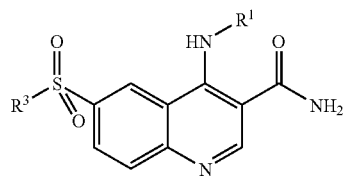

| Ex. No. (a) | R¹NH | R³SO₂ | Starting Material | Amine reagent/ Source | Isolation Method (b) | LCMS MH⁺ | LCMS R_t (min) |
|---|---|---|---|---|---|---|---|
| 111 | (1-methylamino-1,2,3,4-tetrahydronaphthalene) | PhSO₂— | Intermediate 8 | 1,2,3,4-tetrahydro-1-naphthalenamine hydrochloride/ Aldrich | (I) | 458 | 2.92 |
| 113 | (cyclohexylmethyl-N-methyl) | PhSO₂— | Intermediate 8 | (cyclohexylmethyl)amine/Aldrich | (I) | 424 | 2.87 |
| 114 | (4-methoxybenzyl-N-methyl) | PhSO₂— | Intermediate 8 | {[4-(methyloxy)phenyl]methyl}amine hydrochloride/ Aldrich | (I) | 448 | 2.69 |
| 115 | (benzyl-N-methyl) | PhSO₂— | Intermediate 8 | (phenylmethyl)amine hydrochloride/ Aldrich | (I) | 418 | 2.67 |
| 116 | (cyclohexyl-N-methyl) | PhSO₂— | Intermediate 8 | cyclohexylamine hydrochloride/ Acros | (II) | 410 | 2.59 |
| 117 | (2-methyl-N-methyl-propanamine) | PhSO₂— | Intermediate 8 | 2-methyl-1-propanamine trifluoroacetate/ Aldrich | (II) | 384 | 2.43 |

-continued

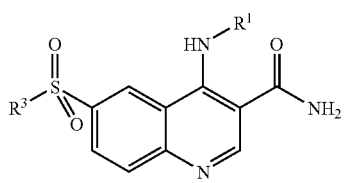

| Ex. No. (a) | R¹NH | R³SO₂ | Starting Material | Amine reagent/ Source | Isolation Method (b) | LCMS MH⁺ | LCMS R$_t$ (min) |
|---|---|---|---|---|---|---|---|
| 118 | (N-pyridin-3-yl)ethyl-NH-Me | PhSO₂— | Intermediate 8 | [2-(3-pyridinyl)ethyl] amine/Lancaster | (II) | 433 | 2.08 |
| 119 | (N-pyridin-4-yl)ethyl-NH-Me | PhSO₂— | Intermediate 8 | [2-(4-pyridinyl)ethyl] amine/Maybridge | (II) | 433 | 2.01 |
| 120 | phenethyl-NH-Me | PhSO₂— | Intermediate 8 | 2-phenylethanamine/ Aldrich | (II) | 432 | 2.68 |
| 121 | (pyridin-3-ylmethyl)-NH-Me | PhSO₂— | Intermediate 8 | (3-pyridinylmethyl) amine/Aldrich | (II) | 419 | 2.12 |
| 122 | (3,5-dimethoxybenzyl)-NH-Me | PhSO₂— | Intermediate 8 | {[3,5-bis(methyloxy)phenyl] methyl}amine hydrochloride/ Aldrich | (II) | 478 | 2.68 |
| 123 | (tetrahydro-2H-pyran-3-yl)-NH-Me | PhSO₂— | Intermediate 8 | tetrahydro-2H-pyran-3-amine hydrochloride/ Anales de Quimica, Serie C: Quimica Organica y Bioquimica, 1988, 84(2), 148-55. | (II) | 412 | 2.20 |

-continued

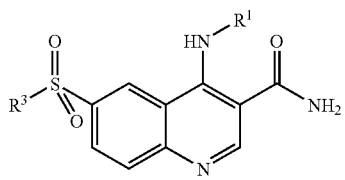

| Ex. No. (a) | R¹NH | R³SO₂ | Starting Material | Amine reagent/ Source | Isolation Method (b) | LCMS MH⁺ | LCMS R_t (min) |
|---|---|---|---|---|---|---|---|
| 124 | (cyclohexanone with NHMe) | PhSO₂— | Intermediate 8 | 4-amino cyclohexanane/ Nouveau Journal de Chimie, 1984, 8(7), 459-67. | (II) | 424 | 2.15 |
| 125 (c) HCl | (3-chloro-4-methoxybenzyl-NHMe) | PhSO₂— | Intermediate 8 | {[3-chloro-4-(methyloxy)phenyl]methyl}amine/ Apin Chemicals | (I) | 482 | 2.56 |
| 126 | (cyclohexyl-NHMe) | (cyclopentyl-SO₂Me) | Intermediate 7 | cyclohexylamine/ Aldrich | (II) | 402 | 2.49 |
| 127 | (isobutyl-NHMe) | (cyclopentyl-SO₂Me) | Intermediate 7 | 2-methyl-1-propanamine/ Aldrich | (II) | 376 | 2.34 |

(a) Salt forms: HCl = hydrochloride (b) Isolation Method:

(I) Filtered off directly from the reaction mixture; it is thought that compounds isolated by this method are free bases, apart from Examples 101 and 125 which are thought to be hydrochloride salts.

(II) Mass Directed preparative HPLC Method A.

(c) No N,N-diisopropylethylamine was used in the preparation of Examples 101 and 125.

The following were made in a similar manner to Example 112:

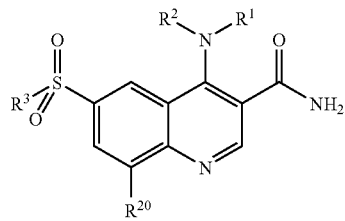

| Ex. No. (a) | $R^1R^2N-$ | $R^3SO_2-$ | $R^{20}-$ | Starting Material | Amine Reagent/ Source | Isolation Method (b) | LCMS $MH^+$ | LCMS $R_t$ (min) |
|---|---|---|---|---|---|---|---|---|
| 319 | 3-methyl-N,N-dimethylaniline | PhSO$_2-$ | H— | Intermediate 8 | N,3-dimethylaniline/ Acros | (II) | 432 | 2.97 |
| 320 | 3-chloro-N,N-dimethylaniline | PhSO$_2-$ | H— | Intermediate 8 | 3-chloro-N-methylaniline/ Maybridge | (II) | 452 | 3.00 |
| 321 TFA | N-methyl-3-aminoquinuclidine | PhSO$_2-$ | H— | Intermediate 8 | 3-aminoquinuclidine dihydrochloride/ Aldrich | (III) | 437 | 1.98 |
| 330 TFA | N-methyl-(3-pyridinylmethyl)amine | PhSO$_2-$ | Me— | Intermediate 16 | (3-pyridinylmethyl) amine/ Aldrich | (III) | 433 | 2.08 |
| 331 HCl | N-methyl-2-(aminomethyl)phenol | 4-MeO-Ph-SO$_2$(Me)— | H— | Intermediate 31 | 2-(aminomethyl) phenol/Buttpark | (I*) | 464 | 2.14 |

-continued

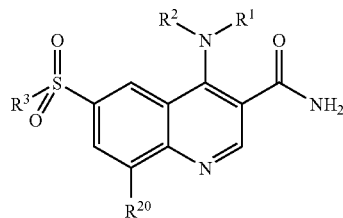

| Ex. No. (a) | R¹R²N— | R³SO₂— | R²⁰— | Starting Material | Amine Reagent/ Source | Isolation Method (b) | LCMS MH⁺ | LCMS R$_t$ (min) |
|---|---|---|---|---|---|---|---|---|
| 332 TFA | HN-CH₂-(3-pyridinyl), N-CH₃ | 4-MeO-C₆H₄-SO₂- (with CH₃ on ring) | H— | Intermediate 31 | (3-pyridinylmethyl)amine/ Aldrich | (III) | 449 | 2.06 |
| 333 TFA | HN-CH₂CH₂-(4-pyridinyl), N-CH₃ | 4-MeO-C₆H₄-SO₂- (with CH₃ on ring) | H— | Intermediate 31 | [2-(4-pyridinyl)ethyl]amine/ Maybridge | (III) | 463 | 1.93 |
| 334 HCl | (H₃C)₃C-NH- | MeSO₂— | Me— | Intermediate 33 | 2-methyl-2-propanamine/Aldrich | (IV) | 336 | 2.04 |

(a) Salt forms: HCl = hydrochloride
TFA = trifluoroacetate
(b) Isolation Method:
(I) Filtered off directly from the reaction mixture; it is thought that compounds isolated by this method are free bases.
(I*) No base is used in the reaction procedure. Filtered off directly from the reaction mixture; it is thought that compounds isolated by this method are hydrochloride salts.
(II) Mass Directed HPLC Method A; it is thought that compounds isolated by this method are free bases unless the R¹ or R³ groups contain basic moieties, in which case formate salts may be formed.
(III) Mass Directed HPLC Method B; it is thought that compounds isolated by this method are trifluoroacetate salts.
(IV) Mass Directed HPLC Method C; it is thought that compounds isolated by this method are hydrochloride salts.

Example 133

6-[(1,1-Dimethylethyl)thio]-4-{[3-(methyloxy)phenyl]amino}-3-quinolinecarboxamide

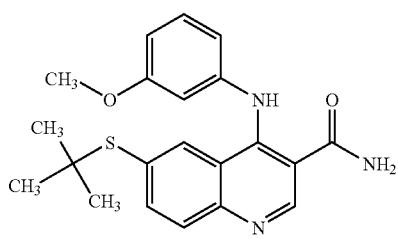

Intermediate 14 (0.050 g), potassium tert-butoxide (0.015 g) and tert-butylmercaptan (0.0135 ml) were added to a stirred solution of tris(dibenzylidineacetone)dipalladium (0) (0.007 g) and (oxydi-2,1-phenylene)bis(diphenylphosphine) (0.005 g) in toluene (2 ml), and the mixture was heated at 100° C. for 3.5 h and left to cool. The solvent was evaporated in vacuo to leave a brown solid (0.072 g), which was purified by Mass Directed Preparative HPLC (Method A) to give the title compound (0.008 g).

LC/MS R$_t$ 2.83 min m/z 382 [MH⁺].

Similarly prepared from Intermediate 14 were the following:

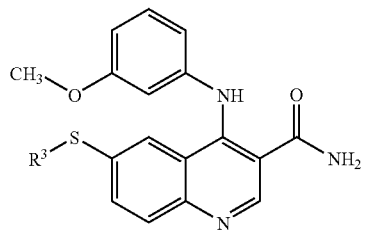

| Ex. No. | R³S— | Thiol reagent/ Source | Isolation Method (b) | LCMS MH+ | LCMS R_t (min) |
|---|---|---|---|---|---|
| 132 | cyclohexyl-S— | cyclohexanethiol/ Aldrich | (II) | 408 | 2.99 |
| 135 | MeC(O)NH-CH₂CH₂-S— | N-(2-mercaptoethyl) acetamide/Aldrich | (II) | 411 | 2.11 |
| 136 | 2,6-dichlorophenyl-S— | 2,6-dichlorobenzene thiol/Aldrich | (II) | 471 | 2.77 |
| 137 | (Me)₂CHCH₂-S— | 2-methyl-1-propanethiol/ Aldrich | (II) | 382 | 2.66 |
| 138 | 1,3-oxazol-2-yl-S— | 1,3-oxazole-2(3H)-thione/ Can. J. Chem., 1972, 50(18), 3082-3. | (II) | 393 | 2.29 |
| 139 | 5-methyl-1,3,4-oxadiazol-2-yl-S— | 5-methyl-1,3,4-oxadiazole-2(3H)-thione/ U.S. Pat. No. 5,670,526 A | (II) | 408 | 2.22 |
| 140 | PhCH₂-S— | phenylmethane thiol/ Aldrich | (II) | 416 | 2.86 |
| 141 | 4-F-C₆H₄-S— | 4-fluorobenzene thiol/ Aldrich | (IV) | 420 | 2.87 |
| 142 | 4-MeO-C₆H₄-S— | 4-(methyloxy) benzenethiol/ Aldrich | (II) | 432 | 2.90 |
| 143 | cyclopentyl-S— | cyclopentanethiol/ Aldrich | (I) | 394 | 2.98 |

-continued

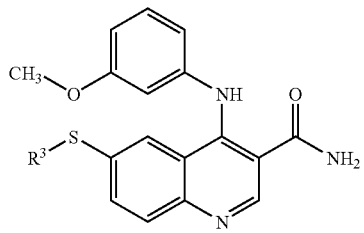

| Ex. No. | R³S— | Thiol reagent/ Source | Isolation Method (b) | LCMS MH+ | LCMS R$_t$ (min) |
|---|---|---|---|---|---|
| 144 | (phenyl-S-) | benzenethiol/ Aldrich | (I) | 402 | 2.96 |

(b) Isolation Method:
(I) Filtered off directly from the reaction mixture; it is thought that compounds isolated by this method are free bases.
(II) Mass Directed preparative HPLC Method A.
(IV) Purified by chromatography on silica gel, eluting with dichloromethane followed by ethyl acetate. It is thought that compounds isolated by this method are free bases.

The following were prepared in a similar manner to Example 133, using N,N-dimethylformamide as the reaction solvent:

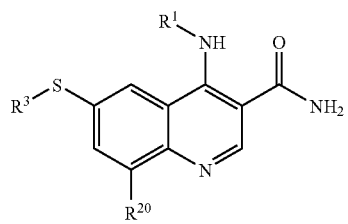

| Ex. No. | R¹NH— | R³S— | R²⁰— | Starting Material | Thiol Reagent/ Source | Isolation Method (b) | LCMS MH+ | LCMS R$_t$ (min) |
|---|---|---|---|---|---|---|---|---|
| 337 | 4-F,3-OMe-aniline | HOCH₂CH₂S— | Me— | Intermediate 35 | 2-mercaptoethanol/ Sigma | (I) | 402 | 2.19 |
| 338 | 4-F,3-OMe-aniline | 1,2,4-triazol-3-yl-S— | Me— | Intermediate 35 | 1,2,4-triazole-3-thiol/Aldrich | (I) | 425 | 2.12 |
| 339 | 4-F,3-OMe-aniline | 1-methyl-imidazol-2-yl-S— | Me— | Intermediate 35 | 1-methyl-2-mercaptoimidazole/ Aldrich | (I) | 438 | 2.15 |

-continued

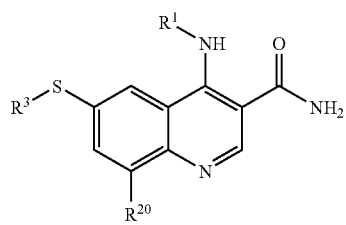

| Ex. No. | R¹NH— | R³S— | R²⁰— | Starting Material | Thiol Reagent/ Source | Isolation Method (b) | LCMS MH⁺ | LCMS R$_t$ (min) |
|---|---|---|---|---|---|---|---|---|
| 340 | 4-F, 3-OCH₃ phenyl N-methyl | 2-(methylthio)-imidazole | Me— | Intermediate 35 | 2-mercaptoimidazole/ Aldrich | (I) | 424 | 1.96 |
| 341 | 4-F, 3-OCH₃ phenyl N-methyl | 2-(methylthio)-benzimidazole | Me— | Intermediate 35 | 2-benzimidazolethiol/ Aldrich | (I) | 474 | 2.54 |
| 342 | 4-F, 3-OCH₃ phenyl N-methyl | 4-methyl-2-(methylthio)-oxazole | Me— | Intermediate 35 | 4-methyl-1,3-oxazole-2(3H)-thione J. Org. Chem., 1967, 32(7), 2079-81. | (I) | 439 | 2.67 |
| 343 | 4-F, 3-OCH₃ phenyl N-methyl | 2-furanyl methylthiomethyl | Me— | Intermediate 35 | 2-furanyl methanethiol/ Aldrich | (I) | 438 | 2.79 |
| 344 | 2,3-dihydrobenzofuran-4-yl N-methyl | Boc-NH-CH₂CH₂-S-methyl | Me— | Intermediate 36 | 1,1-dimethylethyl (2-mercaptoethyl) carbamate/Aldrich | (V) | 495 | 2.73 |
| 345 | 2,3-dihydrobenzofuran-4-yl N-methyl | N-Boc-4-(methylthio)piperidine | Me— | Intermediate 36 | 1,1-dimethylethyl 4-mercapto-1-piperidine-carboxylate/ U.S. Pat. No. 5,317,025 A | (V) | 535 | 3.22 |
| 563 | pyridin-3-yl N-methyl | tetrahydrofuran-3-yl methylthio | Me— | Intermediate 62 | tetrahydro-3-furanthiol/Advan. Carbohydrate Chem. (1963), 18 123-99 | (I) | 381 | 2.17 |

-continued

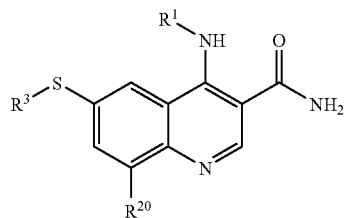

| Ex. No. | R¹NH— | R³S— | R²⁰— | Starting Material | Thiol Reagent/ Source | Isolation Method (b) | LCMS MH⁺ | LCMS $R_t$ (min) |
|---|---|---|---|---|---|---|---|---|
| 564 | 3-fluoro-N-methylanilino | (tetrahydrofuran-3-yl)thiomethyl | Me— | Intermediate 61 | tetrahydro-3-furanthiol/Advan. Carbohydrate Chem. (1963), 18 123-99 | (I) | 398 | 2.65 |
| 565 | 3-fluoro-N-methylanilino | (tetrahydro-2H-pyran-4-yl)thiomethyl | Me— | Intermediate 61 | tetrahydro-2H-pyran-4-thiol/ WO98/05635 | (I) | 412 | 2.70 |
| 566 | N-methyl-pyridin-3-ylamino | (tetrahydro-2H-pyran-4-yl)thiomethyl | Me— | Intermediate 62 | tetrahydro-2H-pyran-4-thiol/ WO98/05635 | (I) | 395 | 2.20 |
| 569 | N-methyl-pyridin-3-ylamino | tert-butyl 4-(methylthio)piperidine-1-carboxylate | Me— | Intermediate 62 | 1,1-dimethylethyl 4-mercapto-1-piperidine carboxylate/U.S. Pat. No. 5,317,025 A | (I) | 494 | 2.80 |
| 570 | 3-fluoro-N-methylanilino | N-(2-(methylthio)ethyl)acetamide | Me— | Intermediate 61 | N-(2-mercaptoethyl)acetamide/Aldrich | (I) | 413 | 2.20 |
| 572 | N-methyl-pyridin-3-ylamino | N-(2-(methylthio)ethyl)acetamide | Me— | Intermediate 62 | N-(2-mercaptoethyl)-acetamide/ Aldrich | (V) | 396 | 1.90 |
| 516 | 4-fluoro-3-methoxy-N-methylanilino | tert-butyl 4-(methylthio)piperidine-1-carboxylate | Me— | Intermediate 35 | 1,1-dimethylethyl 4-mercapto-1-piperidine carboxylate/ U.S. Pat. No. 5,317,025A | (V) | 541 | 3.10 |

-continued

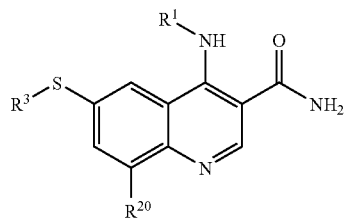

| Ex. No. | R¹NH— | R³S— | R²⁰— | Starting Material | Thiol Reagent/ Source | Isolation Method (b) | LCMS MH⁺ | LCMS $R_t$ (min) |
|---|---|---|---|---|---|---|---|---|
| 517 | 4-fluoro-3-methoxy-N-methylaniline | 1,1-dimethylethyl (2-mercaptoethyl) carbamate | Me— | Intermediate 35 | 1,1-dimethylethyl (2-mercaptoethyl) carbamate/Aldrich | (V) | 501 | 3.68 |
| 528 | 2,3-dihydrobenzofuran-4-ylamine | HO-CH₂CH₂-S-Me | Me— | Intermediate 36 | 2-mercaptoethanol/ Aldrich | (I) | 396 | 2.20 |
| 603 | 3-fluoro-N-methylaniline | 1,1-dimethylethyl (2-mercaptoethyl) carbamate | Me— | Intermediate 61 | 1,1-dimethylethyl (2-mercaptoethyl) carbamate | (I) | 471 | 2.80 |
| 634 | N-methylpyridin-3-ylamine | Me-CH₂-S-Me | Me— | Intermediate 62 | ethanethiol/ Aldrich | (I) | 339 | 2.32 |
| 635 | N-methylpyridin-3-ylamine | Me-CH₂CH₂-S-Me | Me— | Intermediate 62 | 1-propanethiol/ Aldrich | (I) | 353 | 2.71 |
| 636 | N-methylpyridin-3-ylamine | (Me)₂CH-S-Me | Me— | Intermediate 62 | 2-propanethiol/ Aldrich | (I) | 353 | 2.47 |
| 637 | N-methylpyridin-3-ylamine | (Me)₃C-S-Me | Me— | Intermediate 62 | 2-methyl-2-propanethiol/ Aldrich | (I) | 367 | 2.58 |

-continued

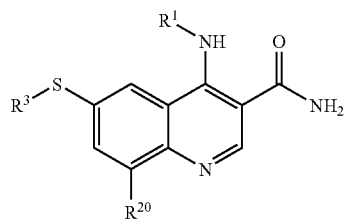

| Ex. No. | R¹NH— | R³S— | R²⁰— | Starting Material | Thiol Reagent/ Source | Isolation Method (b) | LCMS MH⁺ | LCMS R$_t$ (min) |
|---|---|---|---|---|---|---|---|---|
| 638 | 3-pyridyl-CH(NH)- | Me-CH₂-S- | Cl— | Intermediate 96 | ethanethiol/ Aldrich | (I) | 359 | 2.59 |
| 639 | 3-pyridyl-CH(NH)- | Me-CH₂CH₂-S- | Cl— | Intermediate 96 | 1-propanethiol/ Aldrich | (I) | 373 | 2.76 |
| 640 | 3-pyridyl-CH(NH)- | Me-CH(Me)-S- | Cl— | Intermediate 96 | 2-propanethiol/ Aldrich | (I) | 373 | 2.71 |
| 641 | 3-pyridyl-CH(NH)- | Me₃C-S- | Cl— | Intermediate 96 | 2-methyl-2-propanethiol/ Aldrich | (I) | 387 | 2.93 |
| 642 | 5-chloro-3-pyridyl-CH(NH)- | Me-CH₂-S- | Me— | Intermediate 62 | ethanethiol/ Aldrich | (I) | 373 | 2.81 |
| 643 | 5-chloro-3-pyridyl-CH(NH)- | Me-CH₂CH₂-S- | Me— | Intermediate 97 | 1-propanethiol/ Aldrich | (I) | 387 | 3.06 |
| 644 | 5-chloro-3-pyridyl-CH(NH)- | Me-CH(Me)-S- | Me— | Intermediate 97 | 2-propanethiol/ Aldrich | (I) | 387 | 2.95 |

-continued

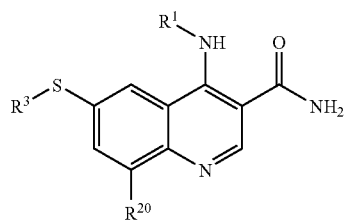

| Ex. No. | R¹NH— | R³S— | R²⁰— | Starting Material | Thiol Reagent/ Source | Isolation Method (b) | LCMS MH⁺ | LCMS R$_t$ (min) |
|---|---|---|---|---|---|---|---|---|
| 645 | 5-chloro-pyridin-3-yl-methylamino | tert-butylthio (Me₃C-S-) | Me— | Intermediate 97 | 2-methyl-2-propanethiol/ Aldrich | (I) | 401 | 3.16 |
| 646 | 5-chloro-pyridin-3-yl-methylamino | ethylthio (MeCH₂-S-) | Cl— | Intermediate 100 | ethanethiol/ Aldrich | (I) | 393 | 3.1 |
| 647 | 5-chloro-pyridin-3-yl-methylamino | n-propylthio | Cl— | Intermediate 100 | 1-propanethiol/ Aldrich | (I) | 407 | 3.3 |
| 648 | 5-chloro-pyridin-3-yl-methylamino | isopropylthio | Cl— | Intermediate 100 | 2-propanethiol/ Aldrich | (I) | 407 | 3.25 |
| 649 | 5-chloro-pyridin-3-yl-methylamino | tert-butylthio | Cl— | Intermediate 100 | 2-methyl-2-propanethiol/ Aldrich | (I) | 421 | 3.33 |
| 650 | 5-fluoro-pyridin-3-yl-methylamino | ethylthio | Me— | Intermediate 98 | ethanethiol/ Aldrich | (I) | 357 | 2.59 |
| 651 | 5-fluoro-pyridin-3-yl-methylamino | n-propylthio | Me— | Intermediate 98 | 1-propanethiol/ Aldrich | (I) | 371 | 2.84 |

-continued

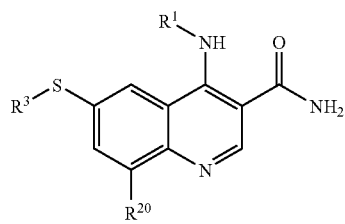

| Ex. No. | R¹NH— | R³S— | R²⁰— | Starting Material | Thiol Reagent/ Source | Isolation Method (b) | LCMS MH⁺ | LCMS R$_t$(min) |
|---|---|---|---|---|---|---|---|---|
| 652 | 5-fluoro-3-(methylamino)pyridine | isopropyl methyl sulfide | Me— | Intermediate 98 | 2-propanethiol/ Aldrich | (I) | 371 | 2.84 |
| 653 | 5-fluoro-3-(methylamino)pyridine | tert-butyl methyl sulfide | Me— | Intermediate 98 | 2-methyl-2-propanethiol/ Aldrich | (I) | 385 | 2.94 |
| 654 | 5-fluoro-3-(methylamino)pyridine | ethyl methyl sulfide | Cl— | Intermediate 99 | ethanethiol/ Aldrich | (I) | 377 | 2.88 |
| 655 | 5-fluoro-3-(methylamino)pyridine | propyl methyl sulfide | Cl— | Intermediate 99 | 1-propanethiol/ Aldrich | (I) | 391 | 3.07 |
| 656 | 5-fluoro-3-(methylamino)pyridine | isopropyl methyl sulfide | Cl— | Intermediate 99 | 2-propanethiol/ Aldrich | (I) | 391 | 3.03 |
| 657 | 5-fluoro-3-(methylamino)pyridine | tert-butyl methyl sulfide | Cl— | Intermediate 99 | 2-methyl-2-propanethiol/ Aldrich | (I) | 405 | 3.14 |
| 658 | 1-ethyl-5-(methylamino)pyrazole | ethyl methyl sulfide | Cl— | Intermediate 102 | ethanethiol/ Aldrich | (I) | 376 | 2.94 |

-continued

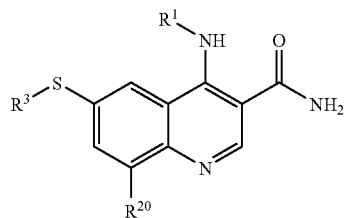

| Ex. No. | R¹NH— | R³S— | R²⁰— | Starting Material | Thiol Reagent/ Source | Isolation Method (b) | LCMS MH⁺ | LCMS R$_t$(min) |
|---|---|---|---|---|---|---|---|---|
| 659 | Me-ethyl-pyrazole-NH | Me-CH₂CH₂-S-Me | Cl— | Intermediate 102 | 1-propanethiol/ Aldrich | (I) | 390 | 3.08 |
| 660 | Me-ethyl-pyrazole-NH | Me₂CH-S-Me | Cl— | Intermediate 102 | 2-propanethiol/ Aldrich | (I) | 390 | 3.02 |
| 661 | Me-ethyl-pyrazole-NH | Me₃C-S-Me | Cl— | Intermediate 102 | 2-methyl-2-propanethiol/ Aldrich | (I) | 404 | 3.21 |
| 662 | Me-ethyl-pyrazole-NH | Me-CH₂-S-Me | Me— | Intermediate 101 | ethanethiol/ Aldrich | (I) | 356 | 2.5 |
| 663 | Me-ethyl-pyrazole-NH | Me-CH₂CH₂-S-Me | Me— | Intermediate 101 | 1-propanethiol/ Aldrich | (I) | 370 | 2.65 |
| 664 | Me-ethyl-pyrazole-NH | Me₂CH-S-Me | Me— | Intermediate 101 | 2-propanethiol/ Aldrich | (I) | 370 | 2.61 |
| 665 | Me-ethyl-pyrazole-NH | Me₃C-S-Me | Me— | Intermediate 101 | 2-methyl-2-propanethiol/ Aldrich | (I) | 384 | 2.89 |

-continued

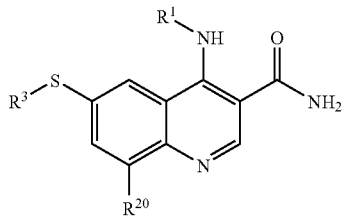

| Ex. No. | R¹NH— | R³S— | R²⁰— | Starting Material | Thiol Reagent/ Source | Isolation Method (b) | LCMS MH⁺ | LCMS $R_t$ (min) |
|---|---|---|---|---|---|---|---|---|
| 681 | 3-fluoro-N-methylanilino | N-(2-methylthioethyl)-N-methylacetamido-S- | Me— | Intermediate 101 | N-(2-mercaptoethyl)-N-methylacetamide/ Tetrahedron 1986, 42 (5), 1449 | (I) | 427 | 2.30 |

(b) Isolation Method:
(I) These were purified by SCX column, eluting with ammonia/methanol.
(V) These were purified by chromatography on silica gel (eluting with ethyl acetate/cyclohexane) followed by trituration with cyclohexane to give the pure product; it is thought that compounds isolated by this method are free bases.

Example 577

4-(2,3-Dihydro-1-benzofuran-4-ylamino)-8-methyl-6-(methylthio)-3-quinolinecarboxamide

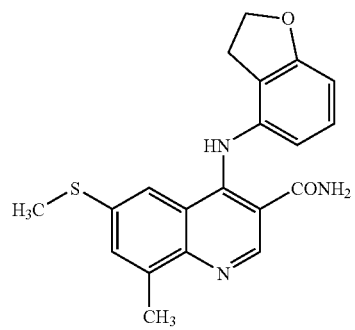

A stirred mixture of Intermediate 36 (0.2 g), sodium thiomethoxide (0.058 g), tris(dibenzylideneacetone)dipalladium(0) (0.076 g), (oxidi-2,1-phenylene)-bis(diphenylphosphine) (0.045 g), and potassium tert-butoxide (0.047 g) in N,N-dimethylformamide (10 ml) was heated at 100° C. under nitrogen for 18 h. The cooled reaction mixture was applied directly to an SCX cartridge (10 g) and eluted with methanol (150 ml) followed by 2M ammonia in methanol (100 ml). Evaporation of the methanol/ammonia fraction gave the title compound as a yellow solid (0.13 g).

LC/MS $R_t$ 2.48 min, m/z 366 [MH⁺]

The following were prepared in a similar manner to Example 577, but without adding potassium tert-butoxide to the reaction mixture:

| Ex. No. | R¹NH— | R²⁰— | Starting Material | LCMS MH⁺ | LCMS $R_t$ (min) |
|---|---|---|---|---|---|
| 577 | 2,3-dihydrobenzofuran-4-yl-N-methylamino | Me— | Intermediate 36 | 382 | 2.00 |
| 604 | 4-fluoro-3-methoxy-N-methylanilino | Et— | Intermediate 74 | 388 | 2.57 |
| 605 | 3-fluoro-N-methylanilino | Et— | Intermediate 75 | 356 | 2.76 |

-continued

Structure: 4-(R¹NH)-6-(methylthio)-8-R²⁰-quinoline-3-carboxamide

| Ex. No. | R¹NH— | R²⁰— | Starting Material | LCMS MH⁺ | LCMS R$_t$ (min) |
|---|---|---|---|---|---|
| 606 | 3-Cl-phenyl-NHMe | Et— | Intermediate 76 | 372 | 2.95 |
| 607 | 3-CN-phenyl-NHMe | Et— | Intermediate 77 | 363 | 2.71 |
| 608 | 3-Me-phenyl-NHMe | Et— | Intermediate 78 | 352 | 2.65 |
| 609 | 1-Me-indazol-6-yl-NHMe | Et— | Intermediate 79 | 392 | 2.44 |
| 610 | 2,3-dihydrobenzofuran-4-yl-NHMe | Et— | Intermediate 80 | 380 | 2.62 |
| 611 | pyridin-3-yl-NHMe | Et— | Intermediate 81 | 339 | 2.2 |
| 612 | 5-F-pyridin-3-yl-NHMe | Et— | Intermediate 82 | 357 | 2.55 |
| 613 | 5-Cl-pyridin-3-yl-NHMe | Et— | Intermediate 83 | 373 | 2.73 |
| 614 | 5-Cl-pyridin-3-yl-NHMe | F— | Intermediate 85 | 363 | 2.69 |
| 615 | pyridin-3-yl-NHMe | F— | Intermediate 86 | 329 | 2.16 |
| 616 | 5-F-pyridin-3-yl-NHMe | F— | Intermediate 84 | 347 | 2.53 |
| 617 | 3-F-phenyl-NHMe | F— | Intermediate 89 | 346 | 2.87 |
| 618 | 3-Cl-phenyl-NHMe | F— | Intermediate 90 | 363 | 3.06 |
| 619 | 3-Me-phenyl-NHMe | F— | Intermediate 91 | 342 | 2.91 |

-continued

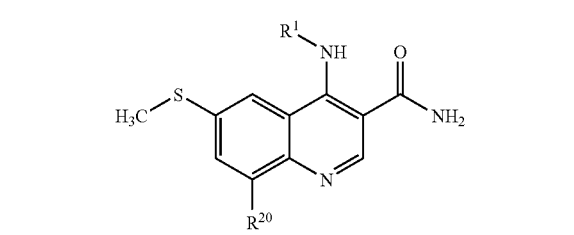

| Ex. No. | R¹NH— | R²⁰— | Starting Material | LCMS MH⁺ | LCMS $R_t$ (min) |
|---|---|---|---|---|---|
| 620 | 3-(methylamino)benzonitrile | F— | Intermediate 92 | 353 | 2.77 |
| 621 | 1-methyl-6-(methylamino)-1H-indazole | F— | Intermediate 93 | 382 | 2.56 |
| 622 | 4-fluoro-3-methoxy-N-methylaniline | F— | Intermediate 94 | 376 | 2.88 |
| 623 | N-methyl-2,3-dihydrobenzofuran-4-amine | F— | Intermediate 88 | 370 | 2.81 |
| 682 | 3,N-dimethylaniline | Cl— | Intermediate 38 | 358 | 3.27 |
| 683 | 4-fluoro-3-methoxy-N-methylaniline | Cl— | Intermediate 39 | 392 | 3.06 |

-continued

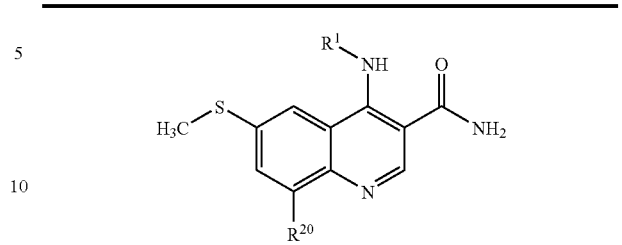

| Ex. No. | R¹NH— | R²⁰— | Starting Material | LCMS MH⁺ | LCMS $R_t$ (min) |
|---|---|---|---|---|---|
| 684 | N-methyl-2,3-dihydrobenzofuran-4-amine | Cl— | Intermediate 40 | 386 | 3.10 |
| 685 | 3-(methylamino)benzonitrile | Cl— | Intermediate 41 | 369 | 3.01 |
| 686 | 3-fluoro-N-methylaniline | Cl— | Intermediate 42 | 362 | 3.20 |
| 687 | 1-methyl-6-(methylamino)-1H-indazole | Cl— | Intermediate 43 | 398 | 2.82 |

Example 134

4-{[3-(Methyloxy)phenyl]amino}-6-({[4-(methyloxy)phenyl]methyl}thio)-3-quinolinecarboxamide

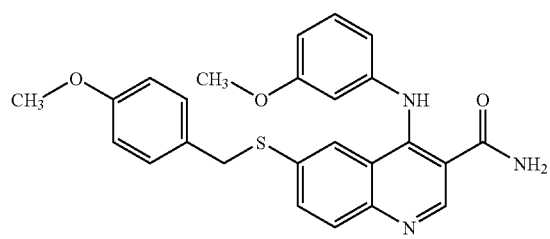

Intermediate 14 (0.020 g), potassium tert-butoxide (0.0061 g) and [4-(methyloxy) phenyl]methanethiol (available from Aldrich) (0.007 ml) were added to a stirred solution of tris(dibenzylidineacetone)dipalladium(0) (0.002 g) and (oxydi-2,1-phenylene)bis (diphenylphosphine) (0.002 g) in N,N-dimethylformamide (1.5 ml), and the mixture was heated under microwave irradiation at 60° C. for 8 min. The solvent was evaporated in vacuo, and the residue purified by Mass Directed Preparative HPLC (Method A) to give the title compound (0.0048 g).

LC/MS $R_t$ 2.93 min m/z 446 [MH$^+$]

Example 129

6-[(1,1-Dimethylethyl)sulfonyl]-4-{[3-(methyloxy)phenyl]amino}-3-quinolinecarboxamide

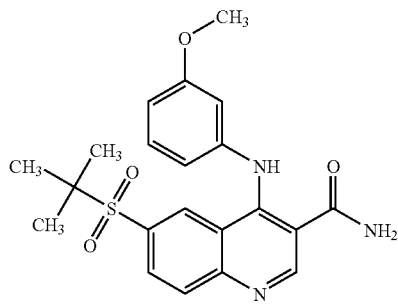

Example 133 (0.010 g) was dissolved in N,N-dimethylformamide (2 ml) and anisole (0.013 ml) was added. Oxone (0.075 g) was added and the mixture stirred for 16 h at room temperature. After quenching with 1M aqueous sodium sulphite, the mixture was extracted with dichloromethane; the organic layer was dried over magnesium sulphate and evaporated in vacuo to give a yellow solid. Purification by mass directed HPLC (Method A) gave the title compound (0.005 g).

LC/MS $R_t$ 2.48 min m/z 414 [MH$^+$].

Similarly prepared were the following:

| Ex. No. | R³SO₂— | Starting Material | Isolation Method (b) | LCMS MH⁺ | LCMS $R_t$ (min) |
|---|---|---|---|---|---|
| 128 | MeO-C₆H₄-S(O)₂- | Example 142 | (II) | 464.09 | 2.83 |
| 130 (a) | Me-C(O)-NH-CH₂CH₂-S(O)₂- | Example 135 | (II) | 443.1 | 2.11 |

(a) No anisole was used in the reaction mixture in this Example.
(b) Isolation Method:
(II) Mass Directed preparative HPLC (Method A).

The following were prepared in a similar manner to Example 129, but without the addition of anisole to the reaction mixture:

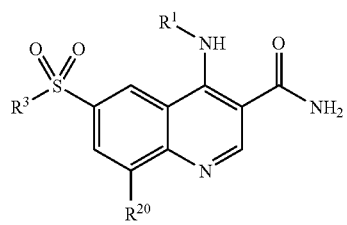

| Ex. No. (a) | R¹NH— | R³SO₂— | R²⁰— | Starting Material | Isolation Method (b) | LCMS MH⁺ | LCMS R$_t$ (min) |
|---|---|---|---|---|---|---|---|
| 346 HCl | H₃C-O-, F-, -NH-CH₃ (phenyl) | HO-CH₂CH₂-SO₂- | Me— | Example 337 | (IV) | 434 | 2.10 |
| 347 HCl | H₃C-O-, F-, -NH-CH₃ (phenyl) | 1,2,4-triazol-3-yl-SO₂- | Me— | Example 338 | (IV) | 457 | 2.30 |
| 348 HCl | H₃C-O-, F-, -NH-CH₃ (phenyl) | 1-methylimidazol-2-yl-SO₂- | Me— | Example 339 | (IV) | 470 | 2.46 |
| 349 HCl | H₃C-O-, F-, -NH-CH₃ (phenyl) | imidazol-2-yl-SO₂- | Me— | Example 340 | (IV) | 456 | 2.27 |
| 350 HCl | H₃C-O-, F-, -NH-CH₃ (phenyl) | benzimidazol-2-yl-SO₂- | Me— | Example 341 | (IV) | 506 | 2.79 |

-continued

| Ex. No. (a) | R¹NH— | R³SO₂— | R²⁰— | Starting Material | Isolation Method (b) | LCMS MH⁺ | LCMS R$_t$ (min) |
|---|---|---|---|---|---|---|---|
| 351 HCl | 4-fluoro-3-methoxy-N-methylanilino | furan-2-ylmethylsulfonyl | Me— | Example 343 | (IV) | 470 | 2.66 |
| 352 | 2,3-dihydrobenzofuran-4-yl(methyl)amino | 1-Boc-piperidin-4-ylsulfonyl | Me— | Example 345 | (V) | 567 | 3.08 |
| 353 | 2,3-dihydrobenzofuran-4-yl(methyl)amino | 2-(Boc-amino)ethylsulfonyl | Me— | Example 344 | (VI) | 527.5 | 2.76 |
| 369 HCl | 3-methyl-N-methylanilino | MeSO₂— | Cl— | Example 682 | (IV) | 390 | 2.77 |
| 370 HCl | 4-fluoro-3-methoxy-N-methylanilino | MeSO₂— | Cl— | Example 683 | (IV) | 424 | 2.63 |
| 371 HCl | 2,3-dihydrobenzofuran-4-yl(methyl)amino | MeSO₂— | Cl— | Example 684 | (IV) | 418 | 2.77 |

-continued

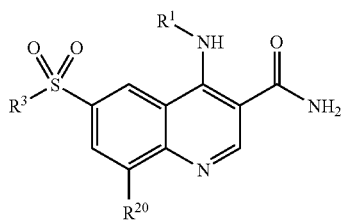

| Ex. No. (a) | R¹NH— | R³SO₂— | R²⁰— | Starting Material | Isolation Method (b) | LCMS MH⁺ | LCMS R_t (min) |
|---|---|---|---|---|---|---|---|
| 372 HCl | 3-cyano-N-methylanilino | MeSO₂— | Cl— | Example 685 | (IV) | 401 | 2.57 |
| 373 HCl | 3-fluoro-N-methylanilino | MeSO₂— | Cl— | Example 686 | (IV) | 394 | 2.70 |
| 374 HCl | 1-methyl-6-(methylamino)indazol-1-yl | MeSO₂— | Cl— | Example 687 | (IV) | 430 | 2.51 |
| 478 | 3-methoxy-N-methylanilino | 3-(N,N-dimethylcarbamoyl)phenylsulfonyl | Me— | Intermediate 29 | (VI) | 519 | 2.55 |
| 602 | 3-fluoro-N-methylanilino | t-butoxycarbonylaminoethylsulfonyl | Me— | Example 603 | (VII) | 503 | 2.90 |

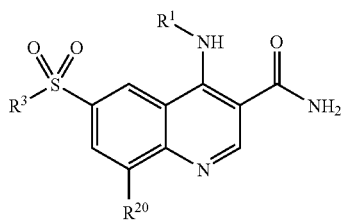

| Ex. No. (a) | R¹NH— | R³SO₂— | R²⁰— | Starting Material | Isolation Method (b) | LCMS MH⁺ | LCMS $R_t$ (min) |
|---|---|---|---|---|---|---|---|
| 515 | H₃C-O-C₆H₄-NH- (3-methoxyphenylamino) | 4-pyridyl-SO₂- | Me— | Example 562 | (VI) | 449 | 2.60 |

(a) Salt forms: HCl = hydrochloride.
(b) Isolation Method:
(IV) Mass Directed preparative HPLC (Method C).
(V) Column chromatography on silica gel.
(VI) Aqueous work-up.
(VII) Trituration from acetonitrile.

The following were prepared in a similar manner to Example 129 without the addition of anisole to the reaction mixture:

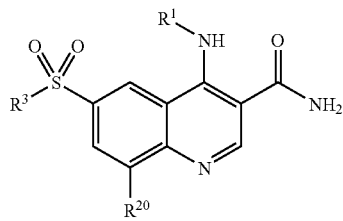

| Ex. No. (a) | R¹NH— | R²⁰— | R³SO₂— | Starting Material | Isolation Method (b) | LCMS MH⁺ | LCMS $R_t$ (min) |
|---|---|---|---|---|---|---|---|
| 522 | H₃C-O, F-phenyl-NH- (4-fluoro-3-methoxyphenylamino) | Me— | Me-O-CH₂CH₂-SO₂- | Example 521 | (II) | 448 | 2.33 |
| 591 HCl | H₃C-O, F-phenyl-NH- (4-fluoro-3-methoxyphenylamino) | Et— | MeSO₂— | Example 604 | (IV) | 418 | 2.39 |

-continued

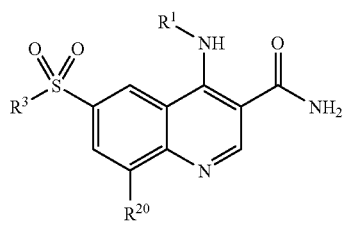

| Ex. No. (a) | R¹NH— | R²⁰— | R³SO₂— | Starting Material | Isolation Method (b) | LCMS MH⁺ | LCMS R$_t$(min) |
|---|---|---|---|---|---|---|---|
| 592 HCl | 3-fluorophenyl(methyl)amino | Et— | MeSO₂— | Example 605 | (IV) | 388 | 2.51 |
| 593 HCl | 3-cyanophenyl(methyl)amino | Et— | MeSO₂— | Example 607 | (IV) | 395 | 2.46 |
| 594 HCl | 5-fluoropyridin-3-yl(methyl)amino | Et— | MeSO₂— | Example 612 | (IV) | 389 | 2.32 |
| 595 HCl | 5-chloropyridin-3-yl(methyl)amino | Et— | MeSO₂— | Example 613 | (IV) | 405 | 2.47 |
| 596 HCl | 3-methylphenyl(methyl)amino | Et— | MeSO₂— | Example 608 | (IV) | 384 | 2.41 |
| 597 HCl | 3-chlorophenyl(methyl)amino | Et— | MeSO₂— | Example 606 | (IV) | 404 | 2.70 |

-continued
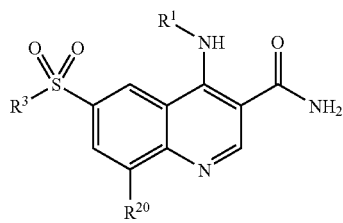
| Ex. No. (a) | R¹NH— | R²⁰— | R³SO₂— | Starting Material | Isolation Method (b) | LCMS MH⁺ | LCMS R$_t$ (min) |
|---|---|---|---|---|---|---|---|
| 598 HCl | 1-methylindazol-6-yl-NH— (N-CH₃) | Et— | MeSO₂— | Example 609 | (IV) | 424 | 2.34 |
| 599 HCl | 2,3-dihydrobenzofuran-4-yl-NH— | Et— | MeSO₂— | Example 610 | (IV) | 412 | 2.44 |
| 600 HCl | pyridin-3-yl-NH— | Et— | MeSO₂— | Example 611 | (IV) | 370 | 1.99 |
| 624 | 2,3-dihydrobenzofuran-4-yl-NH— | F— | MeSO₂— | Example 623 | (II) | 402 | 2.52 |
| 625 | 3-fluorophenyl-NH— | F— | MeSO₂— | Example 617 | (II) | 378 | 2.54 |
| 626 | 3-chlorophenyl-NH— | F— | MeSO₂— | Example 618 | (II) | 395 | 2.70 |

-continued
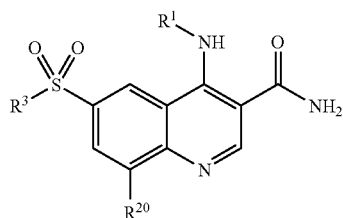
| Ex. No. (a) | R¹NH— | R²⁰— | R³SO₂— | Starting Material | Isolation Method (b) | LCMS MH⁺ | LCMS R_t (min) |
|---|---|---|---|---|---|---|---|
| 627 | 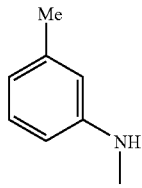 | F— | MeSO₂— | Example 619 | (II) | 374 | 2.61 |
| 628 | 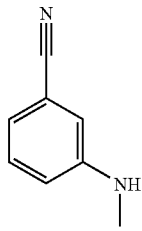 | F— | MeSO₂— | Example 620 | (II) | 385 | 2.42 |
| 629 | 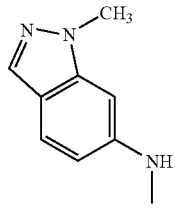 | F— | MeSO₂— | Example 621 | (II) | 414 | 2.27 |
| 630 | 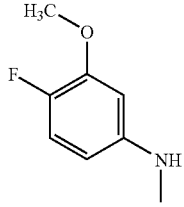 | F— | MeSO₂— | Example 622 | (II) | 408 | 2.45 |

-continued

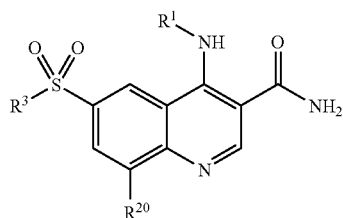

| Ex. No. (a) | R¹NH— | R²⁰— | R³SO₂— | Starting Material | Isolation Method (b) | LCMS MH⁺ | LCMS R$_t$ (min) |
|---|---|---|---|---|---|---|---|
| 631 | 3-(methylamino)pyridine | F— | MeSO₂— | Example 615 | (II) | 361 | 1.91 |
| 632 | 5-chloro-3-(methylamino)pyridine | F— | MeSO₂— | Example 614 | (II) | 395 | 2.32 |
| 633 | 5-fluoro-3-(methylamino)pyridine | F— | MeSO₂— | Example 616 | (II) | 379 | 2.09 |

(a) Salt forms: HCl = hydrochoride.
(b) Isolation method:
(II) Mass Directed preparative HPLC (Method A).
(IV) Mass Directed preparative HPLC (Method C).

Example 184

8-Methyl-4-{[3-(methyloxy)phenyl]amino}-6-(phenylsulfonyl)-3-quinolinecarboxamide hydrochloride

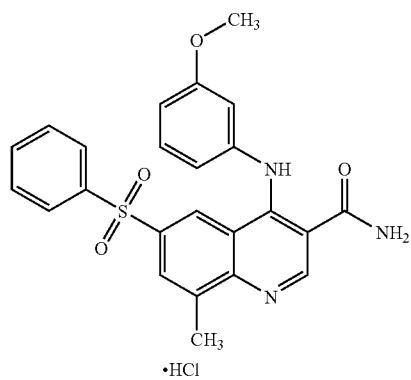

Intermediate 16 (0.036 g) was suspended in acetonitrile (2 ml), 3-methoxyaniline (available from Aldrich) (0.012 g) was added, and the mixture was heated under reflux for 16 h. After cooling to room temperature the mixture was filtered and the residue dried to give the title compound as a beige solid (0.020 g).

LC/MS $R_t$ 2.86 min m/z 448 [MH$^+$]
Similarly prepared was:

Example 186

7-Methyl-4-{[3-(methyloxy)phenyl]amino}-6-(methylsulfonyl)-3-quinolinecarboxamide hydrochloride

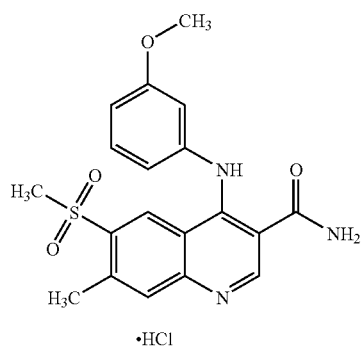

Intermediate 17 (0.058 g) was suspended in acetonitrile (2 ml), 3-methoxyaniline (0.024 g) (available from Aldrich) was added, and the mixture was heated under reflux for 4 h. After cooling to room temperature the mixture was filtered and the residue dried to give the title compound as a beige solid (0.042 g).

LC/MS $R_t$ 2.21 min m/z 386 [MH$^+$]

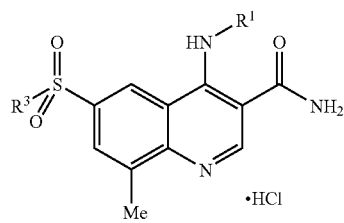

| Ex. No. (a) | R$^1$NH— | R$^3$SO$_2$— | Starting Material | Amine Reagent/ Source | Isolation Method (b) | LCMS MH$^+$ | LCMS R$_t$ (min) |
|---|---|---|---|---|---|---|---|
| 185 HCl | ![structure] | PhSO$_2$— | Intermediate 16 | 4-fluoro-3-methoxyaniline/ Apollo-Chem | (I) | 466 | 2.89 |

(b) Isolation method:
(I) Filtered off from the reaction mixture.

Example 335

4-[(3-Aminophenyl)amino]-6-(methylsulfonyl)-3-quinolinecarboxamide trifluoroacetate

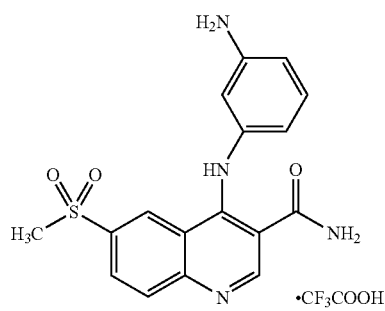

To a stirred mixture of Example 187 (0.130 g) in dichloromethane (5 ml) was added trifluoroacetic acid (1 ml). The mixture was stirred at 20° C. for 1 h and then the solvent was removed in vacuo to give the title compound as a yellow gum (0.100 g).

LC/MS $R_t$ 1.87 min m/z 357 [MH$^+$]

Similarly prepared from example 188 was:

Example 336

4-{[3-(Aminomethyl)phenyl]amino}-6-(methylsulfonyl)-3-quinolinecarboxamide trifluoroacetate

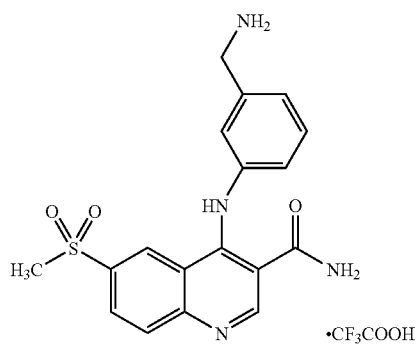

Example 376

1,1-Dimethylethyl 4-({3-(aminocarbonyl)-8-methyl-4-[(1-methyl-1H-benzimidazol-6-yl)amino]-6-quinolinyl}sulfonyl)-1-piperidinecarboxylate

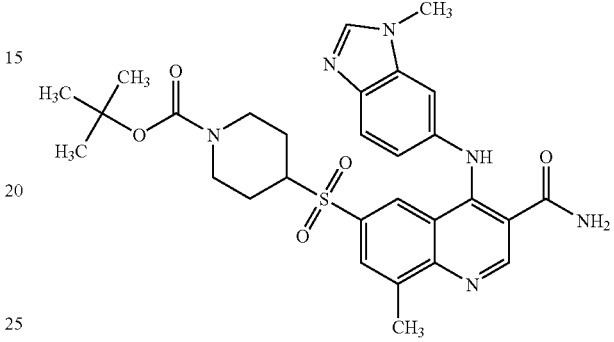

A mixture containing Intermediate 44 (0.500 g), 1,1-dimethylethyl 4-mercapto-1-piperidinecarboxylate (0.442 g, synthesised according to U.S. Pat. No. 5,317,025A), potassium tert-butoxide (0.248 g), tris(dibenzylideneacetone)dipalladium (0.093 g) and (oxydi-2,1-phenylene)bis(diphenylphosphine) (0.091 g) was dissolved in N,N-dimethylformamide (20 ml) and stirred under an atmosphere of nitrogen at 100° C. for 2 h. The solvents were concentrated in vacuo and the residue partitioned between ethyl acetate (100 ml) and water (100 ml). The organic extract was washed with sodium bicarbonate solution followed by brine, dried over magnesium sulfate and concentrated in vacuo to an orange solid. This was purified by flash chromatography on silica gel eluting with a gradient of ethanol (0% to 10%) in ethyl acetate, to give the intermediate sulphide 1,1-dimethylethyl 4-({3-(aminocarbonyl)-8-methyl-4-[(1-methyl-1H-benzimidazol-6-yl)amino]-6-quinolinyl}thio)-1-piperidinecarboxylate as a yellow solid (0.375 g).

LC/MS $R_t$ 2.63 min, m/z 547 [MH$^+$]

Oxone (1.6 g) was added to a solution of the sulphide (0.370 g) in N,N-dimethylformamide (10 ml). The mixture was stirred at room temperature for 1 h and was quenched with a solution of sodium sulphite (4 g) in water (150 ml). The mixture was extracted with ethyl acetate (2×100 ml) and the combined organic suspension washed with water (2×100 ml) and extracted in vacuo to a pale yellow solid. This was purified by recrystallisation from boiling methanol to give the title compound as a pale yellow powder (0.265 g).

LC/MS $R_t$ 2.47 min, m/z 579 [MH$^+$]

Similarly prepared were the following:

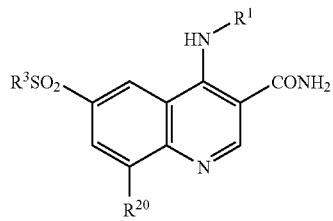

| Ex. No. (a) | R¹NH— | R³SO₂— | R²⁰— | Starting Material | Thiol Reagent/ Source |
|---|---|---|---|---|---|
| 354 | 3-methoxy-N-methylanilino | 4-(methylsulfonyl)benzoic acid methyl ester | H— | Intermediate 37 | Methyl 4-mercaptobenzoate/ Toronto Research Chemicals |
| 355 | 3-methoxy-N-methylanilino | 3-(methylsulfonyl)benzoic acid methyl ester | H— | Intermediate 37 | Methyl 3-mercaptobenzoate/ Toronto Research Chemicals |
| 356 | 3-methoxy-N-methylanilino | 3-methylphenyl methyl sulfone | H— | Intermediate 37 | 3-methylbenzene thiol/ Aldrich |
| 357 HCl | 3-methoxy-N-methylanilino | 3,4-dimethylphenyl methyl sulfone | H— | Intermediate 14 | 3,4-dimethylthiophenol/Aldrich |
| 358 | 3-methoxy-N-methylanilino | 3-fluorophenyl methyl sulfone | H— | Intermediate 14 | 3-fluorobenzene thiol/Avocado |
| 359 HCl | 3-methoxy-N-methylanilino | 4-(trifluoromethyl)phenyl methyl sulfone | H— | Intermediate 14 | 4-(trifluoromethyl) thiophenol/ Fluorochem |

-continued
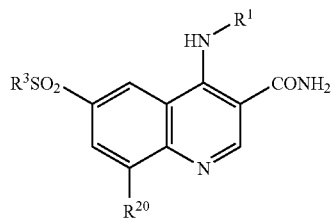
| | | | | |
|---|---|---|---|---|
| 361 | 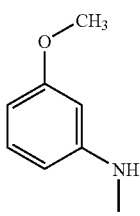 | 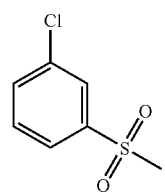 | H— | Intermediate 37 3-chlorothiophenol/ Adrich |
| 362 | 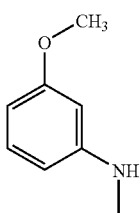 | 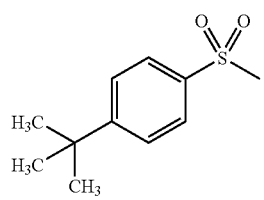 | H— | Intermediate 37 4-tert-butylthio phenol/ Lancaster |
| 363 | 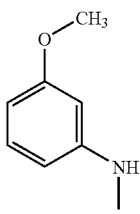 | 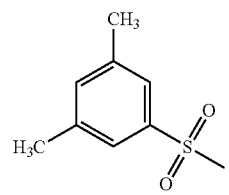 | H— | Intermediate 37 3,5-dimethyl benzenethiol/ Aldrich |
| 364 | 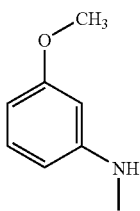 | 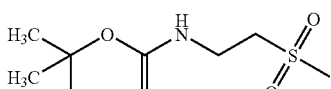 | H— | Intermediate 37 1,1-dimethylethyl (2-mercaptoethyl) carbamate/Aldrich |
| 365 HCl | 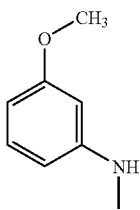 | 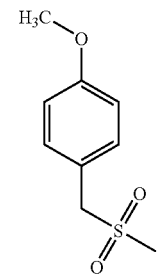 | H— | Intermediate 37 [4-(methyloxy) phenyl] methanethiol/ Aldrich |
| 366 | 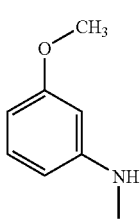 | 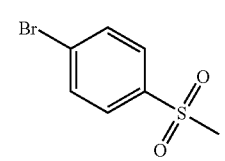 | H— | Intermediate 37 4-bromothiophenol/ Aldrich |

-continued

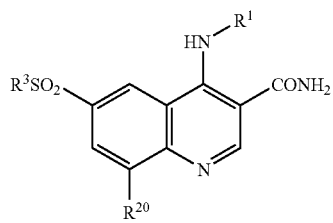

| | | | | | |
|---|---|---|---|---|---|
| 367 HCl | 3-methoxy-N-methylanilino | 2-methoxyphenyl methylsulfonyl | H— | Intermediate 37 | 2-mercaptoanisole/ Lancaster |
| 368 HCl | 3-methoxy-N-methylanilino | (4-chlorophenyl)methyl sulfonyl | H— | Intermediate 37 | (4-chlorophenyl) methanethiol/ Aldrich |
| 375 HCl | 3-methoxy-N-methylanilino | 3-methoxyphenyl sulfonyl | H— | Intermediate 37 | 3-methoxybenzene thiol/ Aldrich |
| 377 | 3-methoxy-N-methylanilino | N-Boc-4-piperidinyl sulfonyl | H— | Intermediate 45 | 1,1-dimethylethyl 4-mercapto-1-piperidine carboxylate/ U.S. Pat. No. 5,317,025 A |
| 378 | 3-cyano-N-methylanilino | N-Boc-4-piperidinyl sulfonyl | H— | Intermediate 46 | 1,1-dimethylethyl 4-mercapto-1-piperidine carboxylate/ U.S. Pat. No. 5,317,025 A |
| 472 | 3-methoxy-N-methylanilino | N-Boc-4-piperidinyl sulfonyl | H— | Intermediate 14 | 1,1-dimethylethyl 4-mercapto-1-piperidine carboxylate/ U.S. Pat. No. 5,317,025 A |

-continued

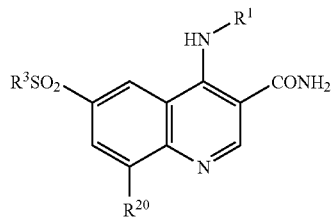

| Ex. No. (a) | Isolation Method (b) | Solvent | LCMS MH$^+$ | LCMS R$_t$ (min) |
|---|---|---|---|---|
| 354 | (II) | Toluene | 492 | 2.76 |
| 355 | (II) | Toluene | 492 | 2.76 |
| 356 | (VII) | Toluene | 448 | 2.90 |
| 357 HCl | (IV) | Toluene | 462 | 3.02 |
| 358 | (V) | Toluene | 452 | 2.83 |
| 359 HCl | (IV) | Toluene | 502 | 3.16 |
| 361 | (II) | Toluene | 468 | 2.96 |
| 362 | (II) | Toluene | 490 | 3.26 |
| 363 | (II) | Toluene | 462 | 3.05 |
| 364 | (V) | Toluene | 469 | 2.59 |
| 365 HCl | (IV) | Toluene | 478 | 2.63 |
| 366 | (VI) | Toluene | 513 | 3.02 |
| 367 HCl | (IV) | Toluene | 464 | 2.52 |
| 368 HCl | (IV) | Toluene | 482 | 2.91 |
| 375 HCl | (VIII) | N,N-dimethylformamide | 464 | 2.76 |
| 377 | (V) | N,N-dimethylformamide | 555 | 2.97 |
| 378 | (V) | N,N-dimethylformamide | 550 | 3.01 |
| 472 | (V) | N,N-dimethylformamide | 541 | 2.89 |

(a) Salt forms: HCl = hydrochloride
(b) Isolation Method:
(II) Mass Directed preparative HPLC (Method A).
(IV) Mass Directed preparative HPLC (Method C).
(V) Column chromatography on silica gel. Compounds isolated by this method are free bases.
(VI) Aqueous workup only with no further chromatography. Compounds isolated by this method are free bases.
(VII) Recrystallised from methanol
(VIII) Mass Directed preparative HPLC (Method A), followed by treatment with 2M HCl in ethanol.

Example 360

6-[(4-Hydroxyphenyl)sulfonyl]-4-[(3-methoxyphenyl)amino]quinoline-3-carboxamide

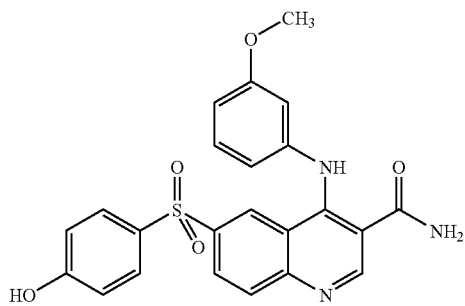

Oxone (3.9 g) was added to a stirred solution of Intermediate 47 (1.1 g) in dry N,N-dimethylformamide (30 ml) at room temperature for 18 h. The mixture was poured into aqueous sodium sulphite solution (200 ml) and extracted with ethyl acetate (3×100 ml). The organic extracts were washed with water (2×100 ml), dried (Na$_2$SO$_4$) and concentrated. A solution of the residual oil in tetrahydrofuran (20 ml) was stirred with a 1M solution of tetrabutylammonium fluoride in tetrahydrofuran (4 ml) for 1 h. The solvent was removed in vacuo and the residue was partitioned between ethyl acetate (2×25 ml) and water (2×50 ml). The organic extracts were dried (Na$_2$SO$_4$) and concentrated to give the title compound as a yellow solid (0.67 g).

LC/MS R$_t$ 2.58 min, m/z 450 [MH$^+$]

Example 379

Methyl 3-[(3-(aminocarbonyl)-8-methyl-4-{[3-(methyloxy)phenyl]amino}-6-quinolinyl)sulfonyl]benzoate

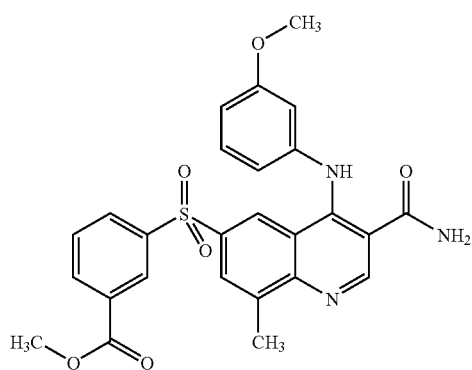

To Intermediate 45 (0.47 g) in dimethoxyethane (10 ml) was added methyl 3-mercaptobenzoate (0.34 ml), potassium phosphate (0.42 g), copper (I) iodide (0.028 g) and N,N-diethylsalicylamide (0.39 g). The mixture was heated at 85° C. for 4 h before adding further methyl 3-mercaptobenzoate (0.34 ml) and copper (I) iodide (0.028 g). After a further 16 h the reaction mixture was concentrated in vacuo and partitioned between ethyl acetate (150 ml) and water (150 ml). The organic layers were washed with brine (100 ml), dried over sodium sulfate and concentrated in vacuo to yield a crude product which was triturated with diethyl ether (20 ml). The solid obtained was collected by filtration, washed with diethyl ether (2×10 ml) to give methyl 3-[(3-(aminocarbonyl)-8-methyl-4-{[3-(methyloxy)phenyl]amino}-6-quinolinyl)thio] benzoate as a beige solid (0.37 g).

LC/MS $R_t$ 3.09 min m/z 474 [MH$^+$]

To a solution of the methyl 3-[(3-(aminocarbonyl)-8-methyl-4-{[3-(methyloxy)phenyl]amino}-6-quinolinyl)thio] benzoate (0.367 g) in N,N-dimethylformamide (10 ml) was added oxone (1.91 g). The mixture was stirred at room temperature for 18 h before quenching with aqueous sodium sulphite solution and extracting with chloroform (3×200 ml). The organic layers were combined, washed with brine, dried over magnesium sulfate and concentrated in vacuo and purified by chromatography on silica gel, eluting with 2:1 ethyl acetate: cyclohexane, to give the title compound as a yellow solid (0.100 g).

LC/MS $R_t$ 3.03 min m/z 506 [MH$^+$]

The following were synthesised in the same manner as Example 379, however potassium carbonate was used as a base instead of potassium phosphate and no N'N-diethylsalicylamide was added.

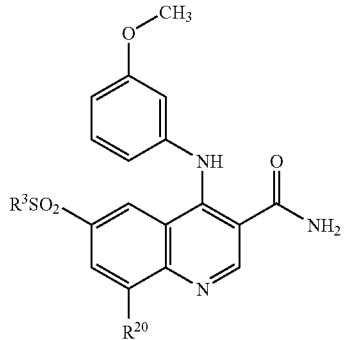

| Ex. No. (a) | $R^3SO_2$— | $R^{20}$— | Starting Material | Thiol Reagent/ Source | Purification Method (b) | LCMS MH$^+$ | LCMS $R_t$ (min) |
|---|---|---|---|---|---|---|---|
| 380 | (3,4-dimethoxyphenylsulfonyl) | Me— | Intermediate 45 | 3,4-dimethoxythiophenol Aldrich | (V) | 508 | 2.81 |
| 381 HCl | (3,4,5-trimethoxyphenylsulfonyl) | Me— | Intermediate 45 | 3,4,5-tris(methyloxy) benzenethiol J. Am. Chem. Soc., 2002, 124(17), 4642-4846 | (IV) | 538 | 2.92 |

-continued

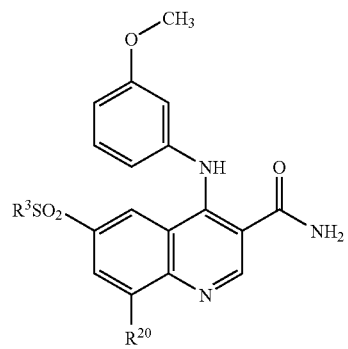

| Ex. No. (a) | R³SO₂— | R²⁰— | Starting Material | Thiol Reagent/ Source | Purification Method (b) | LCMS MH⁺ | LCMS R$_t$ (min) |
|---|---|---|---|---|---|---|---|
| 382 HCl | (3,4-dimethoxyphenyl)SO₂CH₃ | H— | Intermediate 14 | 3,4-dimethoxythiophenol/ Avocado | (IV) | 494 | 2.59 |
| 383 HCl | (3-ethoxyphenyl)SO₂CH₃ | Me— | Intermediate 45 | 3-ethoxythiophenol/ Aldrich | (IV) | 492 | 3.08 |

(a) Salt forms: HCl = hydrochloride
(b) Isolation Method:
(IV) Mass Directed preparative HPLC (Method C).
(V) Column chromatography on silica gel; it is thought that compounds isolated by this method are free bases.

Example 386

6-(Ethylsulfonyl)-4-{[3-(methyloxy)phenyl]amino}-3-quinolinecarboxamide hydrochloride

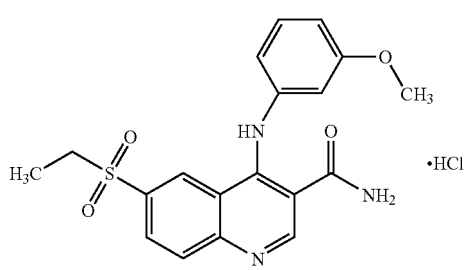

Intermediate 37 (0.100 g) was combined with (oxydi-2,1-phenylene)bis(diphenylphosphine) (0.011 g), potassium tert-butoxide (0.025 g) and tris(dibenzylideneacetone)dipalladium(o) (0.008 g) in 1,4-dioxane (1 ml). Ethanethiol (available from Aldrich, 0.023 ml) was added and the mixture was stirred under microwave irradiation (power 40 W) for 8 min at 90° C. The reaction was quenched by addition of 4M HCl in dioxane, then partitioned between ethyl acetate and sodium bicarbonate solution. The organic layer was concentrated in vacuo to give 0.090 g of crude 6-(ethylthio)-4-{[3-(methyloxy)phenyl]amino}-3-quinolinecarboxamide.

The crude sulphide was dissolved in N,N-dimethylformamide (5 ml) and treated with an excess of oxone (0.375 g) and stirred at room temperature for 4 h. The reaction was quenched by the addition of 1M aqueous sodium sulphite solution, then partitioned between dichloromethane and sodium bicarbonate solution. The solvent was removed in vacuo and the residue was purified by mass directed preparative HPLC (Method C). After evaporation of solvent the title compound was obtained as a yellow solid.

LC/MS R$_t$ 2.30 min, m/z 386 [MH⁺]

The following were prepared in the same manner as Example 386:

[Structure: quinoline core with 4-(3-methoxyphenylamino), 6-R³SO₂, 8-R²⁰, 3-carboxamide (NH₂)]

| Ex. No. (a) | R³SO₂— | R²⁰— | Starting Material | Thiol Reagent/ Source | LCMS MH⁺ | LCMS R$_t$ (min) |
|---|---|---|---|---|---|---|
| 384 (b) | H₃C-CH(CH₃)-CH₂-S(O)₂-CH₃ (isobutyl methylsulfonyl... actually methanesulfonyl via isobutyl) | H— | Intermediate 14 | Isobutyl mercaptan/ Aldrich | 414 | 2.56 |
| 387 HCl | H₃C-CH₂-CH₂-CH₂-S(O)₂- (methyl)  | H— | Intermediate 37 | 1-butanethiol/ Aldrich | 414 | 2.67 |
| 388 HCl | CH₃O-C(O)-CH₂-CH₂-S(O)₂-CH₃ | H— | Intermediate 37 | Methyl-3-mercaptopropionate/ Fluka | 444 | 2.39 |
| 389 HCl | Ph-CH₂-CH₂-S(O)₂-CH₃ | H— | Intermediate 37 | Phenethyl mercaptan/Aldrich | 462 | 2.88 |
| 390 HCl | 2-furanyl-CH₂-S(O)₂-CH₃ | H— | Intermediate 37 | 2-furanylmethanethiol/ Aldrich | 438 | 2.46 |
| 391 HCl | CF₃-CH₂-S(O)₂-CH₃ | H— | Intermediate 37 | 2,2,2-trifluoroethanethiol/ Aldrich | 440 | 2.6 |
| 392 HCl | H₃C-C(O)-NH-CH₂-CH₂-S(O)₂-CH₃ | Me— | Intermediate 45 | N-(2-mercaptoethyl) acetamide/Aldrich | 457 | 2.25 |

(a) Salt forms: HCl = hydrochloride
(b) Isolation method: Mass Directed preparative HPLC (Method A).

Example 393

3-[(3-(Aminocarbonyl)-8-methyl-4-{[3-(methyloxy)phenyl]amino}-6-quinolinyl)sulfonyl]benzoic acid

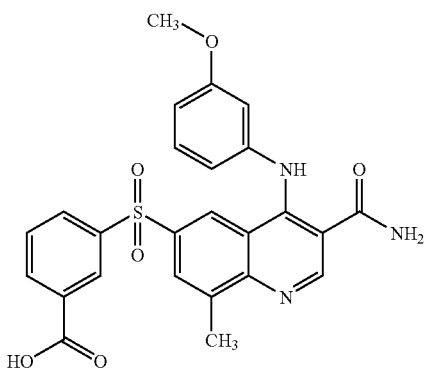

Example 379 (0.1 g) was dissolved in methanol (5 ml) and 2M aqueous sodium hydroxide (1 ml). The mixture was heated to 75° C. for 4 h before cooling and standing at ambient temperature for 18 h. The solvent was removed in vacuo and the residue partitioned between ethyl acetate (100 ml) and water (100 ml). The layers were separated and the aqueous layer was washed with diethyl ether (50 ml), acidifed to pH4 (2M hydrochloric acid) and extracted with ethyl acetate (2×150 ml). The combined ethyl acetate layers were washed with brine (100 ml), dried over magnesium sulfate and concentrated in vacuo to yield the title compound as a beige solid (0.082 g).

LC/MS $R_t$ 2.82 min m/z 492 [MH$^+$].

Similarly prepared were the following:

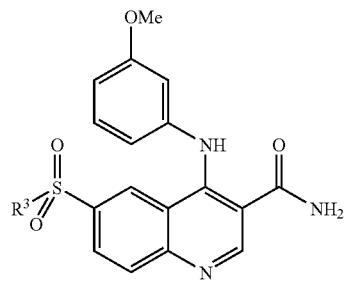

| Example Number | R$^3$SO$_2$— | Starting Material | Isolation Method (b) | LCMS MH$^+$ | LCMS $R_t$ (min) |
|---|---|---|---|---|---|
| 394 | ![structure] | Example 354 | (II) | 478 | 2.67 |
| 395 | ![structure] | Example 355 | (II) | 478 | 2.65 |

(b) Isolation Method: (II) Mass Directed HPLC Method A

The following were prepared from the intermediates shown in the table in a similar manner to the method by which Example 393 was prepared, via Example 379, from Intermediate 45.

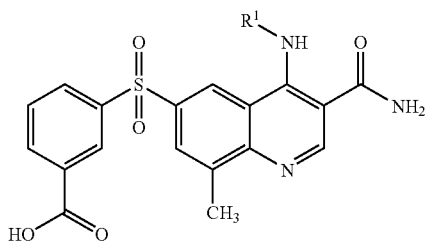

| Example Number (a) | R¹NH— | Starting Material | Isolation Method (b) | LCMS MH⁺ | LCMS R$_t$ (min) |
|---|---|---|---|---|---|
| 396 HCl | | Intermediate 44 | (IV) | 516 | 2.25 |
| 397 HCl | | Intermediate 46 | (IV) | 487 | 2.9 |
| 398 | | Intermediate 36 | (I) | 504 | 2.83 |

(a) Salt forms: HCl = hydrochloride
(b) Isolation Method:
(I) filtered off and used crude.
(IV) Mass Directed HPLC Method C; it is thought that compounds isolated by this method are hydrochloride salts.

Example 399

6-({3-[(Dimethylamino)carbonyl]phenyl}sulfonyl)-8-methyl-4-{[3-(methyloxy)phenyl]amino}-3-quinolinecarboxamide hydrochloride

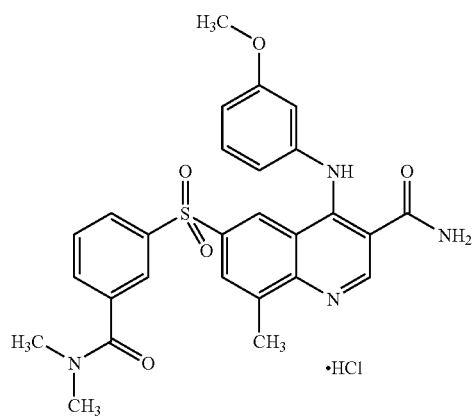

To a solution of Example 393 (0.082 g) in N,N-dimethylformamide (3 ml) was added N,N-diisopropylethylamine (0.12 ml) and O-(7-azabenzotriazol-1-yl)-N,N,N',N'-tetramethyluronium hexafluorophosphate (0.071 g). The mixture was stirred for 20 min before adding a solution of dimethylamine in tetrahydrofuran (2M, 0.8 ml, Aldrich). After a further 1 h more dimethylamine in tetrahydrofuran (2M, 0.8 ml) was added. After 1 h the reaction mixture was concentrated in vacuo and partitioned between ethyl acetate (200 ml) and aqueous sodium bicarbonate (100 ml). The organic layers were washed with brine (100 ml), dried over magnesium sulfate and concentrated in vacuo. Purification by mass directed HPLC (Method C) gave the title compound as a yellow solid (0.022 g).

LC/MS $R_t$ 2.61 min m/z 519 [MH$^+$].
Similarly prepared were the following:

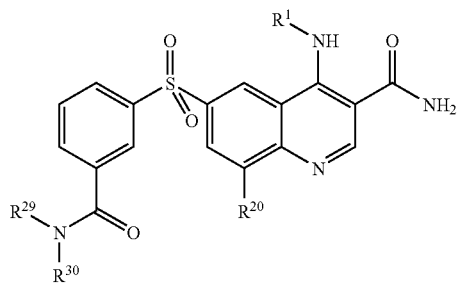

| Example Number (a) | R$^1$NH— | R$^{20}$— | R$^{29}$R$^{30}$N— | Amine Starting Material | Reagent/ Source | LCMS MH$^+$ | LCMS R$_t$ (min) |
|---|---|---|---|---|---|---|---|
| 400 HCl | ![3-methoxyphenylamino] | H— | Me$_2$N— | Example 395 | dimethylamine 2M solution in tetrahydrofuran/ Aldrich | 505 | 2.52 |
| 401 HCl | ![4-methoxy-3-pyridylamino] | H— | H$_2$N— | Example 395 | Ammonia solution 880/Merck | 477 | 2.42 |

-continued

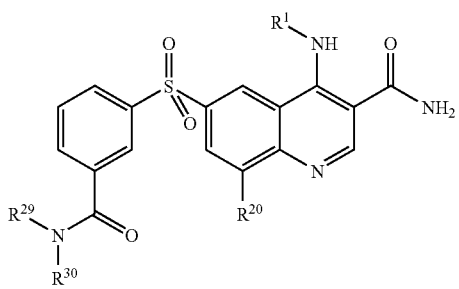

| Example Number (a) | R¹NH— | R²⁰— | R²⁹R³⁰N— | Starting Material | Amine Reagent/ Source | LCMS MH⁺ | LCMS R$_t$ (min) |
|---|---|---|---|---|---|---|---|
| 402 HCl | 3-methoxy-N-methylanilino | H— | MeNH— | Example 395 | methylamine 2M solution in tetrahydrofuran/ Aldrich | 491 | 2.47 |
| 403 HCl | 3-methoxy-N-methylanilino | H— | pyrrolidinyl | Example 395 | Pyrrolidine/ Lancaster | 531 | 2.64 |
| 404 HCl | 3-methoxy-N-methylanilino | H— | propylNH— | Example 395 | propylamine/ Aldrich | 519 | 2.74 |
| 405 (b) | 3-methoxy-N-methylanilino | H— | isobutylNH— | Example 395 | Isobutylamine/ Aldrich | 533 | 2.76 |
| 406 HCl | 3-methoxy-N-methylanilino | H— | morpholinyl | Example 395 | Morpholine/ Lancaster | 547 | 2.51 |

-continued

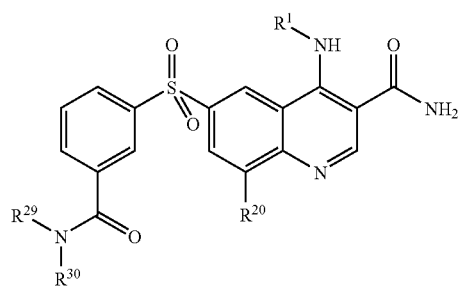

| Example Number (a) | R¹NH— | R²⁰— | R²⁹R³⁰N— | Starting Material | Amine Reagent/ Source | LCMS MH⁺ | LCMS $R_t$ (min) |
|---|---|---|---|---|---|---|---|
| 407 HCl | 3-methoxy-N-methylanilino | H— | HO-CH₂CH₂-NH- (methyl) | Example 395 | Ethanolamine/ Aldrich | 521 | 2.38 |
| 408 HCl | 3-cyano-N-methylanilino | Me— | Me₂N— | Example 397 | dimethylamine 2M solution in tetrahydrofuran/ Aldrich | 514 | 2.71 |
| 409 HCl | 1-methyl-benzimidazol-6-yl(methyl)amino | Me— | Me₂N— | Example 396 | dimethylamine 2M solution in tetrahydrofuran/ Aldrich | 543 | 2.19 |
| 410 HCl | 1-methyl-benzimidazol-6-yl(methyl)amino | Me— | H₂N— | Example 396 | Ammonia solution 880/Merck | 515 | 2.13 |
| 411 HCl | 1-methyl-benzimidazol-6-yl(methyl)amino | Me— | MeNH— | Example 396 | methylamine 2M solution in tetrahydrofuran/ Aldrich | 529 | 2.17 |
| 412 HCl | 3-cyano-N-methylanilino | Me— | H₂N— | Example 397 | dimethylamine 2M solution in tetrahydrofuran/ Aldrich | 486 | 2.61 |

-continued

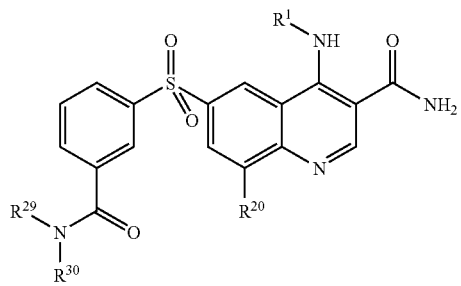

| Example Number (a) | R¹NH— | R²⁰— | R²⁹R³⁰N— | Starting Material | Amine Reagent/ Source | LCMS MH⁺ | LCMS $R_t$ (min) |
|---|---|---|---|---|---|---|---|
| 413 HCl | 3-cyanophenyl-N(Me)— | Me— | MeNH— | Example 397 | methylamine 2M solution in tetrahydrofuran/ Aldrich | 500 | 2.69 |
| 414 (c) | 2,3-dihydrobenzofuran-4-yl-N(Me)— | Me— | Me₂N— | Example 398 | dimethylamine 2M solution in tetrahydrofuran/ Aldrich | 531 | 2.65 |

(a) Salt form: HCl = hydrochloride
(b) Example 405 was isolated by Mass Directed preparative HPLC (Method A).
(c) Example 414 was isolated by aqueous work up.

Similarly prepared from Example 394 were the following:

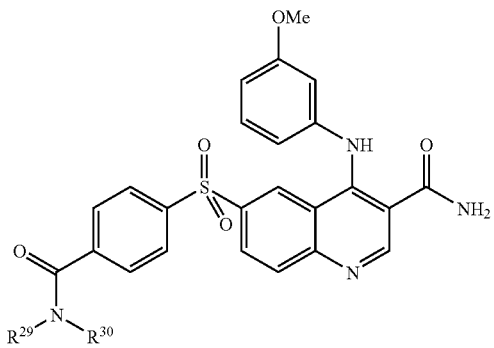

| Example Number (a) | R²⁹R³⁰N— | Amine Reagent/ Source | Isolation method (b) | LCMS MH⁺ | LCMS $R_t$ (min) |
|---|---|---|---|---|---|
| 415 HCl | H₂N— | Ammonia solution 880/Merck | (I) | 477 | 2.45 |
| 416 HCl | MeHN— | methylamine 2M solution in tetrahydrofuran/ Aldrich | (I) | 491 | 2.51 |

-continued

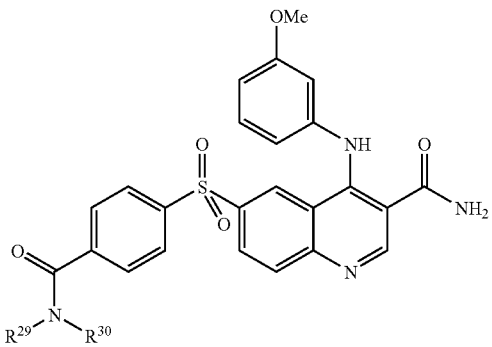

| Example Number (a) | $R^{29}R^{30}N$— | Amine Reagent/ Source | Isolation method (b) | LCMS $MH^+$ | LCMS $R_t$ (min) |
|---|---|---|---|---|---|
| 417 HCl | | Pyrrolidine/Lancaster | (I) | 531 | 2.66 |
| 418 HCl | | propylamine/Aldrich | (I) | 519 | 2.75 |
| 419 HCl | $Me_2N$— | dimethylamine 2M solution in tetrahydrofuran/ Aldrich | (I) | 505 | 2.53 |
| 420 | | Isobutylamine/Aldrich | (II) | 533 | 2.8 |

(a) Salt form: HCl = hydrochloride
(b) Isolation Method:
(I) Mass Directed preparative HPLC (Method C).
(II) Mass Directed preparative HPLC (Method A).

Example 421

4-{[3-(Methyloxy)phenyl]amino}-6-(4-piperidinyl-sulfonyl)-3-quinolinecarboxamide

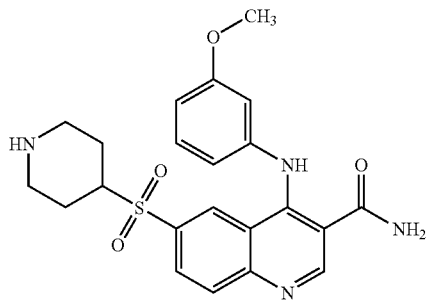

To a mixture containing Example 472 (1.3 g) in anisole (9 ml) was added a solution of 95% trifluoroacetic acid in water (45 ml). The mixture was stirred for 2 h at room temperature and was then concentrated in vacuo. The residue was co-evaporated with toluene (2×20 ml) and triturated with diethyl ether to give a yellow solid. The solid was partitioned between aqueous potassium carbonate (300 ml) and chloroform (300 ml) and the aqueous phase extracted with chloroform (3×200 ml). The combined organic extracts were washed with water (100 ml), dried and concentrated in vacuo to give the title compound as a yellow solid (1.1 g).

LC/MS $R_t$ 1.94 min, m/z 441 [MH$^+$]
Similarly prepared were the following:

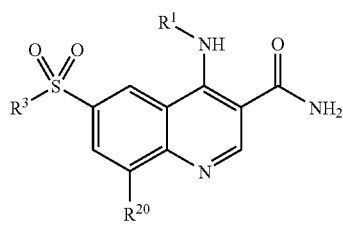

| Ex. No. (a) | R¹NH— | R²⁰— | R³SO₂— | Starting Material | Isolation Method (b) | LCMS MH⁺ | LCMS R_f (min) |
|---|---|---|---|---|---|---|---|
| 422 TFA | 2,3-dihydrobenzofuran-4-yl(methyl)amino | Me— | H₂N-CH₂CH₂-SO₂Me | Example 353 | (I) | 1.98 | 427 |
| 423 | 2,3-dihydrobenzofuran-4-yl(methyl)amino | Me— | 4-(methylsulfonyl)piperidinyl | Example 352 | (II) | 467 | 1.97 |
| 470 TFA | 3-cyanophenyl(methyl)amino | Me— | 4-(methylsulfonyl)piperidinyl | Example 378 | (III) | 450 | 2.03 |
| 474 TFA | 1-methyl-1H-benzimidazol-6-yl(methyl)amino | Me— | 4-(methylsulfonyl)piperidinyl | Example 376 | (I) | 479 | 1.77 |
| 476 | 4-fluoro-3-methoxyphenyl(methyl)amino | Me— | 4-(methylsulfonyl)piperidinyl | Intermediate 55 | (II) | 473 | 2.10 |
| 477 | 4-fluoro-3-methoxyphenyl(methyl)amino | Me— | H₂N-CH₂CH₂-SO₂Me | Intermediate 56 | (II) | 433 | 2.03 |

-continued

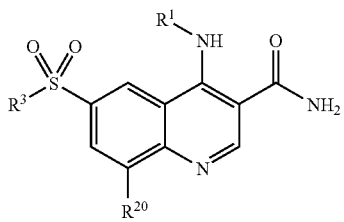

| Ex. No. (a) | R¹NH— | R²⁰— | R³SO₂— | Starting Material | Isolation Method (b) | LCMS MH⁺ | LCMS R_t (min) |
|---|---|---|---|---|---|---|---|
| 561 | 3-fluoro-N-methylphenylamino | Me— | H₂N-CH₂CH₂-SO₂-Me | Example 602 | (IV) | 403 | 1.93 |
| 567 HCl | N-methyl-(pyridin-3-yl)amino | Me— | 4-(methylsulfonyl)piperidin-HN— | Example 568 | (V) | 426 | 1.80 |

(a) Salt forms: TFA = trifluoroacetate (b) Isolation Method:

(I) Filtered off directly from the reaction mixture; it is thought that compounds isolated by this method are trifluoroacetate salts.

(II) Aqueous workup of the crude reaction mixture without further purification; it is thought that compounds isolated by this method are free bases.

(III) Crude product was triturated to give the desired product and no further purification was carried out; it is thought that compounds isolated by this method are trifluoroacetate salts.

(IV) Product isolated by SCX ion exchange to give the free base (V) Reaction mixture evaporated to dryness; it is assumed that this method gave the hydrochloride salt.

Example 424

4-{[3-(Methyloxy)phenyl]amino}-6-{[1-(phenylcarbonyl)-4-piperidinyl]sulfonyl}-3-quinolinecarboxamide

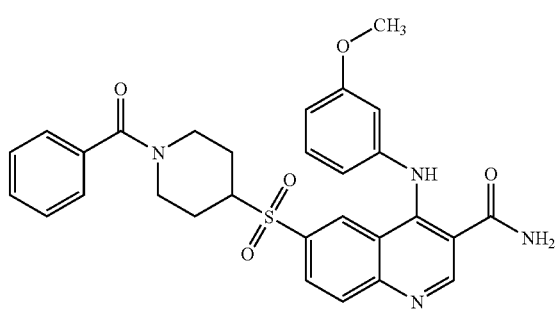

To a mixture containing Example 421 (0.050 g) and triethylamine (0.025 ml) in dioxane (2 ml) was added benzoyl chloride (0.020 ml). The mixture was stirred under nitrogen for 18 h at room temperature and was then diluted with methanol (5 ml). The solution was applied to an aminopropyl cartridge and eluted with methanol. The eluent was evaporated and the residual gum purified by chromatography on SPE eluting with a gradient of methanol in chloroform (0% to 10%) to give the title compound as a yellow solid (0.043 g).

LC/MS R_t 2.63 min, m/z 545 [MH⁺]

Similarly prepared were the following:

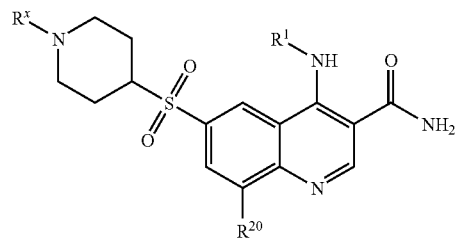

| Ex. No. (a) | R¹NH— | R²⁰— | Rˣ— | Starting Material | Electrophile/ Source | Isolation Method (b) | LCMS MH⁺ | LCMS $R_t$ (min) |
|---|---|---|---|---|---|---|---|---|
| 425 | 3-methoxy-N-methylanilino | H— | methoxycarbonyl (methyl carbamate) | Example 421 | Methyl chloroformate/ Aldrich | (II) | 499 | 2.48 |
| 426 | 3-methoxy-N-methylanilino | H— | acetyl | Example 421 | Acetyl chloride/ Aldrich | (II) | 483 | 2.27 |
| 427 | 3-methoxy-N-methylanilino | H— | methanesulfonyl | Example 421 | Methane sulphonyl chloride/ Aldrich | (V) | 519 | 2.43 |
| 428 | 3-methoxy-N-methylanilino | H— | 3-methylbutanoyl | Example 421 | 3-methylbutanoyl chloride/Aldrich | (III) | 525 | 2.61 |
| 429 | 3-methoxy-N-methylanilino | H— | cyclopropanecarbonyl | Example 421 | Cyclopropane carbonyl chloride/ Aldrich | (III) | 509 | 2.42 |

-continued

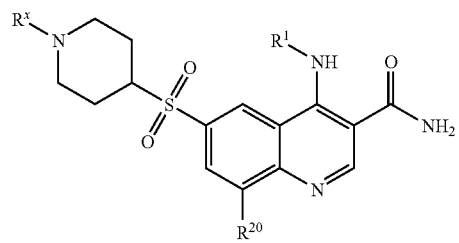

| Ex. No. (a) | R¹NH— | R²⁰— | Rˣ— | Starting Material | Electrophile/ Source | Isolation Method (b) | LCMS MH⁺ | LCMS R$_t$ (min) |
|---|---|---|---|---|---|---|---|---|
| 430 | 3-methoxy-N-methylanilino | H— | 2-furoyl | Example 421 | 2-furancarbonyl chloride/Aldrich | (III) | 535 | 2.5 |
| 431 | 3-methoxy-N-methylanilino | H— | 5-methyl-3-isoxazolecarbonyl | Example 421 | 5-methyl-3-isoxazolecarbonyl chloride/ Maybridge | (III) | 550 | 2.55 |
| 432 | 3-methoxy-N-methylanilino | H— | phenylsulfonyl | Example 421 | Benzene sulphonyl chloride/ Aldrich | (IV) | 581 | 2.9 |
| 433 | 3-methoxy-N-methylanilino | H— | 3,5-dimethyl-4-isoxazolesulfonyl | Example 421 | 3,5-dimethyl-4-isoxazolesulfonyl chloride/Avocado | (IV) | 600 | 2.88 |
| 434 | 3-methoxy-N-methylanilino | H— | 2-(acetylamino)-4-methyl-1,3-thiazole-5-sulfonyl | Example 421 | 2-(acetylamino)-4-methyl-1,3-thiazole-5-sulfonyl chloride/Aldrich | (IV) | 659 | 2.69 |

-continued

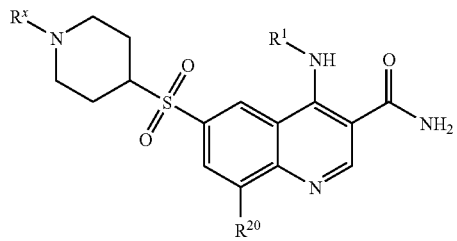

| Ex. No. (a) | R¹NH— | R²⁰— | Rˣ— | Starting Material | Electrophile/ Source | Isolation Method (b) | LCMS MH⁺ | LCMS R_t (min) |
|---|---|---|---|---|---|---|---|---|
| 435 | 3-methoxy-N-methylanilino | H— | butylsulfonyl | Example 421 | 1-butanesulphonyl chloride/Aldrich | (IV) | 561 | 2.75 |
| 436 | 3-methoxy-N-methylanilino | H— | 1-methylimidazol-4-ylsulfonyl | Example 421 | 1-methylimidazole 4-sulphonyl chloride/ Maybridge | (IV) | 585 | 2.35 |
| 437 | 3-methoxy-N-methylanilino | H— | isoxazol-5-ylcarbonyl | Example 421 | Isoxazole-5-carbonyl chloride/ Lancaster | (III) | 536 | 2.37 |
| 438 | 3-methoxy-N-methylanilino | H— | furan-3-ylcarbonyl | Example 421 | 2-furancarbonyl chloride/ Maybridge | (III) | 535 | 2.42 |
| 439 | 3-methoxy-N-methylanilino | H— | isobutyryl | Example 421 | isobutyryl chloride/ Aldrich | (III) | 511 | 2.42 |
| 440 | 3-methoxy-N-methylanilino | H— | propionyl | Example 421 | Propionyl chloride/ Aldrich | (III) | 497 | 2.31 |

-continued

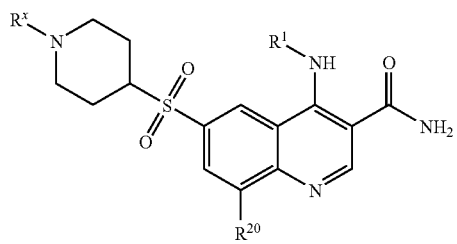

| Ex. No. (a) | R¹NH— | R²⁰— | Rˣ— | Starting Material | Electrophile/ Source | Isolation Method (b) | LCMS MH⁺ | LCMS R$_t$ (min) |
|---|---|---|---|---|---|---|---|---|
| 441 | 3-methoxy-N-methylanilino | H— | pyrrolidine-N-acetyl | Example 421 | 1-pyrrolidinecarbonyl chloride/Lancaster | (III) | 538 | 2.44 |
| 442 | 3-methoxy-N-methylanilino | Me— | 2-furoyl | Intermediate 54 | 2-furancarbonyl chloride/Aldrich | (I) | 549 | 2.65 |
| 443 | 3-cyano-N-methylanilino | Me— | 2-furoyl | Example 470 | 2-furancarbonyl chloride/Aldrich | (I) | 544 | 2.69 |
| 444 | 3-cyano-N-methylanilino | Me— | cyclopropanecarbonyl | Example 470 | Cyclopropane carbonyl chloride/Aldrich | (I) | 518 | 2.63 |
| 445 | 3-methoxy-N-methylanilino | Me— | cyclopropanecarbonyl | Intermediate 54 | Cyclopropane carbonyl chloride/Aldrich | (I) | 523 | 2.57 |

-continued

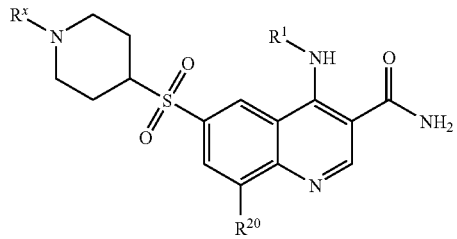

| Ex. No. (a) | R¹NH— | R²⁰— | Rˣ— | Starting Material | Electrophile/ Source | Isolation Method (b) | LCMS MH⁺ | LCMS $R_t$ (min) |
|---|---|---|---|---|---|---|---|---|
| 446 | 2,3-dihydrobenzofuran-4-yl(methyl)amino | Me— | 2-furyl ketone | Example 423 | 2-furancarbonyl chloride/Aldrich | (I) | 561 | 2.66 |
| 447 | 2,3-dihydrobenzofuran-4-yl(methyl)amino | Me— | cyclopropyl ketone | Example 423 | Cyclopropane carbonyl chloride/Aldrich | (I) | 535 | 2.58 |
| 448 HCl | 2,3-dihydrobenzofuran-4-yl(methyl)amino | Me— | methyl carbonate | Example 423 | Methyl chloroformate/Aldrich | (VI) | 525 | 2.57 |

(a) Salt forms: HCl = hydrochloride
(b) Isolation Method:
(I) Purified by chromatography on an SPE column.
(II) Aqueous workup of the crude reaction mixture without further purification.
(III) Purified using an SPE cartridge (aminopropyl solid phase) followed by chromatography using a silica SPE column.
(IV) Purified using an SPE cartridge (aminopropyl solid phase) followed by trituration.
(V) Aqueous workup of the crude reaction followed by trituration of the crude product.
(VI) Aqueous workup of the crude reaction followed by addition of dilute HCl in dioxane and evaporation; it is thought that compounds isolated by this method are hydrochloride salts.

Example 449

4-(2,3-Dihydro-1-benzofuran-4-ylamino)-8-methyl-6-[(1-methyl-4-piperidinyl)sulfonyl]-3-quinolinecarboxamide hydrochloride

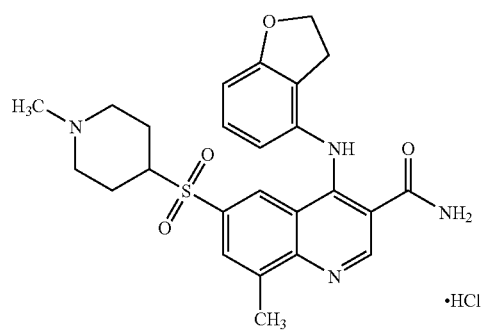

To a mixture containing Example 423 (0.050 g) and triethylamine (0.025 ml) in N,N-dimethylformamide (2 ml) was added methyl iodide (0.0075 ml). The mixture was stirred under nitrogen for 18 h at room temperature and was concentrated by blowing down under nitrogen. Purification by chromatography on silica gel, eluting with dichloromethane/methanol (95:5), gave a white solid which was dissolved in dioxane (10 ml) and treated with 4M hydrogen chloride in 1,4 dioxane (0.100 ml). After evaporation by blowing down under nitrogen the title compound was obtained as a yellow solid (0.028 g).

LC/MS $R_t$ 1.99 min, m/z 481 [MH⁺]

Example 450

6-[(1-Acetyl-4-piperidinyl)sulfonyl]-4-(2,3-dihydro-1-benzofuran-4-ylamino)-8-methyl-3-quinolinecarboxamide hydrochloride

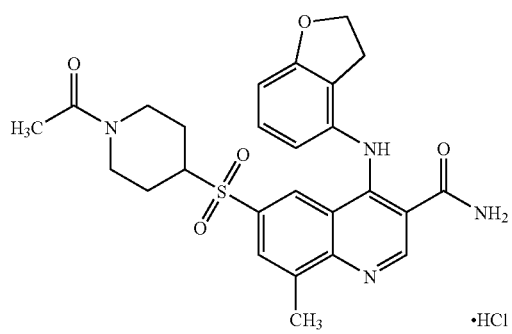

To a mixture containing Example 423 (0.050 g) in pyridine (2 ml) was added acetic anhydride (0.011 ml). The mixture was stirred under nitrogen for 18 h at room temperature, partitioned between chloroform (100 ml) and 10% sodium carbonate solution (100 ml), the layers separated by hydrophobic frit and the organic layer treated with 4M hydrogen chloride in 1,4-dioxane (0.100 ml). After evaporation by blowing down under nitrogen the title compound was obtained as a pale yellow solid (0.021 g).

LC/MS $R_t$ 2.32 min, m/z 509 [MH$^+$]

Similarly prepared were the following:

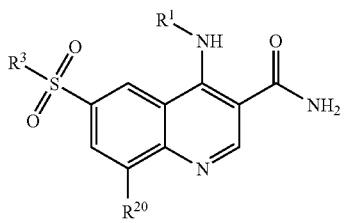

| Ex. No. (a) | R$^1$NH— | R$^{20}$— | R$^3$SO$_2$— | Starting Material | Electrophile/ Source | Isolation Method (b) | LCMS MH$^+$ | LCMS R$_t$ (min) |
|---|---|---|---|---|---|---|---|---|
| 451 | 4-fluoro-3-methoxyphenyl(methyl)amine | Me— | 1-acetyl-4-piperidinyl sulfonyl | Example 476 | Acetic anhydride/ Aldrich | (II) | 515 | 2.31 |
| 452 HCl | 2,3-dihydrobenzofuran-4-yl(methyl)amine | Me— | acetamidoethyl sulfonyl | Example 422 | Acetyl chloride/ Aldrich | (V) | 469 | 2.14 |
| 453 HCl | 4-fluoro-3-methoxyphenyl(methyl)amine | Me— | acetamidoethyl sulfonyl | Example 477 | Acetic anhydride/ Aldrich | (I) | 475 | 2.15 |

-continued

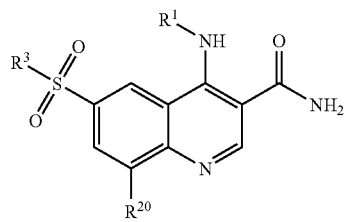

| Ex. No. (a) | R¹NH— | R²⁰— | R³SO₂— | Starting Material | Electrophile/ Source | Isolation Method (b) | LCMS MH⁺ | LCMS R$_t$ (min) |
|---|---|---|---|---|---|---|---|---|
| 454 HCl | 4-fluoro-3-methoxyphenyl-N(Me)— | Me— | H₃C-SO₂-NH-CH₂CH₂-SO₂-Me | Example 477 | Methane-sulphonyl chloride/ Aldrich | (IV) | 511 | 2.23 |
| 455 HCl | 4-fluoro-3-methoxyphenyl-N(Me)— | Me— | H₃CO-C(O)-NH-CH₂CH₂-SO₂-Me | Example 477 | Methyl chloroformate/ Aldrich | (IV) | 491 | 2.29 |
| 456 | 2,3-dihydrobenzofuran-4-yl-N(Me)— | Me— | H₃CO-C(O)-NH-CH₂CH₂-SO₂-Me | Example 422 | Methyl chloroformate/ Aldrich | (VI) | 485 | 2.36 |
| 457 | 2,3-dihydrobenzofuran-4-yl-N(Me)— | Me— | H₃C-SO₂-NH-CH₂CH₂-SO₂-Me | Example 422 | Methane-sulphonyl chloride/ Aldrich | (VI) | 505 | 2.31 |
| 531 | pyridin-3-yl-N(Me)— | Me— | Me-C(O)-N(piperidin-4-yl)-SO₂- | Example 567 | Acetic anhydride/ Aldrich | (III) | 468 | 2.00 |

(a) Salt forms: HCl = hydrochloride.
(c) Isolation Method:
(I) As for Example 450
(II) Mass Directed HPLC (Method A)
(III) Purified by silica SPE eluting with ethyl acetate/methanol
(IV) Mass Directed preparative HPLC (Method C).
(V) Aqueous work-up followed by addition of 4M HCl in 1,4-dioxane to a chloroform solution of the free base to give the hydrochloride salt.
(VI) Aminopropyl SPE column.

Example 473

4-{[3-(Methyloxy)phenyl]amino}-6-({2-[(2-methyl-propanoyl)amino]ethyl}sulfonyl)-3-quinolinecarboxamide

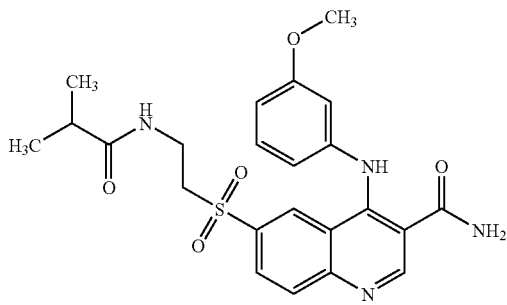

A solution of Example 364 (0.052 g) in anisole (1 ml) was treated with a solution of 95% trifluoroacetic acid in water (5 ml). The mixture was stirred for 3 h at room temperature and was then concentrated in vacuo. The residue was triturated with ethyl acetate, and the resulting solid was collected by filtration, washed with ethyl acetate and ether and dried to give a yellow solid (0.031 g). The solid was treated with dioxane (2 ml) and the suspension treated with N,N-diisopropylethylamine (0.04 ml) followed by isobutyryl chloride (0.015 ml, Aldrich) and the resulting solution stirred at room temperature under nitrogen for 2 h. The solution was diluted with methanol (5 ml) and applied to an aminopropyl SPE cartridge. Elution with methanol gave a gum after evaporation of solvent. The gum was purified by chromatography on silica gel eluting with a gradient of 0% to 6% methanol in chloroform to give the title compound as a yellow solid (0.017 g).

LC/MS $R_t$ 2.22 min, m/z 471 [MH$^+$]

Example 458

6-{[1-(1H-Imidazol-4-ylcarbonyl)-4-piperidinyl]sulfonyl}-8-methyl-4-{[3-(methyloxy)phenyl]amino}-3-quinolinecarboxamide

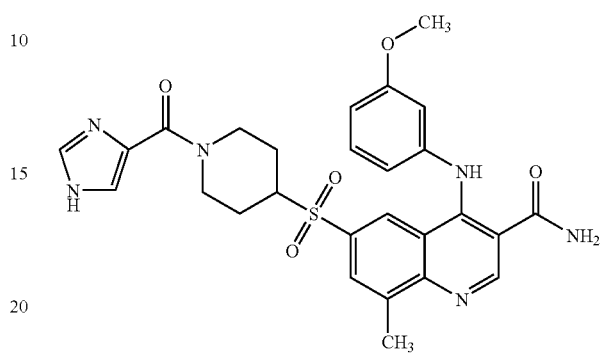

To a solution containing Intermediate 54 (0.041 g) in N,N-dimethylformamide (3 ml) were added imidazole-4-carboxylic acid (0.012 g, Aldrich), (1H-1,2,3-benzotriazol-1-yloxy)(tri-1-pyrrolidinyl)phosphonium hexafluorophosphate (PyBop) (0.053 g) and N,N-diisopropylethylamine (0.03 ml). The solution was stirred under nitrogen at room temperature for 18 h and was then concentrated in vacuo. The residual gum was purified using an aminopropyl SPE cartridge eluting with methanol followed by chromatography on silica gel (SPE cartridge), eluting with a gradient of 0% to 8% methanol in chloroform, to give the title compound as a yellow solid (0.031 g).

LC/MS $R_t$ 2.32 min, m/z 549 [MH$^+$]

Similarly prepared were the following:

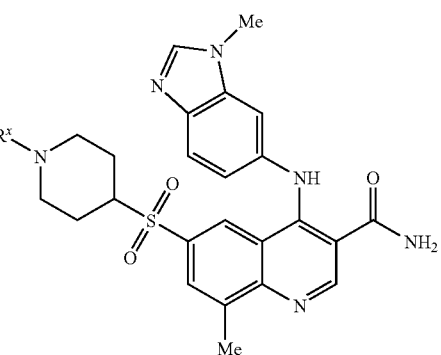

| Example Number (a) | R$^x$— | Starting Material | Amine Reagent/Source | LCMS MH$^+$ | LCMS $R_t$ (min) |
|---|---|---|---|---|---|
| 459 | 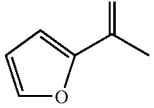 | Example 474 | 2-furoic acid/Aldrich | 573 | 2.15 |

-continued

| Example Number (a) | $R^x$— | Starting Material | Amine Reagent/ Source | LCMS $MH^+$ | LCMS $R_t$ (min) |
|---|---|---|---|---|---|
| 460 | cyclopropyl-CH(=O)- | Example 474 | Cyclopropylmethanoic acid/Aldrich | 547 | 2.12 |

Example 461

4-(2,3-Dihydro-1-benzofuran-4-ylamino)-8-methyl-6-{[1-(methylsulfonyl)-4-piperidinyl]sulfonyl}-3-quinolinecarboxamide hydrochloride

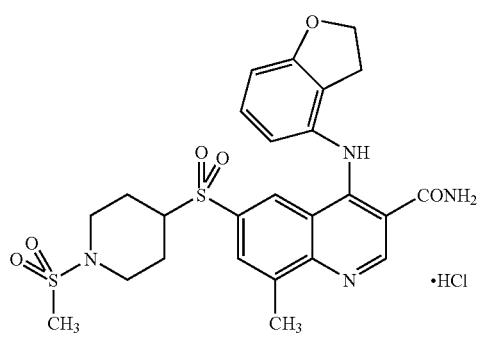

To a mixture containing Example 423 (0.050 g) in 1,4-dioxane (2 ml) was added methanesulphonyl chloride (0.009 ml). The mixture was stirred under nitrogen for 18h at room temperature, partitioned between ethyl acetate (100 ml) and 10% sodium bicarbonate solution (100 ml), separated and dried. The solid obtained was dissolved in 1,4-dioxane and treated with 4M hydrogen chloride in 1,4-dioxane (0.100 ml). After evaporation the title compound was obtained as a pale yellow solid (0.021 g).

LC/MS $R_t$ 2.5 min, m/z 545 [$MH^+$]

Example 462

6-{[4-(Cyclopropylmethoxy)phenyl]sulfonyl}-4-[(3-methoxyphenyl)amino]quinoline-3-carboxamide hydrochloride

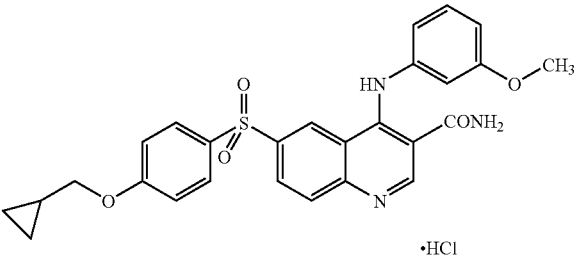

Tributyl phosphine (0.05 ml) was added to a stirred mixture of Example 360 (0.052 g), cyclopropylmethanol (0.028 g) and di-tert-butylazodicarboxylate (0.06 g) in tetrahydrofuran (1.5 ml) at 20° under nitrogen, and stirring was continued at 20° for 3 h. The solvent was concentrated and the residue purified by mass directed preparative HPLC (Method C) to give the title compound as a yellow solid (0.09 g).

LC/MS $R_t$ 3.4 min, m/z 504 [$MH^+$]

Example 463

6-[(4-Ethoxyphenyl)sulfonyl]-4-[(3-methoxyphenyl)amino]quinoline-3-carboxamide hydrochloride

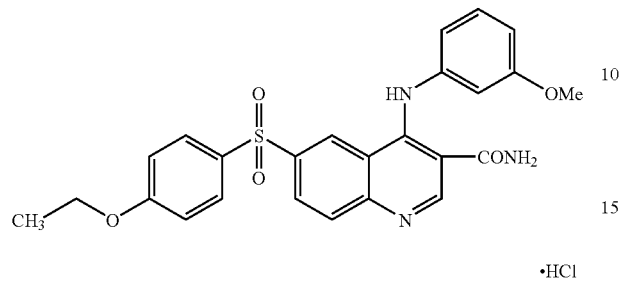

A stirred mixture of Example 360 (0.05 g), iodoethane (0.35 ml) and potassium carbonate (0.02 g) in acetonitrile (1.5 ml) was heated under reflux temperature for 1 h. The solvent was evaporated to dryness. The resulting solid was partitioned between dichloromethane (2×15 ml) and water (30 ml). The extracts were dried ($Na_2SO_4$) and concentrated. The residual solid was purified by mass directed HPLC (Method C) to give the title compound as a pale yellow solid (0.033 g).

LC/MS $R_t$ 2.87 min, m/z 478 [MH$^+$]

The following examples were similarly prepared:

Example 467

4-{[3-(3-Furyl)phenyl]amino}-6-[(4methoxyphenyl)sulfonyl]quinoline-3-carboxamide hydrochloride

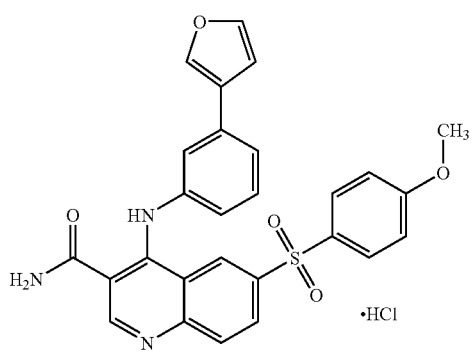

A stirred mixture of Example 254 (0.051 g), 3-furanboronic acid (0.017 g, Aldrich), tetrakis(triphenylphosphine)palladium(0) (0.059) and 2M sodium carbonate solution (1 ml) in dimethoxyethane (2 ml) was heated at 100° C. for 1 h. The mixture was cooled and poured into 2M sodium carbonate solution and extracted into dichloromethane (2×15 ml). The extracts were dried ($Na_2SO_4$) and concentrated. The

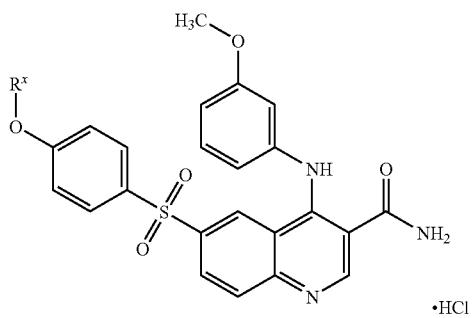

| Example Number (a) | R$^x$O— | Starting Material | Alkylating Agent/ Source | LCMS MH$^+$ | LCMS $R_t$ (min) |
|---|---|---|---|---|---|
| 464 HCl | H$_3$C⁀⁀O⁀ | Example 360 | 1-iodopropane/ Aldrich | 492 | 3.07 |
| 465 HCl | (H$_3$C)(CH$_3$)CH—O— | Example 360 | 2-iodopropane/ Aldrich | 492 | 3.00 |
| 466 HCl | cyclopentyl-O— | Example 360 | Iodocyclopentane/ Aldrich | 518 | 3.24 |

(a) Salt form: HCl = hydrochloride.

residue was purified by mass directed HPLC (Method C) to give the title compound as a yellow solid (0.026 g).

LC/MS $R_t$ 2.93min, m/z 500 [MH$^+$]

Similarly prepared were the following:

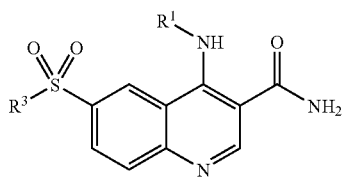

| Ex. No. | R$^1$NH— | R$^3$SO$_2$— | Starting Material | Boronic Acid/ Source | LCMS MH$^+$ | LCMS $R_t$ (min) |
|---|---|---|---|---|---|---|
| 468 (a) | | | Example 366 | [4-(methyloxy)phenyl] boronic acid/Aldrich | 540 | 3.18 |
| 469 (b) | | | Example 366 | 3-furanboronic acid/ Aldrich | 500 | 3.02 |

(a) Example 468 was isolated as the free base by trituration with ether.
(b) Example 469 was isolated as the free base by chromatography on silica gel, eluting with ethyl acetate.

Example 475

6-{[3-(Dimethylamino)-3-oxypropyl]sulfonyl}-4-{[4-fluoro-3-(methyloxy)phenyl]amino}-8-methyl-3-quinolinecarboxamide hydrochloride

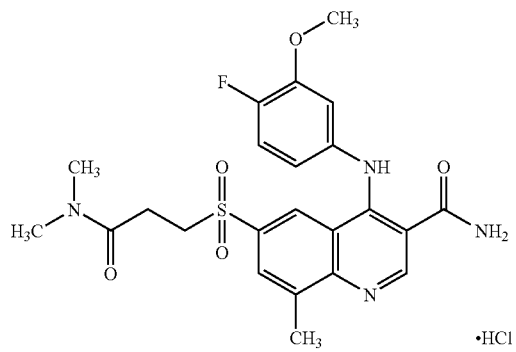

A solution of Intermediate 53 (0.04 g) in N,N-dimethylformamide (3 ml) was treated with oxone (0.22 g) and the resulting solution was stirred at room temperature overnight. The reaction was quenched by the addition on 1M sodium sulphite solution (1 ml) and extracted into dichloromethane. The combined organic layers were dried using a hydrophobic frit and evaporated in vacuo, and the product was dissolved in N,N-dimethylformamide (2 ml) and treated with O-(7-azabenzotriazole-1-yl)-N,N,N',N'-tetramethyluronium hexafluorophosphate (0.016 g). After 5 min, dimethylamine hydrochloride (0.065 g) and N,N-diisopropylethylamine (0.015 ml) in N,N-dimethylformamide (2 ml) were added. The resulting solution was left standing at room temperature overnight. Chromatographic purification by SCX (IST Isolute™, 10 g), eluting with methanol and 2M ammonia/methanol gave a yellow oil. Further purification by mass-directed HPLC (Method C) gave the title compound as a yellow solid (0.009 g).

LC/MS $R_t$ 2.34 min, m/z 489 [MH$^+$]

Example 540

4-[(5-Chloro-3-pyridinyl)amino]-8-methyl-6-(methylsulfonyl)-3-quinolinecarboxamide hydrochloride

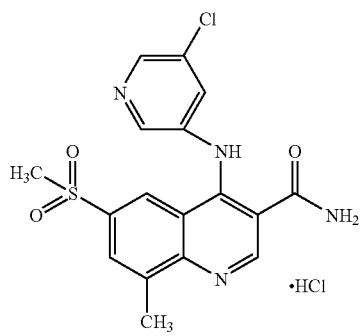

To a solution of Intermediate 33 (0.050 g) in N,N-dimethylformamide was added 5-chloro-3-pyridinamine (0.032 g; Specs) and pyridine hydrochloride (0.029 g) and the mixture heated at 90° C. for 16 h. The solvent was blown off under a stream of nitrogen at 45° C. The residue was triturated with acetonitrile and the resultant precipitate collected by filtration to give the title compound as a brown solid.

LC/MS $R_t$ 2.25 min m/z 391 [MH$^+$]

Similarly prepared were the following:

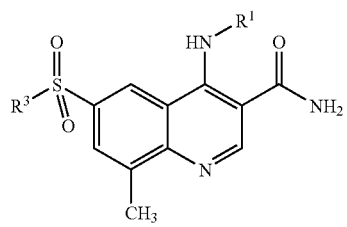

| Ex. No. (a) | R¹NH— | R³SO₂— | Starting Material | Amine Reagent/ Source | Isolation Method (b) | LCMS MH⁺ | LCMS $R_t$ (min) |
|---|---|---|---|---|---|---|---|
| 539 | 3-(methylamino)-5-fluoropyridine | MeSO₂— | Intermediate 33 | 5-Fluoro-3-pyridinamine/ Synchem OHG | (I) | 375 | 2.2 |
| 541 HCl | 5-(methylamino)-2-methylpyridine | MeSO₂— | Intermediate 33 | 6-Methyl-3-pyridinamine/ AsymChem | (IV) | 371 | 1.79 |
| 543 HCl | 4-(methylamino)isobenzofuran-1(3H)-one | MeSO₂— | Intermediate 33 | 4-Amino-2-benzofuran-1(3H)-one/ EP0529636A1 | (II) | 412 | 2.25 |
| 601 | 3-(methylamino)-2,6-dimethylpyridine | MeSO₂— | Intermediate 33 | 2,6-dimethyl-3-pyridylamine/ Lancaster | (III) | 385 | 1.76 |

(a) Salt form: HCl = hydrochoride
(b) Isolation method:
(I) Trituration with acetonitrile followed by elution through an aminopropyl SPE cartridge with methanol.
(II) Reaction was performed at 80° C. in acetonitrile and the product isolated by filtration of the reaction mixture.
(III) Mass Directed preparative HPLC (Method A) followed by chromatography on silica gel eluting with 3% methanol in dichloromethane.
(IV) Trituration with acetonitrile followed by isolation of the product by filtration.

Example 480

Ethyl 3-{[3-(aminocarbonyl)-4-(2,3-dihydro-1-benzofuran-4-ylamino)-8-methyl-6-quinolinyl]sulfonyl}propanoate

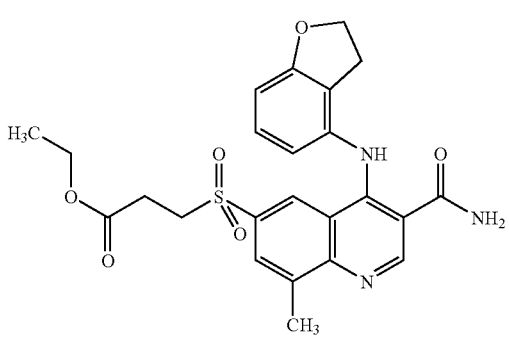

To a solution of Intermediate 57 (0.82 g) in N,N-dimethylformamide (25 ml) was added oxone (4.5 g). The mixture was stirred at room temperature for 2 h before quenching with aqueous sodium sulphite solution and extracting with dichloromethane (2×25 ml). The organic layers were combined, washed with water, dried using a hydrophobic frit, concentrated in vacuo and purified by chromatography on silica gel, eluting with an ethyl acetate: cyclohexane gradient, to give the title compound as a yellow solid (0.12 g).

LC/MS $R_t$ 2.61 min m/z 484 [MH$^+$].

Example 481

3-[(3-(Aminocarbonyl)-4-{[4-fluoro-3-(methyloxy)phenyl]amino}-8-methyl-6-quinolinyl)sulfonyl]propanoic acid hydrochloride

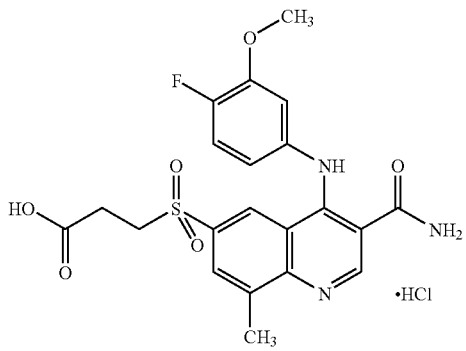

To a solution of Intermediate 53 (0.8 g) in N,N-dimethylformamide (10 ml) was added oxone (4.6 g). The mixture was stirred at room temperature for 48 h before quenching with aqueous sodium sulphite solution and extracting with dichloromethane (3×25 ml). The aqueous layers were combined and applied to an Oasis cartridge, eluting with water and methanol. The methanol fractions were combined and concentrated in vacuo. The residue was applied to an SPE cartridge (Isolute, aminopropyl solid phase), eluting with methanol and 2M ammonia/methanol; evaporation of the methanol/ammonia fraction gave an orange oil. Further purification by mass directed preparative HPLC (Method C) gave the title compound as a yellow oil (0.003 g).

LC/MS $R_t$ 2.23 min m/z 462 [MH$^+$].

Similarly prepared were the following:

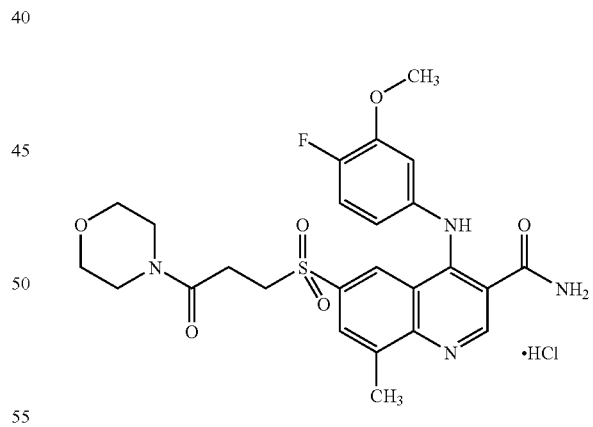

| Example Number (a) | R$^1$NH— | Starting Material | LCMS MH$^+$ | LCMS $R_t$ (min) |
|---|---|---|---|---|
| 549 HCl | (3-fluorophenyl)amino | Intermediate 59 | 432 | 2.38 |
| 550 HCl | (pyridin-3-yl)amino | Intermediate 60 | 415 | 1.92 |

(a) Salt forms: HCl = hydrochloride

Example 482

4-{[4-Fluoro-3-(methyloxy)phenyl]amino}-8-methyl-6-{[3-(4-morpholinyl)-3-oxopropyl]sulfonyl}-3-quinolinecarboxamide hydrochloride To a solution of Example 481 (0.035 g) in N,N-dimethylformamide (2 ml) was added O-(7-azabenzotriazole-1-yl)-N,N,N',N'-tetramethyluronium hexafluorophosphate (0.029 g). After 5 min, morpholine (0.007 ml, available from Aldrich) and N,N-diisopropylethylamine (0.026 ml) were added. The resulting solution was stirred at room temperature overnight, and applied directly to an SCX cartridge (IST Isolute™, 5 g). Elution with methanol and 2M ammonia/methanol gave an orange residue, which was further purified by mass directed preparative HPLC (Method C) to give the title compound as a yellow solid (0.006 g)

LC/MS $R_t$ 2.37 min m/z 531 [MH$^+$]..

Similarly prepared were the following:

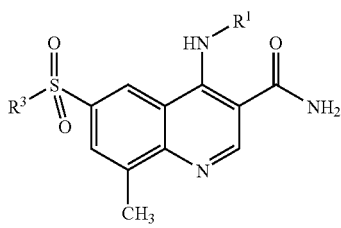

| Example Number (a) | R³SO₂— | R¹NH— | Starting Material | Amine reagent/ Source | Isolation Method (b) | LCMS MH⁺ | LCMS R_t (min) |
|---|---|---|---|---|---|---|---|
| 483 HCl | | | Example 481 | tetrahydro-2H-pyran-4-amine/ Aldrich | (II) | 545 | 2.22 |
| 484 HCl | | | Example 481 | 1-methyl piperazine/ Aldrich | (II) | 544 | 1.84 |
| 506 HCl | | | Example 550 | 1-methyl piperazine/ Aldrich | (II) | 497 | 1.75 |
| 507 HCl | | | Example 549 | 1-methyl piperazine/ Aldrich | (II) | 514 | 1.98 |

(a) Salt form HCl = hydrochloride
(b) Isolation Method:
(II) Mass Directed preparative HPLC (Method C).

Example 551

6-{[3-(Dimethylamino)-3-oxopropyl]thio}-4-[(3-fluorophenyl)amino]-8-methyl-3-quinolinecarboxamide

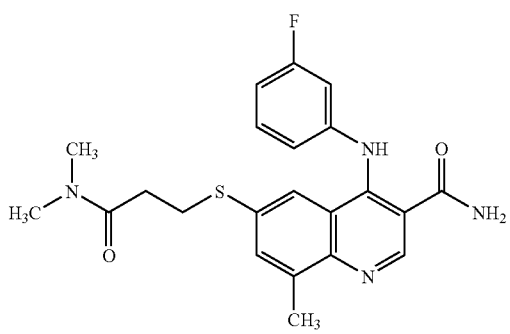

To a solution of Intermediate 59 (0.04 g) in N,N-dimethylformamide (1 ml) was added O-(7-azabenzotriazole-1-yl)-N,N,N',N'-tetramethyluronium hexafluorophosphate (0.038 g). After 5 min, dimethylamine hydrochloride (0.026 g) and N,N-diisopropylethylamine (0.07 ml) were added. The resulting solution was stirred at room temperature overnight, and applied directly to an SCX cartridge (IST Isolute™, 5 g), eluting with methanol followed by 2M ammonia in methanol to give the title compound as an orange oil (0.038 g).

LC/MS $R_t$ 2.39 min m/z 427 [MH$^+$].

Similarly prepared were the following:

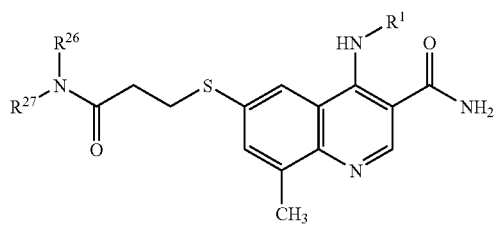

| Example Number | $R^{28}R^{27}N$— | $R^1NH$— | Starting Material | Amine reagent/Source | LCMS MH$^+$ | LCMS $R_t$ (min) |
|---|---|---|---|---|---|---|
| 552 | (tetrahydropyran-4-yl)(methyl)amino | 3-fluoro-N-methylanilino | Intermediate 59 | tetrahydro-2H-pyran-4-amine/Aldrich | 483 | 2.34 |
| 553 | cyclopropyl(methyl)amino | 3-fluoro-N-methylanilino | Intermediate 59 | cyclopropyl(methyl)amine/Karl Industries | 453 | 2.56 |
| 554 | morpholino | 3-fluoro-N-methylanilino | Intermediate 59 | Morpholine/Aldrich | 469 | 2.36 |
| 555 | pyrrolidin-1-yl | 3-fluoro-N-methylanilino | Intermediate 59 | Pyrrolidine/Aldrich | 453 | 2.49 |

-continued

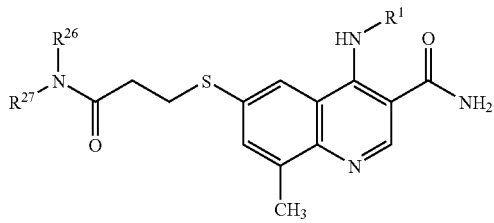

| Example Number | R²⁸R²⁷N— | R¹NH— | Starting Material | Amine reagent/ Source | LCMS MH⁺ | LCMS $R_t$ (min) |
| --- | --- | --- | --- | --- | --- | --- |
| 556 | Me₂N— | 3-pyridyl-NH-CH₂— | Intermediate 60 | Dimethylamine/ Aldrich | 410 | 2.03 |
| 557 | tetrahydropyran-4-yl-N(Me)— | 3-pyridyl-NH-CH₂— | Intermediate 60 | tetrahydro-2H-pyran-4-amine/ Aldrich | 466 | 2.01 |
| 558 | cyclopropyl-N(Me)— | 3-pyridyl-NH-CH₂— | Intermediate 60 | cyclopropyl(methyl)amine/Karl Industries | 436 | 2.20 |
| 559 | morpholin-4-yl— | 3-pyridyl-NH-CH₂— | Intermediate 60 | Morpholine/ Aldrich | 452 | 2.03 |
| 560 | pyrrolidin-1-yl— | 3-pyridyl-NH-CH₂— | Intermediate 60 | Pyrrolidine/Aldrich | 436 | 2.13 |

Example 485

6-{[3-(Dimethylamino)-3-oxopropyl]sulfonyl}-4-[(3-fluorophenyl)amino]-8-methyl-3-quinolinecarboxamide hydrochloride

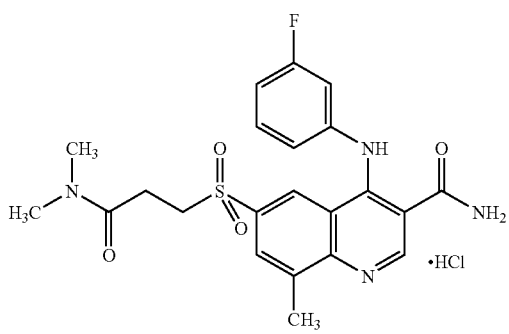

To a solution of the Example 551 (0.038 g) in N,N-dimethylformamide (2 ml) was added oxone (0.22 g). The mixture was stirred at room temperature for 2 h before quenching with aqueous sodium sulphite solution and extracting with dichloromethane. The organic layers were combined, dried by filtration through a hydrophobic frit and concentrated in vacuo. Purification by mass directed preparative HPLC (Method C) gave the title compound as a yellow solid (0.015 g).

LC/MS $R_t$ 2.31 min m/z 459 [MH⁺].

Similarly prepared were the following:

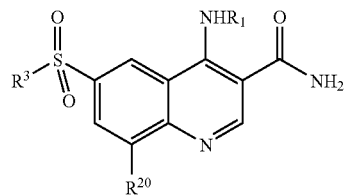

| Example Number (a) | R³SO₂— | Starting Material | R²⁸— | R¹NH— | Isolation Method (b) | LCMS MH⁺ | LCMS R_t (min) |
|---|---|---|---|---|---|---|---|
| 486 HCl | tetrahydropyran-NH-C(O)-CH₂CH₂-S(O)₂-CH₃ | Example 552 | Me— | 3-F-C₆H₄-NH-CH₃ | (II) | 515 | 2.39 |
| 487 HCl | cyclopropyl-N(CH₃)-C(O)-CH₂CH₂-S(O)₂-CH₃ | Example 553 | Me— | 3-F-C₆H₄-NH-CH₃ | (II) | 485 | 2.62 |
| 488 HCl | morpholino-C(O)-CH₂CH₂-S(O)₂-CH₃ | Example 554 | Me— | 3-F-C₆H₄-NH-CH₃ | (II) | 501 | 2.38 |
| 489 HCl | pyrrolidino-C(O)-CH₂CH₂-S(O)₂-CH₃ | Example 555 | Me— | 3-F-C₆H₄-NH-CH₃ | (II) | 485 | 2.49 |
| 490 HCl | (CH₃)₂N-C(O)-CH₂CH₂-S(O)₂-CH₃ | Example 556 | Me— | pyridin-3-yl-NH-CH₃ | (II) | 442 | 1.98 |
| 491 HCl | tetrahydropyran-NH-C(O)-CH₂CH₂-S(O)₂-CH₃ | Example 557 | Me— | pyridin-3-yl-NH-CH₃ | (II) | 498 | 1.95 |
| 492 HCl | cyclopropyl-N(CH₃)-C(O)-CH₂CH₂-S(O)₂-CH₃ | Example 558 | Me— | pyridin-3-yl-NH-CH₃ | (II) | 468 | 2.1 |

-continued

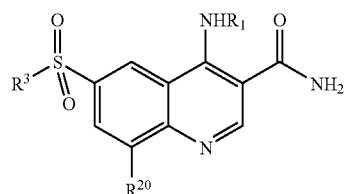

| Example Number (a) | R³SO₂— | Starting Material | R²⁸— | R¹NH— | Isolation Method (b) | LCMS MH⁺ | LCMS R_t (min) |
|---|---|---|---|---|---|---|---|
| 493 HCl | morpholine-C(O)-CH₂CH₂-SO₂- | Example 559 | Me— | 3-pyridyl-NH(Me)- | (II) | 484 | 1.96 |
| 494 HCl | pyrrolidine-C(O)-CH₂CH₂-SO₂- | Example 560 | Me— | 3-pyridyl-NH(Me)- | (II) | 468 | 2.04 |
| 525 HCOOH | tetrahydrofuran-3-yl-SO₂- | Example 563 | Me— | 3-pyridyl-NH(Me)- | (I) | 413 | 2.00 |
| 526 | tetrahydrofuran-3-yl-SO₂- | Example 564 | Me— | 3-pyridyl-NH(Me)- | (I) | 430 | 2.50 |
| 527 | MeC(O)N(Me)CH₂CH₂-SO₂- | Example 681 | Me— | 3-fluorophenyl-NH(Me)- | (III) | 459 | 2.30 |
| 529 | tetrahydropyran-4-yl-SO₂- | Example 565 | Me— | 3-fluorophenyl-NH(Me)- | (IV) | 444 | 2.5 |
| 530 HCl | tetrahydropyran-4-yl-SO₂- | Example 566 | Me— | 3-pyridyl-NH(Me)- | (II) | 427 | 2.00 |

-continued

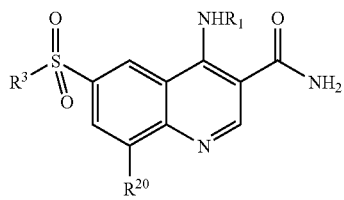

| Example Number (a) | R³SO₂— | Starting Material | R²⁸— | R¹NH— | Isolation Method (b) | LCMS MH⁺ | LCMS R_t (min) |
|---|---|---|---|---|---|---|---|
| 532 | Me-C(O)-NH-CH₂CH₂-S(O)₂-Me | Example 570 | Me— | 3-F, N-Me anilino | (V) | 445 | 2.20 |
| 533 HCl | MeO-CH₂CH₂-S(O)₂-Me | Example 571 | Me— | 2,3-dihydrobenzofuran-4-yl-N(Me)— | (II) | 442 | 2.3 |
| 534 HCOOH | Me-C(O)-NH-CH₂CH₂-S(O)₂-Me | Example 572 | Me— | pyridin-3-yl-N(Me)— | (I) | 428 | 1.8 |
| 535 HCOOH | pyridin-3-yl-S(O)₂-Me | Example 573 | Me— | 4-F, 3-OMe-phenyl-N(Me)— | (I) | 467 | 2.6 |
| 538 HCl | 3,4-diMeO-phenyl-S(O)₂-Me | Example 574 | Me— | 2,3-dihydrobenzofuran-4-yl-N(Me)— | (II) | 520 | 2.83 |
| 568 | N-Boc-piperidin-4-yl-S(O)₂-Me | Example 569 | Me— | pyridin-3-yl-N(Me)— | (VI) | 526 | 2.60 |
| 578 HCl | Me-CH₂CH₂-S(O)₂-Me | Example 635 | Me— | pyridin-3-yl-N(Me)— | (II) | 385 | 2.13 |

-continued

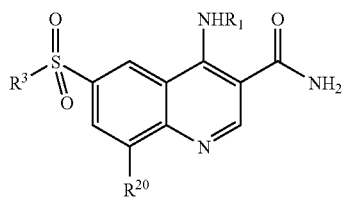

| Example Number (a) | R³SO₂— | Starting Material | R²⁸— | R¹NH— | Isolation Method (b) | LCMS MH⁺ | LCMS R_t (min) |
|---|---|---|---|---|---|---|---|
| 579 HCl | Me—S(O)(O)—CH(Me)— (isopropylsulfonyl) | Example 636 | Me— | 3-pyridyl-NHMe | (II) | 385 | 2.08 |
| 580 HCl | Me,Me,Me—C—S(O)(O)— (tert-butylsulfonyl) | Example 637 | Me— | 3-pyridyl-NHMe | (II) | 399 | 2.22 |
| 581 HCl | Me—CH₂—S(O)(O)— (ethylsulfonyl) | Example 634 | Me— | 3-pyridyl-NHMe | (II) | 371 | 1.95 |
| 582 HCl | Me—CH₂—S(O)(O)— | Example 638 | Cl— | 3-pyridyl-NHMe | (II) | 391 | 2.07 |
| 583 HCl | Me—CH₂—S(O)(O)— | Example 662 | Me— | 1-ethyl-pyrazol-5-yl-NHMe | (II) | 388 | 2.33 |
| 584 HCl | Me—CH(Me)—S(O)(O)— | Example 664 | Me— | 1-ethyl-pyrazol-5-yl-NHMe | (II) | 402 | 2.4 |
| 585 HCl | Me,Me,Me—C—S(O)(O)— | Example 665 | Me— | 1-ethyl-pyrazol-5-yl-NHMe | (II) | 416 | 2.54 |

-continued

| Example Number (a) | R³SO₂— | Starting Material | R²⁸— | R¹NH— | Isolation Method (b) | LCMS MH⁺ | LCMS R_t (min) |
|---|---|---|---|---|---|---|---|
| 666 HCl | Me-CH₂-SO₂-Me | Example 646 | Cl— | 5-chloro-3-(methylamino)pyridine | (II) | 425 | 2.52 |
| 667 HCl | Me-CH₂CH₂-SO₂-Me | Example 647 | Cl— | 5-chloro-3-(methylamino)pyridine | (II) | 439 | 2.73 |
| 668 HCl | (Me)₂CH-SO₂-Me | Example 648 | Cl— | 5-chloro-3-(methylamino)pyridine | (II) | 439 | 2.56 |
| 669 HCl | (Me)₃C-SO₂-Me | Example 649 | Cl— | 5-chloro-3-(methylamino)pyridine | (II) | 453 | 2.66 |
| 670 HCl | (Me)₂CH-SO₂-Me | Example 644 | Me— | 5-chloro-3-(methylamino)pyridine | (II) | 419 | 2.47 |
| 671 HCl | Me-CH₂-SO₂-Me | Example 650 | Me— | 5-fluoro-3-(methylamino)pyridine | (II) | 389 | 2.28 |
| 672 HCl | Me-CH₂CH₂-SO₂-Me | Example 651 | Me— | 5-fluoro-3-(methylamino)pyridine | (II) | 403 | 2.49 |

-continued

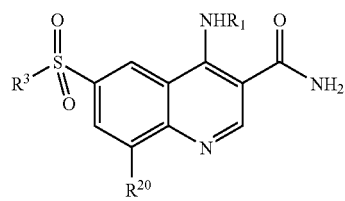

| Example Number (a) | R³SO₂— | Starting Material | R²⁸— | R¹NH— | Isolation Method (b) | LCMS MH⁺ | LCMS R_t (min) |
|---|---|---|---|---|---|---|---|
| 673 HCl | Me-CH(Me)-SO₂- | Example 652 | Me— | 3-F-5-(MeNH)-pyridin-yl | (II) | 403 | 2.35 |
| 674 HCl | Me₃C-SO₂-Me | Example 653 | Me— | 3-F-5-(MeNH)-pyridin-yl | (II) | 417 | 2.47 |
| 675 HCl | MeCH₂CH₂-SO₂-Me | Example 655 | Cl— | 3-F-5-(MeNH)-pyridin-yl | (II) | 423 | 2.49 |
| 676 HCl | Me₂CH-SO₂-Me | Example 656 | Cl— | 3-F-5-(MeNH)-pyridin-yl | (II) | 423 | 2.43 |
| 677 HCl | Me₃C-SO₂-Me | Example 657 | Cl— | 3-F-5-(MeNH)-pyridin-yl | (II) | 437 | 2.54 |
| 678 HCl | MeCH₂-SO₂-Me | Example 642 | Me— | 3-Cl-5-(MeNH)-pyridin-yl | (II) | 405 | 2.38 |
| 679 HCl | MeCH₂CH₂-SO₂-Me | Example 643 | Me— | 3-Cl-5-(MeNH)-pyridin-yl | (II) | 419 | 2.53 |

-continued

| Example Number (a) | R³SO₂— | Starting Material | R²⁸— | R¹NH— | Isolation Method (b) | LCMS MH⁺ | LCMS R$_t$ (min) |
|---|---|---|---|---|---|---|---|
| 680 HCl | (Me)₃C-SO₂— | Example 645 | Me— | 3-chloro-5-(methylamino)pyridine | (II) | 433 | 2.67 |

(a) Salt form HCl = hydrochloride
HCOOH = formate
(b) Isolation Method:
(I) Mass Directed Preparative HPLC (Method A)
(II) Mass Directed Preparative HPLC (Method C)
(III) Aqueous work-up
(IV) SCX ion exchange eluting with 2M ammonia in methanol
(V) Trituration with methanol and collection of the product by filtration
(VI) Chromatography on silica gel eluting with methanol/ethyl acetate mixtures

Example 495

4-{[4-Fluoro-3-(methyloxy)phenyl]amino}-8-methyl-6-{[2-(2-oxo-1-pyrrolidinyl)ethyl]sulfonyl}-3-quinolinecarboxamide hydrochloride

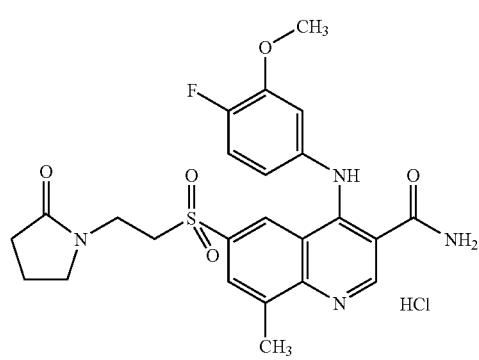

To a solution of Example 477 (0.03 g) in 1,4-dioxan (5 ml) was added ethyl 4-bromobutyrate (0.01 ml, available from Aldrich). The mixture was heated at 120° C. for 48h. The solvent was evaporated in vacuo. Purification by mass directed preparative HPLC (Method C) gave the title compound as a yellow solid (0.007 g).

LC/MS R$_t$ 2.3 min m/z 501 [MH⁺].

Similarly prepared were the following:

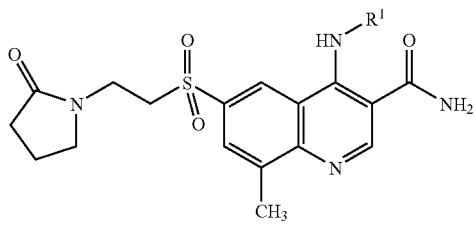

| Example Number (a) | R¹NH— | Starting Material | LCMS MH⁺ | LCMS R$_t$ (min) |
|---|---|---|---|---|
| 514 HCl | 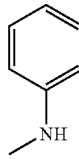 | Example 561 | 471 | 2.29 |

(a) Salt form HCl = hydrochloride

Example 518

6-{[2-(Dimethylamino)ethyl]sulfonyl}-4-{[4-fluoro-3-(methyloxy)phenyl]amino}8-methyl-3-quinolinecarboxamide formate salt

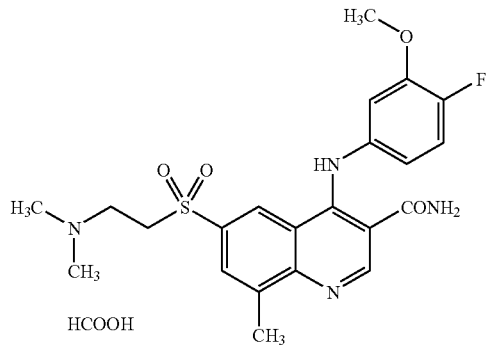

To a stirred mixture of Example 477 (0.05 g) in dry N,N-dimethylformamide (1 ml) was added methyl iodide (0.033 g) and triethylamine (0.032 ml), and the mixture was stirred under nitrogen for 18 h. The mixture was applied directly to an SPE cartridge (1 g) and eluted with 4% methanol in chloroform; the eluent was evaporated in vacuo and the residue purified using mass directed preparative HPLC (Method A) to give the title compound as a yellow solid (0.003 g).

LC/MS $R_t$ 2.01 min, m/z 461 [MH$^+$]

Example 519

4-(2,3-Dihydro-1-benzofuran-4-ylamino)-6-{[2-(dimethylamino)ethyl]sulfonyl}-8-methyl-3-quinolinecarboxamide formate salt Example 519 was prepared by a similar method to Example 518 from Example 422 to give the title compound as a yellow solid (0.005 g)

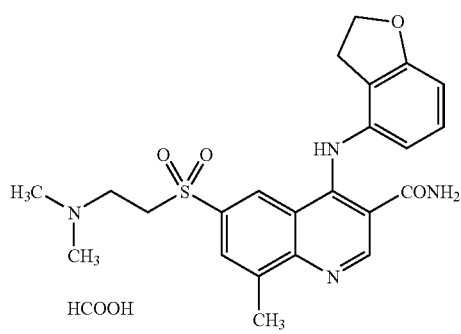

LC/MS $R_t$ 1.94 min, m/z 455 [MH$^+$]

Example 521

4-{[4-Fluoro-3-(methyloxy)phenyl]amino}-8-methyl-6-{[2-(methyloxy)ethyl]thio}-3-quinolinecarboxamide.

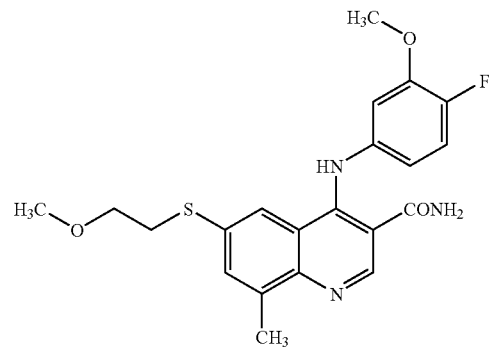

To a solution of Example 337 (0.05 g) in dry N,N-dimethylformamide (2 ml) under nitrogen was added sodium hydride (60% dispersion in mineral oil, 0.015 g). The mixture was stirred at room temperature for 10 min when methyl iodide (0.0078 ml) was added; the mixture was stirred at room temperature for 18 h and the solvent evaporated in vacuo. The residue was partitioned between chloroform and water, the layers separated by hydrophobic frit, and the organic layer evaporated. The crude product was purified using mass directed preparative HPLC (Method A) to give the title compound as a yellow solid (0.025 g).

LC/MS $R_t$ 2.46 min, m/z 416 [MH$^+$]

Similarly prepared from Example 528 was the following:

Example 571

4-(2,3-Dihydro-1-benzofuran-4-ylamino)-8-methyl-6-{[2-(methyloxy)ethyl]thio}-3-quinolinecarboxamide

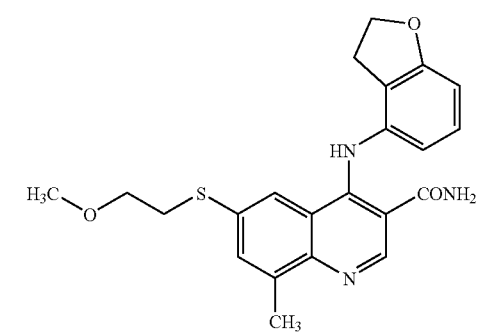

LC/MS $R_t$ 2.40 min, m/z 410 [MH$^+$]

Example 523

4-(2,3-Dihydro-1-benzofuran-4-ylamino)-6-[(2-hydroxyethyl)sulfonyl]-8-methyl-3-quinolinecarboxamide

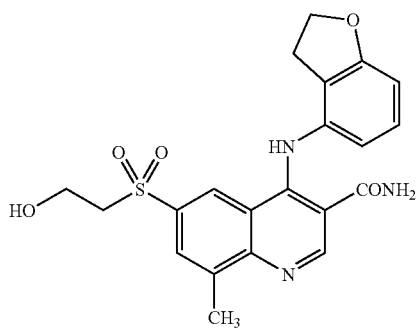

To a solution of Example 528 (0.05 g) in N,N-dimethylformamide (2 ml) was added oxone (0.311 g). The mixture was stirred at room temperature for 3 h before quenching with aqueous sodium sulphite solution and extracting with ethyl acetate (50 ml). The organic layer was dried ($Na_2SO_4$) and concentrated in vacuo, and the mixture purified by mass directed preparative HPLC (Method A) to give the title compound as a white solid (0.035 g).

LC/MS $R_t$ 2.1 min m/z 428 [MH$^+$].

Example 524

4-(2,3-Dihydro-1-benzofuran-4-ylamino)-8-methyl-6-{[2-(methyloxy)ethyl]sulfonyl}-3-quinolinecarboxamide

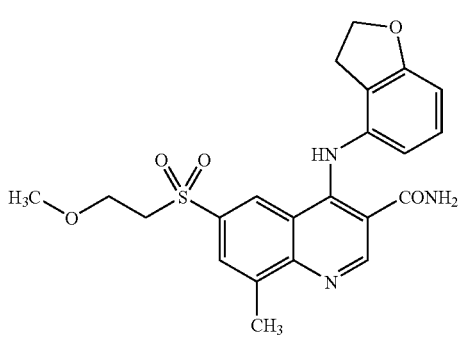

To a solution of Example 523 (0.018 g) in dry N,N-dimethylformamide (1 ml) under nitrogen was added sodium hydride (60% dispersion in mineral oil, 0.0017 g). The mixture was stirred at room temperature for 10 min when methyl iodide (0.0026 ml) was added, stirring was continued for 18 h at room temperature and the solvent evaporated in vacuo. The residue was partitioned between ethyl acetate and water and the organic layer dried ($MgSO_4$) and evaporated. The crude product was purified using mass directed preparative HPLC (Method A) to give the title compound as a yellow solid (0.0024 g)

LC/MS $R_t$ 2.3 min, m/z 442 [MH$^+$].

Example 536

6-({3-[(Dimethylamino)carbonyl]phenyl}sulfinyl)-8-methyl-4-{[3-(methyloxy)phenyl]amino}-3-quinolinecarboxamide

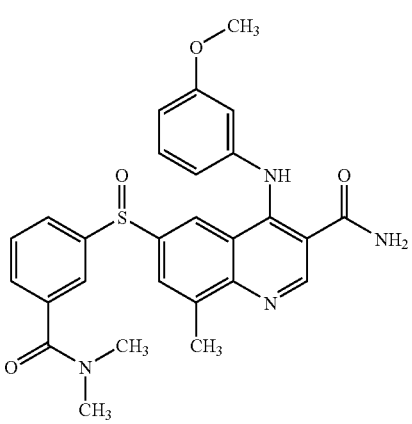

To a mixture containing Example 544 (0.10 g) in N,N-dimethylformamide (10 ml) was added oxone (0.253 g). The mixture was stirred under nitrogen for 3 h at room temperature and was then quenched with a solution of sodium sulphite (0.25 g) in water (10 ml), diluted with water (30 ml) and extracted with ethyl acetate (2×30 ml). The combined organic extracts were evaporated to dryness and the residue purified by mass directed preparative HPLC (Method A) to give the title compound as a yellow solid (0.028 g).

LC/MS $R_t$ 2.24 min, m/z 503 [MH$^+$]

Example 537

6-({3-[(Dimethylamino)carbonyl]phenyl}sulfonyl)-4-[(3-hydroxyphenyl)amino]-8-methyl-3-quinolinecarboxamide

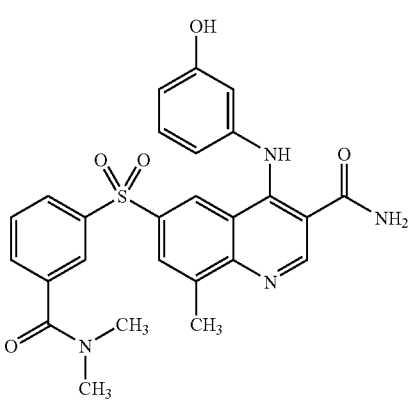

A solution of borontribromide in dichloromethane (1.0 M, 2.2 ml) was added dropwise to an ice-cooled mixture containing Example 478 (0.35 g) in dichloromethane (25 ml) under nitrogen. The mixture was stirred at room temperature for 20 h, and was then treated with a further portion of borontribromide in dichloromethane (1.0 M, 2.2 ml) and stirred for a further 5 h. The mixture was quenched with methanol (10 ml) and evaporated to dryness in vacuo. The residue was partitioned between ethyl acetate (30 ml) and saturated aqueous sodium bicarbonate (30 ml), the organic extract evaporated to dryness in vacuo, and the residue purified by mass directed preparative HPLC (Method A) to give the title compound as a yellow solid (0.075 g).

LC/MS $R_t$ 2.46 min, m/z 505 [MH$^+$]

Example 575

7-({3-[(Dimethylamino)carbonyl]phenyl}sulfinyl)-4-{[3-(methyloxy)phenyl]amino}-3-quinolinecarboxamide

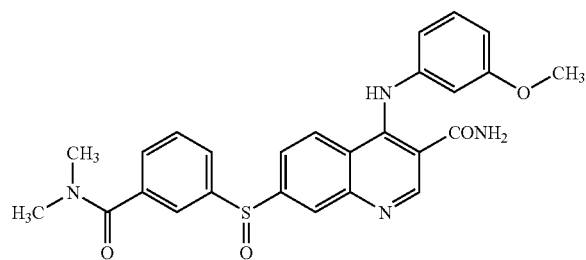

A mixture containing Intermediate 65 (0.15 g), 10% palladium on activated carbon (0.04 g) and triethylamine (5 ml) in ethanol (25 ml) and N,N-dimethylformamide (10 ml) was hydrogenated at room temperature for 4 h. The suspension was filtered through celite, the residue washed with ethanol/N,N-dimethylformamide (3:1, 50 ml), and the filtrate concentrated in vacuo. The residue was purified by mass directed preparative HPLC (Method A) to give the title compound as a yellow solid (0.035 g).

LC/MS $R_t$ 2.32 min, m/z 489 [MH$^+$]

Example 545

7-({3-[(Dimethylamino)carbonyl]phenyl}sulfonyl)-4-{[3-(methyloxy)phenyl]amino}-3-quinolinecarboxamide

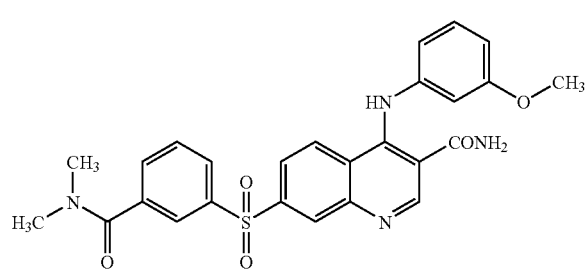

Oxone (0.22 g) was added portionwise to a stirred solution of Example 575 (0.035 g) in N,N-dimethylformamide (4 ml). The mixture was stirred at room temperature under nitrogen for 24 h, a further portion of oxone (0.17 g) was added, and the mixture stirred for a further 5 h. The reaction was quenched with a solution of sodium sulphite (1.2 g) in water (15 ml), diluted with water (10 ml) and extracted with ethyl acetate (3×30 ml). The combined organic extracts were dried over magnesium sulphate and concentrated in vacuo to give the title compound as a buff solid (0.035 g).

LC/MS $R_t$ 2.66 min, m/z 505 [MH$^+$]

Example 576

6-({5-[(Dimethylamino)carbonyl]-3-pyridinyl}thio)-8-methyl-4-{[3-(methyloxy)phenyl]amino}-3-quinolinecarboxamide, formate salt

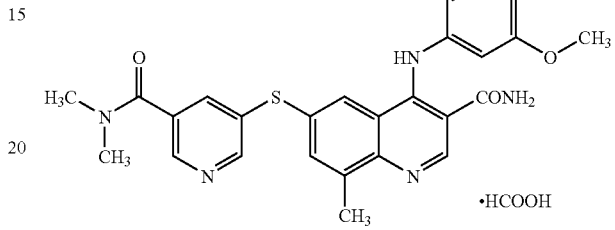

A stirred mixture of Intermediate 45 (0.47 g), Intermediate 69 (0.37 g), copper iodide (0.06 g), and potassium carbonate (0.47 g) in 1,3-dimethyl-3,4,5,6-tetrahydro-2(1H)-pyrimidinone (10 m) was heated at 100° C. under nitrogen for 4 h. The mixture was diluted with water (150 ml) and extracted with ethyl acetate (3×200 ml). The combined organic extracts were washed with water (2×200 ml) and brine (200 ml), and the organic layers dried over magnesium sulphate and concentrated in vacuo. The residue was purified by mass directed preparative HPLC (Method A) to give the title compound as a yellow solid (0.1 g).

LC/MS $R_t$ 2.35 min, m/z 488 [MH$^+$]

Example 547

6-({5-[(Dimethylamino)carbonyl]-3-pyridinyl}sulfinyl)-8-methyl-4-{[3-(methyloxy)phenyl]amino}-3-quinolinecarboxamide hydrochloride and Example 546

6-({5-[(Dimethylamino)carbonyl]-3-pyridinyl}sulfonyl)-8-methyl-4-{[3-(methyloxy)phenyl]amino}-3-quinolinecarboxamide hydrochloride Example 547

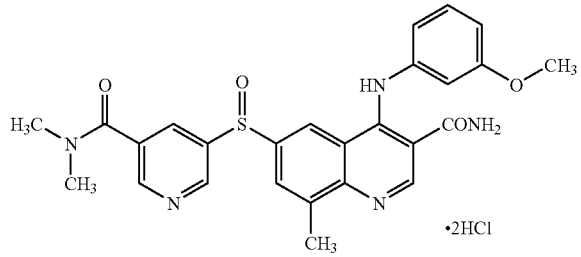

Example 546

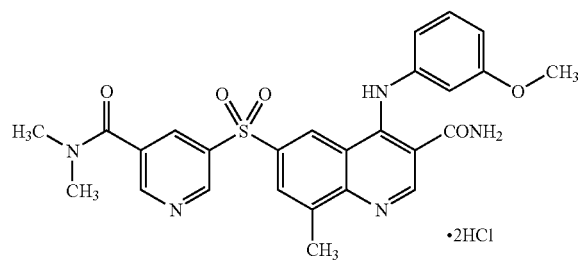

Oxone (1.2 g) was added portionwise to a stirred solution of Example 576 (0.1 g) in N,N-dimethylformamide (6 ml). The solution was stirred at room temperature under nitrogen for 2 h and then quenched with a solution of sodium sulphite (3 g) in water (30 ml). The mixture was diluted with water (25 ml) and extracted with ethyl acetate (4×50 ml) and the combined organic layers were washed with water (2×50 ml) and brine (50 ml), dried over magnesium sulphate and concentrated in vacuo. The residue was purified using mass directed preparative HPLC (Method C) to give Example 546 as a yellow solid (0.010 g) and Example 547 as a yellow solid (0.041 g).

Example 546: LC/MS $R_t$ 2.57 min, m/z 520 [MH$^+$]
Example 547: LC/MS $R_t$ 2.12 min, m/z 504 [MH$^+$]

Example 586

8-Methyl-4-[(3-methyl-5-isoxazolyl)amino]-6-(methylsulfonyl)-3-quinolinecarboxamide hydrochloride

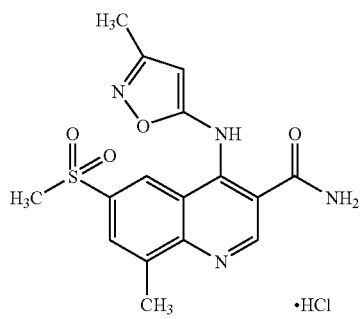

To a stirred suspension of sodium hydride (0.008 g; 60% dispersion in mineral oil) in dry N,N-dimethylformamide (1 ml) was added [(3-methyl-5-isoxazolyl)methyl]amine (available from Aldrich) (0.020 g) and the mixture heated at 80° C. for 30 min. A suspension of Intermediate 33 (0.020 g) in dry N,N-dimethylformamide (0.5 ml) was added and the mixture heated at 80° C. for 3 h. The mixture was quenched by the dropwise addition of ethanol (0.1 ml). The mixture was loaded onto a 2 g SCX cartridge, washed with methanol, and the product eluted with 10% '880' ammonia in methanol. The solvent was removed in vacuo and the residue purified by mass directed preparative HPLC (Method C) to give the title compound as a pale yellow solid (0.009 g)

LC/MS $R_t$ 2.23 min, m/z 361 [MH$^+$]

Example 544

6-({3-[(Dimethylamino)carbonyl]phenyl}thio)-8-methyl-4-{[3-(methyloxy)phenyl]amino}-3-quinolinecarboxamide

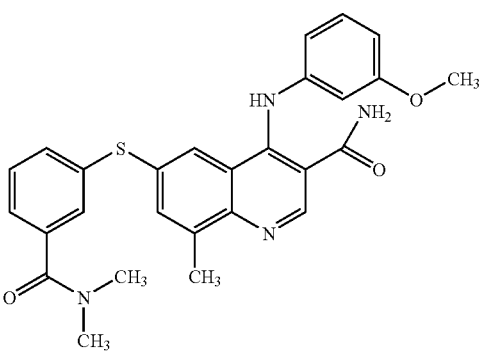

A stirred mixture of Intermediate 45 (50 g), Intermediate 28 (40 g), and potassium carbonate (40 g) in 1,3-dimethyl-3,4,5,6-tetrahydro-2(1H)-pyrimidinone (500 ml) was purged of air (by evacuation of the vessel and refilling with nitrogen three times) and left under nitrogen. Copper (I) iodide (5 g) was added and the mixture was warmed at 90° C. for 23 h. The mixture was cooled to 20° C. and poured into water (2.5 L). The precipitated solid was filtered off, washed with water and sucked partially dry. The damp solid was dissolved in chloroform (4 L) and washed with IN sodium hydroxide solution (1 L), followed by water (2×1 L) and brine (1 L). The organic phase was dried over sodium sulphate and the solvent evaporated to leave a sticky solid. The solid was crystallised from hot ethanol (650 ml) to give the title compound as a solid (45.1 g).

LC/MS $R_t$ 2.60 min m/z 487 [MH$^+$].

Similarly prepared were the following:

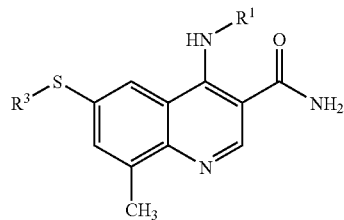

| Example Number (a) | R¹NH— | R³S— | Starting Material | Isolation Method (b) | LCMS MH⁺ | LCMS $R_t$ (min) |
|---|---|---|---|---|---|---|
| 562 | 3-methoxy-N-methylanilino | 4-(methylthio)pyridine | Intermediate 45 | (I) | 417 | 2.27 |
| 573 HCl | 4-fluoro-3-methoxy-N-methylanilino | 3-(methylthio)pyridine | Intermediate 35 | (II) | 435 | 2.56 |
| 574 | 2,3-dihydrobenzofuran-4-yl-N-methylamino | 3,4-dimethoxy-(methylthio)phenyl | Intermediate 36 | (III) | 487 | 2.86 |

(a) Salt form: HCl = hydrochoride
(b) Isolation method:
(I) Aqueous work-up followed by trituration with ether and filtration.
(II) Mass directed preparative HPLC (Method C).
(III) Trituration with ether and filtration.

Example 544

6-({3-[(Dimethylamino)carbonyl]phenyl}thio)-8-methyl-4-{[3-(methyloxy)phenyl]amino}-3-quinolinecarboxamide (alternative synthesis)

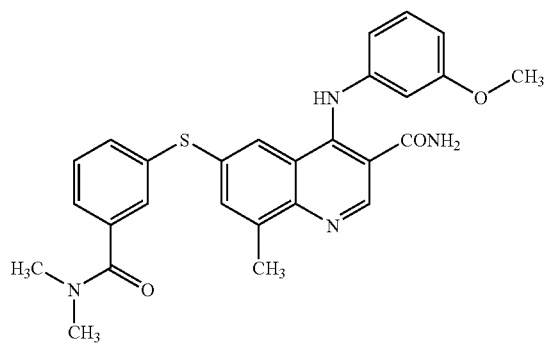

Intermediate 45 (5.0 g), Intermediate 28 (2.89 g), copper iodide (0.506 g) and potassium carbonate (2.94 g) were added to 1,3-dimethyl-3,4,5,6-tetrahydro-2(1H)-pyrimidinone (DMPU, 25 ml) and the resulting stirred slurry was heated to 100° C. under nitrogen. The mixture was stirred at 100° C. for 7 h, allowed to cooled to room temperature and stirred overnight. DMPU (20 ml) and water (80 ml) containing pyridine (0.43 ml) were added and the slurry was heated to 100° C. The resulting solution was seeded with crystals of Example 544 and stirred for 1 h at 100° C. The suspension was cooled gradually over 6 h, allowing the product to crystallise. The product was isolated by filtration, washed with water (2×50 ml) and dried at 40° C. in vacuo to give the title compound as a pale yellow solid (3.9 g).

LC/MS $R_t$ 2.58 min m/z 487 [MH⁺].

Example 478

6-({3-[(Dimethylamino)carbonyl]phenyl}sulfonyl)-8-methyl-4-{[3-(methyloxy)phenyl]amino}-3-quinolinecarboxamide (alternative synthesis)

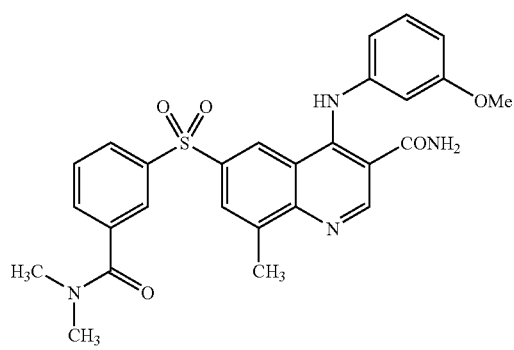

To a solution of Example 544 (29 g) in N,N-dimethylformamide (290 ml) cooled in a water bath was added oxone (87 g) in portions over 10 min. The mixture was stirred for 2 h, then poured into a cold (5° C.) solution of sodium metabisulphite (45 g) in water (2 L). After stirring for 35 min the mixture was extracted with chloroform (2 L+3×800 ml). The combined chloroform extracts were washed with water (3×600 ml), and the aqueous washes were extracted with chloroform (600 ml). The combined organic phases were dried over sodium sulphate and the solvent evaporated to leave a solid which was dried in vacuo at 40° C. for 3 days providing the title compound (27.8 g).

LC/MS $R_t$ 2.62 min m/z 519 [MH$^+$].

The solid was crystallised from hot ethanol containing 20% water (5 L) to give the title compound (20.2 g).

LC/MS $R_t$ 2.62 min m/z 519 [MH$^+$].

Example 478

6-({3-[(Dimethylamino)carbonyl]phenyl}sulfonyl)-8-methyl-4-{[3-(methyloxy)phenyl]amino}-3-quinolinecarboxamide (alternative procedure)

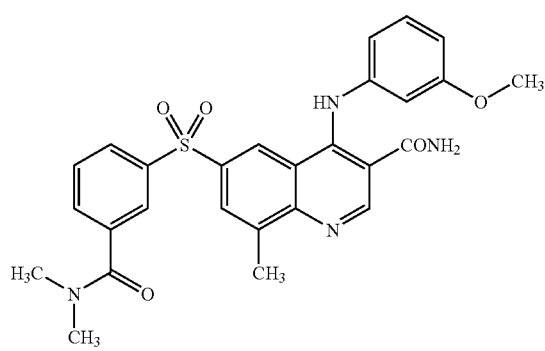

To a solution of Example 544 (3.5 g) in glacial acetic acid (18 ml) and water (3.5 ml) was added oxone (5.76 g) portionwise over 15 min. The mixture was stirred for 1.5 h at 20° C. and excess oxone quenched with a solution of sodium sulphite (0.545 g) in water (3.5 ml). The mixture was diluted with glacial acetic acid (11 ml) and water (21 ml), heated to 90°, treated dropwise over 30 min with 2M aqueous sodium hydroxide (20 ml), and cooled to 25° C. over 30 min. The resulting precipitate was collected by filtration, washed with water (25 ml×3) and dried in vacuo to give the title compound as a pale yellow solid (3.0 g).

LC/MS $R_t$ 2.54 min m/z 519 [MH$^+$].

Example 588

4-(2,3-Dihydro-1-benzofuran-4-ylamino)-8-methyl-6-(methylsulfinyl)-3-quinolinecarboxamide formate salt

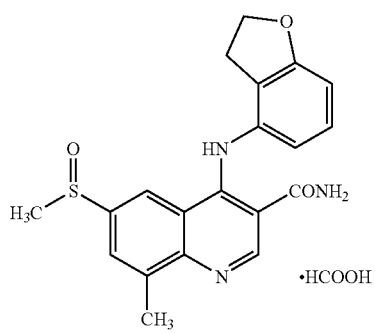

To a suspension of Example 577 (0.04 g) in methanol (10 ml) was added sodium periodate (0.023 g) in water (0.2 ml). The mixture was stirred at room temperature for 4 days and the solvents evaporated in vacuo. The residue was purified using mass directed preparative HPLC (Method A) to give the title compound as a yellow solid (0.017 g).

LC/MS $R_t$ 2.0 min, m/z 382 [MH$^+$]

Example 307

4-(2,3-Dihydro-1-benzofuran-4-ylamino)-8-methyl-6-(methylsulfonyl)-3-quinolinecarboxamide hydrochloride (alternative synthesis)

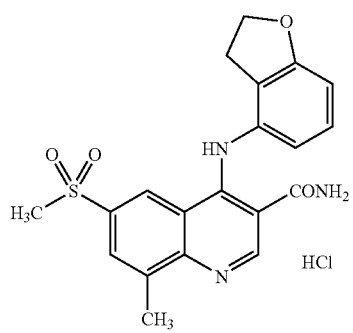

To a solution of Example 577 (0.04 g) in N,N-dimethylformamide (1 ml) was added oxone (0.337 g). The mixture was stirred at room temperature for 18 h, and quenched by addition of 10% sodium sulphite solution (15 ml). The mixture was extracted with ethyl acetate (50 ml), and the organic layer dried (Na$_2$SO$_4$) and evaporated in vacuo. The residue was purified using mass directed preparative HPLC (Method C) to give the title compound as a yellow solid (0.018 g)

LC/MS $R_t$ 2.2 min, m/z 398 [MH$^+$].

Example 688

4-(2,3-Dihydro-1-benzofuran-4-ylamino)-8-methyl-7-(methylthio)-3-quinolinecarboxamide

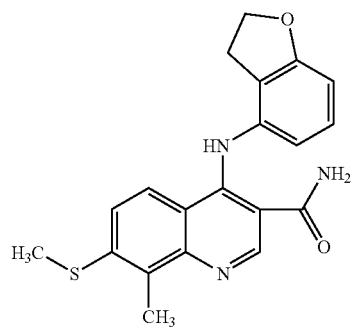

A stirred mixture of Intermediate 104 (0.50 g), sodium methanethiolate (0.35 g), potassium carbonate (0.43 g) and copper (I) iodide (0.025 g) in dry N,N-dimethylformamide (3 ml) was heated at 100° under nitrogen for 18 h. The mixture was cooled, poured into water (50 ml) and stirred for 15 min. The solid material was filtered off, dried in vacuo at 80° for 2 h, and boiled in ethanol:water 15:1 (50 ml) for 30 min. The insoluble material was filtered off, and the filtrate evaporated to dryness to give the title compound as a pale yellow solid (0.163 g).

LC/MS $R_t$ 2.40 min m/z 366 [MH$^+$]

Example 548

4-(2,3-Dihydro-1-benzofuran-4-ylamino)-8-methyl-7-(methylsulfonyl)-3-quinolinecarboxamide hydrochloride

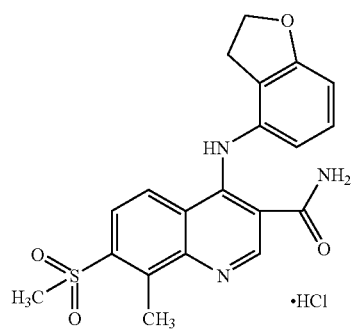

Example 548 was prepared from Example 688 by a similar method to Example 129, but without the addition of anisole to the reaction mixture, using 10:1 N,N-dimethylformamide:water as solvent, and purifying by mass directed preparative HPLC (method C).

LC/MS $R_t$ 2.50 min m/z 398 [MH$^+$]

What is claimed is:

1. A compound of formula (I)

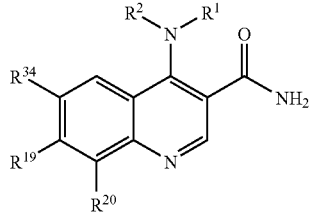

or a pharmaceutically acceptable salt thereof, wherein:

$R^1$ is $C_{1-6}$ alkyl;

$C_{3-7}$ cycloalkyl or $C_{3-7}$ cycloalkyl($C_{1-4}$ alkyl)- wherein the $C_{3-7}$ cycloalkyl is optionally substituted by one or more substituents selected from =O and OH;

$C_{4-7}$ cycloalkyl fused to an aryl ring;

Aryl or aryl($C_{1-6}$ alkyl)- wherein the aryl is optionally substituted by one or more substituents selected from $C_{1-6}$ alkyl, $C_{1-6}$ alkylCONR$^6$—, $C_{1-6}$ alkylCO—, halogen, —CF$_3$, —(CH$_2$)$_m$OH, —OCF$_3$, $C_{1-6}$ alkoxy-, $C_{1-6}$ alkoxy($C_{1-4}$ alkyl)-, $C_{1-6}$ alkoxy$C_{2-6}$ alkoxy-, $C_{1-6}$ alkoxycarbonyl, —CN, R$^4$R$^5$NCO, R$^7$R$^8$N—, R$^9$R$^{10}$NCONR$^{11}$—, HO(CH$_2$)$_{2-6}$O—, R$^{12}$R$^{13}$NSO$_2$(CH$_2$)$_m$—, (4-morpholinyl)$C_{2-6}$ alkoxy, —NR$^{14}$SO$_2$C$_{1-6}$ alkyl, aryloxy, heteroaryl(optionally substituted by $C_{1-6}$ alkyl), CO$_2$H, R$^{21}$R$^{22}$N($C_{1-4}$ alkyl)-, $C_{1-6}$ alkoxyCONR$^{23}$(CH$_2$)$_m$—, aryl(optionally substituted by $C_{1-6}$ alkyl);

Aryl fused to a $C_{4-7}$ cycloalkyl ring, wherein the cycloalkyl ring is optionally substituted by one or more =O;

Aryl fused to a heterocyclyl ring, wherein the heterocyclyl ring is optionally substituted by one or more substituents selected from =O, —COC$_{1-4}$ alkyl, $C_{1-4}$ alkyl;

Heteroaryl or heteroaryl($C_{1-6}$ alkyl)- wherein the heteroaryl is optionally substituted by one or more substituents selected from: $C_{1-6}$ alkyl, aryl($C_{1-4}$ alkyl), $C_{1-6}$ alkoxy, halogen, $C_{1-6}$ alkoxyCO; or Heterocyclyl optionally fused to an aryl or heteroaryl ring;

$R^2$ is hydrogen or $C_{1-6}$ alkyl;

$R^{34}$ is hydrogen or a group of formula:

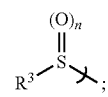

$R^3$ is $C_{1-6}$ alkyl optionally substituted by one or more substituents selected from —OH, —NR$^{16}$COR$^{15}$, —NR$^{17}$R$^{18}$, —CO$_2$R$^{24}$, $C_{1-6}$ alkoxyCONR$^{25}$—, —CONR$^{26}$R$^{27}$, $C_{1-6}$ alkoxy-, $C_{1-6}$ alkylSO$_2$NR$^{33}$—, or a group having one of the following formulae:

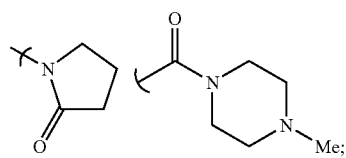

$C_{1-7}$ cycloalkyl;

Aryl or aryl($C_{1-6}$alkyl)- wherein the aryl is optionally substituted by one or more substituents selected from $C_{1-6}$alkyl-, halogen-, $C_{1-6}$alkoxy-, —$CO_2R^{28}$, —$CH_2CO_2H$, —OH, aryl(optionally substituted by a $C_{1-6}$alkoxy group), heteroaryl, —$CONR^{29}R^{30}$, $C_{3-7}$cycloalkoxy, $C^{3-7}$cycloalkyl($C_{1-6}$alkoxy)-, —$CF_3$;

Heteroaryl or heteroaryl($C_{1-6}$alkyl)- wherein the heteroaryl is optionally substituted by one or more $C_{1-6}$alkyl or —$CONR^{29}R^{30}$ groups; or Heterocyclyl linked to the S(=O)$_n$ moiety through a carbon atom which is optionally substituted by one of more substituents selected from $C_{1-6}$alkyl-, $C_{1-6}$alkylCO—, $C_{3-7}$cycloalkylCO—, heteroarylCO—, optionally substituted by one or more $C_{1-4}$alkyl-groups), $C_{1-6}$alkoxyCO—, arylCO—, $R^{31}R^{32}$NCO—, $C_{1-6}$alkylSO$_2$—, arylSO$_2$, -heteroarylSO$_2$ (optionally substituted by one or more $C_{1-4}$alkyl or $C_{1-4}$alkyl-CONH— groups;

m is 0-6;

n is 0, 1 or 2;

$R^{19}$ is hydrogen, $C_{1-6}$alkyl;

$R^{20}$ is hydrogen, $C_{1-6}$alkyl, halogen or $C_{1-6}$alkoxy;

$R^{4-18}$, $R^{21-25}$, $R^{28}$ and $R^{31-33}$ all independently represent H, $C_{1-6}$ alkyl;

$R^{26}$ and $R^{27}$ independently represent H, $C_{1-6}$ alkyl, $C_{3-7}$cycloalkyl or heterocyclyl;

$R^{29}$ and $R^{30}$ independently represent H, $C_{1-6}$alkyl optionally substituted by OH;

$R^7$ and $R^8$ together with the nitrogen atom to which they are attached may form a heterocyclyl ring;

$R^9$ and $R^{10}$ together with the nitrogen atom to which they are attached may form a heterocyclyl ring;

$R^{17}$ and $R^{18}$ together with the nitrogen atom to which they are attached may form a heterocyclyl ring such as morpholine;

$R^{21}$ and $R^{22}$ together with the nitrogen atom to which they are attached may form a heterocyclyl ring;

$R^{26}$ and $R^{27}$ together with the nitrogen atom to which they are attached may form a heterocyclyl ring;

$R^{29}$ and $R^{30}$ together with the nitrogen atom to which they are attached may form a heterocyclyl ring such as morpholine;

$R^{31}$ and $R^{32}$ together with the nitrogen atom to which they are attached may form a heterocyclyl ring.

2. A compound according to claim 1 wherein $R^1$ is selected from

Aryl optionally substituted by one or more substituents selected from $C_{1-6}$alkyl, halogen, $C_{1-6}$alkoxy-, —CN, —$(CH_2)_m(OH)$, and $C_{1-6}$alkylCO—;

Aryl fused to a heterocyclyl ring, and

Heteroaryl optionally substituted by one or more substituents selected from: $C_{1-6}$alkyl, halogen, and $C_{1-6}$alkoxy groups.

3. A compound according to claim 1 wherein $R^1$ is selected from benzothiazolyl, benzimidazolyl, indazolyl, pyridyl and pyrazolyl.

4. A compound according to claim 1 wherein $R^1$ is selected from

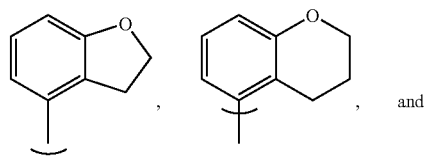
, and

-continued

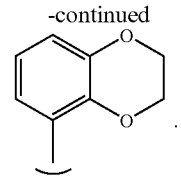
.

5. A compound according to claim 1 wherein $R^1$ is selected from

Aryl optionally substituted by one or more substituents selected from: methyl, fluorine, chlorine, —CN, —OMe, —OH, COMe; and Heteroaryl optionally substituted by one or more methyl, ethyl, flourine, chlorine or methoxy groups.

6. A compound according to claim 1 wherein $R^1$ is selected from 3-(methyloxy)phenyl, 3-methylphenyl, 3-cyanophenyl, 3-fluorophenyl, 3-chlorophenyl, 4-fluoro-3-(methyloxy)phenyl, 3-acetylphenyl, 4-hydroxy-3-(methyloxy)phenyl, 2-fluoro-3-chlorophenyl, 2,3-difluorophenyl, 3,5-difluorophenyl, 1-methyl-1H-benzimidazolyl-6-yl, 1-methyl-1H-indazol-6-yl, 5-(methyloxy)-3-pyridinyl, 3-pyridinyl, 1-ethyl-1H-pyrazol-5-yl, 5-methyl-3-pyridinyl, 1,3-benzothiazol-6-yl, 5-fluoro-3-pyridinyl, and 5-chloro-3-pyridinyl.

7. A compound according to claim 1 wherein $R^2$ is hydrogen.

8. A compound according to claim 1 wherein $R^3$ is selected from:

$C_{1-6}$ alkyl which is optionally substituted by one or more substituents selected from —$NR^{16}COR^{15}$ and —$CONR^{26}R^{27}$;

$C_{3-7}$cycloalkyl;

Aryl optionally substituted by one or more substituents selected from $C_{1-6}$alkyl-, $C_{1-6}$alkoxy-, and $CONR^{29}R^{30}$; and Heterocyclyl which is optionally substituted by one or more substituents selected from $C_{1-6}$alkylCO—, $C_{3-7}$cycloalkylCO—, heteroarylCO—.

9. A compound according to claim 1 wherein $R^3$ is selected from methyl, ethyl, n-propyl, tert-butyl, isopropyl, MeCONH$(CH_2)_2$—, $Me_2NCO(CH_2)_2$—;

Cyclopentyl;

Aryl optionally substituted by one or more methoxy, methyl, —$CONMe_2$ groups; and Heterocyclyl which is optionally substituted by one of more substituents selected from MeCO—, cyclopropylCO, 2-furylCO—.

10. A compound according to claim 8 wherein $R^3$ is selected from 4-(methyloxy)phenyl, phenyl, 3-[(dimethylamino)carbonyl]phenyl, 4-methylphenyl, 3,4-bis(methyloxy)phenyl, 3,4,5-tris(methyloxy)phenyl, 3-(ethyloxy)phenyl.

11. A compound according to claim 1 wherein $R^3$ is a piperidinyl group substituted by one or more substituents selected from MeCO—, cyclopropylCO, and 2-furylCO—.

12. A compound according to claim 1 wherein $R^3$ is 1-acetyl-4-piperidinyl, 1-(2-furanylcarbonyl)-4-piperidinyl, or 1-(cyclopropylcarbonyl)-4-piperidinyl.

13. A compound according to claim 1 wherein $R^{20}$ is hydrogen, methyl, ethyl, fluorine or chlorine.

14. A compound according to claim 1 wherein n is 2.

15. A compound selected from

4-[(3-methylphenyl)amino]-6-(methylsulfonyl)-3-quinolinecarboxamide,
4-[(3-cyanophenyl)amino]-6-(methylsulfonyl)-3-quinolinecarboxamide,
4-(2,3-dihydro-1-benzofuran-4-ylamino)-6-(methylsulfonyl)-3-quinolinecarboxamide,
4-{[3-(methyloxy)phenyl]amino}-6-(methylsulfonyl)-3-quinolinecarboxamide,
4-{[4-fluoro-3-(methyloxy)phenyl]amino}-6-(methylsulfonyl)-3-quinolinecarboxamide,
4-[(3-chlorophenyl)amino]-6-(methylsulfonyl)-3-quinolinecarboxamide,
4-(1,3-benzothiazol-6-ylamino)-6-(phenylsulfonyl-3-quinolinecarboxamide,
4-[(1-methyl-1H-benzimidazol-6-yl)amino]-6-(phenylsulfonyl)-3-quinolinecarboxamide,
4-[(3-cyanophenyl)amino]-6-(phenylsulfonyl)-3-quinolinecarboxamide,
4-(2,3-dihydro-1-benzofuran-4-ylamino)-6-(phenylsulfonyl)-3-quinolinecarboxamide,
4-{[3-(methyloxy)phenyl]amino}-6-(phenylsulfonyl)-3-quinolinecarboxamide,
6-(cyclopentylsulfonyl)-4-[(3-fluorophenyl)amino]-3-quinolinecarboxamide,
4-{[3-(methyloxy)phenyl]amino}-6-{[4-(methyloxy)phenyl]sulfonyl}-3-quinolinecarboxamide,
6-[(1,1-dimethylethyl)sulfonyl]-4-{[3-(methyloxy)phenyl]amino}-3-quinolinecarboxamide,
6-{[2-(acetylamino)ethyl]sulfonyl}-4-{[3-(methyloxy)phenyl]amino}-3-quinolinecarboxamide,
6-[(1,1-dimethylethyl)thio]-4-{[3-(methyloxy)phenyl]amino}-3-quinolinecarboxamide,
6-{[2-(acetylamino)ethyl]thio}-4-{[3-(methyloxy)phenyl]amino}-3-quinolinecarboxamide,
4-[(1-methyl-1H-indazol-6-yl)amino]-6-(phenylsulfonyl)-3-quinolinecarboxamide,
4-{[4-hydroxy-3-(methyloxy)phenyl]amino}-6-(phenylsulfonyl)-3-quinolinecarboxamide,
4-[(3-acetylphenyl)amino]-6-(phenylsulfonyl)-3-quinolinecarboxamide,
8-methyl-4-{[3-(methyloxy)phenyl]amino}-6-(phenylsulfonyl)-3-quinolinecarboxamide,
4-{[4-fluoro-3-(methyloxy)phenyl]amino}-8-methyl-6-(phenylsulfonyl)-3-quinolinecarboxamide,
7-methyl-4-{[3-(methyloxy)phenyl]amino}-6-(methylsulfonyl)-3-quinolinecarboxamide,
8-methyl-4-{[3-(methyloxy)phenyl]amino}-6-{[4-(methyloxy)phenyl]sulfonyl}-3-quinolinecarboxamide,
4-(2,3-dihydro-1-benzofuran-4-ylamino)-8-methyl-6-{[4-(methyloxy)phenyl]sulfonyl}-3-quinolinecarboxamide,
4-[(3-acetylphenyl)amino]-8-methyl-6-{[4-(methyloxy)phenyl]sulfonyl}-3-quinolinecarboxamide,
8-methyl-4-[(1-methyl-1H-indazol-6-yl)amino]-6-{[4-(methyloxy)phenyl]sulfonyl}-3-quinolinecarboxamide,
4-(2,3-dihydro-1,4-benzodioxin-5-ylamino)-8-methyl-6-{[4-(methyloxy)phenyl]sulfonyl}-3-quinolinecarboxamide,
4-[(3-chlorophenyl)amino]-8-methyl-6-{[4-(methyloxy)phenyl]sulfonyl}-3-quinolinecarboxamide,
4-[(3-cyanophenyl)amino]-8-methyl-6-{[4-(methyloxy)phenyl]sulfonyl}-3-quinolinecarboxamide,
4-(1,3-benzothiazol-6-ylamino)-8-methyl-6-{[4-(methyloxy)phenyl]sulfonyl}-3-quinolinecarboxamide,
4-[(3-fluorophenyl)amino]-8-methyl-6-{[4-(methyloxy)phenyl]sulfonyl}-3-quinolinecarboxamide,
4-(2,3-dihydro-1-benzofuran-4-ylamino)-8-methyl-6-[(4-methylphenyl)sulfonyl]-3-quinolinecarboxamide,
8-methyl-4-[(1-methyl-1H-indazol-6-yl)amino]-6-[(4-methylphenyl)sulfonyl]-3-quinolinecarboxamide,
8-methyl-4-{[3-(methyloxy)phenyl]amino}-6-[(4-methylphenyl)sulfonyl]-3-quinolinecarboxamide,
4-{[4-fluoro-3-(methyloxy)phenyl]amino}-8-methyl-6-(methylsulfonyl)-3-quinolinecarboxamide,
8-methyl-4-[(1-methyl-1H-indazol-6-yl)amino]-6-(phenylsulfonyl)-3-quinolinecarboxamide,
4-(2,3-dihydro-1-benzofuran-4-ylamino)-8-methyl-6-(methylsulfonyl)-3-quinolinecarboxamide,
8-methyl-6-(methylsulfonyl)-4-(3-pyridinylamino)-3-quinolinecarboxamide 8-methyl-4-[(1-methyl-1H-indazol-6-yl)amino]-6-(methylsulfonyl)-3-quinolinecarboxamide,
4-[(3-fluorophenyl)amino]-8-methyl-6-(methylsulfonyl)-3-quinolinecarboxamide,
4-[(3-cyanophenyl)amino]-8-methyl-6-(methylsulfonyl)-3-quinolinecarboxamide,
4-[(1-ethyl-1H-pyrazol-5-yl)amino]-8-methyl-6-(methylsulfonyl)-3-quinolinecarboxamide,
8-methyl-4-{[5-(methyloxy)-3-pyridinyl]amino}-6-(methylsulfonyl)-3-quinolinecarboxamide,
8-methyl-4-[(5-methyl-3-pyridinyl)amino]-6-(methylsulfonyl)-3-quinolinecarboxamide,
8-chloro-4-[(3-methylphenyl)amino]-6-(methylsulfonyl)-3-quinolinecarboxamide,
8-chloro4-{[4-fluoro-3-(methyloxy)phenyl]amino}-6-(methylsulfonyl)-3-quinolinecarboxamide,
8-chloro-4-(2,3-dihydro-1-benzofuran-4-ylamino)-6-(methylsulfonyl)-3-quinolinecarboxamide,
8-chloro-4-[(3-cyanophenyl)amino]-6-(methylsulfonyl)-3-quinolinecarboxamide,
8-chloro-4-[(3-fluorophenyl)amino]-6-(methylsulfonyl)-3-quinolinecarboxamide,
8-chloro-4-[(1-methyl-1H-indazol-6-yl)amino]-6-(methylsulfonyl)-3-quinolinecarboxamide,
methyl 3-[(3-(aminocarbonyl)-8-methyl-4-{[3-(methyloxy)phenyl]amino}-6-quinolinyl)sulfonyl]benzoate,
6-{[3,4-bis(methyloxy)phenyl]sulfonyl}-8-methyl-4-{[3-(methyloxy)phenyl]amino}-3-quinolinecarboxamide,
8-methyl-4-{[3-(methyloxy)phenyl]amino}-6-{[3,4,5-tris(methyloxy)phenyl]sulfonyl}-3-quinolinecarboxamide hydrochloride,
6-{[3,4-bis(methyloxy)phenyl]sulfonyl}-4-{[3-(methyloxy)phenyl]amino}-3-quinolinecarboxamide,
6-{[3-(ethyloxy)phenyl]sulfonyl}-8-methyl-4-{[3-(methyloxy)phenyl]amino}-3-quinolinecarboxamide,
6-{[2-(acetylamino)ethyl]sulfonyl}-8-methyl-4-{[3-(methyloxy)phenyl]amino}-3-quinolinecarboxamide,
6-({3-[(dimethylamino)carbonyl]phenyl}sulfonyl)-8-methyl-4-{[3-(methyloxy)phenyl]amino}-3-quinolinecarboxamide,
6-({3-[(dimethylamino)carbonyl]phenyl}sulfonyl)-4-{[3-(methyloxy)phenyl]amino}-3-quinolinecarboxamide,
4-[(3-cyanophenyl)amino]-6-({3-[(dimethylamino)carbonyl]phenyl}sulfonyl)-8-methyl-3-quinolinecarboxamide,
6-({3-[(dimethylamino)carbonyl]phenyl}sulfonyl)-8-methyl-4-[(1-methyl-1H -benzimidazol-6-yl)amino]-3-quinolinecarboxamide,
4-(2,3-dihydro-1-benzofuran-4-ylamino)-6-({3-[(dimethylamino)carbonyl]phenyl}sulfonyl)-8-methyl-3-quinolinecarboxamide,
6-[(1-acetyl-4-piperidinyl)sulfonyl]-4-{[3-(methyloxy)phenyl]amino}-3-quinolinecarboxamide, 6-{[1-(2-furanylcarbonyl)-4-piperidinyl]sulfonyl}-8-methyl-4-{[3-(methyloxy)phenyl]amino}-3-quinolinecarboxamide,
4-[(3-cyanophenyl)amino]-6-{[1-(2-furanylcarbonyl)-4-piperidinyl]sulfonyl}-8-methyl-3-quinolinecarboxamide,
6-{[1-(cyclopropylcarbonyl)-4piperidinyl]sulfonyl}-8-methyl-4-{[3-(methyloxy) phenyl]amino}3-quinolinecarboxamide,
4-(2,3-dihydro-1-benzofuran-4-ylamino)-6-{[1-(2-furanylcarbonyl)-4-piperidinyl]sulfonyl}-8-methyl-3-quinolinecarboxamide,
6-{[1-(cyclopropylcarbonyl)-4-piperidinyl]sulfonyl}-4-(2,3-dihydro-1-benzofuran-4-ylamino)-8-methyl-3-quinolinecarboxamide,
6-[(1-acetyl-4-piperidinyl)sulfonyl]-4-{[4-fluoro-3-(methyloxy)phenyl]amino}-8-methyl-3-quinolinecarboxamide,
4-(2,3-dihydro-1-benzofuran-4-ylamino)-8-methyl-6-({2-[(methylsulfonyl) amino]ethyl}sulfonyl)-3-quinolinecarboxamide,
6-{[1-(2-furanylcarbonyl)-4-piperidinyl]sulfonyl}-8-methyl-4-[(1-methyl-1H-benzimidazol-6-yl)amino]-3-quinolinecarboxamide,
6-{[3-(dimethylamino)-3-oxopropyl]sulfonyl}-4-{[4-fluoro-3-(methyloxy)phenyl]amino}-8-methyl-3-quinolinecarboxamide,
4-[(2,3-difluorophenyl)amino]-8-methyl-6-(methylsulfonyl)-3-quinolinecarboxamide,
4-[(3-chloro-2-fluorophenyl)amino]-8-methyl-6-(methylsulfonyl)-3-quinolinecarboxamide,
4-[(3,5-difluorophenyl)amino]-8-methyl-6-(methylsulfonyl)-3-quinolinecarboxamide,
4-[(5-fluoro-3-pyridinyl)amino]-8-methyl-6-(methylsulfonyl)-3-quinolinecarboxamide,
4-[(5-chloro-3-pyridinyl)amino]-8-methyl-6-(methylsulfonyl)-3-quinolinecarboxamide,
6-({5-[(dimethylamino)carbonyl]-3-pyridinyl}sulfonyl)-8-methyl-4-{[3-(methyloxy)phenyl]amino}-3-quinolinecarboxamide hydrochloride,
8-methyl-6-[(1-methylethyl)sulfonyl]-4-(3-pyridinylamino)-3-quinolinecarboxamide,
6-[(1,1-dimethylethyl)sulfonyl]-8-methyl-4-(3-pyridinylamino)-3-quinolinecarboxamide,
4-[(1-ethyl-1H-pyrazol-5-yl)amino]-8-methyl-6-[(1-methylethyl)sulfonyl]-3-quinolinecarboxamide,
6-[(1,1-dimethylethyl)sulfonyl]-4-[(1-ethyl-1H-pyrazol-5-yl)amino]-8-methyl-3-quinolinecarboxamide,
4-(3,4-dihydro-2H-chromen-5-ylamino)-8-methyl-6-(methylsulfonyl)-3-quinolinecarboxamide,
4-(2,3-dihydro-1-benzofuran-4-ylamino)-8-methyl-6-(methylsulfinyl)-3-quinolinecarboxamide,
4-[(5-chloro-3-pyridinyl)amino]-6-[(1,1-dimethylethyl)sulfonyl]-3-quinolinecarboxamide,
8-ethyl-4-{[4-fluoro-3-(methyloxy)phenyl]amino}-6-(methylsulfonyl)-3-quinolinecarboxamide,
8-ethyl-4-[(3-fluorophenyl)amino]-6-(methylsulfonyl)-3-quinolinecarboxamide,
4-[(3-cyanophenyl)amino]-8-ethyl-6-(methylsulfonyl)-3-quinolinecarboxamide,
8-ethyl-4-[(1-methyl-1H-indazol-6-yl)amino]-6-(methylsulfonyl)-3-quinolinecarboxamide,
4-(2,3-dihydro-1-benzofuran-4-ylamino)-8-ethyl-6-(methylsulfonyl)-3-quinolinecarboxamide,
8-ethyl-6-(methylsulfonyl)-4-(3-pyridinylamino)-3-quinolinecarboxamide 4-(2,3-dihydro-1-benzofuran-4-ylamino)-8-fluoro-6-(methylsulfonyl)-3-quinolinecarboxamide,
8-chloro-4-[(5-chloro-3-pyridinyl)amino]-6-(ethylsulfonyl)-3-quinolinecarboxamide,
8-chloro-4-[(5-chloro-3-pyridinyl)amino]-6-(propylsulfonyl)-3-quinolinecarboxamide,
8-chloro-4-[(5-chloro-3-pyridinyl)amino]-6-[(1-methylethyl)sulfonyl]-3-quinolinecarboxamide,
8-chloro-4-[(5-chloro-3-pyridinyl)amino]-6-[(1,1-dimethylethyl)sulfonyl]-3-quinolinecarboxamide,
4-[(5-chloro-3-pyridinyl)amino]-8-methyl-6-[(1-methylethyl)sulfonyl]-3-quinolinecarboxamide,
6-(ethylsulfonyl)-4-[(5-fluoro-3-pyridinyl)amino]-8-methyl-3-quinolinecarboxamide,
6-[(1,1-dimethylethyl)sulfonyl]-4-[(5-fluoro-3-pyridinyl)amino]-8-methyl-3-quinolinecarboxamide,
8-chloro-4-[(5-fluoro-3-pyridinyl)amino]-6-[(1-methylethyl)sulfonyl]-3-quinolinecarboxamide,
8-chloro-6-[(1,1-dimethylethyl)sulfonyl]-4-[(5-fluoro-3-pyridinyl)amino]-3-quinolinecarboxamide,
4-[(5-chloro-3-pyridinyl)amino]-6-(ethylsulfonyl)-8-methyl-3-quinolinecarboxamide,
4-[(5-chloro-3-pyridinyl)amino]-8-methyl-6-(propylsulfonyl)-3-quinolinecarboxamide,
4-[(5-chloro-3-pyridinyl)amino]-6-[(1,1-dimethylethyl)sulfonyl]-8-methyl-3-quinolinecarboxamide,and
or a pharmaceutically acceptable salt thereof.

16. A compound according to claim 15 selected from
4-(2,3-dihydro-1-benzofuran-4-ylamino)-8-methyl-6-(methylsulfonyl)-3-quinolinecarboxamide,
8-methyl-4-[(1-methyl-1H-indazol-6-yl)amino]-6-(methylsulfonyl)-3-quinolinecarboxamide,
4-[(3-cyanophenyl)amino]-8-methyl-6-(methylsulfonyl)-3-quinolinecarboxamide,
8-methyl-4-[(5-methyl-3-pyridinyl)amino]-6-(methylsulfonyl)-3-quinolinecarboxamide,
4-[(3,5-difluorophenyl)amino]-8-methyl-6-(methylsulfonyl)-3-quinolinecarboxamide,
4-[(1-ethyl-1H-pyrazol-5-yl)amino]-8-methyl-6-[(1-methylethyl)sulfonyl]-3-quinolinecarboxamide,
6-[(1,1-dimethylethyl)sulfonyl]-4-[(5-fluoro-3-pyridinyl)amino]-8-methyl-3-quinolinecarboxamide,
8-chloro-6-[(1,1-dimethylethyl)sulfonyl]-4-[(5-fluoro-3-pyridinyl)amino]-3-quinolinecarboxamide,and pharmaceutically acceptable salts therof.

17. A compound according to claim 15 selected from
8-methyl-4-{[3-(methyloxy)phenyl]amino}-6-{[4-(methyloxy)phenyl]sulfonyl}-3-quinolinecarboxamide,
6-({3-[(dimethylamino)carbonyl]phenyl}sulfonyl)-8-methyl-4-{[3-(methyloxy)phenyl]amino}-3-quinolinecarboxamide hydrochloride,
6-({3-[(dimethylamino)carbonyl]phenyl}sulfonyl)-4-{[3-(methyloxy)phenyl]amino}-3-quinolinecarboxamide,
4-[(3-cyanophenyl)amino]-6-({3-[(dimethylamino)carbonyl]phenyl}sulfonyl)-8-methyl-3-quinolinecarboxamide,
4-(2,3-dihydro-1-benzofuran-4-ylamino)-6-{[1-(2-furanylcarbonyl)-4-piperidinyl]sulfonyl}-8-methyl-3-quinolinecarboxamide,
4-(2,3-dihydro-1-benzofuran-4-ylamino)-8-methyl-6-({2-[(methylsulfonyl)amino]ethyl}sulfonyl)-3-quinolinecarboxamide,
6-({5-[(dimethylamino)carbonyl]-3-pyridinyl}sulfonyl)-8-methyl-4-{[3-(methyloxy)phenyl]amino}-3-quinolinecarboxamide hydrochloride, and
a pharmaceutically acceptable salt thereof.

18. A pharmaceutical formulation comprising a compound of formula (I) according to claim 1 or a pharmaceutically acceptable salt thereof, and a pharmaceutically acceptable carrier or excipient, and optionally one or more other therapeutic ingredients.

19. A combination comprising a compound of formula (I) according to claim 1 or a pharmaceutically acceptable salt and one or more other therapeutic ingredients.

20. A process for preparing a compound of formula (I) as claimed in claim 1 which process comprises:
(i) treating a compound of formula II:

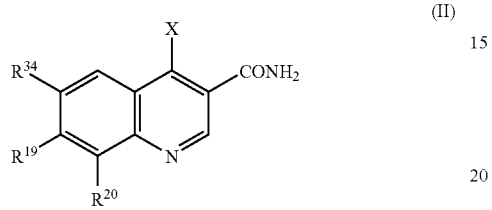

(II)

wherein $R^{34}$, $R^{19}$, and $R^{20}$ are as defined in claim 1, and X represents a halogen atom, with an amine of formula $R^1R^2NH$, wherein $R^1$ and $R^2$ are as defined in claim 1, to make a compound of formula (I).

21. The process of claim 20, further comprising the step of deprotecting the compound of formula (I) to form another compound of formula (I).

22. The process of claim 20, further comprising the step of converting the compound of formula (I) into a further compound of formula (I).

23. The process of claim 20, further comprising the step of converting the compound of formula (I) into a salt thereof.

* * * * *

UNITED STATES PATENT AND TRADEMARK OFFICE
CERTIFICATE OF CORRECTION

| | | |
|---|---|---|
| PATENT NO. | : 7,566,786 B2 | Page 1 of 1 |
| APPLICATION NO. | : 10/557079 | |
| DATED | : July 28, 2009 | |
| INVENTOR(S) | : Baldwin et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 420 days Delete the phrase "by 420 days" and insert -- by 669 days --

Signed and Sealed this

Eleventh Day of May, 2010

David J. Kappos
*Director of the United States Patent and Trademark Office*